(12) United States Patent
Abend et al.

(10) Patent No.: US 12,077,571 B2
(45) Date of Patent: Sep. 3, 2024

(54) POLYOMAVIRUS NEUTRALIZING ANTIBODIES

(71) Applicant: Novartis AG, Basel (CH)

(72) Inventors: Johanna Abend, Emeryville, CA (US); Zorica Dragic, Basel (CH); Adam Lloyd Feire, Hull, MA (US); Mark Knapp, Oakland, CA (US); Steven Kovacs, Randolph, NJ (US); Elisabetta Traggiai, Basel (CH); Lichun Wang, Shanghai (CN); Yongqiang Wang, Shanghai (CN); Danqing Wu, Shanghai (CN); Qilong Wu, Shanghai (CN); Fangmin Xu, Belmont, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 18/186,064

(22) Filed: Mar. 17, 2023

(65) Prior Publication Data

US 2023/0399382 A1    Dec. 14, 2023

Related U.S. Application Data

(63) Continuation of application No. 17/502,910, filed on Oct. 15, 2021, now Pat. No. 11,639,378, which is a continuation of application No. 16/657,855, filed on Oct. 18, 2019, now Pat. No. 11,161,894, which is a continuation of application No. 15/758,491, filed as application No. PCT/IB2016/055339 on Sep. 8, 2016, now Pat. No. 10,450,366.

(51) Int. Cl.
| | |
|---|---|
| A61K 45/06 | (2006.01) |
| A61K 9/19 | (2006.01) |
| A61K 39/42 | (2006.01) |
| C07K 16/08 | (2006.01) |

(52) U.S. Cl.
CPC ............ *C07K 16/084* (2013.01); *A61K 9/19* (2013.01); *A61K 39/42* (2013.01); *A61K 45/06* (2013.01); *C07K 2317/20* (2013.01); *C07K 2317/21* (2013.01); *C07K 2317/24* (2013.01); *C07K 2317/33* (2013.01); *C07K 2317/34* (2013.01); *C07K 2317/41* (2013.01); *C07K 2317/56* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,946,778 A | 8/1990 | Ladner et al. |
| 5,091,513 A | 2/1992 | Huston et al. |
| 5,132,405 A | 7/1992 | Huston et al. |
| 5,641,870 A | 6/1997 | Rinderknecht et al. |
| 6,596,541 B2 | 7/2003 | Murphy et al. |
| 7,244,592 B2 | 7/2007 | Hoogenboom et al. |
| 7,462,697 B2 | 12/2008 | Couto et al. |
| 8,470,979 B2 | 6/2013 | Bondensgaard et al. |
| 9,771,413 B2 | 9/2017 | Martin et al. |
| 9,862,760 B2 | 1/2018 | Abend et al. |
| 10,011,648 B2 | 7/2018 | Burioni et al. |
| 10,435,460 B2 | 10/2019 | Abend et al. |
| 10,450,365 B2 | 10/2019 | Grimm et al. |
| 10,450,366 B2 | 10/2019 | Abend et al. |
| 10,654,914 B2 | 5/2020 | Abend et al. |
| 11,161,894 B2 | 11/2021 | Abend et al. |
| 11,433,132 B2 | 9/2022 | Abend et al. |
| 11,639,378 B2 | 5/2023 | Abend et al. |
| 2008/0107658 A1 | 5/2008 | Franks et al. |
| 2010/0215662 A1 | 8/2010 | Bradbury |
| 2013/0337438 A1 | 12/2013 | Mori et al. |
| 2014/0294841 A1 | 10/2014 | Scheinberg et al. |
| 2015/0056188 A1 | 2/2015 | Simon et al. |
| 2020/0155673 A1 | 5/2020 | Rosario et al. |
| 2020/0190167 A1 | 6/2020 | Abend et al. |
| 2022/0363735 A1 | 11/2022 | Abend et al. |
| 2023/0079587 A1 | 3/2023 | Abend et al. |
| 2023/0220051 A1 | 7/2023 | Abend et al. |

FOREIGN PATENT DOCUMENTS

| | | |
|---|---|---|
| CN | 104520318 A | 4/2015 |
| CN | 104936980 A | 9/2015 |
| JP | 2015524389 A | 8/2015 |
| JP | 2016513072 A | 5/2016 |
| WO | WO-03105894 A1 | 12/2003 |
| WO | WO-2013142299 A1 | 9/2013 |
| WO | WO-2013142300 A2 | 9/2013 |
| WO | WO-2014002035 A2 | 1/2014 |
| WO | WO-2014102399 A1 | 7/2014 |
| WO | WO-2015095770 A1 | 6/2015 |
| WO | WO-2015114150 A1 | 8/2015 |
| WO | WO-2017046676 A1 | 3/2017 |
| WO | WO-2019106578 A2 | 6/2019 |

(Continued)

OTHER PUBLICATIONS

Abend et al., "Inhibitory Effect of Gamma Interferon on BK Virus Gene Expression and Replication," J. Virology, 2007, vol. 81, pp. 272-279.

(Continued)

*Primary Examiner* — Nianxiang Zou
(74) *Attorney, Agent, or Firm* — COOLEY LLP

(57) ABSTRACT

The present invention relates to anti-VP1 antibodies, antibody fragments, and their uses for the prevention and treatment of polyoma virus infection and associated diseases.

20 Claims, 45 Drawing Sheets
Specification includes a Sequence Listing.

(56) References Cited

FOREIGN PATENT DOCUMENTS

| WO | WO-2021250097 A1 | 12/2021 |
|---|---|---|
| WO | WO-2021252835 A1 | 12/2021 |

OTHER PUBLICATIONS

Altschul, S. F., et al., "Gapped Blast and PSI-Blast: a new generation of protein database search programs", Nucleic Acids Research (Sep. 1, 1997); 25(17): 3389-3402.
Ambalathingal, George R. et al., "BK Polyomavirus: Clinical Aspects, Immune Regulation, and Emerging Therapies," Clin Microbiol Rev, Feb. 22, 2017, vol. 30(2), pp. 503-528.
Antinori et al., "Clinical Epidemiology and Survival of Progressive Multifocal Leukoencephalopathy in the Era of Highly Active Antiretroviral Therapy: Data from the Italian Registry Investigative Neuro Aids (IRINA)," Journal of NeuroVirology, 2003, vol. 9. Supp. 1, pp. 47-53.
Astrom et al., "Progressive Multifocal Leuko-Encephalopathy a Hitherto Unrecognized Complication of Chronic Lymphatic Leukemia and Hodgkin's Disease," Brain, 1958, vol. 81, No. 1, pp. 93-111.
Bennett et al., "BK Polyomavirus: Emerging Pathogen," Microbes and Infection, 2012, vol. 14, No. 9, pp. 672-683.
Binet et al., "Polyomavirus Disease Under New Immunosuppressive Drugs: A Cause of Renal Graft Dysfunction and Graft Loss," Transplantation, 1999, vol. 67, No. 6, pp. 918-922.
Brennan et al., "Incidence of BK with Tacrolimus Versus Cyclosporine and Impact of Preemptive Immunosuppression Reduction," Am. J. Transplant, 2005, vol. 5. No. 3, pp. 582-593.
Bressollette-Bodin et al., "A Prospective Longitudinal Study of BK Virus Infection in 104 Renal Transplant Recipients," American Journal of Transplantation, 2005, vol. 5, No. 8, pp. 1926-1933.
Broekema et al., "A System for the Analysis of BKV Non-Coding Control Regions: Application to Clinical Isolates from an HIV/AIDS Patient," Virology, 2010, vol. 407, pp. 368-373.
Caldes, Cristina et al., "Humanization of the anti-CD18 antibody 6.7: an unexpected effect of a framework residue in binding to antigen," Molecular Immunology, vol. 39, No. 15, May 1, 2003, pp. 941-952.
Carter et al., "Humanization of an anti-p185HER2 antibody for human cancer therapy," Proceedings of the National Academy of Sciences, May 1992, 89(10), pp. 4285-4289.
Carter et al. Lack of Serologic Evidence for Prevalent Simian Virus 40 Infection in Humans. J Natl Cancer Inst 2003;95:1522-30.
Casadevall, A. et al., "Immunoglobulin isotype influences affinity and specificity," Proceedings of the National Academy of Sciences, vol. 109, No. 31, Jul. 31, 2012, pp. 12272-12273.
Chang, D., et al., "Production of the antigen and the antibody of the JC virus major capsid protein VP1", Journal of Virological Methods, 1996, vol. 59, No. 1-2, pp. 177-187.
Chao et al., "Isolating and engineering human antibodies using yeast surface display," Nature Protocols, Aug. 2006, 1(2), pp. 755-768.
Chatterjee et al., "Identification of Archetype and Rearranged Forms of BK Virus in Leukocytes from Healthy Individuals," Journal of Medical Virology, 2000, vol. 60, pp. 353-362.
Chen et al., "Synthetic Antibodies and Peptides Recognizing Progressive Multifocal Leukoencephalopathy specific Point Mutations in Polyomavirus JC Capsid Viral Protein 1," mABS, 2015, vol. 7, No. 4, pp. 681-692.
Chothia, C. et al., "Canonical Structures for the Hypervariable Regions of Immunoglobins", Journal of Molecular Biology, Aug. 1987, vol. 196, No. 4, pp. 901-917.
Chothia, et al., "Conformations of immunoglobulin hypervariable regions," Nature, Dec. 28, 1989, vol. 342, pp. 877-883.
Chothia, et al., "Structural repertoire of the human VH segments," Journal of Molecular Biology, Oct. 5, 1992, vol. 227, No. 3, pp. 799-817.
ClinicalTrials.gov, "A Safety, Pharmacokinetics and Efficacy Study of MAU868 for the Treatment of BK Viremia in Kidney Transplant Recipients," ClinicalTrials.gov Identifier: NCT04294472, Jul. 22, 2022, 7 pages.
Co, M., et al., "Chimeric and humanized antibodies with specificity for the CD33 antigen," Journal of Immunology, Feb. 15, 1992, vol. 148, No. 4, pp. 1149-1154.
Co, M. S., et al., "Humanized antibodies for antiviral therapy", Proceedings of the National Academy of Sciences (1991) 88(7): 2869-2873.
Cohen-Bucay, A. et al., "Advances in BK Virus Complications in Organ Transplantation and Beyond," Kidney Medicine, vol. 2, Issue 6, Nov.-Dec. 2020, pp. 771-786.
Dakroub, F., "The impact of pre-graft serology on the risk of BKPyV infection reactivation post-renal transplantation," Doctorate Thesis, Human Health and Pathology, Université de Picardie Jules Verne, Université Libanaise, Oct. 2020, 195 pages.
Derienzo et al., "Evaluation of the Half-Life of Intravenous Human Cytomegalovirus Immune Globulin in Patients Receiving Partially Mismatched Related Donor Bone Marrow Transplantation," Pharmacotherapy, 2000, vol. 20, pp. 1175-1178.
Du, J. et al., "Molecular basis of recognition of human osteopontin by 23C3, a potential therapeutic antibody for treatment of rheumatoid athritis," Journal of Molecular Biology, Academic Press, United Kingdom, by vol. 382, No. 4, Oct. 17, 2008, pp. 835-842.
Ehrlich, P. et al., "Isolation of an active heavy-chain variable domain from a homogeneous rabbit antibody by cathepsin B digestion of the aminoethylated heavy chain," Biochemistry, Aug. 1, 1980, vol. 19, No. 17, pp. 4091-4096.
Gambarino, S. et al., "Genotyping of polyomavirus BK by real time PCR for VP1 gene," Molecular biotechnology, Oct. 2011, vol. 49, pp. 151-158.
Garcia-Suarez et al., "Changes in the Natural History of Progressive Multifocal Leukoencephalopathy in HIV-Negative Lymphoproliferative Disorders: Impact of Novel Therapies," Am. J. Hematol., 2005, vol. 80, No. 4, pp. 271-281.
Gardner, "New Human Papovavirus (B.K.) Isolated from Urine after Renal Transplantation," Lancet, 1971, vol. 297, No. 7712, pp. 1253-1257.
Geoghegan, Eileen M. E et al., "Infectious Entry and Neutralization of Pathogenic JC Polyomaviruses," Cell Rep, Oct. 31, 2017, vol. 21,pp. 1169-1179.
Gorelik et al., "Progressive Multifocal Leukoencephalopathy (PML) Development is Associated with Mutations in JC Virus Capsid Protein VP1 that Change its Receptor Specificity," Journal of Infectious Diseases, 2011, vol. 204, pp. 237-244.
Gorman et al. "Reshaping a therapeutic CD4 antibody." Proceedings of the National Academy of Sciences (1991); 88.10: 4181-4185.
Goudsmit et al., "The Role of BK Virus in Acute Respiratory Tract Disease and the Presence of BKV DNA in Tonsils," Journal of Medical Virology, 1992, vol. 10, pp. 91-99.
Henmi, C., et al., "Establishment of an immunoscreening system using recombinant VP1 protein for the isolation of a monoclonal antibody that blocks JC virus infection", Biochemical and Biophysical Research Communications, 2005, 327, No. 1, pp. 242-251.
Heritage et al., "The Persistence of Papovavirus BK DNA Sequences in Normal Human Renal Tissue," Journal of Medical Virology, 1981, vol. 8, pp. 143-150.
Hirsch et al., "Polyomavirus-Associated Nephropathy in Renal Transplantation: Interdisciplinary Analyses and Recommendations," Transplantation, 2005, vol. 79, No. 1, pp. 1277-1286.
Hirsch et al., "Prospective Study of Polyomavirus Type BK Replication and Nephropathy in Renal-Transplant Recipients," New England J. Medicine, Aug. 15, 2002, vol. 347, No. 7, pp. 488-496.
Hirsch, "Polyomavirus BK Nephropathy: A (Re-)Emerging Complication in Renal Transplantation," Am. J. Transplant., 2002, vol. 2, No. 1, pp. 25-30.
Hochman, J. et al., "Folding and interaction of subunits at the antibody combining site," Biochemistry, Jun. 1, 1976, vol. 15, No. 12, pp. 2706-2710.
Holliger et al., "'Diabodies': Small bivalent and bispecific antibody fragments," Proceedings of the National Academy of Sciences, Jul. 1993, 90(14), pp. 6444-6448.

(56) References Cited

OTHER PUBLICATIONS

Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the United States of America, Aug. 1988, vol. 85, pp. 5879-5883.
Ill, C. et al., "Design and construction of a hybrid immunoglobulin domain with properties of both heavy and light chain variable regions," Protein Engineering, Design and Selection, Aug. 1997, vol. 10, Issue 8, pp. 949-957.
Inbar et al. (1972). "Localization of Antibody-Combining Sites within the Variable Portions of Heavy and Light Chains". Proc Natl Acad Sci USA. 69(9): 2659-2662.
International Search Report and Written Opinion for PCT/IB2018/059429, mailed Jun. 4, 2019, 19 pages.
International Search Report and Written Opinion in PCT/IB2016/055339, dated Feb. 1, 2017, 15 pages.
International Search Report and Written Opinion in PCT/US2021/036923, dated Dec. 16, 2021, 16 pages.
Jelcic, Ivan et al., "Broadly neutralizing human monoclonal JC polyomavirus VP1-specific antibodies as candidate therapeutics for progressive multifocal leukoencephalopathy," Sci Transl Med, 2015, vol. 7(306),pp. 306ra150.
Jiang et al., "The Role of Polyomaviruses in Human Disease," Virology, Feb. 2009, vol. 384, No. 2, pp. 266-273.
Johne et al., "Nuclear Localization of Avian Polyomavirus Structural Protein VP1 is a Prerequisite for the Formation of Virus-Like Particles," Journal of Virology, Jan. 2004, vol. 78, No. 2, pp. 930-937.
Johne et al., "Taxonomical Developments in the Family Polyomaviridae," Arch. Virol., Sep. 2011, vol. 156, No. 9, pp. 1627-1634.
Johnson, et al., "Kabat Database and its applications: future directions," Nucleic Acids Research, Jan. 1, 2001, vol. 29, No. 1, pp. 205-206.
Jordan, S.C. et al., "Efficacy of MAU868, a Novel BKV Neutralizing Monoclonal Antibody (mAb), for the Treatment of Severe BK Virus Nephropathy (BKVN) After Kidney Transplant," [abstract]. Am J Transplant, 2021, vol. 21. Suppl. 3, 4 pages.
Jordan, S.C. et al., "Experience with a BKV-Specific, Neutralizing Monoclonal Antibody (MAU868) for Treatment of Severe BK Virus Nephropathy (BKVN) after Kidney Transplant (FDA EIND #139112)," [abstract]. Am J Transplant., 2020; vol. 20, Suppl. 3, 4 pages.
Kettleborough et al., "Humanization of a mouse monoclonal antibody by CDR-grafting: the importance of framework residues on loop conformation." Protein Engineering (1991); 4.7: 773-783.
Knowles et al., "Discovery and Epidemiology of the Human Polyomaviruses BK Virus (BKV) and JC Virus (JCV)," Adv. Exp. Med. Biol., 2006, vol. 577, pp. 19-45.
Kovacs, Steven J., "2367 A First-in-Human Study of MAU868, a Novel Neutralizing Antibody Against BK Virus," 2nd ASH Annual Meeting and Exposition, Dec. 6, 2020, 1 page.
Kunik, Vared et al., "Structural Consensus among Antibodies Defines the Antigen Binding Site," PLoS Computational Biology, vol. 8, No. 2, Feb. 23, 2012, pp. e1002388.
Lipshutz et al., "BK Nephropathy in Kidney Transplant Recipients Treated with a Calcineurin Inhibitor-Free Immunosuppression Regimen," American Journal of Transplantation, 2004, vol. 4, pp. 2132-2134.
Liu, "Antibody glycosylation and its impact on the pharmacokinetics and pharmacodynamics of monoclonal antibodies and Fc-fusion proteins," J Pharm Sci., Jun. 2015, vol. 104, No. 6, pp. 1866-1884.
Lobuglio et al., "Mouse/human chimeric monoclonal antibody in man: kinetics and immune response." Proceedings of the National Academy of Sciences (1989); 86.11: 4220-4224.
Lonberg and Huszar, "Human Antibodies from Transgenic Mice," International Reviews of Immunology, Jan. 1995, 13(1), pp. 65-93.
Lonberg, N., "Transgenic approaches to human monoclonal antibodies," The Pharmacology of Monoclonal Antibodies, Handbook of Experimental Pharmacology, 1994, vol. 113, pp. 49-101.
Low, J. et al., "BKV and SV40 infection of human kidney tubular epithelial cells in vitro," Virology, Jun. 1, 2004, vol. 323, No. 2, pp. 182-188.
Luo, C., "Genotyping schemes for polyomavirus BK, using gene-specific phylogenetic trees and single nucleotide polymorphism analysis," Journal of virology, Mar. 1, 2009, vol. 83, No. 5, pp. 2285-2297.
Maeda et al. "Construction of reshaped human antibodies with HIV-neutralizing activity." Human Antibodies (1991); 2.3: 124-134.
Martin, F. et al., "The affinity-selection of a minibody polypeptide inhibitor of human interleukin-6," EMBO Journal, Nov. 15, 1994, vol. 13, No. 22, pp. 5305-5309.
Matsuda, Y. et al., "A rapid and efficient method BK polyomavirus genotyping by high-resolution melting analysis," Journal of Medical Virology, Dec. 2011, vol. 83, No. 12, pp. 2128-2134.
Mengelle et al., "JC virus DNA in the peripheral blood of renal transplant patients: a 1-year prospective follow-up in France," J Med Virol., Jan. 2011, vol. 83, No. 1, pp. 132-136.
Neu, U. et al., "A Structure-Guided Mutation in the Major Capsid Protein Retargets BK Polyomavirus," PLoS Pathogens, Oct. 10, 2013, vol. 9, No. 10, 13 pages.
Neuberger, M., "Generating high-avidity human Mabs in mice," Nature Biotechnology, Jul. 1996, 14(7), pp. 826.
Nickeleit et al., "Polyomavirus Infection of Renal Allograft Recipients: From Latent Infection to Manifest Disease," J. Am. Seo. Neprol., 1999, vol. 10, No. 5, pp. 1080-1089.
O'Hara et al., "Gallic Acid-Based Small-Molecule Inhibitors of JC and BK Polyomaviral Infection," Virus Research, 2014, vol. 189, pp. 280-285.
Padgett et al., "Cultivation of Papova-Like Virus from Human Brain with Progressive Multifocal Leukoencephalopathy," Lancet, , 1971, vol. 297, No. 7712, pp. 1257-1260.
Padgett et al., "Prevalence of Antibodies in Human Sera against JC Virus, an Isolate from a Case of Progressive Multifocal Leukoencephalopathy," Journal of Infectious Diseases, 1973, vol. 127, No. 4, pp. 467-470.
Paruli, S. et al., "Role of Virus-Specific T Cell Therapy for Cytomegalovirus and BK Infections in Kidney Transplant Recipients," Kidney 360, May 27, 2021, vol. 2, No. 5, pp. 905-915.
Pastrana et al., "Neutralization Serotyping of BK Polyomavirus Infection in Kidney Transplant Recipients" PLoS Pathogens, Apr. 2012, vol. 8, No. 4, e1002650, pp. 1-11.
Pearson, WR., et al. "Improved tools for biological sequence comparison." Proceedings of the National Academy of Sciences 85.8 (1988): 2444-2448.
Purighalla et al., BK Virus Infection in a Kidney Allograft Diagnosed by Needle Biopsy American Journal of Kidney Diseases, Oct. 1995, vol. 26, No. 4, pp. 671-673.
Qian et al., "Lipids and Proteins Act in Opposing Manners to Regulate Polyomavirus Infection," Journal of Virology, 2010, pp. 9840-9852, vol. 84, No. 19.
Queen C. et al. (Dec. 1989), "A Humanized Antibody That Binds To The Interleukin 2 Receptor," Proceedings of the National Academy of Sciences, vol. 86, No. 24, pp. 10029-10033.
Randhawa et al., "BK Virus Infection in Transplant Recipients: An Overview and Update," American Journal of Transplantation, 2006, vol. 6, No. 9, pp. 2000-2005.
Randhawa et al., "Commercially available immunoglobulins contain virus neutralizing antibodies against all major genotypes of polyomavirus BK," Am J Transplant., 2015, vol. 15, No. 4, pp. 1014-1020.
Randhawa et al., "Human Polyoma Virus-Associated Interstitial Nephritis in the Allograft Kidney," Transplantation, 1999, vol. 67, pp. 103-109.
Randhawa et al., "Identification of species-specific and cross-reactive epitopes in human polyomavirus capsids using monoclonal antibodies," Journal of General Virology, 2009, pp. 634-639.
Reid et al., "Sequencing and Analysis of JC Virus DNA from Natalizumab-Treated PML Patients," J. Infect. Dis., 2011, vol. 204, pp. 237-244.
Reploeg et al., "BK Virus: A Clinical Review," Clin. Infect. Dis., 2001, vol. 33, No. 2, pp. 191-202.

(56) References Cited

OTHER PUBLICATIONS

Richardson, "Progressive Multifocal Leukoencephalopathy," New England Journal of Medicine, 1961, vol. 265, No. 17, pp. 815-823.
Riechmann, L., et al., "Reshaping human antibodies for therapy", Nature (1988); 332(6162): 323-327.
Rudikoff, S. et al. "Single amino acid substitution altering antigen-binding specificity", Proc Natl Acad Sci, (Mar. 1982); 79:1979-1983.
Sabath et al., "Traffic of JC Virus from Sites of Initial Infection to the Brain: The Path to Progressive Multifocal Leukoencephalopathy," Journal Infectious Diseases, 2002, vol. 186, pp. S180-S186.
Sato et al. "Reshaping a human antibody to inhibit the interleukin 6-dependent tumor cell growth." Cancer Research (1993); 53.4: 851-856.
Shinohara et al., "BK Virus Infection of the Human Urinary Tract," Journal of Medical Virology, Dec. 1993, vol. 41, No. 4, pp. 301-305.
Tempest P.R., et al., "Reshaping A Human Monoclonal Antibody To Inhibit Human Respiratory Syncytial Virus Infection In Vivo." Nature Biotechnology, Mar. 1991, vol. 9 (3), pp. 266-271.
Toan, P. et al., "Identification of BK Virus Genotypes in Recipients of Renal Transplant in Vietnam," Transplantation Proceedings, Oct. 2019, vol. 51, No. 8, pp. 2683-2688.
Traunecker, A. et al., "Janusin: new molecular design for bispecific reagents," Int J Cancer Suppl., Jan. 1992, vol. 7, pp. 51-52.
Traunecker et al., "Bispecific single chain molecules (Janusins) target cytotoxic lymphocytes on HIV infected cells," The EMBO Journal, Dec. 1991, 10(12), pp. 3655-3659.
Verhoeyen, M., et al., "Reshaping human antibodies: grafting an antilysozyme activity", Science, Mar. 1988, 239(4847), pp. 1534-1536.
Wang, Dianli, JC Virus VP2 Egg White antigen antibody preparation and nuclear localization signal and nuclear import and translocation body identification, Excellent Master's Degree Thesis in China Text database (Medical and health science and technology Series), Feb. 15, 2009, vol. 2009, No. 2, 118 pages [with machine translation].
Wang, Xinxin, "Early Kidney Transplantation," Studies on BK virus activation in post-recipients Study, Excellent Master's Degree Thesis in China Text database (Medical and health science and technology Series), Jan. 15, 2014, vol. 2014, Issue 1, 181 pages [with machine translation].
Wiseman et al., "Polyomavirus Nephropathy: A Current Perspective and Clinical Considerations," Am. J. Kidney Dis., 2009, vol. 54, No. 1, pp. 131-142.
National Institute of Health, "Immunoglobulin lambda light chain VLJ region, partial [*Homo sapiens*]," GenBank: BAC01663.1, Jul. 26, 2016, 2 pages.

SET BKV VP1-serotype I Affinity Assay

SET BKV VP1-serotype II Affinity Assay

SET BKV VP1-serotype III Affinity Assay

SET BKV VP1-serotype IV Affinity Assay

FIGURE 2

SET affinity assay on BKV VP1 from all four serotypes

Solution Equilibrium Titration (SET) assay, $K_D$ (pM)

| Antigen (VP1) | P165E2 | NEG447 | NEG447A | P7G11 | P7G11A | P8D11 | P8D11A | P8D11B | P8D11C | P8D11D | P8D11E |
|---|---|---|---|---|---|---|---|---|---|---|---|
| serotype I | 1.5 ± 0.1 | 1.0 ± 0.2 | 0.9 ± 0.3 | 4.2 ± 0.2 | 3.0 ± 0.8 | 4.3 ± 1.4 | 4.4 ± 1.2 | 3.8 ± 0.2 | 4.5 ± 1.2 | 5.0 ± 2.0 | 4.3 ± 1.4 |
| serotype II | 154 ± 8 | 29 ± 24.6 | 9.6 ± 2.4 | 1877 ± 118 | 12 ± 2.4 | 2.1 ± 0.4 | 2.5 ± 0.7 | 1.8 ± 0.6 | 2.7 ± 0.9 | 2.0 ± 0.5 | 1.7 ± 0.4 |
| serotype III | >10000 | >10000 | >10000 | >10000 | >10000 | 6.0 ± 3.0 | 3.7 ± 0.5 | 2.5 ± 0.06 | 4.8 ± 1.3 | 5.0 ± 2.0 | 6.0 ± 4.0 |
| serotype IV | 1769 ± 112 | 1049 ± 166 | 185 ± 11 | 2117 ± 140 | 153 ± 17 | 3.0 ± 1.0 | 2.9 ± 1.7 | 2.9 ± 0.4 | 2.7 ± 0.7 | 3.2 ± 0.3 | 2.7 ± 1.2 |

FIGURE 3A

Binding to BKV serotype I VP1 pentamers by SPR

Binding to BKV serotype I VLPs by SPR

Binding to BKV serotype II VP1 pentamers by SPR

Binding to BKV serotype III VLPs by SPR

Binding to BKV serotype IV VP1 pentamers by SPR

Binding to BKV serotype I VLPs by ELISA

Binding to BKV serotype IV VLPs by ELISA

Binding to BKV serotype IV VP1 pentamers by ELISA

FIGURE 7

Binding to BKV serotype I VLPs or serotype IV VLPs or pentamers by ELISA

| Antibody | Serotype I VLP IC50 (nM) | Serotype IV VLP IC50 (nM) | Serotype IV pentamer IC50 (nM) |
|---|---|---|---|
| EBB-C1975-A3 | 14.53 | 0.045 | 0.064 |
| EBB-C1975-A7 | 85.7 | 0.081 | 0.078 |
| EBB-C1975-E7 | 4.32 | 0.044 | 0.026 |
| EBB-C1975-B5 | 55.07 | 0.10 | 0.078 |

Binding to BKV serotype I VLPs by ELISA

FIGURE 9

Binding to BKV serotype I VLPs by ELISA

| Antibody | BKV serotype I VLP IC50 (nM) |
|---|---|
| 2081-20-8 | 0.053 |
| 2075-16-1 | 0.104 |
| 2075-456-4 | 0.052 |
| 2081-36-8 | 0.267 |
| 2081-66-5 | 0.067 |
| 2081-38-5 | 0.046 |
| 2081-25-6 | 0.097 |

Binding to JCV VLPs by ELISA

FIGURE 11

| Antibody | JCV VLP IC50 (nM) |
|---|---|
| 2077-4-1 | 0.034 |
| 2077-7-5 | 0.651 |
| 2077-10-1 | 0.100 |
| 2077-26-1 | 0.067 |
| 2077-28-2 | 0.088 |

Binding to JCV VLPs by ELISA

FIGURE 12A-B
Anti-VP1 antibodies bind to a conformational epitope
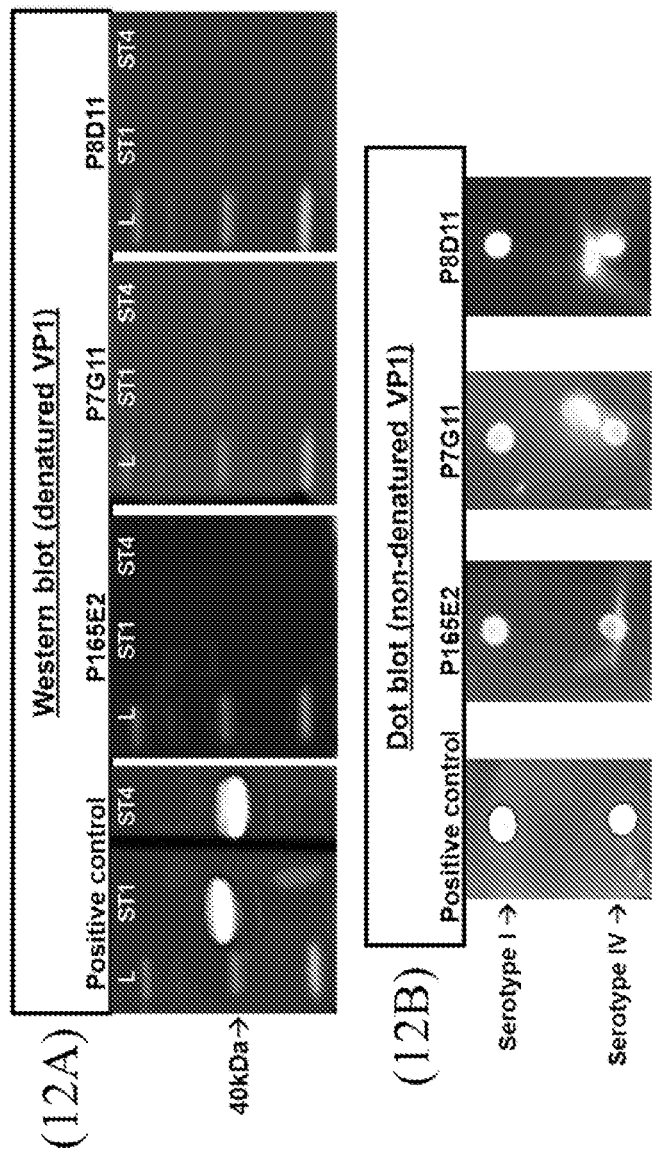

Anti-VP1 antibodies bind to a conformational epitope: Reference BKV serotype I VP1

Anti-VP1 antibodies bind to a conformational epitope: BKV VP1 F66A

Anti-VP1 antibodies bind to a conformational epitope: BKV VP1 L68A

Anti-VP1 antibodies bind to a conformational epitope: BVK VP1 K69A

Anti-VP1 antibodies bind to a conformational epitope: BKV VP1 E82A

Anti-VP1 antibodies bind to a conformational epitope: BKV VP1 I145A

FIGURE 14

Anti-VP1 antibodies bind to a conformational epitope

| Antibody | Residues identified |
|---|---|
| P165E2 | F66, K69, E82, I145 |
| NEG447 | F66, K69, E82, I145 |
| P7G11A | F66, K69, E82, I145 |
| P8D11 | F66, I145 |

| Name | Location | P165E2 | NEG447 | P7G11A | P8D11 |
|---|---|---|---|---|---|
| E61A | BC loop | + | + | + | + |
| N62A | BC loop | + | + | + | + |
| F66A | BC loop | ? | ? | ? | ? |
| L68A | BC loop | + | + | + | + |
| K69A | BC loop | ? | ? | ? | + |
| H69K (III) | BC loop | + | + | + | + |
| S71A | BC loop | + | + | + | + |
| N74A | BC loop | + | + | + | + |
| D75A | BC loop | + | + | + | + |
| S77A | BC loop | + | + | + | + |
| E82A | BC loop | + | ? | ? | + |
| R83A | BC loop | + | + | + | + |
| I145A | DE loop | ? | ? | ? | ? |
| E175A | EF loop | + | + | + | + |

Neutralization of BKV serotype I infection by anti-VP1 antibodies

Neutralization of BKV serotype II infection by anti-VP1 antibodies

Neutralization of BKV serotype III infection by anti-VP1 antibodies

Neutralization of BKV serotype IV infection by anti-VP1 antibodies

FIGURE 19

Summary of neutralization of BKV and JCV infection by anti-VP1 antibodies

Neutralization (μg/ml)

| Antibody | Serotype I | | Serotype II | | Serotype III | | Serotype IV | | JCV | |
|---|---|---|---|---|---|---|---|---|---|---|
| | EC50 | EC90 | EC50 | EC90 | EC50 | EC90 | EC50 | EC90 | EC50 | EC90 |
| P165E2 | 0.009 | 0.37 | 0.081 | 7.98 | >100 | >100 | 0.012 | 0.46 | >100 | >100 |
| NEG447 | 0.004 | 0.27 | 0.024 | 6.72 | >100 | >100 | 0.012 | 0.34 | >100 | >100 |
| NEG447A | 0.0001 | 0.094 | 0.110 | 0.84 | >100 | >100 | 0.011 | 0.26 | ND | ND |
| P7G11 | 0.007 | 0.37 | 0.187 | 1.79 | >100 | >100 | 0.011 | 0.48 | >100 | >100 |
| P7G11A | 0.0008 | 0.34 | 0.074 | 2.89 | >100 | >100 | 0.015 | 0.53 | >100 | >100 |
| P8D11 | 0.015 | 0.24 | 0.089 | 6.34 | 0.092 | 0.53 | 0.023 | 0.39 | 0.090 | 2.76 |
| P8D11A | 0.005 | 0.19 | 0.029 | 8.68 | 0.010 | 0.59 | 0.015 | 0.064 | ND | ND |
| P8D11B | 0.003 | 0.30 | 0.088 | 1.93 | 0.014 | 0.50 | 0.005 | 0.54 | ND | ND |
| P8D11C | 0.0003 | 0.34 | 0.180 | 0.50 | 0.049 | 0.51 | 0.005 | 0.54 | ND | ND |
| P8D11D | 0.034 | 0.15 | 0.161 | 1.64 | 0.185 | 0.87 | 0.003 | 0.063 | ND | ND |
| P8D11E | 0.032 | 0.11 | 0.144 | 2.52 | 0.236 | 0.90 | 0.002 | 0.087 | ND | ND |
| P46F4 | 0.004 | 0.29 | >100 | >100 | >100 | >100 | >100 | >100 | ND | ND |

FIGURE 21

Neutralization of BKV infection by anti-VP1 antibodies

Neutralization (µg/ml)

| Antibody | Serotype I | | Serotype II | | Serotype III | | Serotype IV | |
|---|---|---|---|---|---|---|---|---|
| | EC50 | EC90 | EC50 | EC90 | EC50 | EC90 | EC50 | EC90 |
| EBB-C1975-A3 | 0.045 | 4.84 | 0.12 | 25.18 | >100 | >100 | 0.13 | 8.18 |
| EBB-C1975-A7 | 0.024 | 5.15 | 0.11 | 14.19 | >100 | >100 | 0.28 | 7.79 |
| EBB-C1975-E7 | 0.010 | 2.62 | 0.33 | 9.61 | >100 | >100 | 0.35 | 8.61 |
| EBB-C1975-B5 | 0.033 | 5.53 | 0.42 | 24.17 | 0.76 | >100 | 0.15 | 7.83 |

Neutralization of BKV serotype I infection by anti-VP1 antibodies

FIGURE 23

Neutralization of BKV serotype I infection by anti-VP1 antibodies

| | Neutralization (μg/ml) | |
|---|---|---|
| Antibody | EC50 | EC90 |
| 2081-20-8 | 0.062 | 0.556 |
| 2075-16-1 | 0.065 | 1.253 |
| 2075-456-4 | 0.092 | 0.503 |
| 2081-36-8 | 0.147 | 0.909 |
| 2081-66-5 | 0.041 | 0.601 |
| 2081-38-5 | 0.053 | 1.799 |
| 2081-25-6 | 0.213 | 0.723 |

Neutralization of JCV infection by anti-VP1 antibodies

FIGURE 26

Neutralization of JCV infection by anti-VP1 antibodies

| Antibody | Neutralization (μg/ml) | |
|---|---|---|
| | EC50 | EC90 |
| 2077-4-1 | 0.138 | 3.06 |
| 2077-7-5 | 0.097 | 1.10 |
| 2077-10-1 | 1.492 | >10 |
| 2077-26-1 | 0.702 | 3.20 |
| 2077-28-2 | 0.

FIGURE 27

SET Affinity Assay of P8D11 on JCV VLPs

Solution Equilibrium Titration (SET) assay, $K_D$ (pM)

| Antigen (VLPs) | P8D11 |
|---|---|
| JCV consensus | 436 ± 212 |
| JCV L55F mutant | 933 ± 205 |
| JCV S269F mutant | 327 ± 44 |

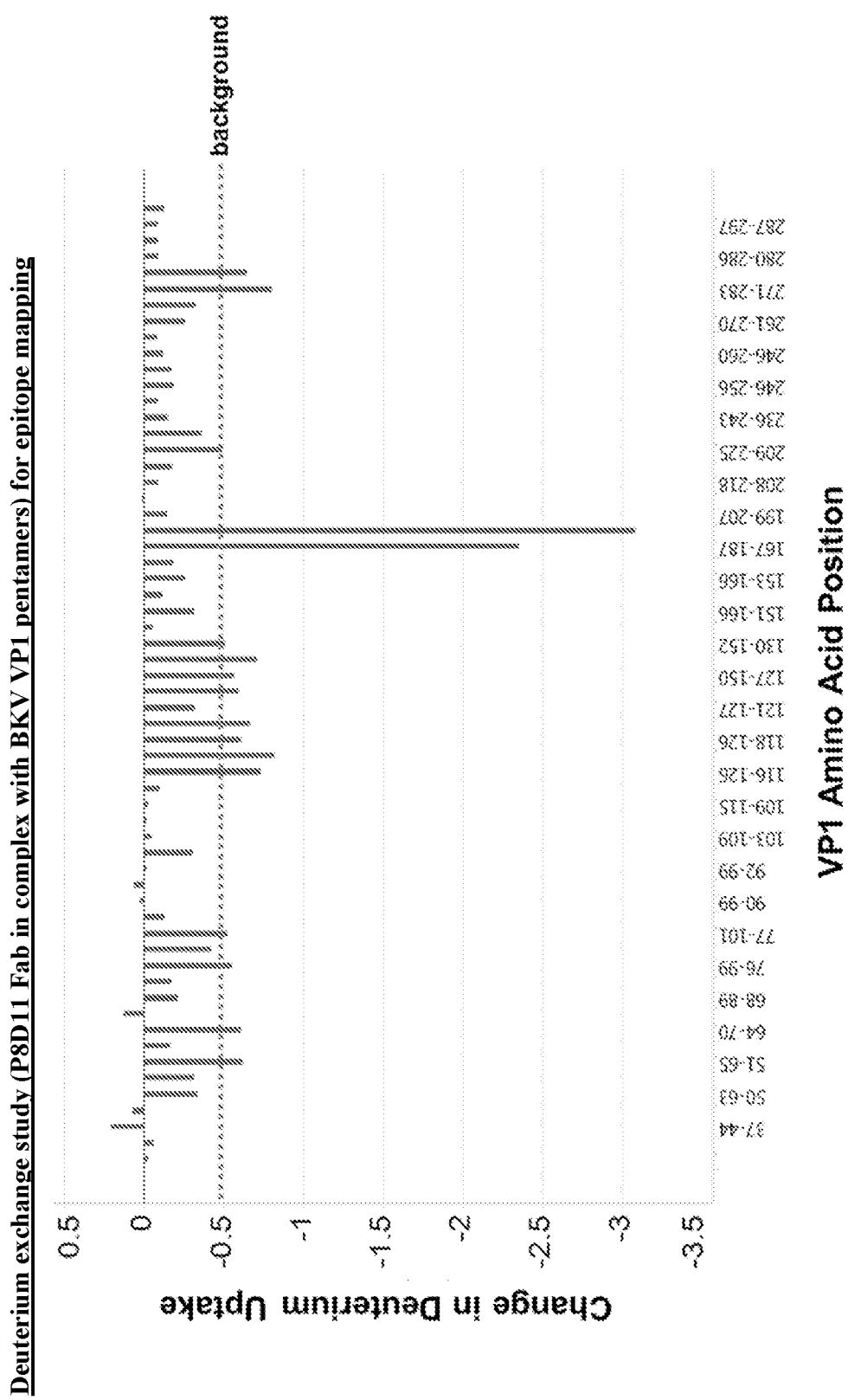

FIGURE 29A

Anti-VP1 antibodies bind to a conformational epitope in BKV VP1 EF loop

| Mutation | P8D11 binding | P7G11A binding |
|---|---|---|
| Y169A | - | - |
| R170A | - | - |
| K172A | - | + |
| E175A | + | + |
| K181A | + | + |
| N182A | + | + |
| T184A | + | + |
| Q186A | + | + |

| Antibody | Contact residues identified |
|---|---|
| P8D11 | Y169, R170, K172 |
| P7G11A | Y169, R170 |

Anti-VP1 antibodies bind to a conformational epitope in BKV VP1 EF loop

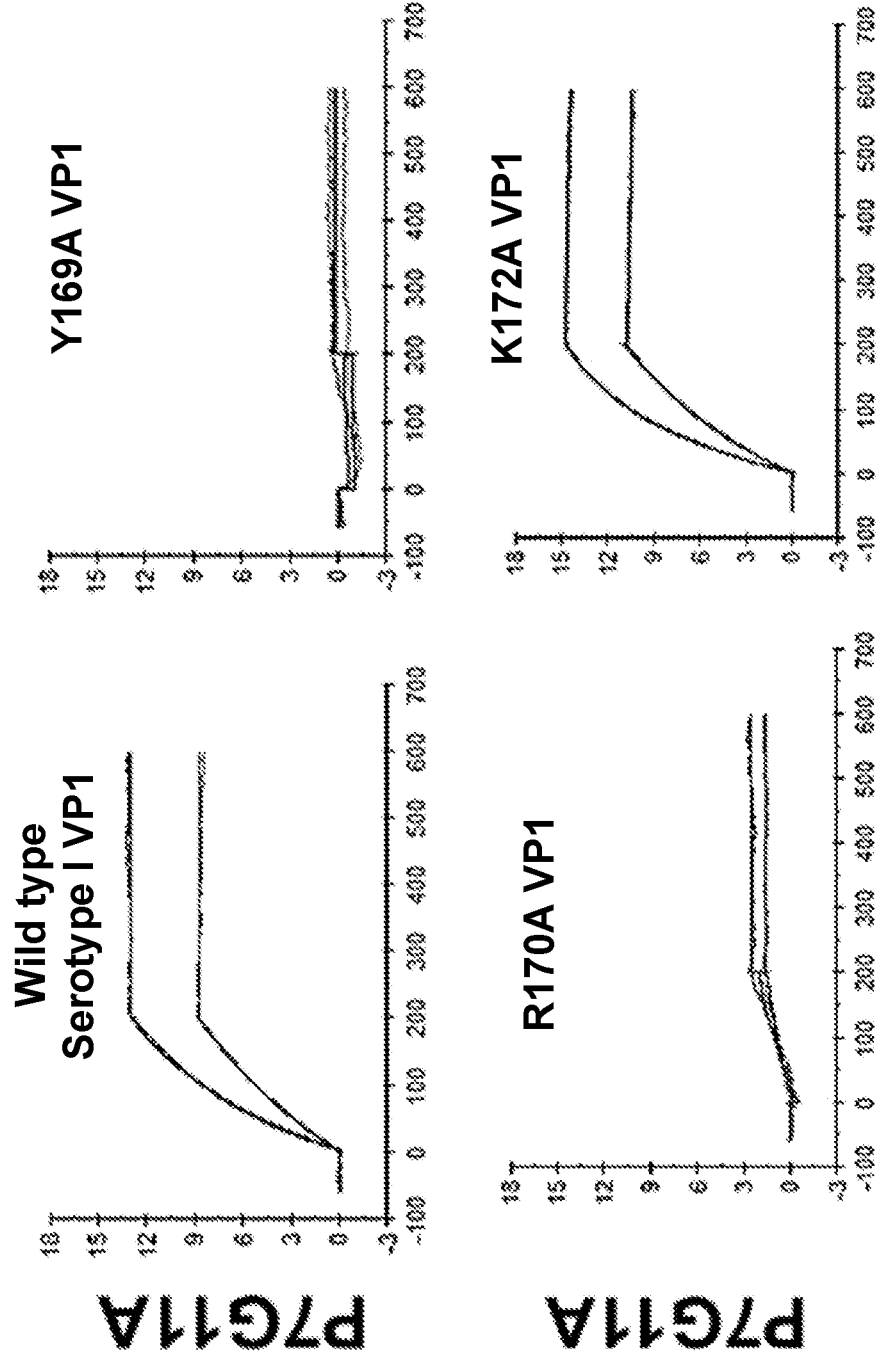

Representation of the scFv chains from P8D11 (black) bound to the BKV capsid protein (VP1) pentamer (gray), each VP1 monomer has a binding site for the scFv.

FIGURE 31A-B

Figure 31A is a representation of the P8D11 scFv (black) bound to the BKV capsid protein (VP1) pentamer (gray), as a single unit removed from the resolution of the larger 5-unit in Figure 30. Figure 31B is a magnification of the contacts between the P8D11 scFv and the VP1 pentamer

POLYOMAVIRUS NEUTRALIZING ANTIBODIES

CROSS-REFERENCE TO RELATED APPLICATIONS

This application is a continuation of U.S. application Ser. No. 17/502,910, filed Oct. 15, 2021, now U.S. Pat. No. 11,639,378, which is a continuation of U.S. application Ser. No. 16/657,855 filed Oct. 18, 2019, now U.S. Pat. No. 11,161,894, which is a continuation of U.S. application Ser. No. 15/758,491 filed Mar. 8, 2018, now U.S. Pat. No. 10,450,366, which is a 371 U.S. National Stage of International Application No. PCT/IB2016/055339, filed Sep. 8, 2016, which claims priority to International Application No. PCT/CN2015/089764, filed Sep. 16, 2015, the disclosures of each of which are incorporated by reference herein in their entirety.

INCORPORATION OF SEQUENCE LISTING

The Sequence Listing associated with this application is provided electronically in XML file format and is hereby incorporated by reference into the specification. The name of the XML file containing the Sequence Listing is VETH_012_06US_SeqList_ST26.xml. The XML file is 551,909 bytes, was created on Mar. 15, 2023, and is being submitted electronically via the USPTO Patent Center.

FIELD OF THE INVENTION

The present disclosure is directed to anti-VP1 antibodies, antibody fragments, and their uses for the reducing the likelihood or treatment of polyoma virus infection.

BACKGROUND OF THE INVENTION

Of the human polyomaviruses, BK virus (BKV) and JC virus (JCV) were the first two identified. These two polyomavirus were isolated from immunosuppressed patients and published in the same issue of Lancet in 1971 (Gardner et al., Lancet 1971 1:1253-1527, and Padgett et al., Lancet 1971 1:1257-1260). Polyomaviruses are icosahedral, non-enveloped, double-stranded DNA viruses. They measure 40-45 nm in diameter and are comprised of 88% protein and 12% DNA.

The BKV genome is a circular double-stranded DNA of approximately 5 Kb in length and contains three major divisions: the early coding region, the late coding region, and a non-coding control region. The early coding region encodes for the three regulatory proteins (large tumor antigen [TAg], small tumor antigen [tAg], and truncated tumor antigen [truncTAg]), which are the first viral proteins expressed in a newly infected cell and are responsible for facilitating viral DNA replication and establishing a favorable cellular environment. The late coding region encodes the three structural proteins (VP1, VP2, and VP3) that make up the viral capsid, as well as the agnoprotein, the role of which during viral replication is less well-defined. The non-coding control region contains the origin of replication as well as the early and late promoters that drive expression of the viral gene products.

BKV has been detected in many different cell types including epithelial cells of the kidney, bladder, and ureter (typical sites of persistence), tonsillar tissue, and lymphocytes (proposed sites of primary infection and dissemination) (Chatterjee et al., J. Med. Virol. 2000; 60:353-362, Goudsmit et al., J. Med. Virol. 1982; 10:91-99, Heritage et al., J. Med. Virol. 1981; 8:143-150, Shinohara et al., J. Med. Virol. 1993; 41(4):301-305). The primary cell surface receptors for BKV are the gangliosides GT1b, GD1b, and GD3, all of which have a terminal a2,8-linked sialic acid and are fairly ubiquitous, allowing infection of various cell types (Neu et al., PLos Patholog. 2013; 9(10):e1003714 and e1003688, see also, O'Hara et al., Virus Res. 2014; 189: 208-285). The non-enveloped icosahedral virion of BKV is composed of three different viral proteins: 360 copies of the major viral capsid protein VP1 arranged in 72 pentamers and 72 copies combined of the minor viral capsid proteins VP2 and VP3, with one VP2 or VP3 molecule associated with each VP1 pentamer. Only VP1 is exposed on the virion surface at entry and each pentamer has five low affinity binding sites for the ganglioside receptor. Binding of VP1 pentamers to ganglioside receptors on the cell surface initiates internalization through a caveolae-mediated endocytic pathway, followed by trafficking of the virus to the endoplasmic reticulum and finally to the nucleus (Tsai and Qian, J. Virol 2010; 84(19):9840-9852).

Infection with the human polyomavirus BK (BKV) is essentially ubiquitous, with estimates ranging between 80 and 90% of the population globally infected (Knowles W. A., Adv. Exp. Med. Biol. 2006; 577:19-45). Primary infection most often occurs during childhood (i.e., before age 10) and results in either a mild, non-specific, self-limited illness or no symptoms at all. Persistent infection is established in the epithelial cells of the renal tubules, ureters, and bladder, and is effectively controlled by the immune system. Transient asymptomatic viral shedding in the urine of immunocompetent adults occurs sporadically but results in no disease or sequelae. However, compromised immune function, particularly with immunosuppression following renal or hematopoietic stem cell transplantation, can lead to uncontrolled BKV replication and ultimately to BKV-associated nephropathy (BKVAN) or hemorrhagic cystitis (HC), a painful disease of the bladder. There are no effective antiviral therapies against BKV and the current standard of care is reduction of immunosuppression, which increases the risk of acute rejection. Even with the current, more aggressive approaches to monitoring and prevention, up to 10% of renal transplant recipients will develop BKVAN and 15-30% of those patients will suffer graft loss due to BKVAN. Among those undergoing reduction in immunosuppressive regimen upon detection of BKV viremia, up to 30% will experience an acute rejection episode as a result.

Although BKV was first described in 1971 (supra), it was not until the 1990s that BK associated nephropathy (BKVAN) was reported in the literature as a cause of kidney transplant injury (Purighalla et al., Am. J. Kidney Dis. 1995; 26:671-673 and Randhawa et al., Transplantation 1999; 67:103-109). In early management of BKVAN, testing positive for BK had severe consequences, with more than 50% of the patients having graft dysfunction and graft loss (Hirsch et al., New Engl. J. Med. 2002; 347:488-496). BK viral reactivation may begin after transplantation, and is seen in about 30%-50% of the patients by 3 months post-transplantation (Bressollette-Bodin et al., Am J. Transplant. 2005; 5(8):1926-1933 and Brennan et al., Am. J. Transplant. 2004; 4(12):2132-2134). BK viral reactivation can be first seen by virus and viral DNA in the urine, then in the plasma and finally in the kidney. (Brennan et al., Am. J. Transplant. 2005; 5(3):582-594 and Hirsch et al., N Eng. J. Med. 2002; 347(7):488-496). About 80% of kidney transplant patients have BK virus in the urine (BK viruria) and 5-10% of these patients progress to BKVAN (Binet et al., Transplantation 1999; 67(6):918-922 and Bressollette-Bodin et al., Am J. Transplant. 2005; 5(8):1926-1933). BKV effects the renal tubular epithelial cells causing necrosis and lytic destruction with denudation of the basement membrane, which allows tubular fluid to accumulate in the interstitum, which results in interstitial fibrosis and tubular atrophy (Nickeleit et al., J. Am. Soc. Neprol. 1999; 10(5):1080-1089) all of which can affect the condition of the transplant. Patients may present with deterioration of renal function, tubule-interstitial nephritis and ureteric stenosis (Garner et al., Lancet 1971; 1(7712):1253-1257 and Hirsch Am. J. Transplant 2002; 2(1)25-30).

BKV can also cause pneumonitis, retinitis and meningoencephalitis in immunocompromised hosts (Reploeg et al., Clin. Infect. Dis. 2001; 33(2):191-202). BKV disease in hematopoietic stem cell transplant (HSCT) recipients typically manifests as hemorrhagic cystitis (HC), which can vary in severity. Viruria (but not viremia) and painful hematuria are associated with the clinical presentation of HC. The current standard of care is supportive in nature, involving primarily forced hydration/diuresis and pain management measures. The most severe cases require blood transfusions, clot evacuation, and can lead to death in some instances. HC of any cause (e.g. drug, radiation, viral) is relatively common among HSCT recipients but BKV-associated HC occurs in approximately 10-12% of patients usually within 6 months after transplantation. There are other viral etiologies of HC, with adenovirus being a more common cause of HC among pediatric HSCT recipients compared with adult HSCT recipients. BK virus has also been observed in other immunocompromised conditions such as systemic lupus erythromatosis, other solid organ transplants and in HIV/AIDS patients (Jiang et al., Virol. 2009; 384:266-273).

At this point, the treatment of BK nephropathy associated with organ transplantation is the reduction of immunosuppression in an attempt to prevent graft dysfunction and graft loss (Wiseman et al., Am. J. Kidney Dis. 2009; 54(1): 131-142 and Hirsch et al., Transplantation 2005; 79(1): 1277-1286). There are no fixed clinical regimes for the reduction, as reduction of the immunosuppression may help to prevent progression from viremia to the extensive damage associated with clinical nephropathy, but this also increases the risk of acute organ rejection (Brennan et al., Am. J. Transplant 2005; 5(3):582-594). Clinicians have reported the use of therapeutics such as cidofovir, leflunomide or quinolones in combination with the reduction of immunosuppressants, however the reports find this approach ineffective, with the added burden of managing additional side effects (Randhawa and Brennan Am. J. Transplant 2006; 6(9):2000-2005). As such, there is an unmet and useful need in the field for therapies that neutralize polyoma viruses such as BK and that can be used in an immunocompromised host.

JC virus is also a polyoma virus which is also highly prevalent in the population (80%), although JC virus is generally acquired later than BK virus (Padgett et al., J. Infect. Dis. 1973; 127(4):467-470 and Sabath et al., J. Infect. Dis. 2002; 186 Suppl. 2:5180-5186). After initial infection, JC virus establishes latency in the lymphoid organs and kidneys and when reactivated, invades the central nervous system via infected B-lymphocytes. Once in the CNS, the JC virus causes progressive multifocal leukoencephalopathy (PML), which is a progressive demyelinating central nervous system disorder. PML most often presents as an opportunistic infection in HIV/AIDS patients and has also been reported in immunosuppressed patients (Angstrom et al., Brain 1958; 81(1):93-111 and Garcia-Suarez et al., Am. J. Hematol. 2005; 80(4):271-281). PML patients present with confusion, mental status changes, gait ataxia, focal neurological defects such as hemi paresis, limb paresis and visual changes (Richardson E. P., N. Eng. J. Med. 1961; 265:815-823). The prognosis of patients with PML is poor and is especially poor in patients with HIV/AIDS (Antinori et al., J. Neurovirol. 2003; 9 suppl. 1:47-53). This further highlights the unmet and useful need in the field for therapies that neutralize polyoma viruses such as JC.

SUMMARY OF THE INVENTION

The present disclosure is directed to neutralizing antibodies to human polyomaviruses and/or fragments thereof, antibodies that recognize BK virus and/or JC virus and their respective VP1 pentamers and fragments thereof.

An antibody, wherein said antibody or antigen binding fragment thereof specifically binds VP1.

The antibody wherein said antibody or antigen binding fragment thereof specifically binds BK virus serotype I-serotype IV VP1. In one embodiment, the antibody or antigen binding fragment thereof binds to BKV serotype I VP1 with a binding affinity of 5.0 pM or less, binds to BKV serotype II VP1 with a binding affinity of 29.0 pM or less, binds to BKV serotype III VP1 with a binding affinity of 6.0 pM or less and/or binds to BKV serotype IV VP1 with a binding affinity of 185.0 pM or less. In another embodiment, the antibody or antigen binding fragment thereof further binds to JCV VP1 and specific JCV VP1 mutants with a binding affinity in the high nanomolar range.

The antibody wherein said antibody or antigen binding fragment specifically binds to a VP1 of Table 1. In one embodiment, the antibody or antigen binding fragment thereof binds to two or more of the VP is of Table 1. In one embodiment, the antibody or antigen binding fragment thereof binds to BKV VP1 serotype I and BKV VP1 serotype II. In another embodiment, the antibody or antigen binding fragment thereof binds to BKV VP1 serotype I and BKV VP1 serotype III. In another embodiment, the antibody or antigen binding fragment thereof binds to BKV VP1 serotype I and BKV VP1 serotype IV. In another embodiment, the antibody or antigen binding fragment thereof binds to BKV VP1 serotype II and BKV VP1 serotype III. In another embodiment, the antibody or antigen binding fragment thereof binds to BKV VP1 serotype II and BKV VP1 serotype IV. In another embodiment, the antibody or antigen binding fragment thereof binds to BKV VP1 serotype I and JCV VP1. In a preferred embodiment, the antibody or antigen binding fragment thereof binds to BKV VP1 serotypes I, II, III and IV. Furthermore, the antibody or antigen binding fragment thereof binds to BKV VP1 serotypes I, II, III and IV and JCV VP1.

The antibody wherein said antibody or antigen binding fragment specifically binds to one or more amino acids residues of a VP1 epitope (SEQ ID NO:500 or SEQ ID NO:501). In one embodiment, the antibody or antigen binding fragment specifically binds to one or more of amino acids Y169, R170 and K172, e.g., binds to Y169 and R170, e.g., as determined by scanning alanine mutagenesis, as described herein.

The antibody wherein said antibody or antigen binding fragment comprises the sequence GFTFXNYWMT (SEQ ID NO. 507), wherein X can be any amino acid (Xaa). In another embodiment, X can be N (Asn), S (Ser), K (Lys) or Q (Gln).

An antibody, wherein said antibody or antigen binding fragment thereof comprises: (i) a heavy chain variable region that comprises (a) a HCDR1 (CDR-Complementarity Determining Region) of SEQ ID NO: 6, (b) a HCDR2 of SEQ ID NO:7, (c) a HCDR3 of SEQ ID NO:8 and a light chain variable region that comprises: (d) a LCDR1 of SEQ ID NO:16, (e) a LCDR2 of SEQ ID NO:17, and (f) a LCDR3 of SEQ ID NO:18;

- (ii) a heavy chain variable region that comprises (a) a HCDR1 of SEQ ID NO:26, (b) a HCDR2 of SEQ ID NO:27, (c) a HCDR3 of SEQ ID NO:28; and a light chain variable region that comprises: (d) a LCDR1 of SEQ ID NO:36, (e) a LCDR2 of SEQ ID NO:37, and (f) a LCDR3 of SEQ ID NO:38;
- (iii) a heavy chain variable region that comprises (a) a HCDR1 of SEQ ID NO:46, (b) a HCDR2 of SEQ ID NO:47, (c) a HCDR3 of SEQ ID NO:48; and a light chain variable region that comprises: (d) a LCDR1 of SEQ ID NO:56, (e) a LCDR2 of SEQ ID NO:57, and (f) a LCDR3 of SEQ ID NO:58;
- (iv) a heavy chain variable region that comprises: (a) a HCDR1 of SEQ ID NO:66, (b) a HCDR2 of SEQ ID NO:67, (c) a HCDR3 of SEQ ID NO:68; and a light chain variable region that comprises: (d) a LCDR1 of SEQ ID NO:76, (e) a LCDR2 of SEQ ID NO:77, and (f) a LCDR3 of SEQ ID NO:78;
- (v) a heavy chain variable region that comprises: (a) a HCDR1 of SEQ ID NO:86, (b) a HCDR2 of SEQ ID NO:87, (c) a HCDR3 of SEQ ID NO:88; and a light chain variable region that comprises: (d) a LCDR1 of SEQ ID NO:96, (e) a LCDR2 of SEQ ID NO:97, and (f) a LCDR3 of SEQ ID NO:98;
- (vi) a heavy chain variable region that comprises: (a) a HCDR1 of SEQ ID NO:106, (b) a HCDR2 of SEQ ID NO: 107, (c) a HCDR3 of SEQ ID NO:108; and a light chain variable region that comprises: (d) a LCDR1 of SEQ ID NO:116, (e) a LCDR2 of SEQ ID NO:117, and (f) a LCDR3 of SEQ ID NO:118;
- (vii) a heavy chain variable region that comprises: (a) a HCDR1 of SEQ ID NO:126, (b) a HCDR2 of SEQ ID NO: 127, (c) a HCDR3 of SEQ ID NO:128; and a light chain variable region that comprises: (d) a LCDR1 of SEQ ID NO:136, (e) a LCDR2 of SEQ ID NO:137, and (f) a LCDR3 of SEQ ID NO:138;
- (viii) a heavy chain variable region that comprises: (a) a HCDR1 of SEQ ID NO:146, (b) a HCDR2 of SEQ ID NO:147, (c) a HCDR3 of SEQ ID NO:148; and a light chain variable region that comprises: (d) a LCDR1 of SEQ ID NO:156, (e) a LCDR2 of SEQ ID NO:157, and (f) a LCDR3 of SEQ ID NO:158;
- (ix) a heavy chain variable region that comprises: (a) a HCDR1 of SEQ ID NO:166, (b) a HCDR2 of SEQ ID NO: 167, (c) a HCDR3 of SEQ ID NO:168; and a light chain variable region that comprises: (d) a LCDR1 of SEQ ID NO:176, (e) a LCDR2 of SEQ ID NO:177, and (f) a LCDR3 of SEQ ID NO: 178;
- (x) a heavy chain variable region that comprises: (a) a HCDR1 of SEQ ID NO:186, (b) a HCDR2 of SEQ ID NO:187, (c) a HCDR3 of SEQ ID NO:188; and a light chain variable region that comprises: (d) a LCDR1 of SEQ ID NO:196, (e) a LCDR2 of SEQ ID NO:197, and (f) a LCDR3 of SEQ ID NO:198;
- (xi) a heavy chain variable region that comprises: (a) a HCDR1 of SEQ ID NO:206, (b) a HCDR2 of SEQ ID NO:207, (c) a HCDR3 of SEQ ID NO:208; and a light chain variable region that comprises: (d) a LCDR1 of SEQ ID NO:216, (e) a LCDR2 of SEQ ID NO:217, and (f) a LCDR3 of SEQ ID NO:218;
- (xii) a heavy chain variable region that comprises: (a) a HCDR1 of SEQ ID NO:226, (b) a HCDR2 of SEQ ID NO:227, (c) a HCDR3 of SEQ ID NO:228; and a light chain variable region that comprises: (d) a LCDR1 of SEQ ID NO:236, (e) a LCDR2 of SEQ ID NO:237, and (f) a LCDR3 of SEQ ID NO:238;
- (xiii) a heavy chain variable region that comprises: (a) a HCDR1 of SEQ ID NO:246, (b) a HCDR2 of SEQ ID NO:247, (c) a HCDR3 of SEQ ID NO:248; and a light chain variable region that comprises: (d) a LCDR1 of SEQ ID NO:256, (e) a LCDR2 of SEQ ID NO:257, and (f) a LCDR3 of SEQ ID NO:258;
- (xiv) a heavy chain variable region that comprises: (a) a HCDR1 of SEQ ID NO:266, (b) a HCDR2 of SEQ ID NO:267, (c) a HCDR3 of SEQ ID NO:268; and a light chain variable region that comprises: (d) a LCDR1 of SEQ ID NO: 276, (e) a LCDR2 of SEQ ID NO:277, and (f) a LCDR3 of SEQ ID NO:278;
- (xv) a heavy chain variable region that comprises: (a) a HCDR1 of SEQ ID NO:286, (b) a HCDR2 of SEQ ID NO:287, (c) a HCDR3 of SEQ ID NO:288; and a light chain variable region that comprises: (d) a LCDR1 of SEQ ID NO:296, (e) a LCDR2 of SEQ ID NO:297, and (f) a LCDR3 of SEQ ID NO:298;
- (xvi) a heavy chain variable region that comprises: (a) a HCDR1 of SEQ ID NO:306, (b) a HCDR2 of SEQ ID NO:307, (c) a HCDR3 of SEQ ID NO:308; and a light chain variable region that comprises: (d) a LCDR1 of SEQ ID NO:314, (e) a LCDR2 of SEQ ID NO:315, and (f) a LCDR3 of SEQ ID NO:316;
- (xvii) a heavy chain variable region that comprises: (a) a HCDR1 of SEQ ID NO:322, (b) a HCDR2 of SEQ ID NO:323, (c) a HCDR3 of SEQ ID NO:324; and a light chain variable region that comprises: (d) a LCDR1 of SEQ ID NO:332, (e) a LCDR2 of SEQ ID NO:333, and (f) a LCDR3 of SEQ ID NO:334;
- (xviii) a heavy chain variable region that comprises: (a) a HCDR1 of SEQ ID NO:342, (b) a HCDR2 of SEQ ID NO:343, (c) a HCDR3 of SEQ ID NO:344; and a light chain variable region that comprises: (d) a LCDR1 of SEQ ID NO:349, (e) a LCDR2 of SEQ ID NO:350, and (f) a LCDR3 of SEQ ID NO:351;
- (xix) a heavy chain variable region that comprises: (a) a HCDR1 of SEQ ID NO:356, (b) a HCDR2 of SEQ ID NO:357, (c) a HCDR3 of SEQ ID NO:358; and a light chain variable region that comprises: (d) a LCDR1 of SEQ ID NO:363, (e) a LCDR2 of SEQ ID NO:364, and (f) a LCDR3 of SEQ ID NO:365;
- (xx) a heavy chain variable region that comprises: (a) a HCDR1 of SEQ ID NO:370, (b) a HCDR2 of SEQ ID NO:371, (c) a HCDR3 of SEQ ID NO:372; and a light chain variable region that comprises: (d) a LCDR1 of SEQ ID NO:377, (e) a LCDR2 of SEQ ID NO:378, and (f) a LCDR3 of SEQ ID NO:379;
- (xxi) a heavy chain variable region that comprises: (a) a HCDR1 of SEQ ID NO:384, (b) a HCDR2 of SEQ ID NO:385, (c) a HCDR3 of SEQ ID NO:386; and a light chain variable region that comprises: (d) a LCDR1 of SEQ ID NO:391, (e) a LCDR2 of SEQ ID NO:392, and (f) a LCDR3 of SEQ ID NO:393;
- (xxii) a heavy chain variable region that comprises: (a) a HCDR1 of SEQ ID NO:398, (b) a HCDR2 of SEQ ID NO:399, (c) a HCDR3 of SEQ ID NO:400; and a light chain variable region that comprises: (d) a LCDR1 of SEQ ID NO:405, (e) a LCDR2 of SEQ ID NO:406, and (f) a LCDR3 of SEQ ID NO:407;

(xxiii) a heavy chain variable region that comprises: (a) a HCDR1 of SEQ ID NO:412, (b) a HCDR2 of SEQ ID NO:413, (c) a HCDR3 of SEQ ID NO:414; and a light chain variable region that comprises: (d) a LCDR1 of SEQ ID NO:419, (e) a LCDR2 of SEQ ID NO:420, and (f) a LCDR3 of SEQ ID NO:421;

(xxiv) a heavy chain variable region that comprises: (a) a HCDR1 of SEQ ID NO:426, (b) a HCDR2 of SEQ ID NO:427, (c) a HCDR3 of SEQ ID NO:428; and a light chain variable region that comprises: (d) a LCDR1 of SEQ ID NO:433, (e) a LCDR2 of SEQ ID NO:434, and (f) a LCDR3 of SEQ ID NO:435;

(xxv) a heavy chain variable region that comprises: (a) a HCDR1 of SEQ ID NO:440, (b) a HCDR2 of SEQ ID NO:441, (c) a HCDR3 of SEQ ID NO:442; and a light chain variable region that comprises: (d) a LCDR1 of SEQ ID NO:447, (e) a LCDR2 of SEQ ID NO:448, and (f) a LCDR3 of SEQ ID NO:449;

(xxvi) a heavy chain variable region that comprises: (a) a HCDR1 of SEQ ID NO:454, (b) a HCDR2 of SEQ ID NO:455, (c) a HCDR3 of SEQ ID NO:456; and a light chain variable region that comprises: (d) a LCDR1 of SEQ ID NO:461, (e) a LCDR2 of SEQ ID NO:462, and (f) a LCDR3 of SEQ ID NO:463;

(xxvii) a heavy chain variable region that comprises: (a) a HCDR1 of SEQ ID NO:468, (b) a HCDR2 of SEQ ID NO:469, (c) a HCDR3 of SEQ ID NO:470; and a light chain variable region that comprises: (d) a LCDR1 of SEQ ID NO:475, (e) a LCDR2 of SEQ ID NO:476, and (f) a LCDR3 of SEQ ID NO:477;

(xxviii) a heavy chain variable region that comprises: (a) a HCDR1 of SEQ ID NO:482, (b) a HCDR2 of SEQ ID NO:483, (c) a HCDR3 of SEQ ID NO:484; and a light chain variable region that comprises: (d) a LCDR1 of SEQ ID NO:489, (e) a LCDR2 of SEQ ID NO:490, and (f) a LCDR3 of SEQ ID NO:491.

An antibody, wherein said antibody or antigen binding fragment thereof comprises: (i) a heavy chain variable region that comprises (a) a HCDR1 (CDR-Complementarity Determining Region) of SEQ ID NO: 508, (b) a HCDR2 of SEQ ID NO:509, (c) a HCDR3 of SEQ ID NO:510 and a light chain variable region that comprises: (d) a LCDR1 of SEQ ID NO:511, (e) a LCDR2 of SEQ ID NO:512, and (f) a LCDR3 of SEQ ID NO:513;

(ii) a heavy chain variable region that comprises (a) a HCDR1 of SEQ ID NO:514, (b) a HCDR2 of SEQ ID NO:515, (c) a HCDR3 of SEQ ID NO:516; and a light chain variable region that comprises: (d) a LCDR1 of SEQ ID NO:517, (e) a LCDR2 of SEQ ID NO:518, and (f) a LCDR3 of SEQ ID NO:519;

(iii) a heavy chain variable region that comprises (a) a HCDR1 of SEQ ID NO:520, (b) a HCDR2 of SEQ ID NO:521, (c) a HCDR3 of SEQ ID NO:522; and a light chain variable region that comprises: (d) a LCDR1 of SEQ ID NO:523, (e) a LCDR2 of SEQ ID NO:524, and (f) a LCDR3 of SEQ ID NO:525;

(iv) a heavy chain variable region that comprises: (a) a HCDR1 of SEQ ID NO:526, (b) a HCDR2 of SEQ ID NO:527, (c) a HCDR3 of SEQ ID NO:528; and a light chain variable region that comprises: (d) a LCDR1 of SEQ ID NO:529, (e) a LCDR2 of SEQ ID NO:530, and (f) a LCDR3 of SEQ ID NO:531;

(v) a heavy chain variable region that comprises: (a) a HCDR1 of SEQ ID NO:532, (b) a HCDR2 of SEQ ID NO:533, (c) a HCDR3 of SEQ ID NO:534; and a light chain variable region that comprises: (d) a LCDR1 of SEQ ID NO:535, (e) a LCDR2 of SEQ ID NO:536, and (f) a LCDR3 of SEQ ID NO:537;

(vi) a heavy chain variable region that comprises: (a) a HCDR1 of SEQ ID NO:538, (b) a HCDR2 of SEQ ID NO:539, (c) a HCDR3 of SEQ ID NO:540; and a light chain variable region that comprises: (d) a LCDR1 of SEQ ID NO:541, (e) a LCDR2 of SEQ ID NO:542, and (f) a LCDR3 of SEQ ID NO:543.

The antibody wherein at least one amino acid within a CDR is substituted by a corresponding residue of a corresponding CDR of another anti-VP1 antibody of Table 2.

The antibody wherein one or two amino acids within a CDR have been modified, deleted or substituted.

The antibody that retains at least 90, 91, 92, 93, 94, 95, 96, 97, 98 or 99% identity over either the variable heavy chain region or the variable light chain region.

The antibody that comprises the modifications in Table 3.

The antibody wherein the antibody is a monoclonal antibody, a chimeric antibody, a humanized antibody, a human engineered antibody, a human antibody, a single chain antibody (scFv) or an antibody fragment.

The antibody wherein said antibody or antigen binding fragment thereof comprises:

(i) a heavy chain variable region (vH) that comprises SEQ ID NO:12, and a light chain variable region (vL) that comprises SEQ ID NO: 22;

(ii) a heavy chain variable region (vH) that comprises SEQ ID NO: 32, and a light chain variable region (vL) that comprises SEQ ID NO: 42;

(iii) a heavy chain variable region (vH) that comprises SEQ ID NO: 52, and a light chain variable region (vL) that comprises SEQ ID NO: 62;

(iv) a heavy chain variable region (vH) that comprises SEQ ID NO: 72, and a light chain variable region (vL) that comprises SEQ ID NO: 82;

(v) a heavy chain variable region (vH) that comprises SEQ ID NO:92, and a light chain variable region (vL) that comprises SEQ ID NO:102;

(vi) a heavy chain variable region (vH) that comprises SEQ ID NO:112, and a light chain variable region (vL) that comprises SEQ ID NO:122;

(vii) a heavy chain variable region (vH) that comprises SEQ ID NO: 132, and a light chain variable region (vL) that comprises SEQ ID NO:142;

(viii) a heavy chain variable region (vH) that comprises SEQ ID NO: 152, and a light chain variable region (vL) that comprises SEQ ID NO:162;

(ix) a heavy chain variable region (vH) that comprises SEQ ID NO:172, and a light chain variable region (vL) that comprises SEQ ID NO:182;

(x) a heavy chain variable region (vH) that comprises SEQ ID NO: 192, and a light chain variable region (vL) that comprises SEQ ID NO:202;

(xi) a heavy chain variable region (vH) that comprises SEQ ID NO:212, and a light chain variable region (vL) that comprises SEQ ID NO:222;

(xii) a heavy chain variable region (vH) that comprises SEQ ID NO:232, and a light chain variable region (vL) that comprises SEQ ID NO:242;

(xiii) a heavy chain variable region (vH) that comprises SEQ ID NO:252, and a light chain variable region (vL) that comprises SEQ ID NO:262;

(xiv) a heavy chain variable region (vH) that comprises SEQ ID NO:272, and a light chain variable region (vL) that comprises SEQ ID NO:282;

(xv) a heavy chain variable region (vH) that comprises SEQ ID NO:292, and a light chain variable region (vL) that comprises SEQ ID NO:302;
(xvi) a heavy chain variable region (vH) that comprises SEQ ID NO:312, and a light chain variable region (vL) that comprises SEQ ID NO:320;
(xvii) a heavy chain variable region (vH) that comprises SEQ ID NO:328, and a light chain variable region (vL) that comprises SEQ ID NO:338;
(xviii) a heavy chain variable region (vH) that comprises SEQ ID NO:348, and a light chain variable region (vL) that comprises SEQ ID NO:355;
(xix) a heavy chain variable region (vH) that comprises SEQ ID NO:362, and a light chain variable region (vL) that comprises SEQ ID NO:369;
(xx) a heavy chain variable region (vH) that comprises SEQ ID NO:376, and a light chain variable region (vL) that comprises SEQ ID NO:383;
(xxi) a heavy chain variable region (vH) that comprises SEQ ID NO:390, and a light chain variable region (vL) that comprises SEQ ID NO:397;
(xxii) a heavy chain variable region (vH) that comprises SEQ ID NO:404, and a light chain variable region (vL) that comprises SEQ ID NO:411;
(xxiii) a heavy chain variable region (vH) that comprises SEQ ID NO:418, and a light chain variable region (vL) that comprises SEQ ID NO:425;
(xxiv) a heavy chain variable region (vH) that comprises SEQ ID NO:432, and a light chain variable region (vL) that comprises SEQ ID NO:439;
(xxv) a heavy chain variable region (vH) that comprises SEQ ID NO: 446, and a light chain variable region (vL) that comprises SEQ ID NO:453;
(xxvi) a heavy chain variable region (vH) that comprises SEQ ID NO:460, and a light chain variable region (vL) that comprises SEQ ID NO:467;
(xxvii) a heavy chain variable region (vH) that comprises SEQ ID NO:474, and a light chain variable region (vL) that comprises SEQ ID NO:481; or
(xxviii) a heavy chain variable region (vH) that comprises SEQ ID NO:488, and a light chain variable region (vL) that comprises SEQ ID NO:495.

The antibody that retains at least 90, 91, 92, 93, 94, 95, 96, 97, 98 or 99% identity over either the variable light or variable heavy region.

The antibody wherein one, two, three, four or five, but less than 10 amino acids within the variable light or variable heavy region have been modified, deleted or substituted.

The antibody wherein the antibody is a monoclonal antibody, a chimeric antibody, a humanized antibody, a human engineered antibody, a human antibody, a single chain antibody (scFv) or an antibody fragment.

The antibody of any of the preceding embodiments wherein the antibody or fragment thereof has reduced glycosylation or no glycosylation or is hypofucosylated.

A composition comprising a plurality of an antibody or antigen binding fragment of any of the preceding embodiments, wherein at least 0.05%, 0.1%, 0.5%, 1%, 2%, 3%, 5% or more of the antibodies in the composition have an α2,3-linked sialic acid residue, and wherein said antibody or antigen binding fragment thereof comprises: (i) a heavy chain variable region that comprises (a) a HCDR1 (CDR-Complementarity Determining Region) of SEQ ID NO: 6, (b) a HCDR2 of SEQ ID NO:7, (c) a HCDR3 of SEQ ID NO:8 and a light chain variable region that comprises: (d) a LCDR1 of SEQ ID NO:16, (e) a LCDR2 of SEQ ID NO:17, and (f) a LCDR3 of SEQ ID NO:18;

(ii) a heavy chain variable region that comprises (a) a HCDR1 of SEQ ID NO:26, (b) a HCDR2 of SEQ ID NO:27, (c) a HCDR3 of SEQ ID NO:28; and a light chain variable region that comprises: (d) a LCDR1 of SEQ ID NO:36, (e) a LCDR2 of SEQ ID NO:37, and (f) a LCDR3 of SEQ ID NO:38;
(iii) a heavy chain variable region that comprises (a) a HCDR1 of SEQ ID NO:46, (b) a HCDR2 of SEQ ID NO:47, (c) a HCDR3 of SEQ ID NO:48; and a light chain variable region that comprises: (d) a LCDR1 of SEQ ID NO:56, (e) a LCDR2 of SEQ ID NO:57, and (f) a LCDR3 of SEQ ID NO:58;
(iv) a heavy chain variable region that comprises: (a) a HCDR1 of SEQ ID NO:66, (b) a HCDR2 of SEQ ID NO:67, (c) a HCDR3 of SEQ ID NO:68; and a light chain variable region that comprises: (d) a LCDR1 of SEQ ID NO:76, (e) a LCDR2 of SEQ ID NO:77, and (f) a LCDR3 of SEQ ID NO:78;
(v) a heavy chain variable region that comprises: (a) a HCDR1 of SEQ ID NO:86, (b) a HCDR2 of SEQ ID NO:87, (c) a HCDR3 of SEQ ID NO:88; and a light chain variable region that comprises: (d) a LCDR1 of SEQ ID NO:96, (e) a LCDR2 of SEQ ID NO:97, and (f) a LCDR3 of SEQ ID NO:98;
(vi) a heavy chain variable region that comprises: (a) a HCDR1 of SEQ ID NO:106, (b) a HCDR2 of SEQ ID NO: 107, (c) a HCDR3 of SEQ ID NO:108; and a light chain variable region that comprises: (d) a LCDR1 of SEQ ID NO:116, (e) a LCDR2 of SEQ ID NO:117, and (f) a LCDR3 of SEQ ID NO:118;
(vii) a heavy chain variable region that comprises: (a) a HCDR1 of SEQ ID NO:126, (b) a HCDR2 of SEQ ID NO: 127, (c) a HCDR3 of SEQ ID NO:128; and a light chain variable region that comprises: (d) a LCDR1 of SEQ ID NO:136, (e) a LCDR2 of SEQ ID NO:137, and (f) a LCDR3 of SEQ ID NO:138;
(viii) a heavy chain variable region that comprises: (a) a HCDR1 of SEQ ID NO:146, (b) a HCDR2 of SEQ ID NO:147, (c) a HCDR3 of SEQ ID NO:148; and a light chain variable region that comprises: (d) a LCDR1 of SEQ ID NO:156, (e) a LCDR2 of SEQ ID NO:157, and (f) a LCDR3 of SEQ ID NO:158;
(ix) a heavy chain variable region that comprises: (a) a HCDR1 of SEQ ID NO:166, (b) a HCDR2 of SEQ ID NO: 167, (c) a HCDR3 of SEQ ID NO:168; and a light chain variable region that comprises: (d) a LCDR1 of SEQ ID NO:176, (e) a LCDR2 of SEQ ID NO:177, and (f) a LCDR3 of SEQ ID NO: 178;
(x) a heavy chain variable region that comprises: (a) a HCDR1 of SEQ ID NO:186, (b) a HCDR2 of SEQ ID NO:187, (c) a HCDR3 of SEQ ID NO:188; and a light chain variable region that comprises: (d) a LCDR1 of SEQ ID NO:196, (e) a LCDR2 of SEQ ID NO:197, and (f) a LCDR3 of SEQ ID NO:198;
(xi) a heavy chain variable region that comprises: (a) a HCDR1 of SEQ ID NO:206, (b) a HCDR2 of SEQ ID NO:207, (c) a HCDR3 of SEQ ID NO:208; and a light chain variable region that comprises: (d) a LCDR1 of SEQ ID NO:216, (e) a LCDR2 of SEQ ID NO:217, and (f) a LCDR3 of SEQ ID NO:218;
(xii) a heavy chain variable region that comprises: (a) a HCDR1 of SEQ ID NO:226, (b) a HCDR2 of SEQ ID NO:227, (c) a HCDR3 of SEQ ID NO:228; and a light chain variable region that comprises: (d) a LCDR1 of SEQ ID NO:236, (e) a LCDR2 of SEQ ID NO:237, and (f) a LCDR3 of SEQ ID NO:238;

(xiii) a heavy chain variable region that comprises: (a) a HCDR1 of SEQ ID NO:246, (b) a HCDR2 of SEQ ID NO:247, (c) a HCDR3 of SEQ ID NO:248; and a light chain variable region that comprises: (d) a LCDR1 of SEQ ID NO:256, (e) a LCDR2 of SEQ ID NO:257, and (f) a LCDR3 of SEQ ID NO:258;

(xiv) a heavy chain variable region that comprises: (a) a HCDR1 of SEQ ID NO:266, (b) a HCDR2 of SEQ ID NO:267, (c) a HCDR3 of SEQ ID NO:268; and a light chain variable region that comprises: (d) a LCDR1 of SEQ ID NO: 276, (e) a LCDR2 of SEQ ID NO:277, and (f) a LCDR3 of SEQ ID NO:278;

(xv) a heavy chain variable region that comprises: (a) a HCDR1 of SEQ ID NO:286, (b) a HCDR2 of SEQ ID NO:287, (c) a HCDR3 of SEQ ID NO:288; and a light chain variable region that comprises: (d) a LCDR1 of SEQ ID NO:296, (e) a LCDR2 of SEQ ID NO:297, and (f) a LCDR3 of SEQ ID NO:298;

(xvi) a heavy chain variable region that comprises: (a) a HCDR1 of SEQ ID NO:306, (b) a HCDR2 of SEQ ID NO:307, (c) a HCDR3 of SEQ ID NO:308; and a light chain variable region that comprises: (d) a LCDR1 of SEQ ID NO:314, (e) a LCDR2 of SEQ ID NO:315, and (f) a LCDR3 of SEQ ID NO:316;

(xvii) a heavy chain variable region that comprises: (a) a HCDR1 of SEQ ID NO:322, (b) a HCDR2 of SEQ ID NO:323, (c) a HCDR3 of SEQ ID NO:324; and a light chain variable region that comprises: (d) a LCDR1 of SEQ ID NO:332, (e) a LCDR2 of SEQ ID NO:333, and (f) a LCDR3 of SEQ ID NO:334;

(xviii) a heavy chain variable region that comprises: (a) a HCDR1 of SEQ ID NO:342, (b) a HCDR2 of SEQ ID NO:343, (c) a HCDR3 of SEQ ID NO:344; and a light chain variable region that comprises: (d) a LCDR1 of SEQ ID NO:349, (e) a LCDR2 of SEQ ID NO:350, and (f) a LCDR3 of SEQ ID NO:351;

(xix) a heavy chain variable region that comprises: (a) a HCDR1 of SEQ ID NO:356, (b) a HCDR2 of SEQ ID NO:357, (c) a HCDR3 of SEQ ID NO:358; and a light chain variable region that comprises: (d) a LCDR1 of SEQ ID NO:363, (e) a LCDR2 of SEQ ID NO:364, and (f) a LCDR3 of SEQ ID NO:365;

(xx) a heavy chain variable region that comprises: (a) a HCDR1 of SEQ ID NO:370, (b) a HCDR2 of SEQ ID NO:371, (c) a HCDR3 of SEQ ID NO:372; and a light chain variable region that comprises: (d) a LCDR1 of SEQ ID NO:377, (e) a LCDR2 of SEQ ID NO:378, and (f) a LCDR3 of SEQ ID NO:379;

(xxi) a heavy chain variable region that comprises: (a) a HCDR1 of SEQ ID NO:384, (b) a HCDR2 of SEQ ID NO:385, (c) a HCDR3 of SEQ ID NO:386; and a light chain variable region that comprises: (d) a LCDR1 of SEQ ID NO:391, (e) a LCDR2 of SEQ ID NO:392, and (f) a LCDR3 of SEQ ID NO:393;

(xxii) a heavy chain variable region that comprises: (a) a HCDR1 of SEQ ID NO:398, (b) a HCDR2 of SEQ ID NO:399, (c) a HCDR3 of SEQ ID NO:400; and a light chain variable region that comprises: (d) a LCDR1 of SEQ ID NO:405, (e) a LCDR2 of SEQ ID NO:406, and (f) a LCDR3 of SEQ ID NO:407;

(xxiii) a heavy chain variable region that comprises: (a) a HCDR1 of SEQ ID NO:412, (b) a HCDR2 of SEQ ID NO:413, (c) a HCDR3 of SEQ ID NO:414; and a light chain variable region that comprises: (d) a LCDR1 of SEQ ID NO:419, (e) a LCDR2 of SEQ ID NO:420, and (f) a LCDR3 of SEQ ID NO:421;

(xxiv) a heavy chain variable region that comprises: (a) a HCDR1 of SEQ ID NO:426, (b) a HCDR2 of SEQ ID NO:427, (c) a HCDR3 of SEQ ID NO:428; and a light chain variable region that comprises: (d) a LCDR1 of SEQ ID NO:433, (e) a LCDR2 of SEQ ID NO:434, and (f) a LCDR3 of SEQ ID NO:435;

(xxv) a heavy chain variable region that comprises: (a) a HCDR1 of SEQ ID NO:440, (b) a HCDR2 of SEQ ID NO:441, (c) a HCDR3 of SEQ ID NO:442; and a light chain variable region that comprises: (d) a LCDR1 of SEQ ID NO:447, (e) a LCDR2 of SEQ ID NO:448, and (f) a LCDR3 of SEQ ID NO:449;

(xxvi) a heavy chain variable region that comprises: (a) a HCDR1 of SEQ ID NO:454, (b) a HCDR2 of SEQ ID NO:455, (c) a HCDR3 of SEQ ID NO:456; and a light chain variable region that comprises: (d) a LCDR1 of SEQ ID NO:461, (e) a LCDR2 of SEQ ID NO:462, and (f) a LCDR3 of SEQ ID NO:463;

(xxvii) a heavy chain variable region that comprises: (a) a HCDR1 of SEQ ID NO:468, (b) a HCDR2 of SEQ ID NO:469, (c) a HCDR3 of SEQ ID NO:470; and a light chain variable region that comprises: (d) a LCDR1 of SEQ ID NO:475, (e) a LCDR2 of SEQ ID NO:476, and (f) a LCDR3 of SEQ ID NO:477;

(xxviii) a heavy chain variable region that comprises: (a) a HCDR1 of SEQ ID NO:482, (b) a HCDR2 of SEQ ID NO:483, (c) a HCDR3 of SEQ ID NO:484; and a light chain variable region that comprises: (d) a LCDR1 of SEQ ID NO:489, (e) a LCDR2 of SEQ ID NO:490, and (f) a LCDR3 of SEQ ID NO:491.

A composition comprising a plurality of an antibody or antigen binding fragment of any of the preceding embodiments, wherein none of the antibodies comprise a bisecting GlcNAc.

A pharmaceutical composition comprising the antibody or fragment thereof, of any of the preceding embodiments wherein the composition is prepared as a lyophilisate.

A pharmaceutical composition comprising the antibody or fragment thereof of any of the preceeding embodiments and a pharmaceutically acceptable carrier. In one embodiment, the carrier is a histidine buffer. In one embodiment, the pharmaceutical composition comprises a sugar (e.g., sucrose).

A method of neutralizing a BK virus or JC virus infection comprising administering via injection or infusion to a patient in need an effective amount of the antibody or the pharmaceutical composition. The method wherein the antibody or antigen binding fragment thereof neutralizes BKV serotype I and BKV serotype II. In another embodiment, the antibody or antigen binding fragment thereof neutralizes BKV serotype I and BKV serotype III. In another embodiment, the antibody or antigen binding fragment thereof neutralizes BKV serotype I and BKV serotype IV. In another embodiment, the antibody or antigen binding fragment thereof neutralizes BKV serotype II and BKV serotype III. In another embodiment, the antibody or antigen binding fragment thereof neutralizes BKV serotype II and BKV serotype IV. In another embodiment, the antibody or antigen binding fragment thereof neutralizes BKV serotype I and JCV. In a specific embodiment, the antibody or antigen binding fragment thereof neutralizes BKV serotypes I, II, III and IV. Furthermore, the antibody or antigen binding fragment thereof neutralizes BKV serotypes I, II, III and IV and JCV. In a preferred embodiment, anti-VP1 antibodies neutralized infection by all four serotypes of BKV (I-IV), these anti-VP1 antibodies specifically include P8D11, the modifications of P8D11, and EBB-C1975-B5.

A method of treating or reducing the likelihood of a BK virus or JC virus associated disorder, comprising administering via injection or infusion to a patient in need an effective amount of the antibody or the pharmaceutical composition, and wherein the disorder is: nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, and immune reconstitution inflammatory syndrome (IRIS).

The method wherein the antibody or composition is reconstituted prior to injection or infusion.

The method wherein the antibody or the pharmaceutical composition is administered in combination with another therapeutic agent.

The method wherein the therapeutic agent is an immunosuppressive agent.

The method wherein the immunosuppressive agent is a monophosphate dehydrogenase inhibitor, a purine synthesis inhibitor, a calcineurin inhibitor or an mTOR inhibitor.

The method wherein the immunosuppressive agent is mycophenolate mofetil (MMF), mycophenolate sodium, azathioprine, tacrolimus, sirolimus or cyclosporine.

The method wherein the therapeutic agent is an additional anti-VP1 antibody.

The antibody or fragment thereof of any of the preceding embodiments for use as a medicament.

The antibody or fragment thereof or the pharmaceutical composition, for use in the neutralization of a BK virus or JC virus infection.

The antibody or fragment thereof, or the pharmaceutical composition, for use in the treatment or reducing the likelihood of: nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, and immune reconstitution inflammatory syndrome (IRIS).

The use of the antibody or fragment thereof, administered in combination with another therapeutic agent.

The use of the antibody or fragment thereof wherein the therapeutic agent is an immunosuppressive agent.

The use of the antibody or fragment thereof wherein the immunosuppressive agent is a monophosphate dehydrogenase inhibitor, a purine synthesis inhibitor, a calcineurin inhibitor or an mTOR inhibitor.

The use of the antibody or fragment thereof, wherein the immunosuppressive agent is: mycophenolate mofetil (MMF), mycophenolate sodium, azathioprine, tacrolimus, sirolimus or cyclosporine.

A nucleic acid that encodes the antibody or antigen binding fragment of any of the preceding embodiments.

A vector comprising the nucleic acid.

A host cell comprising the vector.

A process for producing an antibody or antigen binding fragment comprising cultivating the host cell and recovering the antibody from the culture.

A diagnostic reagent comprising the antibody or antigen binding fragment thereof which is labeled.

The diagnostic reagent wherein the label is selected from the group consisting of a radiolabel, a fluorophore, a chromophore, an imaging agent, and a metal ion.

Definitions

Unless stated otherwise, the following terms and phrases as used herein are intended to have the following meanings:

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementary-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HC CDR1), 50-65 (HC CDR2), and 95-102 (HC CDR3) in a VH, e.g., a mammalian VH, e.g., a human VH; and amino acid residues 24-34 (LC CDR1), 50-56 (LC CDR2), and 89-97 (LC CDR3) in a VL, e.g., a mammalian VL, e.g., a human VL.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment," as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody," as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)). A "paratope" is the part of the antibody which recognizes the epitope of the antigen.

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91% 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD, M)" refers to the dissociation rate constant (kd, time-1) divided by the association rate constant (ka, time-1, M-1). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an anti-VP1 antibody of the present disclosure. In some aspects, the phrase "consisting essentially of" expressly excludes the inclusion of one or more additional active agents other than an anti-VP1 antibody of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=-4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, (Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, (J. Mol. Biol. 48:444-453, 1970), algorithm which has been incorporated into the GAP program in the GCG software package (available from University of South Florida), using either a BLOSUM 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "BKV" or "BK virus" refer to a member of the family Polyomaviridae, genus Orthopolyomavirus. Polyomaviruses are icosahedral, non-enveloped, double-stranded DNA viruses with a genome of approximately 5,000 base pairs. They measure approximately 40-45 nM in diameter (Bennett et al., Microbes and Infection. 2012:14(9):672-683).

"JCV" or "JC virus" refers to a member of the family Polyomaviridae, genus Orthopolyomavirus. JCV is related to BKV, and is also an icosahedral, non-enveloped, double-stranded DNA virus with a genome of approximately 5,000 base pairs. They measure approximately 40-45 nM in diameter (Johne et al., Arch. Virol. 2011; 156(9):1627-1634).

The terms "BKV nephropathy" or "BKV-associated nephropathy" or "BKVAN" refer to the inflammatory interstitial nephropathy resulting from the lytic infection with BKV, characterized by viral cytopathogenic changes and viral gene expression, primarily in the renal tubular epithelium.

The term "VP1" refers to the major polyoma virus capsid subunit protein. "VP1 pentamers" are composed of five monomers of VP1.

TABLE 1-VP1 sequences

| Name | Sequence | SEQ ID NO |
|---|---|---|
| VP1 BKV serotype I | MAPTKRKGECPGAAPKKPKEPVQVPKLLIKGGVEVLEV KTGVDAITEVECFLNPEMGDPDENLRGFSLKLSAENDFS SDSPERKMLPCYSTARIPLPNLNEDLTCGNLLMWEAVTV QTEVIGITSMLNLHAGSQKVHEHGGGKPIQGSNFHFFAV GGDPLEMQGVLMNYRTKYPEGTITPKNPTAQSQVMN TDHKAYLDKNNAYPVECWIPDPSRNENTRYFGTFTGGE NVPPVLHVTNTATTVLLDEQGVGPLCKADSLYVSAADIC GLFTNSSGTQQWRGLARYFKIRLRKRSVKNPYPISFLLSD LINRRTQRVDGQPMYGMESQVEEVRVFDGTERLPGDPD MIRYIDKQGQLQTKML | (SEQ ID NO: 1) |
| VP1 BKV serotype II | MAPTKRKGECPGAAPKKPKEPVQVPKLLIKGGVEVLEV KTGVDAITEVECFLNPEMGDPDDNLRGYSLKLTAENAFD SDSPDKKMLPCYSTARIPLPNLNEDLTCGNLLMWEAVTV KTEVIGITSMLNLHAGSQKVHENGGGKPVQGSNFHFFAV GGDPLEMQGVLMNYRTKYPQGTITPKNPTAQSQVMN | (SEQ ID NO: 2) |

TABLE 1-VP1-continued

| Name | Sequence | SEQ ID NO |
|---|---|---|
|  | TDHKAYLDKNNAYPVECWIPDPSRNENTRYFGTYTGGE<br>NVPPVLHVTNTATTVLLDEQGVGPLCKADSLYVSAADIC<br>GLFTNSSGTQQWRGLARYFKIRLRKRSVKNPYPISFLLSD<br>LINRRTQKVDGQPMYGMESQVEEVRVFDGTEQLPGDPD<br>MIRYIDRQGQLQTKMV |  |
| VP1 BKV<br>serotype III | MAPTKRKGECPGAAPKKPKEPVQVPKLLIKGGVEVLEV<br>KTGVDAITEVECFLNPEMGDPDDHLRGYSQHLSAENAF<br>DSDSPDKKMLPCYSTARIPLPNLNEDLTCGNLLMWEAVT<br>VKTEVIGITSMLNLHAGSQKVHENGGGKPVQGSNFHFFA<br>VGGDPLEMQGVLMNYRTKYPQGTITPKNPTAQSQVM<br>NTDHKAYLDKNNAYPVECWIPDPSKNENTRYFGTYTGG<br>ENVPPVLHVTNTATTVLLDEQGVGPLCKADSLYVSAADI<br>CGLFTNSSGTQQWRGLARYFKIRLRKRSVKNPYPISFLLS<br>DLINRRTQKVDGQPMYGMESQVEEVRVFDGTEQLPGDP<br>DMIRYIDRQGQLQTKMV | (SEQ ID<br>NO: 3) |
| VP1 BKV<br>serotype IV | MAPTKRKGECPGAAPKKPKEPVQVPKLLIKGGVEVLEV<br>KTGVDAITEVECFLNPEMGDPDNDLRGYSLRLTAETAFD<br>SDSPDRKMLPCYSTARIPLPNLNEDLTCGNLLMWEAVTV<br>KTEVIGITSMLNLHAGSQKVHENGGGKPIQGSNFHFFAV<br>GGDPLEMQGVLMNYRTKYPEGTVTPKNPTAQSQVMN<br>TDHKAYLDKNNAYPVECWIPDPSRNENTRYFGTYTGGE<br>NVPPVLHVTNTATTVLLDEQGVGPLCKADSLYVSAADIC<br>GLFTNSSGTQQWRGLPRYFKIRLRKRSVKNPYPISFLLSD<br>LINRRTQRVDGQPMYGMESQVEEVRVFDGTEQLPGDPD<br>MIRYIDRQGQLQTKMV | (SEQ ID<br>NO: 4) |
| JCVVP1 | MAPTKRKGERKDPVQVPKLLIRGGVEVLEVKTGVDSITE<br>VECFLTPEMGDPDEHLRGFSKSISISDTFESDSPNKDMLP<br>CYSVARIPLPNLNEDLTCGNILMWEAVTLKTEVIGVTTL<br>MNVHSNGQATHDNGAGKPVQGTSFHFFSVGGEALELQG<br>VVFNYRTKYPDGTIFPKNATVQSQVMNTEHKAYLDKN<br>KAYPVECWVPDPTRNENTRYFGTLTGGENVPPVLHITNT<br>ATTVLLDEFGVGPLCKGDNLYLSAVDVCGMFTNRSGSQ<br>QWRGLSRYFKVQLRKRRVKNPYPISFLLTDLINRRTPRV<br>DGQPMYGMDAQVEEVRVFEGTEELPGDPDMMRYVDRY<br>GQLQTKML | (SEQ ID<br>NO: 5) |

"Virus-like particles" or "VLP" are an assembly of VP1 pentamers into viral capsids. VLPs are composed of 72 VP1 pentamers. VLPs are structurally very similar to actual virus but lack the minor capsid proteins (VP2 and VP3) as well as the viral DNA genome, and therefore are non-infectious. VLPs are useful as viral epitopes are presented in a similar conformation to the actual virus.

"IC50" (half-maximal inhibitory concentration) refers to the concentration of a particular antibody which induces a signal halfway (50%) between the baseline control and the maximum possible signal. For example, the IC50 is the concentration of antibody at which 50% of the available binding sites on the VP1 antigen are occupied.

"EC50" (half-maximal effective concentration) refers to the concentration of a particular antibody which induces a response halfway (50%) between the baseline control and the maximum possible effect after a specific exposure or treatment time. For example, the EC50 is the concentration of antibody at which virus infection is neutralized by 50%.

"EC90" refers to the concentration of a particular antibody which induces a response corresponding to 90% of the maximum possible effect after a specific exposure or treatment time. For example, the EC90 is the concentration of antibody at which virus infection is neutralized by 90%.

"Neutralization" refers to the inhibition of viral infection of a host cell, as demonstrated by the absence of viral gene expression. Without being held to any one theory, mechanisms of neutralization by a particular antibody could include blocking the interaction of viral capsid proteins with cell surface receptors or disruption of any stage of the entry and trafficking process prior to delivery of the viral genome to the nucleus of the host cell.

As used herein, the terms "treat," "treating," or "treatment" of any disease or disorder refer in one aspect, to ameliorating the disease or disorder (i.e., slowing or arresting or reducing the development of the disease or at least one of the clinical symptoms thereof). In another aspect, "treat," "treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both.

The phrase "reducing the likelihood" refers to delaying the onset or development or progression of the disease, infection or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of the molecules of the present disclosure can prevent the onset of, or result in a decrease in severity of, respectively, disease symptoms, including symptoms associated polyoma viral infection.

The term "co-administer" refers to the simultaneous presence of two active agents in the blood of an individual. Active agents that are co-administered can be concurrently or sequentially delivered.

BRIEF DESCRIPTION OF THE DRAWINGS

FIG. 2 is a table of SET affinity values ($K_D$) for anti-VP1 antibodies on VP1 pentamers for BKV serotypes I-IV.

FIG. 3A-3E graphically represents affinity measurements for anti-VP1 antibodies on VP1 pentamers or VLPs for BKV serotypes I-IV by Biacore.

FIG. 7 is a table of IC50 values generated by ELISA for anti-VP1 antibodies binding to VLPs or VP1 pentamers for BKV serotypes I and IV.

FIG. 9 is a table of IC50 values generated by ELISA for anti-VP1 antibodies binding to BKV serotype I VLPs.

FIG. 11 is a table of IC50 values generated by ELISA for anti-VP1 antibodies binding to JCV VLPs.

FIG. 12A-B shows two blots. The upper panel (FIG. 12A) is a Western blot demonstrating no binding of anti-VP1 antibodies to denatured BKV VP1. The lower panel (FIG. 12B) is a dot-blot of non-denatured BKV VP1 pentamers, demonstrating binding of anti-VP1 antibodies to non-denatured VP1 pentamers.

FIG. 14 is a table summarizing the key residues for binding identified in the epitopes of anti-VP1 antibodies.

FIG. 19 is a table summarizing the neutralizing activity (EC50 and EC90) of anti-VP1 antibodies on BKV serotypes I-IV and JC virus.

FIG. 21 is a table summarizing the neutralizing activity (EC50 and EC90) of anti-VP1 antibodies on BKV serotypes I-IV.

FIG. 23 is a table summarizing the neutralizing activity (EC50 and EC90) of anti-VP1 antibodies on BKV serotype I.

FIG. 26 is table summarizing the neutralizing activity (EC50 and EC90) of anti-VP1 antibodies on JCV infection.

FIG. 27 is table of antibody P8D11 affinity on JC virus VLPs and VLPs containing point mutations.

FIG. 28 is deuterium exchange epitope mapping of a P8D11 Fab bound to BKV VP1 pentamers.

FIG. 29A is a table that shows anti-BKV antibody contact residues in the EF loop when certain mutations are introduced by alanine scanning. FIG. 29B-29C shows the SPR graphs of anti-BKV antibody binding to wild type and mutated residues in VP1.

DETAILED DESCRIPTION

Figure 1A:
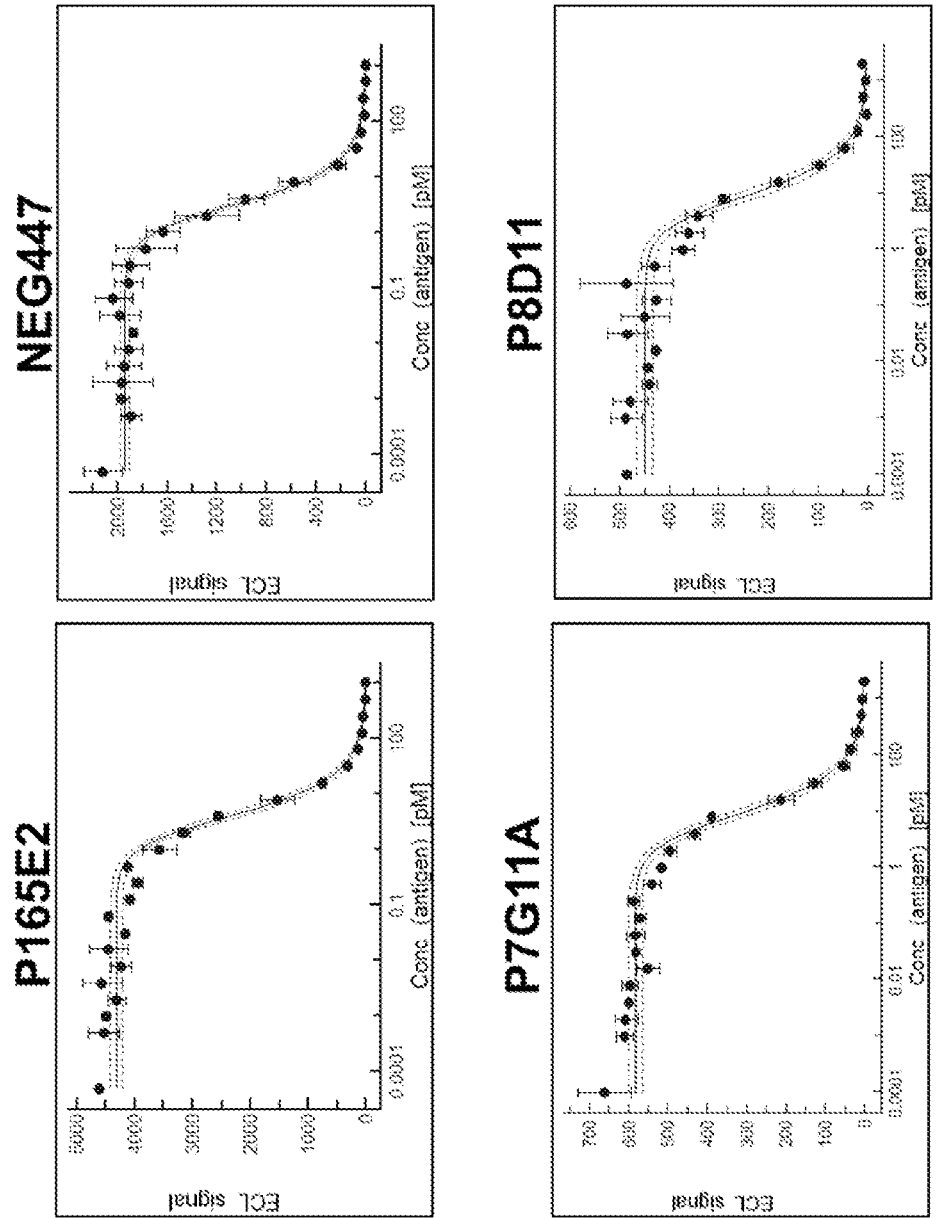
FIG. 1A-1D graphically represents affinity measurements for anti-VP1 antibodies on VP1 pentamers for BKV serotypes I-IV by SET assay.
Figure 1B:
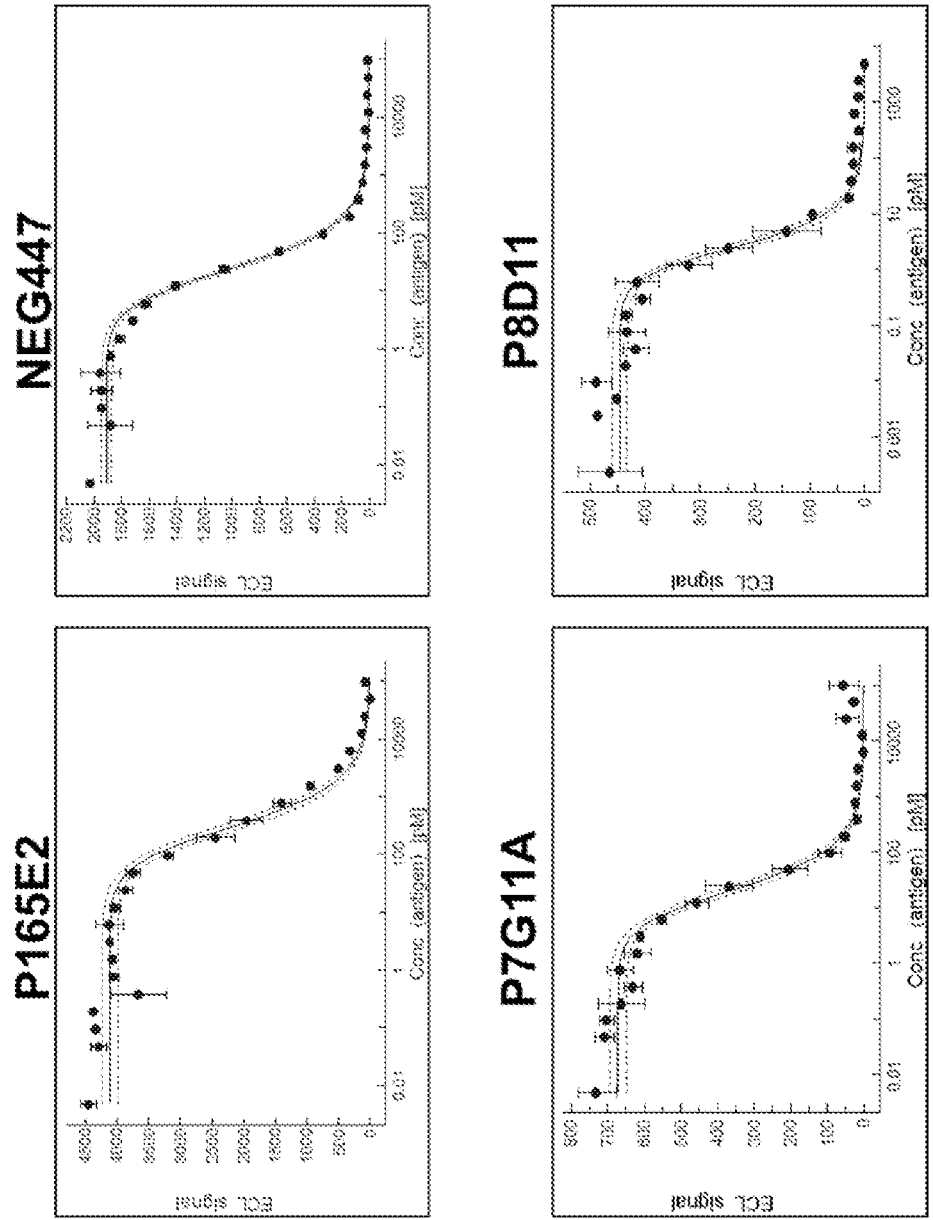
Figure 1C:
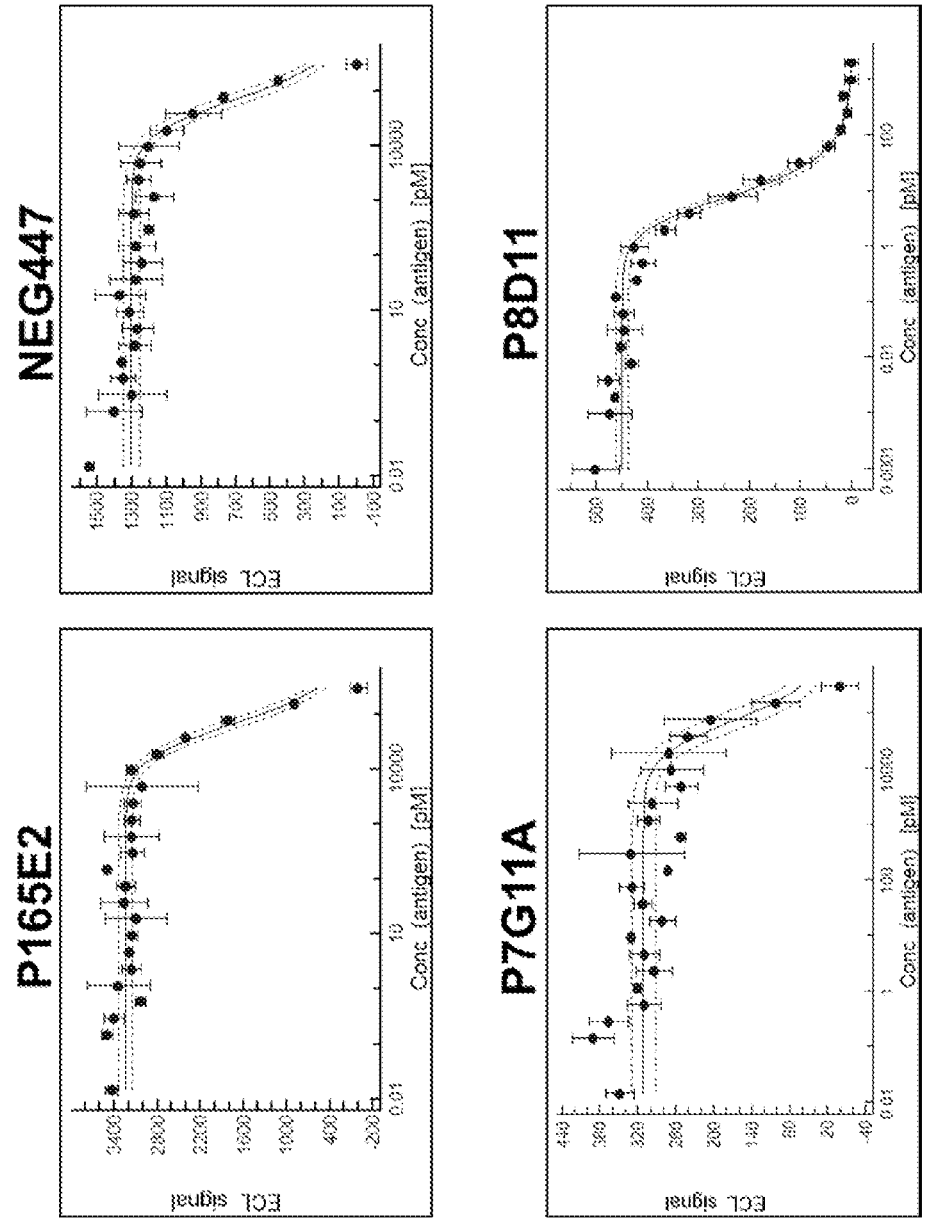
Figure 1D:
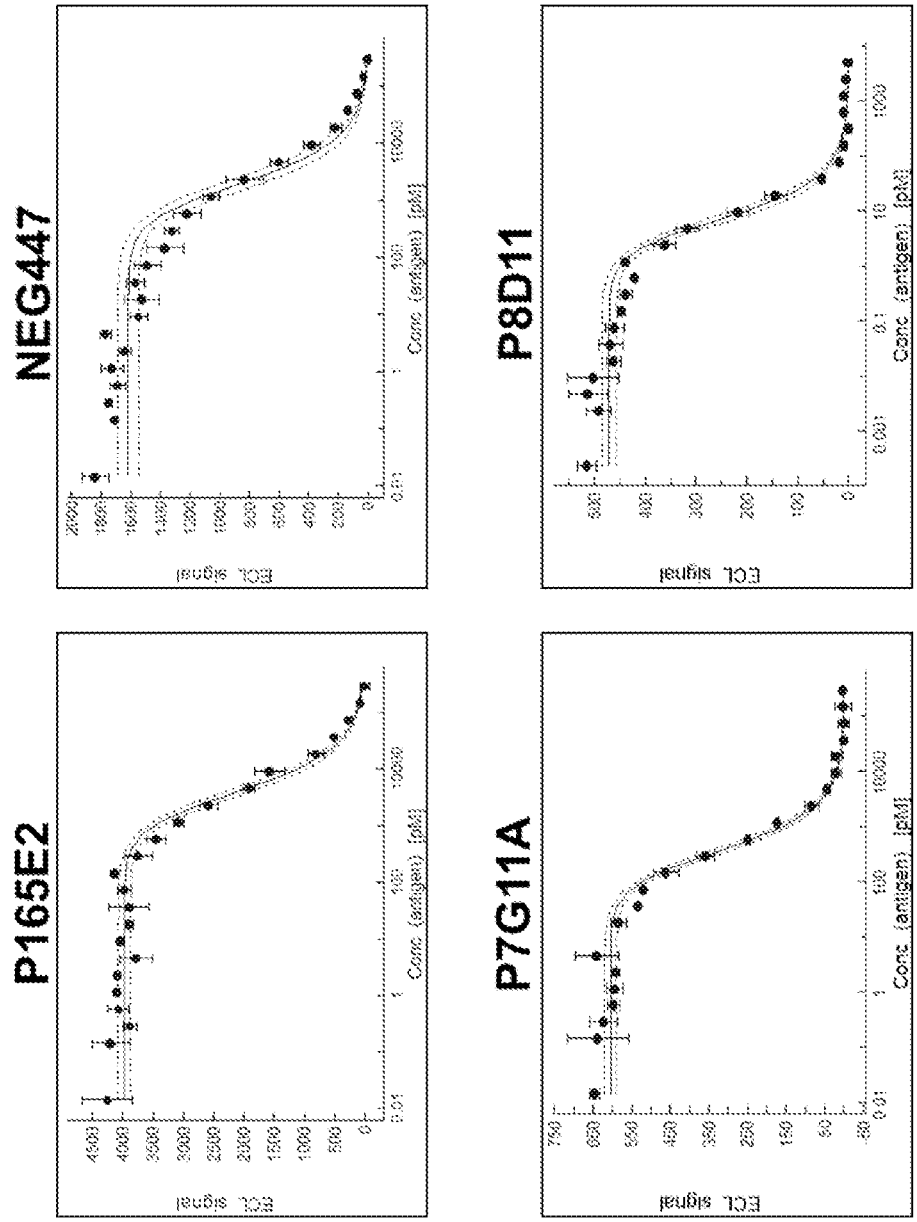

The present disclosure provides for antibodies, antibody fragments (e.g., antigen binding fragments), that bind and neutralize BKV. In particular, the present disclosure is directed to antibodies and antibody fragments (e.g., antigen binding fragments) that bind to VP1 proteins, and neutralize viral infection upon such binding. Furthermore, the present disclosure provides antibodies that have desirable pharmacokinetic characteristics and other desirable attributes, and thus can be used for reducing the likelihood of or treating BK virus-associated nephropathy (e.g. BKVAN). The present disclosure further provides pharmaceutical compositions comprising the antibodies and methods of making and using such pharmaceutical compositions for the prevention and treatment of polyoma virus infection and associated disorders.

Anti-VP1 Antibodies

The present disclosure provides for antibodies or antibody fragments (e.g., antigen binding fragments) that specifically bind to VP1. Antibodies or antibody fragments (e.g., antigen binding fragments) of the present disclosure include, but are not limited to, the human monoclonal antibodies or fragments thereof, isolated as described, in the Examples below.

The present disclosure in certain aspects provides antibodies or antibody fragments (e.g., antigen binding fragments) that specifically bind to VP1, said antibodies or antibody fragments (e.g., antigen binding fragments) comprise a VH domain having an amino acid sequence of SEQ ID NO:12, 32, 52, 72, 92, 112, 132, 152, 172, 192, 212, 232, 252, 272, 292, 312, 328, 348, 362, 376, 390, 404, 418, 432, 446, 460, 474, and 488 (Table 2). The present disclosure also provides antibodies or antibody fragments (e.g., antigen binding fragments) that specifically bind to VP1, said antibodies or antibody fragments (e.g., antigen binding fragments) comprise a VH CDR having an amino acid sequence of any one of the VH CDRs listed in Table 2. In particular aspects, the present disclosure provides antibodies or antibody fragments (e.g., antigen binding fragments) that specifically bind to VP1, said antibodies comprising (or alternatively, consist of) one, two, three, or more VH CDRs having an amino acid sequence of any of the VH CDRs listed in Table 2.

The present disclosure provides antibodies or antibody fragments (e.g., antigen binding fragments) that specifically bind to VP1, said antibodies or antibody fragments (e.g., antigen binding fragments) comprise a VL domain having an amino acid sequence of SEQ ID NO: 22, 42, 62, 82, 102, 122, 142, 162, 182, 202, 222, 242, 262, 282, 302, 320, 338, 355, 369, 383, 397, 411, 425, 439, 453, 467, 481, and 495 (Table 2). The present disclosure also provides antibodies or antibody fragments (e.g., antigen binding fragments) that specifically bind to VP1, said antibodies or antibody fragments (e.g., antigen binding fragments) comprise a VL CDR having an amino acid sequence of any one of the VL CDRs listed in Table 2. In particular, the disclosure provides antibodies or antibody fragments (e.g., antigen binding fragments) that specifically bind to VP1, said antibodies or antibody fragments (e.g., antigen binding fragments) comprise (or alternatively, consist of) one, two, three or more VL CDRs having an amino acid sequence of any of the VL CDRs listed in Table 2.

Other antibodies or antibody fragments (e.g., antigen binding fragments) of the present disclosure include amino acids that have been mutated, yet have at least 60, 70, 80, 90 or 95 percent identity in the CDR regions with the CDR regions depicted in the sequences described in Table 2. In some aspects, it includes mutant amino acid sequences wherein no more than 1, 2, 3, 4 or 5 amino acids have been mutated in the CDR regions when compared with the CDR regions depicted in the sequence described in Table 2.

The present disclosure also provides nucleic acid sequences that encode VH, VL, the full length heavy chain, and the full length light chain of the antibodies that specifically bind to VP1. Such nucleic acid sequences can be optimized for expression in mammalian cells.

TABLE 2

| anti-VP1 Antibodies | | |
|---|---|---|
| P8D11 | | |
| SEQ ID NO: 6 (Kabat) | HCDR1 | NYWMT |
| SEQ ID NO: 7 (Kabat) | HCDR2 | NIKKDGSEKYYVDSVRG |
| SEQ ID NO: 8 (Kabat) | HCDR3 | VRSGRYFALDD |
| SEQ ID NO: 9 (Chothia) | HCDR1 | GFTFNNY |
| SEQ ID NO: 10 (Chothia) | HCDR2 | KKDGSE |
| SEQ ID NO: 11 (Chothia) | HCDR3 | VRSGRYFALDD |
| SEQ ID NO: 12 | VH | QVQLVESGGTLVQPGGSLRLSCAASGFTFNNYWM<br>TWVRQAPGKGLEWVANIKKDGSEKYYVDSVRGR<br>FTISRDNAKNSLFLQMNSLRPEDTAVYFCATVRSG<br>RYFALDDWGQGTLVTVSS |
| SEQ ID NO: 13 | DNA VH | CAGGTGCAGCTGGTGGAATCAGGCGGCACACTG<br>GTGCAGCCTGGCGGTAGCCTGAGACTGAGCTGCG<br>CTGCTAGTGGCTTCACCTTTAACAACTACTGGAT<br>GACCTGGGTTAGGCAGGCCCCTGGTAAAGGCCTC<br>GAGTGGGTGGCAAATATCAAGAAGGACGGTAGC<br>GAGAAGTACTACGTGGACTCAGTCAGAGGCCGG<br>TTCACTATCTCTAGGGATAACGCTAAGAATAGCC<br>TGTTCCTGCAGATGAACTCACTGAGGCCCGAGGA<br>TACCGCCGTCTACTTCTGTGCTACCGTCAGATCA<br>GGCCGCTACTTCGCCCTGGACGACTGGGGTCAAG<br>GCACACTGGTCACCGTGTCTAGC |
| SEQ ID NO: 14 | Heavy Chain | QVQLVESGGTLVQPGGSLRLSCAASGFTFNNYWM<br>TWVRQAPGKGLEWVANIKKDGSEKYYVDSVRGRF<br>TISRDNAKNSLFLQMNSLRPEDTAVYFCATVRSGR<br>YFALDDWGQGTLVTVSSASTKGPSVFPLAPSSKSTS<br>GGTAALGCLVKDYFPEPVTVSWNSGALTSGVHTFP<br>AVLQSSGLYSLSSVVTVPSSSLGTQTYICNVNHKPS<br>NTKVDKRVEPKSCDKTHTCPPCPAPELLGGPSVFLF<br>PPKPKDTLMISRTPEVTCVVVDVSHEDPEVKFNWY<br>VDGVEVHNAKTKPREEQYNSTYRVVSVLTVLHQD<br>WLNGKEYKCKVSNKALPAPIEKTISKAKGQPREPQ<br>VYTLPPSREEMTKNQVSLTCLVKGFYPSDIAVEWE<br>SNGQPENNYKTTPPVLDSDGSFFLYSKLTVDKSRW<br>QQGNVFSCSVMHEALHNHYTQKSLSLSPGK |
| SEQ ID NO: 15 | DNA Heavy Chain | CAGGTGCAGCTGGTGGAATCAGGCGGCACACTG<br>GTGCAGCCTGGCGGTAGCCTGAGACTGAGCTGC<br>GCTGCTAGTGGCTTCACCTTTAACAACTACTGGA<br>TGACCTGGGTTAGGCAGGCCCCTGGTAAAGGCCT<br>CGAGTGGGTGGCAAATATCAAGAAGGACGGTAG |

TABLE 2-continued

| anti-VP1 Antibodies ||||
|---|---|---|---|
| | | CGAGAAGTACTACGTGGACTCAGTCAGAGGCCG GTTCACTATCTCTAGGGATAACGCTAAGAATAGC CTGTTCCTGCAGATGAACTCACTGAGGCCCGAGG ATACCGCCGTCTACTTCTGTGCTACCGTCAGATC AGGCCGCTACTTCGCCCTGGACGACTGGGGTCAA GGCACACTGGTCACCGTGTCTAGCGCTAGCACTA AGGGCCCAAGTGTGTTTCCCCTGGCCCCCAGCAG CAAGTCTACTTCCGGCGGAACTGCTGCCCTGGGT TGCCTGGTGAAGGACTACTTCCCCGAGCCCGTGA CAGTGTCCTGGAACTCTGGGGCTCTGACTTCCGG CGTGCACACCTTCCCCGCCGTGCTGCAGAGCAGC GGCCTGTACAGCCTGAGCAGCGTGGTGACAGTG CCCTCCAGCTCTCTGGGAACCCAGACCTATATCT GCAACGTGAACCACAAGCCCAGCAACACCAAGG TGGACAAGAGAGTGGAGCCCAAGAGCTGCGACA AGACCCACACCTGCCCCCCCTGCCCAGCTCCAGA ACTGCTGGGAGGGCCTTCCGTGTTCCTGTTCCCC CCCAAGCCCAAGGACACCCTGATGATCAGCAGG ACCCCCGAGGTGACCTGCGTGGTGGTGGACGTGT CCCACGAGGACCCAGAGGTGAAGTTCAACTGGT ACGTGGACGGCGTGGAGGTGCACAACGCCAAGA CCAAGCCCAGAGAGGAGCAGTACAACAGCACCT ACAGGGTGGTGTCCGTGCTGACCGTGCTGCACCA GGACTGGCTGAACGGCAAAGAATACAAGTGCAA AGTCTCCAACAAGGCCCTGCCAGCCCCAATCGA AAAGACAATCAGCAAGGCCAAGGGCCAGCCACG GGAGCCCCAGGTGTACACCCTGCCCCCCAGCCG GGAGGAGATGACCAAGAACCAGGTGTCCCTGAC CTGTCTGGTGAAGGGCTTCTACCCCAGCGATATC GCCGTGGAGTGGGAGAGCAACGGCCAGCCCGAG AACAACTACAAGACCACCCCCCCAGTGCTGGAC AGCGACGGCAGCTTCTTCCTGTACAGCAAGCTGA CCGTGGACAAGTCCAGGTGGCAGCAGGGCAACG TGTTCAGCTGCAGCGTGATGCACGAGGCCCTGCA CAACCACTACACCCAGAAGTCCCTGAGCCTGAG CCCCGGCAAG |
| SEQ ID NO: 16 (Kabat) | LCDR1 | GGDNIGSRPVH |
| SEQ ID NO: 17 (Kabat) | LCDR2 | DDSNRPS |
| SEQ ID NO: 18 (Kabat) | LCDR3 | QVWSSSTDHP |
| SEQ ID NO: 19 (Chothia) | LCDR1 | DNIGSRP |
| SEQ ID NO: 20 (Chothia) | LCDR2 | DDS |
| SEQ ID NO: 21 (Chothia) | LCDR3 | WSSSTDH |
| SEQ ID NO: 22 | VL | QSVLTQPPSVSVAPGKTARITCGGDNIGSRPVHWY QQKPGQAPILVVYDDSNRPSGIPERFSGSNSGNTAT LTISRVEAGDEADYYCQVWSSSTDHPFGGGTKVTV L |
| SEQ ID NO: 23 | DNA VL | CAGTCAGTCCTGACTCAGCCCCCTAGCGTCAGCG TGGCCCCTGGTAAAACCGCTAGAATCACCTGTGG CGGCGATAATATCGGCTCTAGGCCCGTGCACTGG TATCAGCAGAAGCCCGGTCAAGCCCCTATCCTGG TGGTCTACGACGACTCTAATAGACCTAGCGGAAT CCCCGAGCGGTTTAGCGGCTCTAATTCTGGTAAT ACCGCTACCCTGACTATCTCTAGGGTGGAAGCCG GCGACGAGGCCGACTACTACTGTCAAGTCTGGTC TAGCTCTACCGATCACCCCTTCGGCGGAGGCACT AAGGTTACAGTGCTG |
| SEQ ID NO: 24 | Light Chain | QSVLTQPPSVSVAPGKTARITCGGDNIGSRPVHWY QQKPGQAPILVVYDDSNRPSGIPERFSGSNSGNTAT LTISRVEAGDEADYYCQVWSSSTDHPFGGGTKVTV LGQPKAAPSVTLFPPSSEELQANKATLVCLISDFYP GAVTVAWKADSSPVKAGVETTTPSKQSNNKYAAS SYLSLTPEQWKSHRSYSCQVTHEGSTVEKTVAPTE CS |

TABLE 2-continued anti-VP1 Antibodies

| SEQ ID NO: 25 | DNA Light Chain | CAGTCAGTCCTGACTCAGCCCCCTAGCGTCAGCG
TGGCCCCTGGTAAAACCGCTAGAATCACCTGTGG
CGGCGATAATATCGGCTCTAGGCCCGTGCACTGG
TATCAGCAGAAGCCCGGTCAAGCCCCTATCCTGG
TGGTCTACGACGACTCTAATAGACCTAGCGGAAT
CCCCGAGCGGTTTAGCGGCTCTAATTCTGGTAAT
ACCGCTACCCTGACTATCTCTAGGGTGGAAGCCG
GCGACGAGGCCGACTACTACTGTCAAGTCTGGTC
TAGCTCTACCGATCACCCCTTCGGCGGAGGCACT
AAGGTTACAGTGCTGGGTCAACCTAAGGCTGCCC
CCAGCGTGACCCTGTTCCCCCCCAGCAGCGAGGA
GCTGCAGGCCAACAAGGCCACCCTGGTGTGCCT
GATCAGCGACTTCTACCCAGGCGCCGTGACCGTG
GCCTGGAAGGCCGACAGCAGCCCCGTGAAGGCC
GGCGTGGAGACCACCACCCCCAGCAAGCAGAGC
AACAACAAGTACGCCGCCAGCAGCTACCTGAGC
CTGACCCCGAGCAGTGGAAGAGCCACAGGTCC
TACAGCTGCCAGGTGACCCACGAGGGCAGCACC
GTGGAAAAGACCGTGGCCCCAACCGAGTGCAGC |

P8D11A

| SEQ ID NO: 26 (Kabat) | HCDR1 | NYWMT |
| SEQ ID NO: 27 (Kabat) | HCDR2 | NIKKDGSEKYYVDSVRG |
| SEQ ID NO: 28 (Kabat) | HCDR3 | VRSGRYFALDD |
| SEQ ID NO: 29 (Chothia) | HCDR1 | GFTFSNY |
| SEQ ID NO: 30 (Chothia) | HCDR2 | KKDGSE |
| SEQ ID NO: 31 (Chothia) | HCDR3 | VRSGRYFALDD |
| SEQ ID NO: 32 | VH | QVQLVESGGTLVQPGGSLRLSCAASGFTFSNYWM
TWVRQAPGKGLEWVANIKKDGSEKYYVDSVRGR
FTISRDNAKNSLFLQMNSLRPEDTAVYFCATVRSG
RYFALDDWGQGTLVTVSS |
| SEQ ID NO: 33 | DNA VH | CAGGTGCAGCTGGTGGAATCAGGCGGCACACTG
GTGCAGCCTGGCGGTAGCCTGAGACTGAGCTGC
GCTGCTAGTGGCTTCACCTTCTCTAACTACTGGA
TGACCTGGGTCAGGCAGGCCCCTGGTAAAGGCC
TCGAGTGGGTGGCAAATATCAAGAAGGACGGTA
GCGAGAAGTACTACGTGGACTCAGTCAGAGGCC
GGTTCACTATCTCTAGGGATAACGCTAAGAATAG
CCTGTTCCTGCAGATGAACTCACTGAGGCCCGAG
GATACCGCCGTCTACTTCTGTGCTACCGTCAGAT
CAGGCCGCTACTTCGCCCTGGACGACTGGGGTCA
AGGCACACTGGTCACCGTGTCTAGC |
| SEQ ID NO: 34 | Heavy Chain | QVQLVESGGTLVQPGGSLRLSCAASGFTFSNYWM
TWVRQAPGKGLEWVANIKKDGSEKYYVDSVRGR
FTISRDNAKNSLFLQMNSLRPEDTAVYFCATVRSG
RYFALDDWGQGTLVTVSSASTKGPSVFPLAPSSKS
TSGGTAALGCLVKDYFPEPVTVSWNSGALTSGVHT
FPAVLQSSGLYSLSSVVTVPSSSLGTQTYICNVNHK
PSNTKVDKRVEPKSCDKTHTCPPCPAPELLGGPSVF
LFPPKPKDTLMISRTPEVTCVVVDVSHEDPEVKFN
WYVDGVEVHNAKTKPREEQYNSTYRVVSVLTVLH
QDWLNGKEYKCKVSNKALPAPIEKTISKAKGQPRE
PQVYTLPPSREEMTKNQVSLTCLVKGFYPSDIAVE
WESNGQPENNYKTTPPVLDSDGSFFLYSKLTVDKS
RWQQGNVFSCSVMHEALHNHYTQKSLSLSPGK |
| SEQ ID NO: 35 | DNA Heavy Chain | CAGGTGCAGCTGGTGGAATCAGGCGGCACACTG
GTGCAGCCTGGCGGTAGCCTGAGACTGAGCTGC
GCTGCTAGTGGCTTCACCTTCTCTAACTACTGGA
TGACCTGGGTCAGGCAGGCCCCTGGTAAAGGCC
TCGAGTGGGTGGCAAATATCAAGAAGGACGGTA
GCGAGAAGTACTACGTGGACTCAGTCAGAGGCC |

TABLE 2-continued

| | | |
|---|---|---|
| | | anti-VP1 Antibodies |
| | | GGTTCACTATCTCTAGGGATAACGCTAAGAATAG<br>CCTGTTCCTGCAGATGAACTCACTGAGGCCCGAG<br>GATACCGCCGTCTACTTCTGTGCTACCGTCAGAT<br>CAGGCCGCTACTTCGCCCTGGACGACTGGGGTCA<br>AGGCACACTGGTCACCGTGTCTAGCGCTAGCACT<br>AAGGGCCCAAGTGTGTTTCCCCTGGCCCCCAGCA<br>GCAAGTCTACTTCCGGCGGAACTGCTGCCCTGGG<br>TTGCCTGGTGAAGGACTACTTCCCCGAGCCCGTG<br>ACAGTGTCCTGGAACTCTGGGGCTCTGACTTCCG<br>GCGTGCACACCTTCCCCGCCGTGCTGCAGAGCAG<br>CGGCCTGTACAGCCTGAGCAGCGTGGTGACAGT<br>GCCCTCCAGCTCTCTGGGAACCCAGACCTATATC<br>TGCAACGTGAACCACAAGCCCAGCAACACCAAG<br>GTGGACAAGAGAGTGGAGCCCAAGAGCTGCGAC<br>AAGACCCACACCTGCCCCCCCTGCCCAGCTCCAG<br>AACTGCTGGGAGGGCCTTCCGTGTTCCTGTTCCC<br>CCCCAAGCCCAAGGACACCCTGATGATCAGCAG<br>GACCCCCGAGGTGACCTGCGTGGTGGTGGACGT<br>GTCCCACGAGGACCCAGAGGTGAAGTTCAACTG<br>GTACGTGGACGGCGTGGAGGTGCACAACGCCAA<br>GACCAAGCCCAGAGAGGAGCAGTACAACAGCAC<br>CTACAGGGTGGTGTCCGTGCTGACCGTGCTGCAC<br>CAGGACTGGCTGAACGGCAAAGAATACAAGTGC<br>AAAGTCTCCAACAAGGCCCTGCCAGCCCCAATC<br>GAAAAGACAATCAGCAAGGCCAAGGGCCAGCCA<br>CGGGAGCCCCAGGTGTACACCCTGCCCCCCAGCC<br>GGGAGGAGATGACCAAGAACCAGGTGTCCCTGA<br>CCTGTCTGGTGAAGGGCTTCTACCCCAGCGATAT<br>CGCCGTGGAGTGGGAGAGCAACGGCCAGCCCGA<br>GAACAACTACAAGACCACCCCCCAGTGCTGGA<br>CAGCGACGGCAGCTTCTTCCTGTACAGCAAGCTG<br>ACCGTGGACAAGTCCAGGTGGCAGCAGGGCAAC<br>GTGTTCAGCTGCAGCGTGATGCACGAGGCCCTGC<br>ACAACCACTACACCCAGAAGTCCCTGAGCCTGA<br>GCCCCGGCAAG |
| SEQ ID NO: 36<br>(Kabat) | LCDR1 | GGDNIGSRPVH |
| SEQ ID NO: 37<br>(Kabat) | LCDR2 | DDSNRPS |
| SEQ ID NO: 38<br>(Kabat) | LCDR3 | QVWSSSTDHP |
| SEQ ID NO: 39<br>(Chothia) | LCDR1 | DNIGSRP |
| SEQ ID NO: 40<br>(Chothia) | LCDR2 | DDS |
| SEQ ID NO: 41<br>(Chothia) | LCDR3 | WSSSTDH |
| SEQ ID NO: 42 | VL | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>L |
| SEQ ID NO: 43 | DNA VL | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTG |
| SEQ ID NO: 44 | Light<br>Chain | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>LGQPKAAPSVTLFPPSSEELQANKATLVCLISDFYP<br>GAVTVAWKADSSPVKAGVETTTPSKQSNNKYAAS<br>SYLSLTPEQWKSHRSYSCQVTHEGSTVEKTVAPTE<br>CS |

TABLE 2-continued

| anti-VP1 Antibodies | | |
|---|---|---|
| SEQ ID NO: 45 | DNA Light Chain | CAGTCAGTCCTGACTCAGCCCCCTAGCGTCAGCG TGGCCCCTGGTAAAACCGCTAGAATCACCTGTGG CGGCGATAATATCGGCTCTAGGCCCGTGCACTGG TATCAGCAGAAGCCCGGTCAAGCCCCTATCCTGG TGGTCTACGACGACTCTAATAGACCTAGCGGAAT CCCCGAGCGGTTTAGCGGCTCTAATTCTGGTAAT ACCGCTACCCTGACTATCTCTAGGGTGGAAGCCG GCGACGAGGCCGACTACTACTGTCAAGTCTGGTC TAGCTCTACCGATCACCCCTTCGGCGGAGGCACT AAGGTTACAGTGCTGGGTCAACCTAAGGCTGCCC CCAGCGTGACCCTGTTCCCCCCCAGCAGCGAGGA GCTGCAGGCCAACAAGGCCACCCTGGTGTGCCT GATCAGCGACTTCTACCCAGGCGCCGTGACCGTG GCCTGGAAGGCCGACAGCAGCCCCGTGAAGGCC GGCGTGGAGACCACCACCCCCAGCAAGCAGAGC AACAACAAGTACGCCGCCAGCAGCTACCTGAGC CTGACCCCCGAGCAGTGGAAGAGCCACAGGTCC TACAGCTGCCAGGTGACCCACGAGGGCAGCACC GTGGAAAAGACCGTGGCCCCAACCGAGTGCAGC |
| P8D11B | | |
| SEQ ID NO: 46 (Kabat) | HCDR1 | NYWMT |
| SEQ ID NO: 47 (Kabat) | HCDR2 | NIKKDGSEKYYVDSVRG |
| SEQ ID NO: 48 (Kabat) | HCDR3 | VRSGRYFALDD |
| SEQ ID NO: 49 (Chothia) | HCDR1 | GFTFKNY |
| SEQ ID NO: 50 (Chothia) | HCDR2 | KKDGSE |
| SEQ ID NO: 51 (Chothia) | HCDR3 | VRSGRYFALDD |
| SEQ ID NO: 52 | VH | QVQLVESGGTLVQPGGSLRLSCAASGFTFKNYWM TWVRQAPGKGLEWVANIKKDGSEKYYVDSVRGR FTISRDNAKNSLFLQMNSLRPEDTAVYFCATVRSG RYFALDDWGQGTLVTVSS |
| SEQ ID NO: 53 | DNA VH | CAGGTGCAGCTGGTGGAATCAGGCGGCACACTG GTGCAGCCTGGCGGTAGCCTGAGACTGAGCTGC GCTGCTAGTGGCTTCACCTTTAAGAACTACTGGA TGACCTGGGTCAGGCAGGCCCCTGGTAAAGGCC TCGAGTGGGTGGCAAATATCAAGAAGGACGGTA GCGAGAAGTACTACGTGGACTCAGTCAGAGGCC GGTTCACTATCTCTAGGGATAACGCTAAGAATAG CCTGTTCCTGCAGATGAACTCACTGAGGCCCGAG GATACCGCCGTCTACTTCTGTGCTACCGTCAGAT CAGGCCGCTACTTCGCCCTGGACGACTGGGGTCA AGGCACACTGGTCACCGTGTCTAGC |
| SEQ ID NO: 54 | Heavy Chain | QVQLVESGGTLVQPGGSLRLSCAASGFTFKNYWM TWVRQAPGKGLEWVANIKKDGSEKYYVDSVRGR FTISRDNAKNSLFLQMNSLRPEDTAVYFCATVRSG RYFALDDWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNHK PSNTKVDKRVEPKSCDKTHTCPPCPAPELLGGPSVF LFPPKPKDTLMISRTPEVTCVVVDVSHEDPEVKFN WYVDGVEVHNAKTKPREEQYNSTYRVVSVLTVLH QDWLNGKEYKCKVSNKALPAPIEKTISKAKGQPRE PQVYTLPPSREEMTKNQVSLTCLVKGFYPSDIAVE WESNGQPENNYKTTPPVLDSDGSFFLYSKLTVDKS RWQQGNVFSCSVMHEALHNHYTQKSLSLSPGK |
| SEQ ID NO: 55 | DNA Heavy Chain | CAGGTGCAGCTGGTGGAATCAGGCGGCACACTG GTGCAGCCTGGCGGTAGCCTGAGACTGAGCTGC GCTGCTAGTGGCTTCACCTTTAAGAACTACTGGA TGACCTGGGTCAGGCAGGCCCCTGGTAAAGGCC TCGAGTGGGTGGCAAATATCAAGAAGGACGGTA GCGAGAAGTACTACGTGGACTCAGTCAGAGGCC GGTTCACTATCTCTAGGGATAACGCTAAGAATAG |

TABLE 2-continued anti-VP1 Antibodies

|  |  |  |
|---|---|---|
|  |  | CCTGTTCCTGCAGATGAACTCACTGAGGCCCGAG<br>GATACCGCCGTCTACTTCTGTGCTACCGTCAGAT<br>CAGGCCGCTACTTCGCCCTGGACGACTGGGGTCA<br>AGGCACACTGGTCACCGTGTCTAGCGCTAGCACT<br>AAGGGCCCAAGTGTGTTTCCCCTGGCCCCCAGCA<br>GCAAGTCTACTTCCGGCGGAACTGCTGCCCTGGG<br>TTGCCTGGTGAAGGACTACTTCCCCGAGCCCGTG<br>ACAGTGTCCTGGAACTCTGGGGCTCTGACTTCCG<br>GCGTGCACACCTTCCCCGCCGTGCTGCAGAGCAG<br>CGGCCTGTACAGCCTGAGCAGCGTGGTGACAGT<br>GCCCTCCAGCTCTCTGGGAACCCAGACCTATATC<br>TGCAACGTGAACCACAAGCCCAGCAACACCAAG<br>GTGGACAAGAGAGTGGAGCCCAAGAGCTGCGAC<br>AAGACCCACACCTGCCCCCCCTGCCCAGCTCCAG<br>AACTGCTGGGAGGGCCTTCCGTGTTCCTGTTCCC<br>CCCCAAGCCCAAGGACACCCTGATGATCAGCAG<br>GACCCCCGAGGTGACCTGCGTGGTGGTGGACGT<br>GTCCCACGAGGACCCAGAGGTGAAGTTCAACTG<br>GTACGTGGACGGCGTGGAGGTGCACAACGCCAA<br>GACCAAGCCCAGAGAGGAGCAGTACAACAGCAC<br>CTACAGGGTGGTGTCCGTGCTGACCGTGCTGCAC<br>CAGGACTGGCTGAACGGCAAAGAATACAAGTGC<br>AAAGTCTCCAACAAGGCCCTGCCAGCCCCAATC<br>GAAAAGACAATCAGCAAGGCCAAGGGCCAGCCA<br>CGGGAGCCCCAGGTGTACACCCTGCCCCCCAGCC<br>GGGAGGAGATGACCAAGAACCAGGTGTCCCTGA<br>CCTGTCTGGTGAAGGGCTTCTACCCCAGCGATAT<br>CGCCGTGGAGTGGGAGAGCAACGGCCAGCCCGA<br>GAACAACTACAAGACCACCCCCCAGTGCTGGA<br>CAGCGACGGCAGCTTCTTCCTGTACAGCAAGCTG<br>ACCGTGGACAAGTCCAGGTGGCAGCAGGGCAAC<br>GTGTTCAGCTGCAGCGTGATGCACGAGGCCCTGC<br>ACAACCACTACACCCAGAAGTCCCTGAGCCTGA<br>GCCCCGGCAAG |
| SEQ ID NO: 56<br>(Kabat) | LCDR1 | GGDNIGSRPVH |
| SEQ ID NO: 57<br>(Kabat) | LCDR2 | DDSNRPS |
| SEQ ID NO: 58<br>(Kabat) | LCDR3 | QVWSSSTDHP |
| SEQ ID NO: 59<br>(Chothia) | LCDR1 | DNIGSRP |
| SEQ ID NO: 60<br>(Chothia) | LCDR2 | DDS |
| SEQ ID NO: 61<br>(Chothia) | LCDR3 | WSSSTDH |
| SEQ ID NO: 62 | VL | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>L |
| SEQ ID NO: 63 | DNA VL | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTG |
| SEQ ID NO: 64 | Light<br>Chain | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>LGQPKAAPSVTLFPPSSEELQANKATLVCLISDFYP<br>GAVTVAWKADSSPVKAGVETTTPSKQSNNKYAAS<br>SYLSLTPEQWKSHRSYSCQVTHEGSTVEKTVAPTE<br>CS |

TABLE 2-continued anti-VP1 Antibodies

| SEQ ID NO: 65 | DNA Light Chain | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTGGGTCAACCTAAGGCTGCCC<br>CCAGCGTGACCCTGTTCCCCCCCAGCAGCGAGGA<br>GCTGCAGGCCAACAAGGCCACCCTGGTGTGCCT<br>GATCAGCGACTTCTACCCAGGCGCCGTGACCGTG<br>GCCTGGAAGGCCGACAGCAGCCCCGTGAAGGCC<br>GGCGTGGAGACCACCACCCCCAGCAAGCAGAGC<br>AACAACAAGTACGCCGCCAGCAGCTACCTGAGC<br>CTGACCCCCGAGCAGTGGAAGAGCCACAGGTCC<br>TACAGCTGCCAGGTGACCCACGAGGGCAGCACC<br>GTGGAAAAGACCGTGGCCCCAACCGAGTGCAGC |
|---|---|---|
| P8D11C | | |
| SEQ ID NO: 66 (Kabat) | HCDR1 | NYWMT |
| SEQ ID NO: 67 (Kabat) | HCDR2 | NIKKDGSEKYYVDSVRG |
| SEQ ID NO: 68 (Kabat) | HCDR3 | VRSGRYFALDD |
| SEQ ID NO: 69 (Chothia) | HCDR1 | GFTFQNY |
| SEQ ID NO: 70 (Chothia) | HCDR2 | KKDGSE |
| SEQ ID NO: 71 (Chothia) | HCDR3 | VRSGRYFALDD |
| SEQ ID NO: 72 | VH | QVQLVESGGTLVQPGGSLRLSCAASGFTFQNYWM<br>TWVRQAPGKGLEWVANIKKDGSEKYYVDSVRGR<br>FTISRDNAKNSLFLQMNSLRPEDTAVYFCATVRSG<br>RYFALDDWGQGTLVTVSS |
| SEQ ID NO: 73 | DNA VH | CAGGTGCAGCTGGTGGAATCAGGCGGCACACTG<br>GTGCAGCCTGGCGGTAGCCTGAGACTGAGCTGC<br>GCCGCTAGTGGATTCACCTTTCAGAACTACTGGA<br>TGACCTGGGTCAGACAGGCCCCTGGTAAAGGCC<br>TCGAGTGGGTGGCAAATATCAAGAAGGACGGTA<br>GCGAGAAGTACTACGTGGACTCAGTCAGAGGCC<br>GGTTCACTATCTCTAGGGATAACGCTAAGAATAG<br>CCTGTTCCTGCAGATGAACTCACTGAGGCCCGAG<br>GATACCGCCGTCTACTTCTGTGCTACCGTCAGAT<br>CAGGCCGCTACTTCGCCCTGGACGACTGGGGTCA<br>AGGCACACTGGTCACCGTGTCTAGC |
| SEQ ID NO: 74 | Heavy Chain | QVQLVESGGTLVQPGGSLRLSCAASGFTFQNYWM<br>TWVRQAPGKGLEWVANIKKDGSEKYYVDSVRGR<br>FTISRDNAKNSLFLQMNSLRPEDTAVYFCATVRSG<br>RYFALDDWGQGTLVTVSSASTKGPSVFPLAPSSKS<br>TSGGTAALGCLVKDYFPEPVTVSWNSGALTSGVHT<br>FPAVLQSSGLYSLSSVVTVPSSSLGTQTYICNVNHK<br>PSNTKVDKRVEPKSCDKTHTCPPCPAPELLGGPSVF<br>LFPPKPKDTLMISRTPEVTCVVVDVSHEDPEVKFN<br>WYVDGVEVHNAKTKPREEQYNSTYRVVSVLTVLH<br>QDWLNGKEYKCKVSNKALPAPIEKTISKAKGQPRE<br>PQVYTLPPSREEMTKNQVSLTCLVKGFYPSDIAVE<br>WESNGQPENNYKTTPPVLDSDGSFFLYSKLTVDKS<br>RWQQGNVFSCSVMHEALHNHYTQKSLSLSPGK |
| SEQ ID NO: 75 | DNA Heavy Chain | CAGGTGCAGCTGGTGGAATCAGGCGGCACACTG<br>GTGCAGCCTGGCGGTAGCCTGAGACTGAGCTGC<br>GCCGCTAGTGGATTCACCTTTCAGAACTACTGGA<br>TGACCTGGGTCAGACAGGCCCCTGGTAAAGGCC<br>TCGAGTGGGTGGCAAATATCAAGAAGGACGGTA<br>GCGAGAAGTACTACGTGGACTCAGTCAGAGGCC<br>GGTTCACTATCTCTAGGGATAACGCTAAGAATAG |

TABLE 2-continued anti-VP1 Antibodies

| | | |
|---|---|---|
| | | CCTGTTCCTGCAGATGAACTCACTGAGGCCCGAG<br>GATACCGCCGTCTACTTCTGTGCTACCGTCAGAT<br>CAGGCCGCTACTTCGCCCTGGACGACTGGGGTCA<br>AGGCACACTGGTCACCGTGTCTAGCGCTAGCACT<br>AAGGGCCCAAGTGTGTTTCCCCTGGCCCCCAGCA<br>GCAAGTCTACTTCCGGCGGAACTGCTGCCCTGGG<br>TTGCCTGGTGAAGGACTACTTCCCCGAGCCCGTG<br>ACAGTGTCCTGGAACTCTGGGGCTCTGACTTCCG<br>GCGTGCACACCTTCCCCGCCGTGCTGCAGAGCAG<br>CGGCCTGTACAGCCTGAGCAGCGTGGTGACAGT<br>GCCCTCCAGCTCTCTGGGAACCCAGACCTATATC<br>TGCAACGTGAACCACAAGCCCAGCAACACCAAG<br>GTGGACAAGAGAGTGGAGCCCAAGAGCTGCGAC<br>AAGACCCACACCTGCCCCCCCTGCCCAGCTCCAG<br>AACTGCTGGGAGGGCCTTCCGTGTTCCTGTTCCC<br>CCCCAAGCCCAAGGACACCCTGATGATCAGCAG<br>GACCCCCGAGGTGACCTGCGTGGTGGTGGACGT<br>GTCCCACGAGGACCCAGAGGTGAAGTTCAACTG<br>GTACGTGGACGGCGTGGAGGTGCACAACGCCAA<br>GACCAAGCCCAGAGAGGAGCAGTACAACAGCAC<br>CTACAGGGTGGTGTCCGTGCTGACCGTGCTGCAC<br>CAGGACTGGCTGAACGGCAAAGAATACAAGTGC<br>AAAGTCTCCAACAAGGCCCTGCCAGCCCCAATC<br>GAAAAGACAATCAGCAAGGCCAAGGGCCAGCCA<br>CGGGAGCCCCAGGTGTACACCCTGCCCCCCAGCC<br>GGGAGGAGATGACCAAGAACCAGGTGTCCCTGA<br>CCTGTCTGGTGAAGGGCTTCTACCCCAGCGATAT<br>CGCCGTGGAGTGGGAGAGCAACGGCCAGCCCGA<br>GAACAACTACAAGACCACCCCCCCAGTGCTGGA<br>CAGCGACGGCAGCTTCTTCCTGTACAGCAAGCTG<br>ACCGTGGACAAGTCCAGGTGGCAGCAGGGCAAC<br>GTGTTCAGCTGCAGCGTGATGCACGAGGCCCTGC<br>ACAACCACTACACCCAGAAGTCCCTGAGCCTGA<br>GCCCCGGCAAG |
| SEQ ID NO: 76<br>(Kabat) | LCDR1 | GGDNIGSRPVH |
| SEQ ID NO: 77<br>(Kabat) | LCDR2 | DDSNRPS |
| SEQ ID NO: 78<br>(Kabat) | LCDR3 | QVWSSSTDHP |
| SEQ ID NO: 79<br>(Chothia) | LCDR1 | DNIGSRP |
| SEQ ID NO: 80<br>(Chothia) | LCDR2 | DDS |
| SEQ ID NO: 81<br>(Chothia) | LCDR3 | WSSSTDH |
| SEQ ID NO: 82 | VL | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>L |
| SEQ ID NO: 83 | DNA VL | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTG |
| SEQ ID NO: 84 | Light<br>Chain | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>LGQPKAAPSVTLFPPSSEELQANKATLVCLISDFYP<br>GAVTVAWKADSSPVKAGVETTTPSKQSNNKYAAS<br>SYLSLTPEQWKSHRSYSCQVTHEGSTVEKTVAPTE<br>CS |

TABLE 2-continued anti-VP1 Antibodies

| SEQ ID NO: 85 | DNA Light Chain | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTGGGTCAACCTAAGGCTGCCC<br>CCAGCGTGACCCTGTTCCCCCCCAGCAGCGAGGA<br>GCTGCAGGCCAACAAGGCCACCCTGGTGTGCCT<br>GATCAGCGACTTCTACCCAGGCGCCGTGACCGTG<br>GCCTGGAAGGCCGACAGCAGCCCCGTGAAGGCC<br>GGCGTGGAGACCACCACCCCCAGCAAGCAGAGC<br>AACAACAAGTACGCCGCCAGCAGCTACCTGAGC<br>CTGACCCCCGAGCAGTGGAAGAGCCACAGGTCC<br>TACAGCTGCCAGGTGACCCACGAGGGCAGCACC<br>GTGGAAAAGACCGTGGCCCCAACCGAGTGCAGC |

P8D11D

| SEQ ID NO: 86 (Kabat) | HCDR1 | NYWMT |
| SEQ ID NO: 87 (Kabat) | HCDR2 | NIKKDGSEKYYVDSVRG |
| SEQ ID NO: 88 (Kabat) | HCDR3 | VRSGRYFALDD |
| SEQ ID NO: 89 (Chothia) | HCDR1 | GFTFNNY |
| SEQ ID NO: 90 (Chothia) | HCDR2 | KKDGSE |
| SEQ ID NO: 91 (Chothia) | HCDR3 | VRSGRYFALDD |
| SEQ ID NO: 92 | VH | QVQLQESGPGLVQPGGSLRLSCAASGFTFNNYWM<br>TWVRQAPGKGLEWVANIKKDGSEKYYVDSVRGR<br>FTISRDNAKNSLFLQMNSLRPEDTAVYFCATVRSG<br>RYFALDDWGQGTLVTVSS |
| SEQ ID NO: 93 | DNA VH | CAGGTGCAGCTGCAGGAATCAGGCCCAGGACTG<br>GTGCAGCCTGGCGGTAGCCTGAGACTGAGCTGC<br>GCTGCTAGTGGCTTCACCTTTAACAACTACTGGA<br>TGACCTGGGTCCGCCAGGCCCCTGGCAAAGGCCT<br>GGAGTGGGTGGCAAATATCAAGAAGGACGGTAG<br>CGAGAAGTACTACGTGGACTCAGTCAGAGGCCG<br>GTTCACTATCTCTAGGGATAACGCTAAGAATAGC<br>CTGTTCCTGCAGATGAACTCACTGAGGCCCGAGG<br>ATACCGCCGTCTACTTCTGTGCTACCGTCAGATC<br>AGGCCGCTACTTCGCCCTGGACGACTGGGGCCA<br>GGGCACCCTGGTCACCGTGTCTTCC |
| SEQ ID NO: 94 | Heavy Chain | QVQLQESGPGLVQPGGSLRLSCAASGFTFNNYWM<br>TWVRQAPGKGLEWVANIKKDGSEKYYVDSVRGR<br>FTISRDNAKNSLFLQMNSLRPEDTAVYFCATVRSG<br>RYFALDDWGQGTLVTVSSASTKGPSVFPLAPSSKS<br>TSGGTAALGCLVKDYFPEPVTVSWNSGALTSGVHT<br>FPAVLQSSGLYSLSSVVTVPSSSLGTQTYICNVNHK<br>PSNTKVDKRVEPKSCDKTHTCPPCPAPELLGGPSVF<br>LFPPKPKDTLMISRTPEVTCVVVDVSHEDPEVKFN<br>WYVDGVEVHNAKTKPREEQYNSTYRVVSVLTVLH<br>QDWLNGKEYKCKVSNKALPAPIEKTISKAKGQPRE<br>PQVYTLPPSREEMTKNQVSLTCLVKGFYPSDIAVE<br>WESNGQPENNYKTTPPVLDSDGSFFLYSKLTVDKS<br>RWQQGNVFSCSVMHEALHNHYTQKSLSLSPGK |
| SEQ ID NO: 95 | DNA Heavy Chain | CAGGTGCAGCTGCAGGAATCAGGCCCAGGACTG<br>GTGCAGCCTGGCGGTAGCCTGAGACTGAGCTGC<br>GCTGCTAGTGGCTTCACCTTTAACAACTACTGGA<br>TGACCTGGGTCCGCCAGGCCCCTGGCAAAGGCCT<br>GGAGTGGGTGGCAAATATCAAGAAGGACGGTAG<br>CGAGAAGTACTACGTGGACTCAGTCAGAGGCCG<br>GTTCACTATCTCTAGGGATAACGCTAAGAATAGC |

TABLE 2-continued anti-VP1 Antibodies

|  |  |  |
|---|---|---|
|  |  | CTGTTCCTGCAGATGAACTCACTGAGGCCCGAGG<br>ATACCGCCGTCTACTTCTGTGCTACCGTCAGATC<br>AGGCCGCTACTTCGCCCTGGACGACTGGGGCCA<br>GGGCACCCTGGTCACCGTGTCTTCCGCTAGCACT<br>AAGGGCCCAAGTGTGTTTCCCCTGGCCCCCAGCA<br>GCAAGTCTACTTCCGGCGGAACTGCTGCCCTGGG<br>TTGCCTGGTGAAGGACTACTTCCCCGAGCCCGTG<br>ACAGTGTCCTGGAACTCTGGGGCTCTGACTTCCG<br>GCGTGCACACCTTCCCCGCCGTGCTGCAGAGCAG<br>CGGCCTGTACAGCCTGAGCAGCGTGGTGACAGT<br>GCCCTCCAGCTCTCTGGGAACCCAGACCTATATC<br>TGCAACGTGAACCACAAGCCCAGCAACACCAAG<br>GTGGACAAGAGAGTGGAGCCCAAGAGCTGCGAC<br>AAGACCCACACCTGCCCCCCCTGCCCAGCTCCAG<br>AACTGCTGGGAGGGCCTTCCGTGTTCCTGTTCCC<br>CCCCAAGCCCAAGGACACCCTGATGATCAGCAG<br>GACCCCCGAGGTGACCTGCGTGGTGGTGGACGT<br>GTCCCACGAGGACCCAGAGGTGAAGTTCAACTG<br>GTACGTGGACGGCGTGGAGGTGCACAACGCCAA<br>GACCAAGCCCAGAGAGGAGCAGTACAACAGCAC<br>CTACAGGGTGGTGTCCGTGCTGACCGTGCTGCAC<br>CAGGACTGGCTGAACGGCAAAGAATACAAGTGC<br>AAAGTCTCCAACAAGGCCCTGCCAGCCCCAATC<br>GAAAAGACAATCAGCAAGGCCAAGGGCCAGCCA<br>CGGGAGCCCCAGGTGTACACCCTGCCCCCCAGCC<br>GGGAGGAGATGACCAAGAACCAGGTGTCCCTGA<br>CCTGTCTGGTGAAGGGCTTCTACCCCAGCGATAT<br>CGCCGTGGAGTGGGAGAGCAACGGCCAGCCCGA<br>GAACAACTACAAGACCACCCCCCAGTGCTGGA<br>CAGCGACGGCAGCTTCTTCCTGTACAGCAAGCTG<br>ACCGTGGACAAGTCCAGGTGGCAGCAGGGCAAC<br>GTGTTCAGCTGCAGCGTGATGCACGAGGCCCTGC<br>ACAACCACTACACCCAGAAGTCCCTGAGCCTGA<br>GCCCCGGCAAG |
| SEQ ID NO: 96<br>(Kabat) | LCDR1 | GGDNIGSRPVH |
| SEQ ID NO: 97<br>(Kabat) | LCDR2 | DDSNRPS |
| SEQ ID NO: 98<br>(Kabat) | LCDR3 | QVWSSSTDHP |
| SEQ ID NO: 99<br>(Chothia) | LCDR1 | DNIGSRP |
| SEQ ID NO: 100<br>(Chothia) | LCDR2 | DDS |
| SEQ ID NO: 101<br>(Chothia) | LCDR3 | WSSSTDH |
| SEQ ID NO: 102 | VL | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>L |
| SEQ ID NO: 103 | DNA VL | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTG |
| SEQ ID NO: 104 | Light<br>Chain | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>LGQPKAAPSVTLFPPSSEELQANKATLVCLISDFYP<br>GAVTVAWKADSSPVKAGVETTTPSKQSNNKYAAS<br>SYLSLTPEQWKSHRSYSCQVTHEGSTVEKTVAPTE<br>CS |

TABLE 2-continued anti-VP1 Antibodies

| | | |
|---|---|---|
| SEQ ID NO: 105 | DNA Light Chain | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTGGGTCAACCTAAGGCTGCCC<br>CCAGCGTGACCCTGTTCCCCCCCAGCAGCGAGGA<br>GCTGCAGGCCAACAAGGCCACCCTGGTGTGCCT<br>GATCAGCGACTTCTACCCAGGCGCCGTGACCGTG<br>GCCTGGAAGGCCGACAGCAGCCCCGTGAAGGCC<br>GGCGTGGAGACCACCACCCCCAGCAAGCAGAGC<br>AACAACAAGTACGCCGCCAGCAGCTACCTGAGC<br>CTGACCCCCGAGCAGTGGAAGAGCCACAGGTCC<br>TACAGCTGCCAGGTGACCCACGAGGGCAGCACC<br>GTGGAAAAGACCGTGGCCCCAACCGAGTGCAGC |
| P8D11E | | |
| SEQ ID NO: 106 (Kabat) | HCDR1 | NYWMT |
| SEQ ID NO: 107 (Kabat) | HCDR2 | NIKKDGSEKYYVDSVRG |
| SEQ ID NO: 108 (Kabat) | HCDR3 | VRSGRYFALDD |
| SEQ ID NO: 109 (Chothia) | HCDR1 | GFTFNNY |
| SEQ ID NO: 110 (Chothia) | HCDR2 | KKDGSE |
| SEQ ID NO: 111 (Chothia) | HCDR3 | VRSGRYFALDD |
| SEQ ID NO: 112 | VH | QVQLVESGGGLVQPGGSLRLSCAASGFTFNNYWM<br>TWVRQAPGKGLEWVANIKKDGSEKYYVDSVRGR<br>FTISRDNAKNSLFLQMNSLRPEDTAVYFCATVRSG<br>RYFALDDWGQGTLVTVSS |
| SEQ ID NO: 113 | DNA VH | CAGGTGCAGCTGGTGGAATCAGGCGGCGGACTG<br>GTGCAGCCTGGCGGTAGCCTGAGACTGAGCTGC<br>GCTGCTAGTGGCTTCACCTTTAACAACTACTGGA<br>TGACCTGGGTTAGGCAGGCCCCTGGTAAAGGCCT<br>CGAGTGGGTGGCAAATATCAAGAAGGACGGTAG<br>CGAGAAGTACTACGTGGACTCAGTCAGAGGCCG<br>GTTCACTATCTCTAGGGATAACGCTAAGAATAGC<br>CTGTTCCTGCAGATGAACTCACTGAGGCCCGAGG<br>ATACCGCCGTCTACTTCTGTGCTACCGTCAGATC<br>AGGCCGCTACTTCGCCCTGGACGACTGGGGTCAA<br>GGCACACTGGTCACCGTGTCTAGC |
| SEQ ID NO: 114 | Heavy Chain | QVQLVESGGGLVQPGGSLRLSCAASGFTFNNYWM<br>TWVRQAPGKGLEWVANIKKDGSEKYYVDSVRGR<br>FTISRDNAKNSLFLQMNSLRPEDTAVYFCATVRSG<br>RYFALDDWGQGTLVTVSSASTKGPSVFPLAPSSKS<br>TSGGTAALGCLVKDYFPEPVTVSWNSGALTSGVHT<br>FPAVLQSSGLYSLSSVVTVPSSSLGTQTYICNVNHK<br>PSNTKVDKRVEPKSCDKTHTCPPCPAPELLGGPSVF<br>LFPPKPKDTLMISRTPEVTCVVVDVSHEDPEVKFN<br>WYVDGVEVHNAKTKPREEQYNSTYRVVSVLTVLH<br>QDWLNGKEYKCKVSNKALPAPIEKTISKAKGQPRE<br>PQVYTLPPSREEMTKNQVSLTCLVKGFYPSDIAVE<br>WESNGQPENNYKTTPPVLDSDGSFFLYSKLTVDKS<br>RWQQGNVFSCSVMHEALHNHYTQKSLSLSPGK |
| SEQ ID NO: 115 | DNA Heavy Chain | CAGGTGCAGCTGGTGGAATCAGGCGGCGGACTG<br>GTGCAGCCTGGCGGTAGCCTGAGACTGAGCTGC<br>GCTGCTAGTGGCTTCACCTTTAACAACTACTGGA<br>TGACCTGGGTTAGGCAGGCCCCTGGTAAAGGCCT<br>CGAGTGGGTGGCAAATATCAAGAAGGACGGTAG<br>CGAGAAGTACTACGTGGACTCAGTCAGAGGCCG<br>GTTCACTATCTCTAGGGATAACGCTAAGAATAGC |

TABLE 2-continued anti-VP1 Antibodies

|  |  |  |
|---|---|---|
|  |  | CTGTTCCTGCAGATGAACTCACTGAGGCCCGAGG<br>ATACCGCCGTCTACTTCTGTGCTACCGTCAGATC<br>AGGCCGCTACTTCGCCCTGGACGACTGGGGTCAA<br>GGCACACTGGTCACCGTGTCTAGCGCTAGCACTA<br>AGGGCCCAAGTGTGTTTCCCCTGGCCCCCAGCAG<br>CAAGTCTACTTCCGGCGGAACTGCTGCCCTGGGT<br>TGCCTGGTGAAGGACTACTTCCCCGAGCCCGTGA<br>CAGTGTCCTGGAACTCTGGGGCTCTGACTTCCGG<br>CGTGCACACCTTCCCCGCCGTGCTGCAGAGCAGC<br>GGCCTGTACAGCCTGAGCAGCGTGGTGACAGTG<br>CCCTCCAGCTCTCTGGGAACCCAGACCTATATCT<br>GCAACGTGAACCACAAGCCCAGCAACACCAAGG<br>TGGACAAGAGAGTGGAGCCCAAGAGCTGCGACA<br>AGACCCACACCTGCCCCCCCTGCCCAGCTCCAGA<br>ACTGCTGGGAGGGCCTTCCGTGTTCCTGTTCCCC<br>CCCAAGCCCAAGGACACCCTGATGATCAGCAGG<br>ACCCCCGAGGTGACCTGCGTGGTGGTGGACGTGT<br>CCCACGAGGACCCAGAGGTGAAGTTCAACTGGT<br>ACGTGGACGGCGTGGAGGTGCACAACGCCAAGA<br>CCAAGCCCAGAGAGGAGCAGTACAACAGCACCT<br>ACAGGGTGGTGTCCGTGCTGACCGTGCTGCACCA<br>GGACTGGCTGAACGGCAAAGAATACAAGTGCAA<br>AGTCTCCAACAAGGCCCTGCCAGCCCCAATCGA<br>AAAGACAATCAGCAAGGCCAAGGGCCAGCCACG<br>GGAGCCCCAGGTGTACACCCTGCCCCCCAGCCG<br>GGAGGAGATGACCAAGAACCAGGTGTCCCTGAC<br>CTGTCTGGTGAAGGGCTTCTACCCCAGCGATATC<br>GCCGTGGAGTGGGAGAGCAACGGCCAGCCCGAG<br>AACAACTACAAGACCACCCCCCCAGTGCTGGAC<br>AGCGACGGCAGCTTCTTCCTGTACAGCAAGCTGA<br>CCGTGGACAAGTCCAGGTGGCAGCAGGGCAACG<br>TGTTCAGCTGCAGCGTGATGCACGAGGCCCTGCA<br>CAACCACTACACCCAGAAGTCCCTGAGCCTGAG<br>CCCCGGCAAG |
| SEQ ID NO: 116<br>(Kabat) | LCDR1 | GGDNIGSRPVH |
| SEQ ID NO: 117<br>(Kabat) | LCDR2 | DDSNRPS |
| SEQ ID NO: 118<br>(Kabat) | LCDR3 | QVWSSSTDHP |
| SEQ ID NO: 119<br>(Chothia) | LCDR1 | DNIGSRP |
| SEQ ID NO: 120<br>(Chothia) | LCDR2 | DDS |
| SEQ ID NO: 121<br>(Chothia) | LCDR3 | WSSSTDH |
| SEQ ID NO: 122 | VL | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>L |
| SEQ ID NO: 123 | DNA VL | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTG |
| SEQ ID NO: 124 | Light<br>Chain | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>LGQPKAAPSVTLFPPSSEELQANKATLVCLISDFYP<br>GAVTVAWKADSSPVKAGVETTTPSKQSNNKYAAS<br>SYLSLTPEQWKSHRSYSCQVTHEGSTVEKTVAPTE<br>CS |

TABLE 2-continued anti-VP1 Antibodies

| | | |
|---|---|---|
| SEQ ID NO: 125 | DNA Light Chain | CAGTCAGTCCTGACTCAGCCCCCTAGCGTCAGCG<br>TGGCCCCTGGTAAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTGGGTCAACCTAAGGCTGCCC<br>CCAGCGTGACCCTGTTCCCCCCCAGCAGCGAGGA<br>GCTGCAGGCCAACAAGGCCACCCTGGTGTGCCT<br>GATCAGCGACTTCTACCCAGGCGCCGTGACCGTG<br>GCCTGGAAGGCCGACAGCAGCCCCGTGAAGGCC<br>GGCGTGGAGACCACCACCCCCAGCAAGCAGAGC<br>AACAACAAGTACGCCGCCAGCAGCTACCTGAGC<br>CTGACCCCCGAGCAGTGGAAGAGCCACAGGTCC<br>TACAGCTGCCAGGTGACCCACGAGGGCAGCACC<br>GTGGAAAAGACCGTGGCCCCAACCGAGTGCAGC |

P165E2

| | | |
|---|---|---|
| SEQ ID NO: 126 (Kabat) | HCDR1 | RDYWT |
| SEQ ID NO: 127 (Kabat) | HCDR2 | NIYYSGSTNYNPSLKS |
| SEQ ID NO: 128 (Kabat) | HCDR3 | VPGCSSTSCIDGWFDP |
| SEQ ID NO: 129 (Chothia) | HCDR1 | GGSISRD |
| SEQ ID NO: 130 (Chothia) | HCDR2 | YYSGS |
| SEQ ID NO: 131 (Chothia) | HCDR3 | VPGCSSTSCIDGWFDP |
| SEQ ID NO: 132 | VH | QVQLQESGPGLVKPSETLSLTCTVSGGSISRDYWT<br>WVRQPPGEGLEWIGNIYYSGSTNYNPSLKSRVTISV<br>AASKKQFSLKLTSVTAADTAVYYCARVPGCSSTSC<br>IDGWFDPWGQGILVTVSS |
| SEQ ID NO: 133 | DNA VH | CAGGTGCAGCTGCAAGAATCAGGCCCTGGCCTG<br>GTCAAGCCTAGCGAGACACTGAGCCTGACCTGC<br>ACCGTCAGCGGCGGCTCTATCTCTAGGGACTACT<br>GGACCTGGGTCCGACAGCCTCCTGGCGAGGGCC<br>TCGAGTGGATCGGTAATATCTACTATAGCGGCTC<br>TACTAACTATAACCCTAGCCTGAAGTCTAGGGTC<br>ACAATTAGCGTGGCCGCCTCTAAGAAGCAGTTTA<br>GCCTGAAGCTGACTAGCGTGACCGCCGCTGACA<br>CCGCCGTCTACTACTGCGCTAGAGTGCCCGGCTG<br>CTCTAGCACTAGCTGTATCGACGGCTGGTTTGAC<br>CCTTGGGGTCAAGGGATCCTGGTCACCGTGTCTA<br>GC |
| SEQ ID NO: 134 | Heavy Chain | QVQLQESGPGLVKPSETLSLTCTVSGGSISRDYWT<br>WVRQPPGEGLEWIGNIYYSGSTNYNPSLKSRVTISV<br>AASKKQFSLKLTSVTAADTAVYYCARVPGCSSTSC<br>IDGWFDPWGQGILVTVSSASTKGPSVFPLAPSSKST<br>SGGTAALGCLVKDYFPEPVTVSWNSGALTSGVHTF<br>PAVLQSSGLYSLSSVVTVPSSSLGTQTYICNVNHKP<br>SNTKVDKRVEPKSCDKTHTCPPCPAPELLGGPSVFL<br>FPPKPKDTLMISRTPEVTCVVVDVSHEDPEVKFNW<br>YVDGVEVHNAKTKPREEQYNSTYRVVSVLTVLHQ<br>DWLNGKEYKCKVSNKALPAPIEKTISKAKGQPREP<br>QVYTLPPSREEMTKNQVSLTCLVKGFYPSDIAVEW<br>ESNGQPENNYKTTPPVLDSDGSFFLYSKLTVDKSR<br>WQQGNVFSCSVMHEALHNHYTQKSLSLSPGK |
| SEQ ID NO: 135 | DNA Heavy Chain | CAGGTGCAGCTGCAAGAATCAGGCCCTGGCCTG<br>GTCAAGCCTAGCGAGACACTGAGCCTGACCTGC<br>ACCGTCAGCGGCGGCTCTATCTCTAGGGACTACT<br>GGACCTGGGTCCGACAGCCTCCTGGCGAGGGCC<br>TCGAGTGGATCGGTAATATCTACTATAGCGGCTC<br>TACTAACTATAACCCTAGCCTGAAGTCTAGGGT |

TABLE 2-continued

| | | anti-VP1 Antibodies |
|---|---|---|
| | | ACAATTAGCGTGGCCGCCTCTAAGAAGCAGTTTA<br>GCCTGAAGCTGACTAGCGTGACCGCCGCTGACA<br>CCGCCGTCTACTACTGCGCTAGAGTGCCCGGCTG<br>CTCTAGCACTAGCTGTATCGACGGCTGGTTTGAC<br>CCTTGGGGTCAAGGGATCCTGGTCACCGTGTCTA<br>GCGCTAGCACTAAGGGCCCAAGTGTGTTTCCCCT<br>GGCCCCCAGCAGCAAGTCTACTTCCGGCGGAACT<br>GCTGCCCTGGGTTGCCTGGTAAGGACTACTTCC<br>CCGAGCCCGTGACAGTGTCCTGGAACTCTGGGGC<br>TCTGACTTCCGGCGTGCACACCTTCCCCGCCGTG<br>CTGCAGAGCAGCGGCCTGTACAGCCTGAGCAGC<br>GTGGTGACAGTGCCCTCCAGCTCTCTGGGAACCC<br>AGACCTATATCTGCAACGTGAACCACAAGCCCA<br>GCAACACCAAGGTGGACAAGAGAGTGGAGCCCA<br>AGAGCTGCGACAAGACCCACACCTGCCCCCCCT<br>GCCCAGCTCCAGAACTGCTGGGAGGGCCTTCCGT<br>GTTCCTGTTCCCCCCCAAGCCCAAGGACACCCTG<br>ATGATCAGCAGGACCCCCGAGGTGACCTGCGTG<br>GTGGTGGACGTGTCCCACGAGGACCCAGAGGTG<br>AAGTTCAACTGGTACGTGGACGGCGTGGAGGTG<br>CACAACGCCAAGACCAAGCCCAGAGAGGAGCAG<br>TACAACAGCACCTACAGGGTGGTGTCCGTGCTGA<br>CCGTGCTGCACCAGGACTGGCTGAACGGCAAAG<br>AATACAAGTGCAAAGTCTCCAACAAGGCCCTGC<br>CAGCCCCAATCGAAAAGACAATCAGCAAGGCCA<br>AGGGCCAGCCACGGGAGCCCCAGGTGTACACCC<br>TGCCCCCCAGCCGGGAGGAGATGACCAAGAACC<br>AGGTGTCCCTGACCTGTCTGGTGAAGGGCTTCTA<br>CCCCAGCGATATCGCCGTGGAGTGGGAGAGCAA<br>CGGCCAGCCCGAGAACAACTACAAGACCACCCC<br>CCCAGTGCTGGACAGCGACGGCAGCTTCTTCCTG<br>TACAGCAAGCTGACCGTGGACAAGTCCAGGTGG<br>CAGCAGGGCAACGTGTTCAGCTGCAGCGTGATG<br>CACGAGGCCCTGCACAACCACTACACCCAGAAG<br>TCCCTGAGCCTGAGCCCCGGCAAG |
| SEQ ID NO: 136<br>(Kabat) | LCDR1 | SGSSSNIGNTYVS |
| SEQ ID NO: 137<br>(Kabat) | LCDR2 | DNNKRPS |
| SEQ ID NO: 138<br>(Kabat) | LCDR3 | GTWDSSLSAWV |
| SEQ ID NO: 139<br>(Chothia) | LCDR1 | SSSNIGNTY |
| SEQ ID NO: 140<br>(Chothia) | LCDR2 | DNN |
| SEQ ID NO: 141<br>(Chothia) | LCDR3 | WDSSLSAW |
| SEQ ID NO: 142 | VL | QSVLTQPPSLSAAPGQRVTISCSGSSSNIGNTYVSW<br>YQQLPGTAPKLLIYDNNKRPSGIPGRFSGSKSGTSA<br>TLGITGLQTGDEAAYYCGTWDSSLSAWVFGGGTR<br>LTVL |
| SEQ ID NO: 143 | DNA VL | CAGTCAGTCCTGACTCAGCCCCCTAGCCTGAGCG<br>CCGCTCCCGGTCAAAGAGTGACTATTAGCTGTAG<br>CGGCTCTAGCTCTAATATCGGTAATACCTACGTC<br>AGCTGGTATCAGCAGCTGCCCGGCACCGCCCCTA<br>AGCTGCTGATCTACGATAACAACAAGCGGCCTA<br>GCGGAATCCCTGGTCGCTTTAGCGGATCTAAATC<br>AGGCACTAGCGCTACCCTGGGAATCACCGGCCT<br>GCAGACCGGCGACGAAGCCGCCTACTACTGCGG<br>CACCTGGGACTCTAGTCTGAGCGCCTGGGTGTTC<br>GGCGGAGGCACTAGACTGACCGTGCTG |
| SEQ ID NO: 144 | Light<br>Chain | QSVLTQPPSLSAAPGQRVTISCSGSSSNIGNTYVSW<br>YQQLPGTAPKLLIYDNNKRPSGIPGRFSGSKSGTSA<br>TLGITGLQTGDEAAYYCGTWDSSLSAWVFGGGTR<br>LTVLGQPKAAPSVTLFPPSSEELQANKATLVCLISD<br>FYPGAVTVAWKADSSPVKAGVETTTPSKQSNNKY<br>AASSYLSLTPEQWKSHRSYSCQVTHEGSTVEKTVA<br>PTECS |

TABLE 2-continued anti-VP1 Antibodies

| SEQ ID NO: 145 | DNA Light Chain | CAGTCAGTCCTGACTCAGCCCCCTAGCCTGAGCG<br>CCGCTCCCGGTCAAAGAGTGACTATTAGCTGTAG<br>CGGCTCTAGCTCTAATATCGGTAATACCTACGTC<br>AGCTGGTATCAGCAGCTGCCCGGCACCGCCCCTA<br>AGCTGCTGATCTACGATAACAACAAGCGGCCTA<br>GCGGAATCCCTGGTCGCTTTAGCGGATCTAAATC<br>AGGCACTAGCGCTACCCTGGGAATCACCGGCCT<br>GCAGACCGGCGACGAAGCCGCCTACTACTGCGG<br>CACCTGGGACTCTAGTCTGAGCGCCTGGGTGTTC<br>GGCGGAGGCACTAGACTGACCGTGCTGGGTCAA<br>CCTAAGGCTGCCCCCAGCGTGACCCTGTTCCCCC<br>CCAGCAGCGAGGAGCTGCAGGCCAACAAGGCCA<br>CCCTGGTGTGCCTGATCAGCGACTTCTACCCAGG<br>CGCCGTGACCGTGGCCTGGAAGGCCGACAGCAG<br>CCCCGTGAAGGCCGGCGTGGAGACCACCACCCC<br>CAGCAAGCAGAGCAACAACAAGTACGCCGCCAG<br>CAGCTACCTGAGCCTGACCCCCGAGCAGTGGAA<br>GAGCCACAGGTCCTACAGCTGCCAGGTGACCCA<br>CGAGGGCAGCACCGTGGAAAAGACCGTGGCCCC<br>AACCGAGTGCAGC |

NEG447

| SEQ ID NO: 146 (Kabat) | HCDR1 | RDYWS |
| SEQ ID NO: 147 (Kabat) | HCDR2 | NIYYSGSTNYNPSLKS |
| SEQ ID NO: 148 (Kabat) | HCDR3 | VPGCSSTSCIDGWFDP |
| SEQ ID NO: 149 (Chothia) | HCDR1 | GGSISRD |
| SEQ ID NO: 150 (Chothia) | HCDR2 | YYSGS |
| SEQ ID NO: 151 (Chothia) | HCDR3 | VPGCSSTSCIDGWFDP |
| SEQ ID NO: 152 | VH | QVQLQESGPGLVKPSETLSLTCTVSGGSISRDYWS<br>WVRQPPGAGLEWIGNIYYSGSTNYNPSLKSRVTISV<br>ATNKKQFSLKLTSVTAADTAVYYCARVPGCSSTSC<br>IDGWFDPWGQGILVTVSS |
| SEQ ID NO: 153 | DNA VH | CAGGTGCAGCTGCAAGAATCAGGCCCTGGCCTG<br>GTCAAGCCTAGCGAGACACTGAGCCTGACCTGC<br>ACCGTCAGCGGCGGCTCTATCTCTAGGGACTACT<br>GGTCCTGGGTCCGACAACCTCCTGGCGCTGGCCT<br>CGAGTGGATCGGTAATATCTACTATAGCGGCTCT<br>ACTAACTATAACCCTAGCCTGAAGTCTAGGGTCA<br>CAATTAGTGTGGCTACTAACAAGAAGCAGTTTAG<br>CCTGAAGCTGACTAGCGTGACCGCCGCTGACACC<br>GCCGTCTACTACTGCGCTAGAGTGCCCGGCTGCT<br>CTAGCACTAGCTGTATCGACGGTTGGTTTGACCC<br>TTGGGGTCAAGGGATCCTGGTCACCGTGTCTAGC |
| SEQ ID NO: 154 | Heavy Chain | QVQLQESGPGLVKPSETLSLTCTVSGGSISRDYWS<br>WVRQPPGAGLEWIGNIYYSGSTNYNPSLKSRVTISV<br>ATNKKQFSLKLTSVTAADTAVYYCARVPGCSSTSC<br>IDGWFDPWGQGILVTVSSASTKGPSVFPLAPSSKST<br>SGGTAALGCLVKDYFPEPVTVSWNSGALTSGVHTF<br>PAVLQSSGLYSLSSVVTVPSSSLGTQTYICNVNHKP<br>SNTKVDKRVEPKSCDKTHTCPPCPAPELLGGPSVFL<br>FPPKPKDTLMISRTPEVTCVVVDVSHEDPEVKFNW<br>YVDGVEVHNAKTKPREEQYNSTYRVVSVLTVLHQ<br>DWLNGKEYKCKVSNKALPAPIEKTISKAKGQPREP<br>QVYTLPPSREEMTKNQVSLTCLVKGFYPSDIAVEW<br>ESNGQPENNYKTTPPVLDSDGSFFLYSKLTVDKSR<br>WQQGNVFSCSVMHEALHNHYTQKSLSLSPGK |
| SEQ ID NO: 155 | DNA Heavy Chain | CAGGTGCAGCTGCAAGAATCAGGCCCTGGCCTG<br>GTCAAGCCTAGCGAGACACTGAGCCTGACCTGC<br>ACCGTCAGCGGCGGCTCTATCTCTAGGGACTACT<br>GGTCCTGGGTCCGACAACCTCCTGGCGCTGGCCT<br>CGAGTGGATCGGTAATATCTACTATAGCGGCTCT |

TABLE 2-continued anti-VP1 Antibodies

| | | |
|---|---|---|
| | | ACTAACTATAACCCTAGCCTGAAGTCTAGGGTCA<br>CAATTAGTGTGGCTACTAACAAGAAGCAGTTTAG<br>CCTGAAGCTGACTAGCGTGACCGCCGCTGACACC<br>GCCGTCTACTACTGCGCTAGAGTGCCCGGCTGCT<br>CTAGCACTAGCTGTATCGACGGTTGGTTTGACCC<br>TTGGGGTCAAGGGATCCTGGTCACCGTGTCTAGC<br>GCTAGCACTAAGGGCCCAAGTGTGTTTCCCCTGG<br>CCCCCAGCAGCAAGTCTACTTCCGGCGGAACTGC<br>TGCCCTGGGTTGCCTGGTGAAGGACTACTTCCCC<br>GAGCCCGTGACAGTGTCCTGGAACTCTGGGGCTC<br>TGACTTCCGGCGTGCACACCTTCCCCGCCGTGCT<br>GCAGAGCAGCGGCCTGTACAGCCTGAGCAGCGT<br>GGTGACAGTGCCCTCCAGCTCTCTGGGAACCCAG<br>ACCTATATCTGCAACGTGAACCACAAGCCCAGC<br>AACACCAAGGTGGACAAGAGAGTGGAGCCCAAG<br>AGCTGCGACAAGACCCACACCTGCCCCCCCTGCC<br>CAGCTCCAGAACTGCTGGGAGGGCCTTCCGTGTT<br>CCTGTTCCCCCCCAAGCCCAAGGACACCCTGATG<br>ATCAGCAGGACCCCCGAGGTGACCTGCGTGGTG<br>GTGGACGTGTCCCACGAGGACCCAGAGGTGAAG<br>TTCAACTGGTACGTGGACGGCGTGGAGGTGCAC<br>AACGCCAAGACCAAGCCCAGAGAGGAGCAGTAC<br>AACAGCACCTACAGGGTGGTGTCCGTGCTGACC<br>GTGCTGCACCAGGACTGGCTGAACGGCAAAGAA<br>TACAAGTGCAAAGTCTCCAACAAGGCCCTGCCA<br>GCCCCAATCGAAAAGACAATCAGCAAGGCCAAG<br>GGCCAGCCACGGGAGCCCCAGGTGTACACCCTG<br>CCCCCCAGCCGGGAGGAGATGACCAAGAACCAG<br>GTGTCCCTGACCTGTCTGGTGAAGGGCTTCTACC<br>CCAGCGATATCGCCGTGGAGTGGGAGAGCAACG<br>GCCAGCCCGAGAACAACTACAAGACCACCCCC<br>CAGTGCTGGACAGCGACGGCAGCTTCTTCCTGTA<br>CAGCAAGCTGACCGTGGACAAGTCCAGGTGGCA<br>GCAGGGCAACGTGTTCAGCTGCAGCGTGATGCA<br>CGAGGCCCTGCACAACCACTACACCCAGAAGTC<br>CCTGAGCCTGAGCCCCGGCAAG |
| SEQ ID NO: 156<br>(Kabat) | LCDR1 | SGSSSNIGNTYVS |
| SEQ ID NO: 157<br>(Kabat) | LCDR2 | DNNKRPS |
| SEQ ID NO: 158<br>(Kabat) | LCDR3 | GTWDSSLSAWV |
| SEQ ID NO: 159<br>(Chothia) | LCDR1 | SSSNIGNTY |
| SEQ ID NO: 160<br>(Chothia) | LCDR2 | DNN |
| SEQ ID NO: 161<br>(Chothia) | LCDR3 | WDSSLSAW |
| SEQ ID NO: 162 | VL | QSVLTQPPSLSAAPGQKVTISCSGSSSNIGNTYVSW<br>YQQLPGTAPKLLIYDNNKRPSGIPDRFSGSKSGTSA<br>TLGITGLQTGDEAVYYCGTWDSSLSAWVFGGGTR<br>LTVL |
| SEQ ID NO: 163 | DNA VL | CAGTCAGTCCTGACTCAGCCCCCTAGCCTGAGCG<br>CCGCTCCCGGTCAAAAAGTGACTATTAGCTGTAG<br>CGGCTCTAGCTCTAATATCGGTAATACCTACGTC<br>AGCTGGTATCAGCAGCTGCCCGGCACCGCCCCTA<br>AGCTGCTGATCTACGATAACAACAAGCGGCCTA<br>GCGGAATCCCCGATAGGTTTAGCGGATCTAAGTC<br>AGGCACTAGCGCTACCCTGGGAATCACCGGCCT<br>GCAGACCGGCGACGAGGCCGTCTACTACTGCGG<br>CACCTGGGACTCTAGTCTGAGCGCCTGGGTGTTC<br>GGCGGAGGCACTAGAGACTGACCGTGCTG |
| SEQ ID NO: 164 | Light<br>Chain | QSVLTQPPSLSAAPGQKVTISCSGSSSNIGNTYVSW<br>YQQLPGTAPKLLIYDNNKRPSGIPDRFSGSKSGTSA<br>TLGITGLQTGDEAVYYCGTWDSSLSAWVFGGGTR<br>LTVLGQPKAAPSVTLFPPSSEELQANKATLVCLISD<br>FYPGAVTVAWKADSSPVKAGVETTTPSKQSNNKY<br>AASSYLSLTPEQWKSHRSYSCQVTHEGSTVEKTVA<br>PTECS |

TABLE 2-continued anti-VP1 Antibodies

| SEQ ID NO: 165 | DNA Light Chain | CAGTCAGTCCTGACTCAGCCCCCTAGCCTGAGCG<br>CCGCTCCCGGTCAAAAAGTGACTATTAGCTGTAG<br>CGGCTCTAGCTCTAATATCGGTAATACCTACGTC<br>AGCTGGTATCAGCAGCTGCCCGGCACCGCCCCTA<br>AGCTGCTGATCTACGATAACAACAAGCGGCCTA<br>GCGGAATCCCCGATAGGTTTAGCGGATCTAAGTC<br>AGGCACTAGCGCTACCCTGGGAATCACCGGCCT<br>GCAGACCGGCGACGAGGCCGTCTACTACTGCGG<br>CACCTGGGACTCTAGTCTGAGCGCCTGGGTGTTC<br>GGCGGAGGCACTAGACTGACCGTGCTGGGTCAA<br>CCTAAGGCTGCCCCCAGCGTGACCCTGTTCCCCC<br>CCAGCAGCGAGGAGCTGCAGGCCAACAAGGCCA<br>CCCTGGTGTGCCTGATCAGCGACTTCTACCCAGG<br>CGCCGTGACCGTGGCCTGGAAGGCCGACAGCAG<br>CCCCGTGAAGGCCGGCGTGGAGACCACCACCCC<br>CAGCAAGCAGAGCAACAACAAGTACGCCGCCAG<br>CAGCTACCTGAGCCTGACCCCCGAGCAGTGGAA<br>GAGCCACAGGTCCTACAGCTGCCAGGTGACCCA<br>CGAGGGCAGCACCGTGGAAAAGACCGTGGCCCC<br>AACCGAGTGCAGC |

NEG447A

| SEQ ID NO: 166 (Kabat) | HCDR1 | RDYWS |
| SEQ ID NO: 167 (Kabat) | HCDR2 | NIYYSGSTNYNPSLKS |
| SEQ ID NO: 168 (Kabat) | HCDR3 | VPGCSSTSCIDGWFDP |
| SEQ ID NO: 169 (Chothia) | HCDR1 | GGSISRD |
| SEQ ID NO: 170 (Chothia) | HCDR2 | YYSGS |
| SEQ ID NO: 171 (Chothia) | HCDR3 | VPGCSSTSCIDGWFDP |
| SEQ ID NO: 172 | VH | QVQLQESGPGLVKPSETLSLTCTVSGGSISRDYWS<br>WVRQPPGAGLEWIGNIYYSGSTNYNPSLKSRVTISV<br>ATNKKQFSLKLTSVTAADTAVYYCARVPGCSSTSC<br>IDGWFDPWGQGILVTVSS |
| SEQ ID NO: 173 | DNA VH | CAGGTGCAATTGCAGGAAAGCGGCCCTGGCCTC<br>GTGAAGCCCAGCGAGACACTGAGCCTGACCTGT<br>ACCGTGTCCGGCGGCAGCATCAGCAGAGACTAC<br>TGGAGCTGGGTTCGCCAGCCTCCAGGCGCAGGA<br>CTGGAATGGATCGGCAACATCTACTACAGCGGC<br>AGCACCAACTACAACCCCAGCCTGAAGTCCAGA<br>GTGACCATCAGCGTGGCCACAAACAAGAAACAG<br>TTCTCCCTGAAGCTGACCAGCGTGACAGCCGCCG<br>ATACCGCCGTGTACTACTGCGCCAGAGTGCCTGG<br>CTGTAGCAGCACCAGCTGCATCGACGGATGGTTC<br>GACCCTTGGGGCCAGGGCATTCTCGTGACCGTCA<br>GCTCA |
| SEQ ID NO: 174 | Heavy Chain | QVQLQESGPGLVKPSETLSLTCTVSGGSISRDYWS<br>WVRQPPGAGLEWIGNIYYSGSTNYNPSLKSRVTISV<br>ATNKKQFSLKLTSVTAADTAVYYCARVPGCSSTSC<br>IDGWFDPWGQGILVTVSSASTKGPSVFPLAPSSKST<br>SGGTAALGCLVKDYFPEPVTVSWNSGALTSGVHTF<br>PAVLQSSGLYSLSSVVTVPSSSLGTQTYICNVNHKP<br>SNTKVDKRVEPKSCDKTHTCPPCPAPELLGGPSVFL<br>FPPKPKDTLMISRTPEVTCVVVDVSHEDPEVKFNW<br>YVDGVEVHNAKTKPREEQYNSTYRVVSVLTVLHQ<br>DWLNGKEYKCKVSNKALPAPIEKTISKAKGQPREP<br>QVYTLPPSREEMTKNQVSLTCLVKGFYPSDIAVEW<br>ESNGQPENNYKTTPPVLDSDGSFFLYSKLTVDKSR<br>WQQGNVFSCSVMHEALHNHYTQKSLSLSPGK |
| SEQ ID NO: 175 | DNA Heavy Chain | CAGGTGCAATTGCAGGAAAGCGGCCCTGGCCTC<br>GTGAAGCCCAGCGAGACACTGAGCCTGACCTGT<br>ACCGTGTCCGGCGGCAGCATCAGCAGAGACTAC<br>TGGAGCTGGGTTCGCCAGCCTCCAGGCGCAGGA |

TABLE 2-continued anti-VP1 Antibodies

|  |  |  |
|---|---|---|
|  |  | CTGGAATGGATCGGCAACATCTACTACAGCGGC<br>AGCACCAACTACAACCCCAGCCTGAAGTCCAGA<br>GTGACCATCAGCGTGGCCACAAACAAGAAACAG<br>TTCTCCCTGAAGCTGACCAGCGTGACAGCCGCC<br>ATACCGCCGTGTACTACTGCGCCAGAGTGCCTGG<br>CTGTAGCAGCACCAGCTGCATCGACGGATGGTTC<br>GACCCTTGGGGCCAGGGCATTCTCGTGACCGTCA<br>GCTCAGCTAGCACCAAGGGCCCCAGCGTGTTCCC<br>CCTGGCCCCCAGCAGCAAGAGCACCAGCGGCGG<br>CACAGCCGCCCTGGGCTGCCTGGTGAAGGACTA<br>CTTCCCCGAGCCCGTGACCGTGTCCTGGAACAGC<br>GGAGCCCTGACCTCCGGCGTGCACACCTTCCCCG<br>CCGTGCTGCAGAGCAGCGGCCTGTACAGCCTGTC<br>CAGCGTGGTGACAGTGCCCAGCAGCAGCCTGGG<br>CACCCAGACCTACATCTGCAACGTGAACCACAA<br>GCCCAGCAACACCAAGGTGGACAAGAGAGTGGA<br>GCCCAAGAGCTGCGACAAGACCCACACCTGCCC<br>CCCCTGCCCAGCCCCAGAGCTGCTGGGCGGACCC<br>TCCGTGTTCCTGTTCCCCCCCAAGCCCAAGGACA<br>CCCTGATGATCAGCAGGACCCCCGAGGTGACCT<br>GCGTGGTGGTGGACGTGAGCCACGAGGACCCAG<br>AGGTGAAGTTCAACTGGTACGTGGACGGCGTGG<br>AGGTGCACAACGCCAAGACCAAGCCCAGAGAGG<br>AGCAGTACAACAGCACCTACAGGGTGGTGTCCG<br>TGCTGACCGTGCTGCACCAGGACTGGCTGAACG<br>GCAAGGAATACAAGTGCAAGGTCTCCAACAAGG<br>CCCTGCCAGCCCCCATCGAAAAGACCATCAGCA<br>AGGCCAAGGGCCAGCCACGGGAGCCCCAGGTGT<br>ACACCCTGCCCCCCTCCCGGGAGGAGATGACCA<br>AGAACCAGGTGTCCCTGACCTGTCTGGTGAAGG<br>GCTTCTACCCCAGCGACATCGCCGTGGAGTGGGA<br>GAGCAACGGCCAGCCCGAGAACAACTACAAGAC<br>CACCCCCCCAGTGCTGGACAGCGACGGCAGCTTC<br>TTCCTGTACAGCAAGCTGACCGTGGACAAGTCCA<br>GGTGGCAGCAGGGCAACGTGTTCAGCTGCAGCG<br>TGATGCACGAGGCCCTGCACAACCACTACACCCC<br>AGAAGAGCCTGAGCCTGTCCCCCGGCAAG |
| SEQ ID NO: 176<br>(Kabat) | LCDR1 | SGSSSNIGNTYVS |
| SEQ ID NO: 177<br>(Kabat) | LCDR2 | DNNKRPS |
| SEQ ID NO: 178<br>(Kabat) | LCDR3 | GTWDSSLSAWV |
| SEQ ID NO: 179<br>(Chothia) | LCDR1 | SSSNIGNTY |
| SEQ ID NO: 180<br>(Chothia) | LCDR2 | DNN |
| SEQ ID NO: 181<br>(Chothia) | LCDR3 | WDSSLSAW |
| SEQ ID NO: 182 | VL | QSVLTQPPSVSAAPGQKVTISCSGSSSNIGNTYVSW<br>YQQLPGTAPKLLIYDNNKRPSGIPDRFSGSKSGTSA<br>TLGITGLQTGDEADYYCGTWDSSLSAWVFGGGTR<br>LTVL |
| SEQ ID NO: 183 | DNA VL | CAAAGCGTGCTGACCCAGCCTCCTAGCGTGTCTG<br>CTGCCCCTGGCCAGAAGGTGACCATCAGCTGTAG<br>CGGCAGCAGCTCCAACATCGGCAACACCTACGT<br>GTCCTGGTATCAGCAGCTGCCCGGCACCGCCCCC<br>AAACTGCTGATCTACGACAACAACAAGCGGCCC<br>AGCGGCATCCCCGATAGATTTTCTGGCAGCAAGA<br>GCGGCACCAGCGCCACCCTGGGAATCACAGGAC<br>TGCAGACAGGGGACGAGGCCGATTACTACTGTG<br>GCACCTGGGATTCTAGCCTGAGCGCCTGGGTGTT<br>CGGCGGAGGCACAAGACTGACAGTGCTG |

TABLE 2-continued

| anti-VP1 Antibodies | | |
|---|---|---|
| SEQ ID NO: 184 | Light Chain | QSVLTQPPSVSAAPGQKVTISCSGSSSNIGNTYVSW YQQLPGTAPKLLIYDNNKRPSGIPDRFSGSKSGTSA TLGITGLQTGDEADYYCGTWDSSLSAWVFGGGTR LTVLGQPKAAPSVTLFPPSSEELQANKATLVCLISD FYPGAVTVAWKADSSPVKAGVETTTPSKQSNNKY AASSYLSLTPEQWKSHRSYSCQVTHEGSTVEKTVA PTECS |
| SEQ ID NO: 185 | DNA Light Chain | CAAAGCGTGCTGACCCAGCCTCCTAGCGTGTCTG CTGCCCCTGGCCAGAAGGTGACCATCAGCTGTAG CGGCAGCAGCTCCAACATCGGCAACACCTACGT GTCCTGGTATCAGCAGCTGCCCGGCACCGCCCCC AAACTGCTGATCTACGACAACAACAAGCGGCCC AGCGGCATCCCCGATAGATTTTCTGGCAGCAAGA GCGGCACCAGCGCCACCCTGGGAATCACAGGAC TGCAGACAGGGGACGAGGCCGATTACTACTGTG GCACCTGGGATTCTAGCCTGAGCGCCTGGGTGTT CGGCGGAGGCACAAGACTGACAGTGCTGGGTCA GCCTAAGGCCGCTCCCTCCGTGACCCTGTTCCCC CCCAGCTCCGAGGAACTGCAGGCCAACAAGGCC ACCCTGGTGTGCCTGATCAGCGACTTCTACCCTG GCGCCGTGACCGTGGCCTGGAAGGCCGACAGCA GCCCCGTGAAGGCCGGCGTGGAGACAACCACCC CCAGCAAGCAGAGCAACAACAAGTACGCCGCCA GCAGCTACCTGAGCCTGACCCCCGAGCAGTGGA AGAGCCACAGAAGCTACAGCTGCCAGGTCACCC ACGAGGGCAGCACCGTGGAGAAAACCGTGGCCC CCACCGAGTGCAGC |
| P7G11 | | |
| SEQ ID NO: 186 (Kabat) | HCDR1 | SGGYSWS |
| SEQ ID NO: 187 (Kabat) | HCDR2 | YIYYRGTTYYNPSLKS |
| SEQ ID NO: 188 (Kabat) | HCDR3 | ALTHLVGVGWFDP |
| SEQ ID NO: 189 (Chothia) | HCDR1 | GGSISSGGY |
| SEQ ID NO: 190 (Chothia) | HCDR2 | YYRGT |
| SEQ ID NO: 191 (Chothia) | HCDR3 | ALTHLVGVGWFDP |
| SEQ ID NO: 192 | VH | QVQLQESGPGLAKPSQTLSLTCSVSGGSISSGGYSW SWIRQPPGKGLEYIGYIYYRGTTYYNPSLKSRITMS VDTSNNQISLKLTSVTAADTAVYYCARALTHLVGV GWFDPWGQGTMVTVSS |
| SEQ ID NO: 193 | DNA VH | CAGGTGCAGCTGCAAGAATCAGGCCCTGGCCTG GCTAAGCCTAGTCAGACCCTGAGCCTGACCTGTA GCGTCAGCGGAGGCTCTATCTCTAGCGGCGGCTA TAGCTGGTCCTGGATTAGACAGCCCCCAGGTAAA GGCCTCGAGTATATCGGCTATATCTACTATAGGG GCACTACCTACTATAACCCTAGCCTGAAGTCTAG GATCACTATGAGCGTGGACACCTCTAACAATCAG ATTAGCCTGAAGCTGACTAGCGTGACCGCCGCTG ACACCGCCGTCTACTACTGCGCTAGAGCCCTGAC TCACCTCGTTGGAGTGGGCTGGTTTGACCCTTGG GGTCAAGGCACTATGGTCACCGTGTCTAGC |

TABLE 2-continued anti-VP1 Antibodies

| | | |
|---|---|---|
| SEQ ID NO: 194 | Heavy Chain | QVQLQESGPGLAKPSQTLSLTCSVSGGSISSGGYSW SWIRQPPGKGLEYIGYIYYRGTTYYNPSLKSRITMS VDTSNNQISLKLTSVTAADTAVYYCARALTHLVGV GWFDPWGQGTMVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| SEQ ID NO: 195 | DNA Heavy Chain | CAGGTGCAGCTGCAAGAATCAGGCCCTGGCCTG GCTAAGCCTAGTCAGACCCTGAGCCTGACCTGTA GCGTCAGCGGAGGCTCTATCTCTAGCGGCGGCTA TAGCTGGTCCTGGATTAGACAGCCCCCAGGTAAA GGCCTCGAGTATATCGGCTATATCTACTATAGGG GCACTACCTACTATAACCCTAGCCTGAAGTCTAG GATCACTATGAGCGTGGACACCTCTAACAATCAG ATTAGCCTGAAGCTGACTAGCGTGACCGCCGCTG ACACCGCCGTCTACTACTGCGCTAGAGCCCTGAC TCACCTCGTTGGAGTGGGCTGGTTTGACCCTTGG GGTCAAGGCACTATGGTCACCGTGTCTAGCGCTA GCACTAAGGGCCCAAGTGTGTTTCCCCTGGCCCC CAGCAGCAAGTCTACTTCCGGCGGAACTGCTGCC CTGGGTTGCCTGGTGAAGGACTACTTCCCCGAGC CCGTGACAGTGTCCTGGAACTCTGGGGCTCTGAC TTCCGGCGTGCACACCTTCCCCGCCGTGCTGCAG AGCAGCGGCCTGTACAGCCTGAGCAGCGTGGTG ACAGTGCCCTCCAGCTCTCTGGGAACCCAGACCT ATATCTGCAACGTGAACCACAAGCCCAGCAACA CCAAGGTGGACAAGAGAGTGGAGCCCAAGAGCT GCGACAAGACCCACACCTGCCCCCCCTGCCCAGC TCCAGAACTGCTGGGAGGGCCTTCCGTGTTCCTG TTCCCCCCCAAGCCCAAGGACACCCTGATGATCA GCAGGACCCCCGAGGTGACCTGCGTGGTGGTGG ACGTGTCCCACGAGGACCCAGAGGTGAAGTTCA ACTGGTACGTGGACGGCGTGGAGGTGCACAACG CCAAGACCAAGCCCAGAGAGGAGCAGTACAACA GCACCTACAGGGTGGTGTCCGTGCTGACCGTGCT GCACCAGGACTGGCTGAACGGCAAGGAATACAA GTGCAAAGTCTCCAACAAGGCCCTGCCAGCCCC AATCGAAAAGACAATCAGCAAGGCCAAGGGCCA GCCACGGGAGCCCCAGGTGTACACCCTGCCCCCC AGCCGGGAGGAGATGACCAAGAACCAGGTGTCC CTGACCTGTCTGGTGAAGGGCTTCTACCCCAGCG ATATCGCCGTGGAGTGGGAGAGCAACGGCCAGC CCGAGAACAACTACAAGACCACCCCCCCAGTGC TGGACAGCGACGGCAGCTTCTTCCTGTACAGCAA GCTGACCGTGGACAAGTCCAGGTGGCAGCAGGG CAACGTGTTCAGCTGCAGCGTGATGCACGAGGC CCTGCACAACCACTACACCCAGAAGTCCCTGAGC CTGAGCCCCGGCAAG |
| SEQ ID NO: 196 (Kabat) | LCDR1 | SGGSSNLGSNYVS |
| SEQ ID NO: 197 (Kabat) | LCDR2 | DNNKRPS |
| SEQ ID NO: 198 (Kabat) | LCDR3 | GTWDGSLSAWV |
| SEQ ID NO: 199 (Chothia) | LCDR1 | GSSNLGSNY |
| SEQ ID NO: 200 (Chothia) | LCDR2 | DNN |
| SEQ ID NO: 201 (Chothia) | LCDR3 | WDGSLSAW |
| SEQ ID NO: 202 | VL | QSVLTQPPSVSAAPGQKVTISCSGGSSNLGSNYVS WYQQLPGTAPKLLIYDNNKRPSGIPDRFSGSKSGTS ATLGITGLQTGDEADYYCGTWDGSLSAWVFGGGT KVTVL |

TABLE 2-continued anti-VP1 Antibodies

| SEQ ID NO: 203 | DNA VL | CAGTCAGTCCTGACTCAGCCCCCTAGCGTCAGCG<br>CCGCTCCCGGTCAAAAAGTGACTATTAGCTGTAG<br>CGGCGGCTCCTCTAACCTGGGCTCTAACTACGTC<br>AGCTGGTATCAGCAGCTGCCCGGCACCGCCCCTA<br>AGCTGCTGATCTACGATAACAACAAGCGGCCTA<br>GCGGAATCCCCGATAGGTTTAGCGGCTCTAAGTC<br>AGGCACTAGCGCTACCCTGGGAATCACCGGCCT<br>GCAGACCGGCGACGAGGCCGACTACTACTGTGG<br>CACCTGGGACGGTAGCCTGAGCGCCTGGGTGTTC<br>GGCGGAGGCACTAAAGTCACAGTGCTG |
| --- | --- | --- |
| SEQ ID NO: 204 | Light Chain | QSVLTQPPSVSAAPGQKVTISCSGGSSNLGSNYVS<br>WYQQLPGTAPKLLIYDNNKRPSGIPDRFSGSKSGTS<br>ATLGITGLQTGDEADYYCGTWDGSLSAWVFGGGT<br>KVTVLGQPKAAPSVTLFPPSSEELQANKATLVCLIS<br>DFYPGAVTVAWKADSSPVKAGVETTTPSKQSNNK<br>YAASSYLSLTPEQWKSHRSYSCQVTHEGSTVEKTV<br>APTECS |
| SEQ ID NO: 205 | DNA Light Chain | CAGTCAGTCCTGACTCAGCCCCCTAGCGTCAGCG<br>CCGCTCCCGGTCAAAAAGTGACTATTAGCTGTAG<br>CGGCGGCTCCTCTAACCTGGGCTCTAACTACGTC<br>AGCTGGTATCAGCAGCTGCCCGGCACCGCCCCTA<br>AGCTGCTGATCTACGATAACAACAAGCGGCCTA<br>GCGGAATCCCCGATAGGTTTAGCGGCTCTAAGTC<br>AGGCACTAGCGCTACCCTGGGAATCACCGGCCT<br>GCAGACCGGCGACGAGGCCGACTACTACTGTGG<br>CACCTGGGACGGTAGCCTGAGCGCCTGGGTGTTC<br>GGCGGAGGCACTAAAGTCACAGTGCTGGGTCAA<br>CCTAAGGCTGCCCCCAGCGTGACCCTGTTCCCCC<br>CAGCAGCGAGGAGCTGCAGGCCAACAAGGCCA<br>CCCTGGTGTGCCTGATCAGCGACTTCTACCCAGG<br>CGCCGTGACCGTGGCCTGGAAGGCCGACAGCAG<br>CCCCGTGAAGGCCGGCGTGGAGACCACCACCCC<br>CAGCAAGCAGAGCAACAACAAGTACGCCGCCAG<br>CAGCTACCTGAGCCTGACCCCCGAGCAGTGGAA<br>GAGCCACAGGTCCTACAGCTGCCAGGTGACCCA<br>CGAGGGCAGCACCGTGGAAAAGACCGTGGCCCC<br>AACCGAGTGCAGC |
| P7G11A | | |
| SEQ ID NO: 206 (Kabat) | HCDR1 | SGGYSWS |
| SEQ ID NO: 207 (Kabat) | HCDR2 | YIYYRGTTYYNPSLKS |
| SEQ ID NO: 208 (Kabat) | HCDR3 | ALTHLVGVGWFDP |
| SEQ ID NO: 209 (Chothia) | HCDR1 | GGSISSGGY |
| SEQ ID NO: 210 (Chothia) | HCDR2 | YYRGT |
| SEQ ID NO: 211 (Chothia) | HCDR3 | ALTHLVGVGWFDP |
| SEQ ID NO: 212 | VH | QVQLQESGPGLVKPSQTLSLTCTVSGGSISSGGYSW<br>SWIRQPPGKGLEYIGYIYYRGTTYYNPSLKSRVTIS<br>VDTSNNQISLKLSSVTAADTAVYYCARALTHLVGV<br>GWFDPWGQGTMVTVSS |
| SEQ ID NO: 213 | DNA VH | CAGGTGCAGCTGCAAGAATCAGGCCCTGGCCTG<br>GTCAAGCCTAGTCAGACCCTGAGCCTGACCTGCA<br>CCGTCAGCGGAGGCTCTATCTCTAGCGGCGGCTA<br>TAGCTGGTCCTGGATTAGACAGCCCCCAGGTAAA<br>GGCCTCGAGTATATCGGCTATATCTACTATAGGG<br>GCACTACCTACTATAACCCTAGCCTGAAGTCTAG<br>GGTCACAATTAGCGTGGACACCTCTAACAATCAG<br>ATTAGCCTGAAGCTGTCTAGCGTGACCGCCGCTG<br>ACACCGCCGTCTACTACTGCGCTAGAGCCCTGAC<br>TCACCTCGTCGGAGTGGGCTGGTTTGACCCTTGG<br>GGTCAAGGCACTATGGTCACCGTGTCTAGC |

TABLE 2-continued anti-VP1 Antibodies

| SEQ ID NO: 214 | Heavy Chain | QVQLQESGPGLVKPSQTLSLTCTVSGGSISSGGYSWSWIRQPPGKGLEYIGYIYYRGTTYYNPSLKSRVTISVDTSNNQISLKLSSVTAADTAVYYCARALTHLVGVGWFDPWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
|---|---|---|
| SEQ ID NO: 215 | DNA Heavy Chain | CAGGTGCAGCTGCAAGAATCAGGCCCTGGCCTGGTCAAGCCTAGTCAGACCCTGAGCCTGACCTGCACCGTCAGCGGAGGCTCTATCTCTAGCGGCGGCTATAGCTGGTCCTGGATTAGACAGCCCCCAGGTAAAGGCCTCGAGTATATCGGCTATATCTACTATAGGGGCACTACCTACTATAACCCTAGCCTGAAGTCTAGGGTCACAATTAGCGTGGACACCTCTAACAATCAGATTAGCCTGAAGCTGTCTAGCGTGACCGCCGCTGACACCGCCGTCTACTACTGCGCTAGAGCCCTGACTCACCTCGTCGGAGTGGGCTGGTTTGACCCTTGGGGTCAAGGCACTATGGTCACCGTGTCTAGCGCTAGCACTAAGGGCCCAAGTGTGTTTCCCCTGGCCCCCAGCAGCAAGTCTACTTCCGGCGGAACTGCTGCCCTGGGTTGCCTGGTAAGGACTACTTCCCCGAGCCCGTGACAGTGTCCTGGAACTCTGGGGCTCTGACTTCCGGCGTGCACACCTTCCCGCCGTGCTGCAGAGCAGCGGCCTGTACAGCCTGAGCAGCGTGGTGACAGTGCCCTCCAGCTCTCTGGGAACCCAGACCTATATCTGCAACGTGAACCACAAGCCCAGCAACACCAAGGTGGACAAGAGAGTGGAGCCCAAGAGCTGCGACAAGACCCACACCTGCCCCCCCTGCCCAGCTCCAGAACTGCTGGGAGGGCCTTCCGTGTTCCTGTTCCCCCCCAAGCCCAAGGACACCCTGATGATCAGCAGGACCCCCGAGGTGACCTGCGTGGTGGTGGACGTGTCCCACGAGGACCCAGAGGTGAAGTTCAACTGGTACGTGGACGGCGTGGAGGTGCACAACGCCAAGACCAAGCCCAGAGAGGAGCAGTACAACAGCACCTACAGGGTGGTGTCCGTGCTGACCGTGCTGCACCAGGACTGGCTGAACGGCAAGGAATACAAGTGCAAAGTCTCCAACAAGGCCCTGCCAGCCCCAATCGAAAAGACAATCAGCAAGGCCAAGGGCCAGCCACGGGAGCCCCAGGTGTACACCCTGCCCCCCAGCCGGGAGGAGATGACCAAGAACCAGGTGTCCCTGACCTGTCTGGTGAAGGGCTTCTACCCCAGCGATATCGCCGTGGAGTGGGAGAGCAACGGCCAGCCCGAGAACAACTACAAGACCACCCCCCCAGTGCTGGACAGCGACGGCAGCTTCTTCCTGTACAGCAAGCTGACCGTGGACAAGTCCAGGTGGCAGCAGGGCAACGTGTTCAGCTGCAGCGTGATGCACGAGGCCCTGCACAACCACTACACCCAGAAGTCCCTGAGCCTGAGCCCCGGCAAG |
| SEQ ID NO: 216 (Kabat) | LCDR1 | SGGSSNLGSNYVS |
| SEQ ID NO: 217 (Kabat) | LCDR2 | DNNKRPS |
| SEQ ID NO: 218 (Kabat) | LCDR3 | GTWDGSLSAWV |
| SEQ ID NO: 219 (Chothia) | LCDR1 | GSSNLGSNY |
| SEQ ID NO: 220 (Chothia) | LCDR2 | DNN |
| SEQ ID NO: 221 (Chothia) | LCDR3 | WDGSLSAW |
| SEQ ID NO: 222 | VL | QSVLTQPPSVSAAPGQKVTISCSGGSSNLGSNYVSWYQQLPGTAPKLLIYDNNKRPSGIPDRFSGSKSGTSATLGITGLQTGDEADYYCGTWDGSLSAWVFGGGTKVTVL |

TABLE 2-continued anti-VP1 Antibodies

| SEQ ID NO: 223 | DNA VL | CAGTCAGTCCTGACTCAGCCCCCTAGCGTCAGCG<br>CCGCTCCCGGTCAAAAAGTGACTATTAGCTGTAG<br>CGGCGGCTCCTCTAACCTGGGCTCTAACTACGTC<br>AGCTGGTATCAGCAGCTGCCCGGCACCGCCCCTA<br>AGCTGCTGATCTACGATAACAACAAGCGGCCTA<br>GCGGAATCCCCGATAGGTTTAGCGGCTCTAAGTC<br>AGGCACTAGCGCTACCCTGGGAATCACCGGCCT<br>GCAGACCGGCGACGAGGCCGACTACTACTGTGG<br>CACCTGGGACGGTAGCCTGAGCGCCTGGGTGTTC<br>GGCGGAGGCACTAAAGTCACAGTGCTG |
| --- | --- | --- |
| SEQ ID NO: 224 | Light<br>Chain | QSVLTQPPSVSAAPGQKVTISCSGGSSNLGSNYVS<br>WYQQLPGTAPKLLIYDNNKRPSGIPDRFSGSKSGTS<br>ATLGITGLQTGDEADYYCGTWDGSLSAWVFGGGT<br>KVTVLGQPKAAPSVTLFPPSSEELQANKATLVCLIS<br>DFYPGAVTVAWKADSSPVKAGVETTTPSKQSNNK<br>YAASSYLSLTPEQWKSHRSYSCQVTHEGSTVEKTV<br>APTECS |
| SEQ ID NO: 225 | DNA<br>Light<br>Chain | CAGTCAGTCCTGACTCAGCCCCCTAGCGTCAGCG<br>CCGCTCCCGGTCAAAAAGTGACTATTAGCTGTAG<br>CGGCGGCTCCTCTAACCTGGGCTCTAACTACGTC<br>AGCTGGTATCAGCAGCTGCCCGGCACCGCCCCTA<br>AGCTGCTGATCTACGATAACAACAAGCGGCCTA<br>GCGGAATCCCCGATAGGTTTAGCGGCTCTAAGTC<br>AGGCACTAGCGCTACCCTGGGAATCACCGGCCT<br>GCAGACCGGCGACGAGGCCGACTACTACTGTGG<br>CACCTGGGACGGTAGCCTGAGCGCCTGGGTGTTC<br>GGCGGAGGCACTAAAGTCACAGTGCTGGGTCAA<br>CCTAAGGCTGCCCCCAGCGTGACCCTGTTCCCCC<br>CAGCAGCGAGGAGCTGCAGGCCAACAAGGCCA<br>CCCTGGTGTGCCTGATCAGCGACTTCTACCCAGG<br>CGCCGTGACCGTGGCCTGGAAGGCCGACAGCAG<br>CCCCGTGAAGGCCGGCGTGGAGACCACCACCCC<br>CAGCAAGCAGAGCAACAACAAGTACGCCGCCAG<br>CAGCTACCTGAGCCTGACCCCCGAGCAGTGGAA<br>GAGCCACAGGTCCTACAGCTGCCAGGTGACCCA<br>CGAGGGCAGCACCGTGGAAAAGACCGTGGCCCC<br>AACCGAGTGCAGC |
| EBB-C1975-B5- | | |
| SEQ ID NO: 226<br>(Kabat) | HCDR1 | AYYWT |
| SEQ ID NO: 227<br>(Kabat) | HCDR2 | YISHSGSTNYNPSLKS |
| SEQ ID NO: 228<br>(Kabat) | HCDR3 | LGDTASLSRFYYYIDV |
| SEQ ID NO: 229<br>(Chothia) | HCDR1 | GGSTSAY |
| SEQ ID NO: 230<br>(Chothia) | HCDR2 | SHSGS |
| SEQ ID NO: 231<br>(Chothia) | HCDR3 | LGDTASLSRFYYYIDV |
| SEQ ID NO: 232 | VH | QVQLVQSGPGLVKPSETLSLTCTVSGGSTSAYYWT<br>WIRQPPGKGLEWIGYISHSGSTNYNPSLKSRVTISA<br>DTSKNQLSLKVNSVTAADTAVYYCARLGDTASLS<br>RFYYYIDVWGKGTTVTVSS |
| SEQ ID NO: 233 | DNA VH | CAGGTGCAGCTGGTGCAGTCTGGCCCAGGACTG<br>GTGAAGCCTTCGGAGACCCTGTCCCTCACCTGCA<br>CTGTCTCTGGTGGCTCCACCAGTGCTTACTACTG<br>GACCTGGATTCGGCAGCCCCAGGGAAGGGACT<br>GGAGTGGATTGGGTATATCTCTCACAGTGGGAGC<br>ACCAACTACAACCCCTCCCTCAAGAGTCGAGTCA<br>CCATATCAGCAGACACGTCCAAGAACCAGCTCTC<br>CCTGAAGGTGAACTCTGTGACCGCCGCAGACAC<br>GGCCGTGTATTACTGTGCGAGACTTGGGGATACA<br>GCTTCACTTAGCCGCTTCTACTACTACATTGACG<br>TCTGGGGCAAAGGGACCACGGTCACCGTCTCCTC<br>A |

TABLE 2-continued

| anti-VP1 Antibodies | | |
|---|---|---|
| SEQ ID NO: 234 | Heavy Chain | QVQLVQSGPGLVKPSETLSLTCTVSGGSTSAYYWT WIRQPPGKGLEWIGYISHSGSTNYNPSLKSRVTISA DTSKNQLSLKVNSVTAADTAVYYCARLGDTASLS RFYYYIDVWGKGTTVTVSSASTKGPSVFPLAPSSKS TSGGTAALGCLVKDYFPEPVTVSWNSGALTSGVHT FPAVLQSSGLYSLSSVVTVPSSSLGTQTYICNVNHK PSNTKVDKRVEPKSCDKTHTCPPCPAPELLGGPSVF LFPPKPKDTLMISRTPEVTCVVVDVSHEDPEVKFN WYVDGVEVHNAKTKPREEQYNSTYRVVSVLTVLH QDWLNGKEYKCKVSNKALPAPIEKTISKAKGQPRE PQVYTLPPSREEMTKNQVSLTCLVKGFYPSDIAVE WESNGQPENNYKTTPPVLDSDGSFFLYSKLTVDKS RWQQGNVFSCSVMHEALHNHYTQKSLSLSPGK |
| SEQ ID NO: 235 | DNA Heavy Chain | CAGGTGCAGCTGGTGCAGTCTGGCCCAGGACTG GTGAAGCCTTCGGAGACCCTGTCCCTCACCTGCA CTGTCTCTGGTGGCTCCACCAGTGCTTACTACTG GACCTGGATTCGGCAGCCCCCAGGGAAGGGACT GGAGTGGATTGGGTATATCTCTCACAGTGGGAGC ACCAACTACAACCCCTCCCTCAAGAGTCGAGTCA CCATATCAGCAGACACGTCCAAGAACCAGCTCTC CCTGAAGGTGAACTCTGTGACCGCCGCAGACAC GGCCGTGTATTACTGTGCGAGACTTGGGGATACA GCTTCACTTAGCCGCTTCTACTACTACATTGACG TCTGGGGCAAAGGGACCACGGTCACCGTCTCCTC AGCTAGCACCAAGGGCCCATCGGTCTTCCCCCTG GCACCCTCCTCCAAGAGCACCTCTGGGGGCACA GCGGCCCTGGGCTGCCTGGTCAAGGACTACTTCC CCGAACCGGTGACGGTGTCGTGGAACTCAGGCG CCCTGACCAGCGGCGTGCACACCTTCCCGGCTGT CCTACAGTCCTCAGGACTCTACTCCCTCAGCAGC GTGGTGACCGTGCCCTCCAGCAGCTTGGGCACCC AGACCTACATCTGCAACGTGAATCACAAGCCCA GCAACACCAAGGTGGACAAGAGAGTTGAGCCCA AATCTTGTGACAAAACTCACACATGCCCACCGTG CCCAGCACCTGAACTCCTGGGGGGACCGTCAGTC TTCCTCTTCCCCCCAAAACCCAAGGACACCCTCA TGATCTCCCGGACCCCTGAGGTCACATGCGTGGT GGTGGACGTGAGCCACGAAGACCCTGAGGTCAA GTTCAACTGGTACGTGGACGGCGTGGAGGTGCA TAATGCCAAGACAAAGCCGCGGGAGGAGCAGTA CAACAGCACGTACCGTGTGGTCAGCGTCCTCACC GTCCTGCACCAGGACTGGCTGAATGGCAAGGAG TACAAGTGCAAGGTCTCCAACAAAGCCCTCCCA GCCCCCATCGAGAAAACCATCTCCAAAGCCAAA GGGCAGCCCCGAGAACCACAGGTGTACACCCTG CCCCCATCCCGGGAGGAGATGACCAAGAACCAG GTCAGCCTGACCTGCCTGGTCAAAGGCTTCTATC CCAGCGACATCGCCGTGGAGTGGGAGAGCAATG GGCAGCCGGAGAACAACTACAAGACCACGCCTC CCGTGCTGGACTCCGACGGCTCCTTCTTCCTCTA CAGCAAGCTCACCGTGGACAAGAGCAGGTGGCA GCAGGGGAACGTCTTCTCATGCTCCGTGATGCAT GAGGCTCTGCACAACCACTACACGCAGAAGAGC CTCTCCCTGTCTCCGGGTAAA |
| SEQ ID NO: 236 (Kabat) | LCDR1 | RASQSVSSNYLA |
| SEQ ID NO: 237 (Kabat) | LCDR2 | GASSRAT |
| SEQ ID NO: 238 (Kabat) | LCDR3 | QQYGSSPPYT |
| SEQ ID NO: 239 (Chothia) | LCDR1 | SQSVSSNY |
| SEQ ID NO: 240 (Chothia) | LCDR2 | GAS |
| SEQ ID NO: 241 (Chothia) | LCDR3 | YGSSPPY |

TABLE 2-continued

| anti-VP1 Antibodies | | |
|---|---|---|
| SEQ ID NO: 242 | VL | EIVMTQSPDTLSLSPGERATLSCRASQSVSSNYLAW<br>YQQKPGEAPRLLIYGASSRATGIPDRFSGSGSGTDF<br>TLTISRLEPEDFAVYYCQQYGSSPPYTFGQGTRLEI<br>K |
| SEQ ID NO: 243 | DNA VL | GAAATTGTAATGACGCAGTCTCCAGACACCCTGT<br>CTTTGTCTCCAGGGGAAAGAGCCACCCTCTCCTG<br>CAGGGCCAGTCAGAGTGTTAGCAGCAACTACTT<br>AGCCTGGTACCAGCAGAAACCTGGCGAGGCTCC<br>CAGGCTCCTCATCTATGGTGCATCCAGCAGGGCC<br>ACTGGCATCCCAGACAGGTTCAGTGGCAGTGGG<br>TCTGGGACAGACTTCACTCTCACCATCAGCAGAC<br>TGGAGCCTGAAGATTTTGCAGTGTATTACTGTCA<br>GCAGTATGGTAGCTCACCTCCGTACACTTTTGGC<br>CAGGGGACACGACTGGAGATTAAAC |
| SEQ ID NO: 244 | Light<br>Chain | EIVMTQSPDTLSLSPGERATLSCRASQSVSSNYLAW<br>YQQKPGEAPRLLIYGASSRATGIPDRFSGSGSGTDF<br>TLTISRLEPEDFAVYYCQQYGSSPPYTFGQGTRLEI<br>KRTVAAPSVFIFPPSDEQLKSGTASVVCLLNNFYPR<br>EAKVQWKVDNALQSGNSQESVTEQDSKDSTYSLS<br>STLTLSKADYEKHKVYACEVTHQGLSSPVTKSFNR<br>GEC |
| SEQ ID NO: 245 | DNA<br>Light<br>Chain | GAAATTGTAATGACGCAGTCTCCAGACACCCTGT<br>CTTTGTCTCCAGGGGAAAGAGCCACCCTCTCCTG<br>CAGGGCCAGTCAGAGTGTTAGCAGCAACTACTT<br>AGCCTGGTACCAGCAGAAACCTGGCGAGGCTCC<br>CAGGCTCCTCATCTATGGTGCATCCAGCAGGGCC<br>ACTGGCATCCCAGACAGGTTCAGTGGCAGTGGG<br>TCTGGGACAGACTTCACTCTCACCATCAGCAGAC<br>TGGAGCCTGAAGATTTTGCAGTGTATTACTGTCA<br>GCAGTATGGTAGCTCACCTCCGTACACTTTTGGC<br>CAGGGGACACGACTGGAGATTAAACGTACGGTG<br>GCTGCACCATCTGTCTTCATCTTCCCGCCATCTGA<br>TGAGCAGTTGAAATCTGGAACTGCCTCTGTTGTG<br>TGCCTGCTGAATAACTTCTATCCCCGCGAGGCCA<br>AAGTACAGTGGAAGGTGGATAACGCCCTCCAAT<br>CGGGTAACTCCCAGGAGAGTGTCACAGAGCAGG<br>ACAGCAAGGACAGCACCTACAGCCTCAGCAGCA<br>CCCTGACGCTGAGCAAAGCAGACTACGAGAAAC<br>ACAAAGTCTACGCCTGCGAAGTCACCCATCAGG<br>GCCTGAGCTCGCCCGTCACAAAGAGCTTCAACCG<br>CGGAGAGTGT |
| EBB-C1975-A3 | | |
| SEQ ID NO: 246<br>(Kabat) | HCDR1 | RNYMS |
| SEQ ID NO: 247<br>(Kabat) | HCDR2 | GIYSGGSTYYADSVKG |
| SEQ ID NO: 248<br>(Kabat) | HCDR3 | EDEFWSGYSAGVD |
| SEQ ID NO: 249<br>(Chothia) | HCDR1 | GFTVRRN |
| SEQ ID NO: 250<br>(Chothia) | HCDR2 | YSGGS |
| SEQ ID NO: 251<br>(Chothia) | HCDR3 | EDEFWSGYSAGVD |
| SEQ ID NO: 252 | VH | EVQLVETGGGLVQPGGSLRLSCAASGFTVRRNYM<br>SWVRQAPGKGLEWVSGIYSGGSTYYADSVKGRFTI<br>SRDYSKNTLSLQMNTLRVEDTAVYFCAREDEFWS<br>GYSAGVDWGQGTLVTVSS |

TABLE 2-continued anti-VP1 Antibodies

| SEQ ID NO: 253 | DNA VH | GAGGTGCAGCTGGTGGAGACTGGAGGAGGCTTG<br>GTCCAGCCGGGGGGGTCCCTGAGACTCTCATGTG<br>CAGCCTCTGGATTCACCGTCAGACGCAATTACAT<br>GAGTTGGGTCCGCCAGGCTCCGGGGAAGGGACT<br>GGAGTGGGTCTCAGGGATCTACAGTGGTGGTAG<br>CACATACTACGCAGACTCCGTGAAGGGCCGATTC<br>ACCATCTCCAGAGACTATTCCAAGAACACACTGT<br>CTCTTCAAATGAACACCCTGAGAGTCGAGGACA<br>CGGCCGTGTATTTCTGTGCGAGAGAAGACGAATT<br>TTGGAGCGGGTATTCCGCTGGGGTCGACTGGGGC<br>CAGGGAACCCTGGTCACCGTCTCCTCAG |
| --- | --- | --- |
| SEQ ID NO: 254 | Heavy<br>Chain | EVQLVETGGGLVQPGGSLRLSCAASGFTVRRNYM<br>SWVRQAPGKGLEWVSGIYSGGSTYYADSVKGRFTI<br>SRDYSKNTLSLQMNTLRVEDTAVYFCAREDEFWS<br>GYSAGVDWGQGTLVTVSSASTKGPSVFPLAPSSKS<br>TSGGTAALGCLVKDYFPEPVTVSWNSGALTSGVHT<br>FPAVLQSSGLYSLSSVVTVPSSSLGTQTYICNVNHK<br>PSNTKVDKRVEPKSCDKTHTCPPCPAPELLGGPSVF<br>LFPPKPKDTLMISRTPEVTCVVVDVSHEDPEVKFN<br>WYVDGVEVHNAKTKPREEQYNSTYRVVSVLTVLH<br>QDWLNGKEYKCKVSNKALPAPIEKTISKAKGQPRE<br>PQVYTLPPSREEMTKNQVSLTCLVKGFYPSDIAVE<br>WESNGQPENNYKTTPPVLDSDGSFFLYSKLTVDKS<br>RWQQGNVFSCSVMHEALHNHYTQKSLSLSPGK |
| SEQ ID NO: 255 | DNA<br>Heavy<br>Chain | GAGGTGCAGCTGGTGGAGACTGGAGGAGGCTTG<br>GTCCAGCCGGGGGGGTCCCTGAGACTCTCATGTG<br>CAGCCTCTGGATTCACCGTCAGACGCAATTACAT<br>GAGTTGGGTCCGCCAGGCTCCGGGGAAGGGACT<br>GGAGTGGGTCTCAGGGATCTACAGTGGTGGTAG<br>CACATACTACGCAGACTCCGTGAAGGGCCGATTC<br>ACCATCTCCAGAGACTATTCCAAGAACACACTGT<br>CTCTTCAAATGAACACCCTGAGAGTCGAGGACA<br>CGGCCGTGTATTTCTGTGCGAGAGAAGACGAATT<br>TTGGAGCGGGTATTCCGCTGGGGTCGACTGGGGC<br>CAGGGAACCCTGGTCACCGTCTCCTCAGCTAGCA<br>CCAAGGGCCCATCGGTCTTCCCCCTGGCACCCTC<br>CTCCAAGAGCACCTCTGGGGGCACAGCGGCCCT<br>GGGCTGCCTGGTCAAGGACTACTTCCCCGAACCG<br>GTGACGGTGTCGTGGAACTCAGGCGCCCTGACC<br>AGCGGCGTGCACACCTTCCCGGCTGTCCTACAGT<br>CCTCAGGACTCTACTCCCTCAGCAGCGTGGTGAC<br>CGTGCCCTCCAGCAGCTTGGGCACCCAGACCTAC<br>ATCTGCAACGTGAATCACAAGCCCAGCAACACC<br>AAGGTGGACAAGAGAGTTGAGCCCAAATCTTGT<br>GACAAAACTCACACATGCCCACCGTGCCCAGCA<br>CCTGAACTCCTGGGGGGACCGTCAGTCTTCCTCT<br>TCCCCCCAAAACCCAAGGACACCCTCATGATCTC<br>CCGGACCCCTGAGGTCACATGCGTGGTGGTGGA<br>CGTGAGCCACGAAGACCCTGAGGTCAAGTTCAA<br>CTGGTACGTGGACGGCGTGGAGGTGCATAATGC<br>CAAGACAAAGCCGCGGGAGGAGCAGTACAACAG<br>CACGTACCGTGTGGTCAGCGTCCTCACCGTCCTG<br>CACCAGGACTGGCTGAATGGCAAGGAGTACAAG<br>TGCAAGGTCTCCAACAAAGCCCTCCCAGCCCCCA<br>TCGAGAAAACCATCTCCAAAGCCAAAGGGCAGC<br>CCCGAGAACCACAGGTGTACACCCTGCCCCCATC<br>CCGGGAGGAGATGACCAAGAACCAGGTCAGCCT<br>GACCTGCCTGGTCAAAGGCTTCTATCCCAGCGAC<br>ATCGCCGTGGAGTGGGAGAGCAATGGGCAGCCG<br>GAGAACAACTACAAGACCACGCCTCCCGTGCTG<br>GACTCCGACGGCTCCTTCTTCCTCTACAGCAAGC<br>TCACCGTGGACAAGAGCAGGTGGCAGCAGGGGA<br>ACGTCTTCTCATGCTCCGTGATGCATGAGGCTCT<br>GCACAACCACTACACGCAGAAGAGCCTCTCCCT<br>GTCTCCGGGTAAA |
| SEQ ID NO: 256<br>(Kabat) | LCDR1 | RASQSISSYLN |
| SEQ ID NO: 257<br>(Kabat) | LCDR2 | AASSLQS |

TABLE 2-continued anti-VP1 Antibodies

| SEQ ID NO: 258 (Kabat) | LCDR3 | QQSYNTPRT |
|---|---|---|
| SEQ ID NO: 259 (Chothia) | LCDR1 | SQSISSY |
| SEQ ID NO: 260 (Chothia) | LCDR2 | AAS |
| SEQ ID NO: 261 (Chothia) | LCDR3 | SYNTPR |
| SEQ ID NO: 262 | VL | DIRLTQSPSSLSASVGDRVTITCRASQSISSYLNWYQ QKPGKAPKLLIYAASSLQSGVPSRFSGSGSGTDFTL TISSLQPEDFATYYCQQSYNTPRTFGQGTKVEIK |
| SEQ ID NO: 263 | DNA VL | GACATCCGGTTGACCCAGTCTCCATCCTCCCTGT CTGCATCTGTAGGAGACAGAGTCACCATCACTTG CCGGGCAAGTCAGAGCATTAGCAGCTATTTGAAT TGGTATCAGCAGAAACCAGGGAAAGCCCCTAAG CTCCTGATCTATGCTGCATCCAGTTTGCAAAGTG GGGTCCCATCAAGGTTCAGTGGCAGTGGATCTGG GACAGATTTCACTCTCACCATCAGCAGTCTGCAA CCTGAAGATTTTGCAACTTACTACTGTCAACAGA GTTACAATACCCCTCGAACGTTCGGCCAAGGGAC CAAGGTGGAGATCAAACG |
| SEQ ID NO: 264 | Light Chain | DIRLTQSPSSLSASVGDRVTITCRASQSISSYLNWYQ QKPGKAPKLLIYAASSLQSGVPSRFSGSGSGTDFTL TISSLQPEDFATYYCQQSYNTPRTFGQGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| SEQ ID NO: 265 | DNA Light Chain | GACATCCGGTTGACCCAGTCTCCATCCTCCCTGT CTGCATCTGTAGGAGACAGAGTCACCATCACTTG CCGGGCAAGTCAGAGCATTAGCAGCTATTTGAAT TGGTATCAGCAGAAACCAGGGAAAGCCCCTAAG CTCCTGATCTATGCTGCATCCAGTTTGCAAAGTG GGGTCCCATCAAGGTTCAGTGGCAGTGGATCTGG GACAGATTTCACTCTCACCATCAGCAGTCTGCAA CCTGAAGATTTTGCAACTTACTACTGTCAACAGA GTTACAATACCCCTCGAACGTTCGGCCAAGGGAC CAAGGTGGAGATCAAACGTACGGTGGCTGCACC ATCTGTCTTCATCTTCCCGCCATCTGATGAGCAG TTGAAATCTGGAACTGCCTCTGTTGTGTGCCTGC TGAATAACTTCTATCCCCGCGAGGCCAAAGTACA GTGGAAGGTGGATAACGCCCTCCAATCGGGTAA CTCCCAGGAGAGTGTCACAGAGCAGGACAGCAA GGACAGCACCTACAGCCTCAGCAGCACCCTGAC GCTGAGCAAAGCAGACTACGAGAAACACAAAGT CTACGCCTGCGAAGTCACCCATCAGGGCCTGAGC TCGCCCGTCACAAAGAGCTTCAACCGCGGAGAG TGT |

EBB-C1975-A7

| SEQ ID NO: 266 (Kabat) | HCDR1 | RNYMS |
|---|---|---|
| SEQ ID NO: 267 (Kabat) | HCDR2 | GIYSGGSTYYADSVKG |
| SEQ ID NO: 268 (Kabat) | HCDR3 | EDEFWSGYSAGVD |
| SEQ ID NO: 269 (Chothia) | HCDR1 | GFTVSRN |
| SEQ ID NO: 270 (Chothia) | HCDR2 | YSGGS |
| SEQ ID NO: 271 (Chothia) | HCDR3 | EDEFWSGYSAGVD |

TABLE 2-continued anti-VP1 Antibodies

| SEQ ID NO: 272 | VH | QVQLVESGGGLVQPGGSLRLSCAASGFTVSRNYMS
WVRQAPGKGLEWVSGIYSGGSTYYADSVKGRFTIS
RDYSKNTLSLQMNTLRVEDTAVYFCAREDEFWSG
YSAGVDWGQGTLVTVSS |
|---|---|---|
| SEQ ID NO: 273 | DNA VH | CAGGTGCAGCTGGTGGAATCTGGAGGAGGCTTG
GTCCAGCCTGGGGGGTCCCTGAGACTCTCATGTG
CAGCCTCTGGATTCACCGTCAGTCGCAATTACAT
GAGTTGGGTCCGCCAGGCTCCGGGGAAGGGACT
GGAGTGGGTCTCAGGGATTTACAGTGGTGGTAG
CACATACTACGCAGACTCCGTGAAGGGCCGATTC
ACCATCTCCAGAGACTATTCCAAGAACACACTGT
CTCTTCAAATGAACACCCTGAGAGTCGAGGACA
CGGCCGTGTATTTCTGTGCGAGAGAAGACGAATT
TTGGAGTGGGTATTCCGCTGGGGTCGACTGGGGC
CAGGGAACCCTGGTCACCGTCTCCTCAGC |
| SEQ ID NO: 274 | Heavy Chain | QVQLVESGGGLVQPGGSLRLSCAASGFTVSRNYMS
WVRQAPGKGLEWVSGIYSGGSTYYADSVKGRFTIS
RDYSKNTLSLQMNTLRVEDTAVYFCAREDEFWSG
YSAGVDWGQGTLVTVSSASTKGPSVFPLAPSSKST
SGGTAALGCLVKDYFPEPVTVSWNSGALTSGVHTF
PAVLQSSGLYSLSSVVTVPSSSLGTQTYICNVNHKP
SNTKVDKRVEPKSCDKTHTCPPCPAPELLGGPSVFL
FPPKPKDTLMISRTPEVTCVVVDVSHEDPEVKFNW
YVDGVEVHNAKTKPREEQYNSTYRVVSVLTVLHQ
DWLNGKEYKCKVSNKALPAPIEKTISKAKGQPREP
QVYTLPPSREEMTKNQVSLTCLVKGFYPSDIAVEW
ESNGQPENNYKTTPPVLDSDGSFFLYSKLTVDKSR
WQQGNVFSCSVMHEALHNHYTQKSLSLSPGK |
| SEQ ID NO: 275 | DNA Heavy Chain | CAGGTGCAGCTGGTGGAATCTGGAGGAGGCTTG
GTCCAGCCTGGGGGGTCCCTGAGACTCTCATGTG
CAGCCTCTGGATTCACCGTCAGTCGCAATTACAT
GAGTTGGGTCCGCCAGGCTCCGGGGAAGGGACT
GGAGTGGGTCTCAGGGATTTACAGTGGTGGTAG
CACATACTACGCAGACTCCGTGAAGGGCCGATTC
ACCATCTCCAGAGACTATTCCAAGAACACACTGT
CTCTTCAAATGAACACCCTGAGAGTCGAGGACA
CGGCCGTGTATTTCTGTGCGAGAGAAGACGAATT
TTGGAGTGGGTATTCCGCTGGGGTCGACTGGGGC
CAGGGAACCCTGGTCACCGTCTCCTCAGCTAGCA
CCAAGGGCCCATCGGTCTTCCCCCTGGCACCCTC
CTCCAAGAGCACCTCTGGGGGCACAGCGGCCCT
GGGCTGCCTGGTCAAGGACTACTTCCCCGAACCG
GTGACGGTGTCGTGGAACTCAGGCGCCCTGACC
AGCGGCGTGCACACCTTCCCGGCTGTCCTACAGT
CCTCAGGACTCTACTCCCTCAGCAGCGTGGTGAC
CGTGCCCTCCAGCAGCTTGGGCACCCAGACCTAC
ATCTGCAACGTGAATCACAAGCCCAGCAACACC
AAGGTGGACAAGAGAGTTGAGCCCAAATCTTGT
GACAAAACTCACACATGCCCACCGTGCCCAGCA
CCTGAACTCCTGGGGGGACCGTCAGTCTTCCTCT
TCCCCCCAAAACCCAAGGACACCCTCATGATCTC
CCGGACCCCTGAGGTCACATGCGTGGTGGTGGA
CGTGAGCCACGAAGACCCTGAGGTCAAGTTCAA
CTGGTACGTGGACGGCGTGGAGGTGCATAATGC
CAAGACAAAGCCGCGGGAGGAGCAGTACAACAG
CACGTACCGTGTGGTCAGCGTCCTCACCGTCCTG
CACCAGGACTGGCTGAATGGCAAGGAGTACAAG
TGCAAGGTCTCCAACAAAGCCCTCCCAGCCCCCA
TCGAGAAAACCATCTCCAAAGCCAAAGGGCAGC
CCCGAGAACCACAGGTGTACACCCTGCCCCCATC
CCGGGAGGAGATGACCAAGAACCAGGTCAGCCT
GACCTGCCTGGTCAAAGGCTTCTATCCCAGCGAC
ATCGCCGTGGAGTGGGAGAGCAATGGGCAGCCG
GAGAACAACTACAAGACCACGCCTCCCGTGCTG
GACTCCGACGGCTCCTTCTTCCTCTACAGCAAGC
TCACCGTGGACAAGAGCAGGTGGCAGCAGGGGA
ACGTCTTCTCATGCTCCGTGATGCATGAGGCTCT
GCACAACCACTACACGCAGAAGAGCCTCTCCCT
GTCTCCGGGTAAA |
| SEQ ID NO: 276 (Kabat) | LCDR1 | RASQSISSYLN |
| SEQ ID NO: 277 (Kabat) | LCDR2 | AASSLQS |

TABLE 2-continued anti-VP1 Antibodies

| SEQ ID NO: 278 (Kabat) | LCDR3 | QQSYSTPRT |
|---|---|---|
| SEQ ID NO: 279 (Chothia) | LCDR1 | SQSISSY |
| SEQ ID NO: 280 (Chothia) | LCDR2 | AAS |
| SEQ ID NO: 281 (Chothia) | LCDR3 | SYSTPR |
| SEQ ID NO: 282 | VL | DIRMTQSPSSLSASVGDRVTITCRASQSISSYLNWY QQKPGKAPTLLIYAASSLQSGVPSRFSGSGSGTDFT LTISSLQPEDFATYYCQQSYSTPRTFGQGTKVEIK |
| SEQ ID NO: 283 | DNA VL | GACATCCGGATGACCCAGTCTCCATCCTCCCTGT CTGCATCTGTAGGAGACAGAGTCACCATCACTTG CCGGGCAAGTCAGAGCATTAGCAGCTATTTAAAT TGGTATCAGCAGAAACCAGGGAAAGCCCCTACG CTCCTGATCTATGCTGCATCCAGTTTGCAAAGTG GGGTCCCATCAAGGTTCAGTGGCAGTGGATCTGG GACAGATTTCACTCTCACCATCAGCAGTCTGCAA CCTGAAGATTTTGCAACTTACTACTGTCAACAGA GTTACAGTACCCCTCGGACGTTCGGCCAAGGGAC CAAGGTGGAGATCAAAC |
| SEQ ID NO: 284 | Light Chain | DIRMTQSPSSLSASVGDRVTITCRASQSISSYLNWY QQKPGKAPTLLIYAASSLQSGVPSRFSGSGSGTDFT LTISSLQPEDFATYYCQQSYSTPRTFGQGTKVEIKR TVAAPSVFIFPPSDEQLKSGTASVVCLLNNFYPREA KVQWKVDNALQSGNSQESVTEQDSKDSTYSLSSTL TLSKADYEKHKVYACEVTHQGLSSPVTKSFNRGEC |
| SEQ ID NO: 285 | DNA Light Chain | GACATCCGGATGACCCAGTCTCCATCCTCCCTGT CTGCATCTGTAGGAGACAGAGTCACCATCACTTG CCGGGCAAGTCAGAGCATTAGCAGCTATTTAAAT TGGTATCAGCAGAAACCAGGGAAAGCCCCTACG CTCCTGATCTATGCTGCATCCAGTTTGCAAAGTG GGGTCCCATCAAGGTTCAGTGGCAGTGGATCTGG GACAGATTTCACTCTCACCATCAGCAGTCTGCAA CCTGAAGATTTTGCAACTTACTACTGTCAACAGA GTTACAGTACCCCTCGGACGTTCGGCCAAGGGAC CAAGGTGGAGATCAAACGTACGGTGGCTGCACC ATCTGTCTTCATCTTCCCGCCATCTGATGAGCAG TTGAAATCTGGAACTGCCTCTGTTGTGTGCCTGC TGAATAACTTCTATCCCCGCGAGGCCAAAGTACA GTGGAAGGTGGATAACGCCCTCCAATCGGGTAA CTCCCAGGAGAGTGTCACAGAGCAGGACAGCAA GGACAGCACCTACAGCCTCAGCAGCACCCTGAC GCTGAGCAAAGCAGACTACGAGAAACACAAAGT CTACGCCTGCGAAGTCACCCATCAGGGCCTGAGC TCGCCCGTCACAAAGAGCTTCAACCGCGGAGAG TGT |

EBB-C1975-E7

| SEQ ID NO: 286 (Kabat) | HCDR1 | RNYMS |
|---|---|---|
| SEQ ID NO: 287 (Kabat) | HCDR2 | GIYGGGRTYYAESVKG |
| SEQ ID NO: 288 (Kabat) | HCDR3 | EDEFWSGYSAGVD |
| SEQ ID NO: 289 (Chothia) | HCDR1 | GFTVSRN |
| SEQ ID NO: 290 (Chothia) | HCDR2 | YGGGR |
| SEQ ID NO: 291 (Chothia) | HCDR3 | EDEFWSGYSAGVD |

TABLE 2-continued

| anti-VP1 Antibodies | | |
|---|---|---|
| SEQ ID NO: 292 | VH | EVQLLESGGGLVRPGGSLRVSCAASGFTVSRNYMS WVRQAPGKGLEWVSGIYGGGRTYYAESVKGRFTI SRDYSKNTLFLQMNTLRVEDTALYFCAREDEFWS GYSAGVDWGQGTLVTVSS |
| SEQ ID NO: 293 | DNA VH | GAGGTGCAGCTGTTGGAGTCCGGGGGAGGCTTG GTCCGGCCTGGGGGGTCCCTGAGAGTCTCATGTG CAGCCTCTGGATTCACCGTCAGTCGCAATTACAT GAGTTGGGTCCGCCAGGCTCCGGGGAAGGGACT GGAGTGGGTCTCAGGGATTTACGGTGGTGGTAG GACTTACTACGCAGAGTCCGTGAAGGGCCGATTC ACCATCTCCAGAGACTATTCCAAGAACACACTGT TTCTTCAAATGAACACCCTGAGAGTCGAGGACAC GGCCCTGTATTTCTGTGCGAGAGAAGACGAATTT TGGAGTGGGTATTCTGCTGGGGTCGACTGGGGCC AGGGAACCCTGGTCACTGTCTCCTCA |
| SEQ ID NO: 294 | Heavy Chain | EVQLLESGGGLVRPGGSLRVSCAASGFTVSRNYMS WVRQAPGKGLEWVSGIYGGGRTYYAESVKGRFTI SRDYSKNTLFLQMNTLRVEDTALYFCAREDEFWS GYSAGVDWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNHK PSNTKVDKRVEPKSCDKTHTCPPCPAPELLGGPSVF LFPPKPKDTLMISRTPEVTCVVVDVSHEDPEVKFN WYVDGVEVHNAKTKPREEQYNSTYRVVSVLTVLH QDWLNGKEYKCKVSNKALPAPIEKTISKAKGQPRE PQVYTLPPSREEMTKNQVSLTCLVKGFYPSDIAVE WESNGQPENNYKTTPPVLDSDGSFFLYSKLTVDKS RWQQGNVFSCSVMHEALHNHYTQKSLSLSPGK |
| SEQ ID NO: 295 | DNA Heavy Chain | GAGGTGCAGCTGTTGGAGTCCGGGGGAGGCTTG GTCCGGCCTGGGGGGTCCCTGAGAGTCTCATGTG CAGCCTCTGGATTCACCGTCAGTCGCAATTACAT GAGTTGGGTCCGCCAGGCTCCGGGGAAGGGACT GGAGTGGGTCTCAGGGATTTACGGTGGTGGTAG GACTTACTACGCAGAGTCCGTGAAGGGCCGATTC ACCATCTCCAGAGACTATTCCAAGAACACACTGT TTCTTCAAATGAACACCCTGAGAGTCGAGGACAC GGCCCTGTATTTCTGTGCGAGAGAAGACGAATTT TGGAGTGGGTATTCTGCTGGGGTCGACTGGGGCC AGGGAACCCTGGTCACTGTCTCCTCAGCTAGCAC CAAGGGCCCATCGGTCTTCCCCCTGGCACCCTCC TCCAAGAGCACCTCTGGGGGCACAGCGGCCCTG GGCTGCCTGGTCAAGGACTACTTCCCCGAACCGG TGACGGTGTCGTGGAACTCAGGCGCCCTGACCA GCGGCGTGCACACCTTCCCGGCTGTCCTACAGTC CTCAGGACTCTACTCCCTCAGCAGCGTGGTGACC GTGCCCTCCAGCAGCTTGGGCACCCAGACCTACA TCTGCAACGTGAATCACAAGCCCAGCAACACCA AGGTGGACAAGAGAGTTGAGCCCAAATCTTGTG ACAAAACTCACACATGCCCACCGTGCCCAGCAC CTGAACTCCTGGGGGGACCGTCAGTCTTCCTCTT CCCCCCAAAACCCAAGGACACCCTCATGATCTCC CGGACCCCTGAGGTCACATGCGTGGTGGTGGAC GTGAGCCACGAAGACCCTGAGGTCAAGTTCAAC TGGTACGTGGACGGCGTGGAGGTGCATAATGCC AAGACAAAGCCGCGGGAGGAGCAGTACAACAGC ACGTACCGTGTGGTCAGCGTCCTCACCGTCCTGC ACCAGGACTGGCTGAATGGCAAGGAGTACAAGT GCAAGGTCTCCAACAAAGCCCTCCCAGCCCCCAT CGAGAAAACCATCTCCAAAGCCAAAGGGCAGCC CCGAGAACCACAGGTGTACACCCTGCCCCCATCC CGGGAGGAGATGACCAAGAACCAGGTCAGCCTG ACCTGCCTGGTCAAAGGCTTCTATCCCAGCGACA TCGCCGTGGAGTGGGAGAGCAATGGGCAGCCGG AGAACAACTACAAGACCACGCCTCCCGTGCTGG ACTCCGACGGCTCCTTCTTCCTCTACAGCAAGCT CACCGTGGACAAGAGCAGGTGGCAGCAGGGGAA CGTCTTCTCATGCTCCGTGATGCATGAGGCTCTG CACAACCACTACACGCAGAAGAGCCTCTCCCTGT CTCCGGGTAAA |
| SEQ ID NO: 296 (Kabat) | LCDR1 | RASQSISSYLN |
| SEQ ID NO: 297 (Kabat) | LCDR2 | AASTLQT |

TABLE 2-continued anti-VP1 Antibodies

| | | |
|---|---|---|
| SEQ ID NO: 298 (Kabat) | LCDR3 | QQSYNTPRT |
| SEQ ID NO: 299 (Chothia) | LCDR1 | SQSISSY |
| SEQ ID NO: 300 (Chothia) | LCDR2 | AAS |
| SEQ ID NO: 301 (Chothia) | LCDR3 | SYNTPR |
| SEQ ID NO: 302 | VL | DIQVTQSPSSLSASVGDRVTITCRASQSISSYLNWY QQEPGKAPKLLIYAASTLQTGVPSRFSGSGSGTDFT LTISSLQPEDFATYYCQQSYNTPRTFGQGTKVEIK |
| SEQ ID NO: 303 | DNA VL | GACATCCAGGTGACCCAGTCTCCATCCTCCCTGT CTGCATCTGTAGGAGACAGAGTCACCATCACTTG CCGGGCAAGTCAGAGCATTAGCAGCTATTTAAAT TGGTATCAGCAGGAACCAGGGAAAGCCCCTAAA CTCCTGATCTACGCTGCATCCACTTTGCAAACTG GGGTCCCATCACGGTTCAGTGGTAGTGGATCTGG GACAGATTTCACTCTCACCATCAGCAGTCTGCAA CCTGAAGATTTTGCAACTTATTACTGTCAACAGA GTTACAATACCCCTCGAACCTTCGGCCAAGGGAC CAAGGTGGAAATCAAACG |
| SEQ ID NO: 304 | Light Chain | DIQVTQSPSSLSASVGDRVTITCRASQSISSYLNWY QQEPGKAPKLLIYAASTLQTGVPSRFSGSGSGTDFT LTISSLQPEDFATYYCQQSYNTPRTFGQGTKVEIKR TVAAPSVFIFPPSDEQLKSGTASVVCLLNNFYPREA KVQWKVDNALQSGNSQESVTEQDSKDSTYSLSSTL TLSKADYEKHKVYACEVTHQGLSSPVTKSFNRGEC |
| SEQ ID NO: 305 | DNA Light Chain | GACATCCAGGTGACCCAGTCTCCATCCTCCCTGT CTGCATCTGTAGGAGACAGAGTCACCATCACTTG CCGGGCAAGTCAGAGCATTAGCAGCTATTTAAAT TGGTATCAGCAGGAACCAGGGAAAGCCCCTAAA CTCCTGATCTACGCTGCATCCACTTTGCAAACTG GGGTCCCATCACGGTTCAGTGGTAGTGGATCTGG GACAGATTTCACTCTCACCATCAGCAGTCTGCAA CCTGAAGATTTTGCAACTTATTACTGTCAACAGA GTTACAATACCCCTCGAACCTTCGGCCAAGGGAC CAAGGTGGAAATCAAACGTACGGTGGCTGCACC ATCTGTCTTCATCTTCCCGCCATCTGATGAGCAG TTGAAATCTGGAACTGCCTCTGTTGTGTGCCTGC TGAATAACTTCTATCCCCGCGAGGCCAAAGTACA GTGGAAGGTGGATAACGCCCTCCAATCGGGTAA CTCCCAGGAGAGTGTCACAGAGCAGGACAGCAA GGACAGCACCTACAGCCTCAGCAGCACCCTGAC GCTGAGCAAAGCAGACTACGAGAAACACAAAGT CTACGCCTGCGAAGTCACCCATCAGGGCCTGAGC TCGCCCGTCACAAAGAGCTTCAACCGCGGAGAG TGT |

P46F4

| | | |
|---|---|---|
| SEQ ID NO: 306 (Kabat) | HCDR1 | NGGYYWS |
| SEQ ID NO: 307 (Kabat) | HCDR2 | CIHYSGGTYYNPSLKS |
| SEQ ID NO: 308 (Kabat) | HCDR3 | ALIAAPGISDWFDP |
| SEQ ID NO: 309 (Chothia) | HCDR1 | GGSISNGGY |
| SEQ ID NO: 310 (Chothia) | HCDR2 | HYSGG |
| SEQ ID NO: 311 (Chothia) | HCDR3 | ALIAAPGISDWFDP |

TABLE 2-continued anti-VP1 Antibodies

| | | |
|---|---|---|
| SEQ ID NO: 312 | VH | QVQLQESGPGLVKPSQTLSLTCTVSGGSISNGGYY WSWIRLHPGKGLEWIGCIHYSGGTYYNPSLKSRVT VSLDTSKNQFSLNLISVTAADTAIYFCARALIAAPGI SDWFDPWGQGTLVTVSS |
| SEQ ID NO: 313 | Heavy Chain | QVQLQESGPGLVKPSQTLSLTCTVSGGSISNGGYY WSWIRLHPGKGLEWIGCIHYSGGTYYNPSLKSRVT VSLDTSKNQFSLNLISVTAADTAIYFCARALIAAPGI SDWFDPWGQGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKKVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| SEQ ID NO: 314 (Kabat) | LCDR1 | SGSNSNVGHNYVS |
| SEQ ID NO: 315 (Kabat) | LCDR2 | DNNKRPS |
| SEQ ID NO: 316 (Kabat) | LCDR3 | GTWDSSLSAGV |
| SEQ ID NO: 317 (Chothia) | LCDR1 | SNSNVGHNY |
| SEQ ID NO: 318 (Chothia) | LCDR2 | DNN |
| SEQ ID NO: 319 (Chothia) | LCDR3 | WDSSLSAG |
| SEQ ID NO: 320 | VL | QSVLTQPPSVSAAPGQKVTISCSGSNSNVGHNYVS WYQQLPGTAPKLLIYDNNKRPSGIPDRFSGSKSGTS ATLGITGLQTGDEADYYCGTWDSSLSAGVFGGGT KVTVL |
| SEQ ID NO: 321 | Light Chain | QSVLTQPPSVSAAPGQKVTISCSGSNSNVGHNYVS WYQQLPGTAPKLLIYDNNKRPSGIPDRFSGSKSGTS ATLGITGLQTGDEADYYCGTWDSSLSAGVFGGGT KVTVLGQPKAAPSVTLFPPSSEELQANKATLVCLIS DFYPGAVTVAWKADSSPVKAGVETTTPSKQSNNK YAASSYLSLTPEQWKSHRSYSCQVTHEGSTVEKTV APTECS |
| 2081-20-8 hz53 | | |
| SEQ ID NO: 322 (Kabat) | HCDR1 | SSWMN |
| SEQ ID NO: 323 (Kabat) | HCDR2 | RIYPGDADTYYSGKFKG |
| SEQ ID NO: 324 (Kabat) | HCDR3 | HSSGFTY |
| SEQ ID NO: 325 (Chothia) | HCDR1 | GYTFSSS |
| SEQ ID NO: 326 (Chothia) | HCDR2 | YPGDAD |
| SEQ ID NO: 327 (Chothia) | HCDR3 | HSSGFTY |
| SEQ ID NO: 328 | VH | QVQLVQSGAEVKKPGASVKVSCKASGYTFSSSWM NWVRQAPGQRLEWMGRIYPGDADTYYSGKFKGR VTITADSSARTAYMELSSLRSEDTAVYYCAIHSSGF TYWGQGTLVTVSS |
| SEQ ID NO: 329 | DNA VH | CAGGTCCAGCTTGTGCAGTCTGGGGCTGAGGTGA AGAAGCCTGGGGCCTCAGTGAAGGTTTCCTGCA AGGCTTCTGGCTATACATTCAGCAGCTCTTGGAT |

TABLE 2-continued anti-VP1 Antibodies

| | | |
|---|---|---|
| | | GAACTGGGTGCGCCAGGCCCCCGGACAAAGGCT<br>TGAGTGGATGGGACGGATCTATCCAGGAGACGC<br>CGATACTTACTACAGTGGGAAATTCAAGGGCAG<br>AGTCACCATTACCGCCGACAGCTCCGCGAGAAC<br>AGCCTACATGGAGCTGAGCAGCCTGAGATCTGA<br>AGACACGGCTGTGTATTACTGTGCGATCCACAGC<br>TCGGGCTTTACTTACTGGGGCCAGGGCACCCTGG<br>TCACCGTCTCCTCAGC |
| SEQ ID NO: 330 | Heavy<br>Chain | QVQLVQSGAEVKKPGASVKVSCKASGYTFSSSWM<br>NWVRQAPGQRLEWMGRIYPGDADTYYSGKFKGR<br>VTITADSSARTAYMELSSLRSEDTAVYYCAIHSSGF<br>TYWGQGTLVTVSSASTKGPSVFPLAPSSKSTSGGT<br>AALGCLVKDYFPEPVTVSWNSGALTSGVHTFPAVL<br>QSSGLYSLSSVVTVPSSSLGTQTYICNVNHKPSNTK<br>VDKRVEPKSCDKTHTCPPCPAPELLGGPSVFLFPPK<br>PKDTLMISRTPEVTCVVVDVSHEDPEVKFNWYVD<br>GVEVHNAKTKPREEQYNSTYRVVSVLTVLHQDWL<br>NGKEYKCKVSNKALPAPIEKTISKAKGQPREPQVY<br>TLPPSREEMTKNQVSLTCLVKGFYPSDIAVEWESN<br>GQPENNYKTTPPVLDSDGSFFLYSKLTVDKSRWQQ<br>GNVFSCSVMHEALHNHYTQKSLSLSPGK |
| SEQ ID NO: 331 | DNA<br>Heavy<br>Chain | CAGGTCCAGCTTGTGCAGTCTGGGGCTGAGGTGA<br>AGAAGCCTGGGGCCTCAGTGAAGGTTTCCTGCA<br>AGGCTTCTGGCTATACATTCAGCAGCTCTTGGAT<br>GAACTGGGTGCGCCAGGCCCCCGGACAAAGGCT<br>TGAGTGGATGGGACGGATCTATCCAGGAGACGC<br>CGATACTTACTACAGTGGGAAATTCAAGGGCAG<br>AGTCACCATTACCGCCGACAGCTCCGCGAGAAC<br>AGCCTACATGGAGCTGAGCAGCCTGAGATCTGA<br>AGACACGGCTGTGTATTACTGTGCGATCCACAGC<br>TCGGGCTTTACTTACTGGGGCCAGGGCACCCTGG<br>TCACCGTCTCCTCAGCTAGCACCAAGGGCCCATC<br>GGTCTTCCCCCTGGCACCCTCCTCCAAGAGCACC<br>TCTGGGGGCACAGCGGCCCTGGGCTGCCTGGTCA<br>AGGACTACTTCCCCGAACCGGTGACGGTGTCGTG<br>GAACTCAGGCGCCCTGACCAGCGGCGTGCACAC<br>CTTCCCGGCTGTCCTACAGTCCTCAGGACTCTAC<br>TCCCTCAGCAGCGTGGTGACCGTGCCCTCCAGCA<br>GCTTGGGCACCCAGACCTACATCTGCAACGTGAA<br>TCACAAGCCCAGCAACACCAAGGTGGACAAGAG<br>AGTTGAGCCCAAATCTTGTGACAAAACTCACACA<br>TGCCCACCGTGCCCAGCACCTGAACTCCTGGGGG<br>GACCGTCAGTCTTCCTCTTCCCCCCAAAACCCAA<br>GGACACCCTCATGATCTCCCGGACCCCTGAGGTC<br>ACATGCGTGGTGGTGGACGTGAGCCACGAAGAC<br>CCTGAGGTCAAGTTCAACTGGTACGTGGACGGC<br>GTGGAGGTGCATAATGCCAAGACAAAGCCGCGG<br>GAGGAGCAGTACAACAGCACGTACCGTGTGGTC<br>AGCGTCCTCACCGTCCTGCACCAGGACTGGCTGA<br>ATGGCAAGGAGTACAAGTGCAAGGTCTCCAACA<br>AAGCCCTCCCAGCCCCCATCGAGAAAACCATCTC<br>CAAAGCCAAAGGGCAGCCCCGAGAACCACAGGT<br>GTACACCCTGCCCCCATCCCGGGAGGAGATGAC<br>CAAGAACCAGGTCAGCCTGACCTGCCTGGTCAA<br>AGGCTTCTATCCCAGCGACATCGCCGTGGAGTGG<br>GAGAGCAATGGGCAGCCGGAGAACAACTACAAG<br>ACCACGCCTCCCGTGCTGGACTCCGACGGCTCCT<br>TCTTCCTCTACAGCAAGCTCACCGTGGACAAGAG<br>CAGGTGGCAGCAGGGGAACGTCTTCTCATGCTCC<br>GTGATGCATGAGGCTCTGCACAACCACTACACGC<br>AGAAGAGCCTCTCCCTGTCTCCGGGTAAA |
| SEQ ID NO: 332<br>(Kabat) | LCDR1 | RASQDISDYLN |
| SEQ ID NO: 333<br>(Kabat) | LCDR2 | YTSRLHS |
| SEQ ID NO: 334<br>(Kabat) | LCDR3 | QQTHTLPFT |
| SEQ ID NO: 335<br>(Chothia) | LCDR1 | SQDISDY |
| SEQ ID NO: 336<br>(Chothia) | LCDR2 | YTS |

TABLE 2-continued anti-VP1 Antibodies

| | | |
|---|---|---|
| SEQ ID NO: 337 (Chothia) | LCDR3 | THTLPF |
| SEQ ID NO: 338 | VL | DIQMTQSPSSLSASVGDRVTITCRASQDISDYLNWY QQKPGKAPKLLIYYTSRLHSGVPSRFSGSGSGTDYT LTISSLQPEDFATYFCQQTHTLPFTFGGGTKVEIK |
| SEQ ID NO: 339 | DNA VL | GACATCCAGATGACCCAGTCTCCATCCTCCCTGT CTGCATCTGTAGGAGACAGAGTCACCATCACTTG CAGGGCAAGTCAGGACATTAGCGATTATTTAAA CTGGTATCAGCAGAAACCAGGGAAAGCCCCTAA GCTCCTGATCTATTATACATCAAGATTACACTCA GGGGTCCCATCAAGGTTCAGTGGCAGTGGATCTG GGACAGATTACACTCTCACCATCAGCAGTCTGCA ACCTGAAGATTTTGCAACTTACTTCTGTCAACAG ACTCATACGCTTCCTTTCACGTTCGGCGGAGGGA CCAAGGTGGAGATCAAACG |
| SEQ ID NO: 340 | Light Chain | DIQMTQSPSSLSASVGDRVTITCRASQDISDYLNWY QQKPGKAPKLLIYYTSRLHSGVPSRFSGSGSGTDYT LTISSLQPEDFATYFCQQTHTLPFTFGGGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| SEQ ID NO: 341 | DNA Light Chain | GACATCCAGATGACCCAGTCTCCATCCTCCCTGT CTGCATCTGTAGGAGACAGAGTCACCATCACTTG CAGGGCAAGTCAGGACATTAGCGATTATTTAAA CTGGTATCAGCAGAAACCAGGGAAAGCCCCTAA GCTCCTGATCTATTATACATCAAGATTACACTCA GGGGTCCCATCAAGGTTCAGTGGCAGTGGATCTG GGACAGATTACACTCTCACCATCAGCAGTCTGCA ACCTGAAGATTTTGCAACTTACTTCTGTCAACAG ACTCATACGCTTCCTTTCACGTTCGGCGGAGGGA CCAAGGTGGAGATCAAACGTACGGTGGCTGCAC CATCTGTCTTCATCTTCCCGCCATCTGATGAGCA GTTGAAATCTGGAACTGCCTCTGTTGTGTGCCTG CTGAATAACTTCTATCCCCGCGAGGCCAAAGTAC AGTGGAAGGTGGATAACGCCCTCCAATCGGGTA ACTCCCAGGAGAGTGTCACAGAGCAGGACAGCA AGGACAGCACCTACAGCCTCAGCAGCACCCTGA CGCTGAGCAAAGCAGACTACGAGAAACACAAAG TCTACGCCTGCGAAGTCACCCATCAGGGCCTGAG CTCGCCCGTCACAAAGAGCTTCAACCGCGGAGA GTGT |

2075-16-1

| | | |
|---|---|---|
| SEQ ID NO: 342 (Kabat) | HCDR1 | NYWMH |
| SEQ ID NO: 343 (Kabat) | HCDR2 | NIYPGSGNTNYGENFKS |
| SEQ ID NO: 344 (Kabat) | HCDR3 | SAIYYGYDGHYFAMDY |
| SEQ ID NO: 345 (Chothia) | HCDR1 | GYTFTNY |
| SEQ ID NO: 346 (Chothia) | HCDR2 | YPGSGN |
| SEQ ID NO: 347 (Chothia) | HCDR3 | SAIYYGYDGHYFAMDY |
| SEQ ID NO: 348 | VH | QVQLQQPGSELVRPGASVKLSCKASGYTFTNYWM HWVKQGHGQLEWIGNIYPGSGNTNYGENFKSKG TLTVDTSSSTAYMHLSRLTSEDSAVYYCSRSAIYYG YDGHYFAMDYWGQGTSVTVSS |
| SEQ ID NO: 349 (Kabat) | LCDR1 | KASQDIRKYIA |
| SEQ ID NO: 350 (Kabat) | LCDR2 | YTSTLQS |

TABLE 2-continued anti-VP1 Antibodies

| | | |
|---|---|---|
| SEQ ID NO: 351 (Kabat) | LCDR3 | LQYDNILFT |
| SEQ ID NO: 352 (Chothia) | LCDR1 | SQDIRKY |
| SEQ ID NO: 353 (Chothia) | LCDR2 | YTS |
| SEQ ID NO: 354 (Chothia) | LCDR3 | YDNILF |
| SEQ ID NO: 355 | VL | DIQMTQSPSSLSASLGGKVTITCKASQDIRKYIAWY QHKPGKGPRLLINYTSTLQSGIPSRFRGSGSGRDYS FSISNLEPEDIATYYCLQYDNILFTFGTGTKLEIK |

2075-456-4

| | | |
|---|---|---|
| SEQ ID NO: 356 (Kabat) | HCDR1 | SCWMN |
| SEQ ID NO: 357 (Kabat) | HCDR2 | RIYPGDGDTKYTEKFKD |
| SEQ ID NO: 358 (Kabat) | HCDR3 | SGSGLPY |
| SEQ ID NO: 359 (Chothia) | HCDR1 | GYSFSSC |
| SEQ ID NO: 360 (Chothia) | HCDR2 | YPGDGD |
| SEQ ID NO: 361 (Chothia) | HCDR3 | SGSGLPY |
| SEQ ID NO: 362 | VH | QVHLQQSGPELVKPGASVTISCKTSGYSFSSCWMN WVKQRPGQGLEWIGRIYPGDGDTKYTEKFKDKAT LTADKSSSTAYMQLSSLTSVDSALYFCAISGSGLPY WGQGTLVTVSE |
| SEQ ID NO: 363 (Kabat) | LCDR1 | RASQDIHNYLN |
| SEQ ID NO: 364 (Kabat) | LCDR2 | STSRLHS |
| SEQ ID NO: 365 (Kabat) | LCDR3 | QQTHTLPLT |
| SEQ ID NO: 366 (Chothia) | LCDR1 | SQDIHNY |
| SEQ ID NO: 367 (Chothia) | LCDR2 | STS |
| SEQ ID NO: 368 (Chothia) | LCDR3 | THTLPL |
| SEQ ID NO: 369 | VL | DIQMTQTTSSLSASLGDRVTISCRASQDIHNYLNWY QQKPDGTIKLLIYSTSRLHSGVPSRFSGSGSGTHYSL TINNLEQEDIATYFCQQTHTLPLTFGAGTKLELK |

2081-36-8

| | | |
|---|---|---|
| SEQ ID NO: 370 (Kabat) | HCDR1 | SYWMN |
| SEQ ID NO: 371 (Kabat) | HCDR2 | QIYPGNGDTNYNGKFKG |
| SEQ ID NO: 372 (Kabat) | HCDR3 | EARQGYHYAMDY |

// TABLE 2-continued
// anti-VP1 Antibodies

| SEQ ID NO: 373 (Chothia) | HCDR1 | GYAFSSY |
| --- | --- | --- |
| SEQ ID NO: 374 (Chothia) | HCDR2 | YPGNGD |
| SEQ ID NO: 375 (Chothia) | HCDR3 | EARQGYHYAMDY |
| SEQ ID NO: 376 | VH | QVQLQQSGAGLVRPGSSVKISCKTSGYAFSSYWM NWVKQRPGQGLEWIGQIYPGNGDTNYNGKFKGK ATLTADKSSNTAYIQLNSLTSEDSAVYFCAREARQ GYHY AMDYWGQGTSVTVSL |
| SEQ ID NO: 377 (Kabat) | LCDR1 | SASSMINSNYLH |
| SEQ ID NO: 378 (Kabat) | LCDR2 | RTSNLAS |
| SEQ ID NO: 379 (Kabat) | LCDR3 | QQGSNIFT |
| SEQ ID NO: 380 (Chothia) | LCDR1 | SSMINSNY |
| SEQ ID NO: 381 (Chothia) | LCDR2 | RTS |
| SEQ ID NO: 382 (Chothia) | LCDR3 | GSNIF |
| SEQ ID NO: 383 | VL | EIVFTQSPTTMAAFPGEKITITCSASSMINSNYLHWY QQKPGFSPKVLIYRTSNLASGVPARFSGTGSGTSFS LTIGTMEAEDVATYYCQQGSNIFTFGSGTKLEIK |

2081-66-5

| SEQ ID NO: 384 (Kabat) | HCDR1 | NSWMN |
| --- | --- | --- |
| SEQ ID NO: 385 (Kabat) | HCDR2 | RIYPGDGDTQYNEKFKG |
| SEQ ID NO: 386 (Kabat) | HCDR3 | SRSGLDY |
| SEQ ID NO: 387 (Chothia) | HCDR1 | GFTFSNS |
| SEQ ID NO: 388 (Chothia) | HCDR2 | YPGDGD |
| SEQ ID NO: 389 (Chothia) | HCDR3 | SRSGLDY |
| SEQ ID NO: 390 | VH | QVQLQQSGPELVKPGASVRISCKVSGFTFSNSWMN WVKQRPGQGLEWIGRIYPGDGDTQYNEKFKGKAT LTADTSSNTAYIQLNSLTSVDSAVFFCARSRSGLDY WGQGTTLTVSS |
| SEQ ID NO: 391 (Kabat) | LCDR1 | RASQDIYNYLN |
| SEQ ID NO: 392 (Kabat) | LCDR2 | STSRLHS |
| SEQ ID NO: 393 (Kabat) | LCDR3 | HQSHTVPFT |
| SEQ ID NO: 394 (Chothia) | LCDR1 | SQDIYNY |
| SEQ ID NO: 395 (Chothia) | LCDR2 | STS |
| SEQ ID NO: 396 (Chothia) | LCDR3 | SHTVPF |

TABLE 2-continued anti-VP1 Antibodies

| SEQ ID NO: 397 | VL | DIQMTQSTSSLSASLGDRVTISCRASQDIYNYLNWF<br>QQKPDGTVKPLIYSTSRLHSGVSSRFSGSGSGTDYS<br>LTISNLEREDIATYFCHQSHTVPFTFGSGTKLEIK |
|---|---|---|
| 2081-38-5 | | |
| SEQ ID NO: 398<br>(Kabat) | HCDR1 | SSWIN |
| SEQ ID NO: 399<br>(Kabat) | HCDR2 | RIYPGDGDTNYNGKFKG |
| SEQ ID NO: 400<br>(Kabat) | HCDR3 | HSSGFPH |
| SEQ ID NO: 401<br>(Chothia) | HCDR1 | GYTFSSS |
| SEQ ID NO: 402<br>(Chothia) | HCDR2 | YPGDGD |
| SEQ ID NO: 403<br>(Chothia) | HCDR3 | HSSGFPH |
| SEQ ID NO: 404 | VH | QVQLQQSGPELVKPGASVKISCKASGYTFSSSWIN<br>WVKQRPGQGLEWIGRIYPGDGDTNYNGKFKGKAT<br>LTADKSSSTVDMHLSSLTYVDSAVYFCAIHSSGFPH<br>WGQGTLVTVSA |
| SEQ ID NO: 405<br>(Kabat) | LCDR1 | RTSQDISDYLN |
| SEQ ID NO: 406<br>(Kabat) | LCDR2 | YTSRLHS |
| SEQ ID NO: 407<br>(Kabat) | LCDR3 | QQTNTLPFT |
| SEQ ID NO: 408<br>(Chothia) | LCDR1 | SQDISDY |
| SEQ ID NO: 409<br>(Chothia) | LCDR2 | YTS |
| SEQ ID NO: 410<br>(Chothia) | LCDR3 | TNTLPF |
| SEQ ID NO: 411 | VL | DIQMTQTTSSLSASLGGRVTISCRTSQDISDYLNWY<br>QQKPDGAVKLLIYYTSRLHSGVPSRFSGSGSGTDYS<br>LTISNLEQEDIATYFCQQTNTLPFTFGGGTKLEIK |
| 2081-25-6 | | |
| SEQ ID NO: 412<br>(Kabat) | HCDR1 | RYWMN |
| SEQ ID NO: 413<br>(Kabat) | HCDR2 | QIYPGDGDTKYNGKFKD |
| SEQ ID NO: 414<br>(Kabat) | HCDR3 | YGNYGMDY |
| SEQ ID NO: 415<br>(Chothia) | HCDR1 | GYAFSRY |
| SEQ ID NO: 416<br>(Chothia) | HCDR2 | YPGDGD |
| SEQ ID NO: 417<br>(Chothia) | HCDR3 | YGNYGMDY |
| SEQ ID NO: 418 | | QVQLQQSGAELVRPGSSVKISCKASGYAFSRYWM<br>NWVKQRPGQGLEWIGQIYPGDGDTKYNGKFKDTA<br>TLTADKSSSTAYLQLSSLTSEDSAVYFCAKYGNYG<br>MDYWGQGTSVTVSS |

TABLE 2-continued anti-VP1 Antibodies

| | | |
|---|---|---|
| SEQ ID NO: 419 (Kabat) | LCDR1 | RSSQSLEYGNGNTYLN |
| SEQ ID NO: 420 (Kabat) | LCDR2 | RVSNRFS |
| SEQ ID NO: 421 (Kabat) | LCDR3 | LQFTHVPYT |
| SEQ ID NO: 422 (Chothia) | LCDR1 | SQSLEYGNGNTY |
| SEQ ID NO: 423 (Chothia) | LCDR2 | RVS |
| SEQ ID NO: 424 (Chothia) | LCDR3 | FTHVPY |
| SEQ ID NO: 425 | VL | DAVMTQTPLSLPVSLGDQASISCRSSQSLEYGNGNTYLNWYLQKPGQSPQLLIYRVSNRFSGVLDRFSGSGSGTDFTLKISRVEAEDLGVYFCLQFTHVPYTFGGGTKLEIK |
| 2077-4-1 | | |
| SEQ ID NO: 426 (Kabat) | HCDR1 | GYTMN |
| SEQ ID NO: 427 (Kabat) | HCDR2 | LFNPYNGGTRYNQKFKG |
| SEQ ID NO: 428 (Kabat) | HCDR3 | LRNYGIGDDFFDY |
| SEQ ID NO: 429 (Chothia) | HCDR1 | GYSFTGY |
| SEQ ID NO: 430 (Chothia) | HCDR2 | NPYNGG |
| SEQ ID NO: 431 (Chothia) | HCDR3 | LRNYGIGDDFFDY |
| SEQ ID NO: 432 | VH | EVQLQQSGPELVKPGASMKISCKASGYSFTGYTMNWVKQSHGENLEWIGLFNPYNGGTRYNQKFKGKATLTVDKSSSTAYMELLSLTSEDSAVYYCARLRNYGIGDDFFDYWGQGTTLTVSS |
| SEQ ID NO: 433 (Kabat) | LCDR1 | KASQDVGTAVA |
| SEQ ID NO: 434 (Kabat) | LCDR2 | WASTRHT |
| SEQ ID NO: 435 (Kabat) | LCDR3 | QQYSNYPYT |
| SEQ ID NO: 436 (Chothia) | LCDR1 | SQDVGTA |
| SEQ ID NO: 437 (Chothia) | LCDR2 | WAS |
| SEQ ID NO: 438 (Chothia) | LCDR3 | YSNYPY |
| SEQ ID NO: 439 | VL | DIVMTQSHKFMSTSVGDRVSITCKASQDVGTAVAWYQQKPGQSPKLLIYWASTRHTGVPDRFTGSGSGTDFTLTISNVQSEDLTDYFCQQYSNYPYTFGGGTKLEIK |
| 2077-7-5 | | |
| SEQ ID NO: 440 (Kabat) | HCDR1 | GYTMN |
| SEQ ID NO: 441 (Kabat) | HCDR2 | LFNPYNGGINYNQKFKG |

TABLE 2-continued anti-VP1 Antibodies

| SEQ ID NO: 442 (Kabat) | HCDR3 | LRYYGIGDDFFDY |
|---|---|---|
| SEQ ID NO: 443 (Chothia) | HCDR1 | GYSFTGY |
| SEQ ID NO: 444 (Chothia) | HCDR2 | NPYNGG |
| SEQ ID NO: 445 (Chothia) | HCDR3 | LRYYGIGDDFFDY |
| SEQ ID NO: 446 | VH | EVQLQQSGPELVKPGASMKISCKASGYSFTGYTMN WVKQSHGKNLEWIGLFNPYNGGINYNQKFKGKAT LTVDKSSSTAYMELLSLTSEDSAVYYCARLRYYGI GDDFFDYWGQGTSLTVSS |
| SEQ ID NO: 447 (Kabat) | LCDR1 | KASRDVGTAVA |
| SEQ ID NO: 448 (Kabat) | LCDR2 | WASTRHT |
| SEQ ID NO: 449 (Kabat) | LCDR3 | QQYSNYPYT |
| SEQ ID NO: 450 (Chothia) | LCDR1 | SRDVGTA |
| SEQ ID NO: 451 (Chothia) | LCDR2 | WAS |
| SEQ ID NO: 452 (Chothia) | LCDR3 | YSNYPY |
| SEQ ID NO: 453 | VL | DIVMTQSHKFMSTSVGDRVSITCKASRDVGTAVA WYQQKPGQSPKLLIYWASTRHTGVPDRFTGSGSGT DFTLTISNVQSEDLADYFCQQYSNYPYTFGGGTKL EMK |

2077-10-1

| SEQ ID NO: 454 (Kabat) | HCDR1 | GYTMN |
|---|---|---|
| SEQ ID NO: 455 (Kabat) | HCDR2 | LFNPYNGGPNYNQKFKG |
| SEQ ID NO: 456 (Kabat) | HCDR3 | LRYYGIGDDFFDY |
| SEQ ID NO: 457 (Chothia) | HCDR1 | GYSFTGY |
| SEQ ID NO: 458 (Chothia) | HCDR2 | NPYNGG |
| SEQ ID NO: 459 (Chothia) | HCDR3 | LRYYGIGDDFFDY |
| SEQ ID NO: 460 | VH | EVQLQQSGPELVKPGASMKISCKASGYSFTGYTMN WMKQGHGKNLEWIGLFNPYNGGPNYNQKFKGKA TLTVDKSSSTAYMELLSLTSEDSAVYYCARLRYYG IGDDFFDYWGQGTTLTVSS |
| SEQ ID NO: 461 (Kabat) | LCDR1 | KASQDVGTAVA |
| SEQ ID NO: 462 (Kabat) | LCDR2 | WASTRHT |
| SEQ ID NO: 463 (Kabat) | LCDR3 | QQYSSYPYT |
| SEQ ID NO: 464 (Chothia) | LCDR1 | SQDVGTA |

| | | |
|---|---|---|
| TABLE 2-continued | | |
| anti-VP1 Antibodies | | |
| SEQ ID NO: 465 (Chothia) | LCDR2 | WAS |
| SEQ ID NO: 466 (Chothia) | LCDR3 | YSSYPY |
| SEQ ID NO: 467 | VL | DIVMTQSHKFMSTSVGDRVSITCKASQDVGTAVA WYQQKPGQSPKLLIYWASTRHTGVPDRFTGSGSGT DFTLTITNVQSEDLTDYFCQQYSSYPYTFGGGTKLE IK |
| 2077-26-1 | | |
| SEQ ID NO: 468 (Kabat) | HCDR1 | GYTMN |
| SEQ ID NO: 469 (Kabat) | HCDR2 | LFNPYNGGPSYNQKFKG |
| SEQ ID NO: 470 (Kabat) | HCDR3 | LRYYGIGDDFFDY |
| SEQ ID NO: 471 (Chothia) | HCDR1 | GYSFTGY |
| SEQ ID NO: 472 (Chothia) | HCDR2 | NPYNGG |
| SEQ ID NO: 473 (Chothia) | HCDR3 | LRYYGIGDDFFDY |
| SEQ ID NO: 474 | VH | EVQLQQSGPDLVKPGASMKLSCKASGYSFTGYTM NWVKQSHGKNLEWIGLFNPYNGGPSYNQKFKGKA TLTVDKSSSTAYMELLSLTPEDSAVYYCARLRYYG IGDDFFDYWGQGTTLTVSS |
| SEQ ID NO: 475 (Kabat) | LCDR1 | KASQDVGTAVA |
| SEQ ID NO: 476 (Kabat) | LCDR2 | WASTRHT |
| SEQ ID NO: 477 (Kabat) | LCDR3 | QQYSNYPYT |
| SEQ ID NO: 478 (Chothia) | LCDR1 | SQDVGTA |
| SEQ ID NO: 479 (Chothia) | LCDR2 | WAS |
| SEQ ID NO: 480 (Chothia) | LCDR3 | YSNYPY |
| SEQ ID NO: 481 | VL | DIVMTQSHKFMSTSVGDRVSITCKASQDVGTAVA WYQEKPGQSPKLLIYWASTRHTGVPDRFTGSGSGT DFTLTISNVQSEDLAYYFCQQYSNYPYTFGGGTKL EIK |
| 2077-28-2 | | |
| SEQ ID NO: 482 (Kabat) | HCDR1 | GYTMN |
| SEQ ID NO: 483 (Kabat) | HCDR2 | LFNPYNGGATYNQRFKG |
| SEQ ID NO: 484 (Kabat) | HCDR3 | LRKYGIGDDFFDY |
| SEQ ID NO: 485 (Chothia) | HCDR1 | GYSFTGY |
| SEQ ID NO: 486 (Chothia) | HCDR2 | NPYNGG |
| SEQ ID NO: 487 (Chothia) | HCDR3 | LRKYGIGDDFFDY |

TABLE 2-continued anti-VP1 Antibodies

| SEQ ID NO: 488 | VH | EVQLQQSGPELVKPGASMKISCKASGYSFTGYTMN WVKQSHGKNLEWIGLFNPYNGGATYNQRFKGKA TLTVDKSSSTAYMDLLSLTSEDSAVYYCTRLRKYG IGDDFFDYWGQGTTLTVSS |
| --- | --- | --- |
| SEQ ID NO: 489 (Kabat) | LCDR1 | KASQDVGTAVA |
| SEQ ID NO: 490 (Kabat) | LCDR2 | WASTRHT |
| SEQ ID NO: 491 (Kabat) | LCDR3 | QQYSTYTYT |
| SEQ ID NO: 492 (Chothia) | LCDR1 | SQDVGTA |
| SEQ ID NO: 493 (Chothia) | LCDR2 | WAS |
| SEQ ID NO: 494 (Chothia) | LCDR3 | YSTYTY |
| SEQ ID NO: 495 | VL | DIVMTQSHKFMSTSVGDRVSITCKASQDVGTAVA WYQQKPGQSPKLLIYWASTRHTGVPDRFTGSGSGT DFTLTISNVQSEDLADYFCQQYSTYTYTFGGGTKL EIK |

P8D11

| SEQ ID NO: 508 (Combined) | HCDR1 | GFTFNNYWMT |
| --- | --- | --- |
| SEQ ID NO: 509 (Combined) | HCDR2 | NIKKDGSEKYYVDSVRG |
| SEQ ID NO: 510 (Combined) | HCDR3 | VRSGRYFALDD |
| SEQ ID NO: 511 (Combined) | LCDR1 | GGDNIGSRPVH |
| SEQ ID NO: 512 (Combined) | LCDR2 | DDSNRPS |
| SEQ ID NO: 513 (Combined) | LCDR3 | QVWSSSTDHP |

P8D11A

| SEQ ID NO: 514 (Combined) | HCDR1 | GFTFSNYWMT |
| --- | --- | --- |
| SEQ ID NO: 515 (Combined) | HCDR2 | NIKKDGSEKYYVDSVRG |
| SEQ ID NO: 516 (Combined) | HCDR3 | VRSGRYFALDD |
| SEQ ID NO: 517 (Combined) | LCDR1 | GGDNIGSRPVH |
| SEQ ID NO: 518 (Combined) | LCDR2 | DDSNRPS |
| SEQ ID NO: 519 (Combined) | LCDR3 | QVWSSSTDHP |

P8D11B

| SEQ ID NO: 520 (Combined) | HCDR1 | GFTFKNYWMT |
| --- | --- | --- |
| SEQ ID NO: 521 (Combined) | HCDR2 | NIKKDGSEKYYVDSVRG |

TABLE 2-continued anti-VP1 Antibodies

| | | |
|---|---|---|
| SEQ ID NO: 522 (Combined) | HCDR3 | VRSGRYFALDD |
| SEQ ID NO: 523 (Combined) | LCDR1 | GGDNIGSRPVH |
| SEQ ID NO: 524 (Combined) | LCDR2 | DDSNRPS |
| SEQ ID NO: 525 (Combined) | LCDR3 | QVWSSSTDHP |

P8D11C

| | | |
|---|---|---|
| SEQ ID NO: 526 (Combined) | HCDR1 | GFTFQNYWMT |
| SEQ ID NO: 527 (Combined) | HCDR2 | NIKKDGSEKYYVDSVRG |
| SEQ ID NO: 528 (Combined) | HCDR3 | VRSGRYFALDD |
| SEQ ID NO: 529 (Combined) | LCDR1 | GGDNIGSRPVH |
| SEQ ID NO: 530 (Combined) | LCDR2 | DDSNRPS |
| SEQ ID NO: 531 (Combined) | LCDR3 | QVWSSSTDHP |

P8D11D

| | | |
|---|---|---|
| SEQ ID NO: 532 (Combined) | HCDR1 | GFTFNNYWMT |
| SEQ ID NO: 533 (Combined) | HCDR2 | NIKKDGSEKYYVDSVRG |
| SEQ ID NO: 534 (Combined) | HCDR3 | VRSGRYFALDD |
| SEQ ID NO: 535 (Combined) | LCDR1 | GGDNIGSRPVH |
| SEQ ID NO: 536 (Combined) | LCDR2 | DDSNRPS |
| SEQ ID NO: 537 (Combined) | LCDR3 | QVWSSSTDHP |

P8D11E

| | | |
|---|---|---|
| SEQ ID NO: 538 (Combined) | HCDR1 | GFTFNNYWMT |
| SEQ ID NO: 539 (Combined) | HCDR2 | NIKKDGSEKYYVDSVRG |
| SEQ ID NO: 540 (Combined) | HCDR3 | VRSGRYFALDD |
| SEQ ID NO: 541 (Combined) | LCDR1 | GGDNIGSRPVH |
| SEQ ID NO: 542 (Combined) | LCDR2 | DDSNRPS |
| SEQ ID NO: 543 (Combined) | LCDR3 | QVWSSSTDHP |

Other antibodies of the present disclosure include those where the amino acids or nucleic acids encoding the amino acids have been mutated; yet have at least 60, 70, 80, 90 or 95 percent identity to the sequences described in Table 2. In some aspects, it includes mutant amino acid sequences wherein no more than 1, 2, 3, 4 or 5 amino acids have been mutated in the variable regions when compared with the variable regions depicted in the sequence described in Table 2, while retaining substantially the same therapeutic activity.

Since each of these antibodies can bind to VP1, the VH, VL, full length light chain, and full length heavy chain sequences (amino acid sequences and the nucleotide sequences encoding the amino acid sequences) can be "mixed and matched" to create other VP1-binding antibodies. Such "mixed and matched" VP1-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise, a full length light chain sequence from a particular full length heavy chain/full length light chain pairing should be replaced with a structurally similar full length light chain sequence. Accordingly, in one aspect, the disclosure provides for an isolated monoclonal antibody or antigen binding region thereof having: a heavy chain variable region comprising an amino acid sequence selected from the group consisting of SEQ ID NO: 12, 32, 52, 72, 92, 112, 132, 152, 172, 192, 212, 232, 252, 272, 292, 312, 328, 348, 362, 376, 390, 404, 418, 432, 446, 460, 474, and 488 (Table 2); and a light chain variable region comprising an amino acid sequence selected from the group consisting of SEQ ID NO: 22, 42, 62, 82, 102, 122, 142, 162, 182, 202, 222, 242, 262, 282, 302, 320, 338, 355, 369, 383, 397, 411, 425, 439, 453, 467, 481 and 495 (Table 2); wherein the antibody specifically binds to VP1.

In another aspect, the disclosure provides (i) an isolated monoclonal antibody having: a full length heavy chain comprising an amino acid sequence that has been optimized for expression in the cell of a mammalian selected from the group consisting of SEQ ID NOs: 14, 34, 54, 74, 94, 114, 134, 154, 174, 194, 214, 234, 254, 274, 294, 313 and 330; and a full length light chain comprising an amino acid sequence that has been optimized for expression in the cell of a mammalian selected from the group consisting of SEQ ID NOs: 24, 44, 64, 84, 104, 124, 144, 164, 184, 204, 224, 244, 264, 284, 304, 321, 340, or (ii) a functional protein comprising an antigen binding portion thereof.

In another aspect, the present disclosure provides VP1-binding antibodies that comprise the heavy chain and light chain CDR1s, CDR2s and CDR3s as described in Table 2, or combinations thereof. The amino acid sequences of the VH CDR1s of the antibodies are shown in SEQ ID NOs: 6, 26, 46, 66, 86, 106, 126, 146, 166, 186, 206, 226, 246, 266, 286, 306, 322, 342, 356, 370, 384, 398, 412, 426, 440, 454, 468, and 482. The amino acid sequences of the VH CDR2s of the antibodies and are shown in SEQ ID NOs: 7, 27, 47, 67, 87, 107, 127, 147, 167, 187, 207, 227, 247, 267, 287, 307, 323, 343, 357, 371, 385, 399, 413, 427, 441, 455, 469, and 483. The amino acid sequences of the VH CDR3s of the antibodies are shown in SEQ ID NOs: 8, 28, 48, 68, 88, 108, 128, 148, 168, 188, 208, 228, 248, 268, 288, 308, 324, 344, 358, 372, 386, 400, 414, 428, 442, 456, 470, and 484. The amino acid sequences of the VL CDR1s of the antibodies are shown in SEQ ID NOs: 16, 36, 56, 76, 96, 116, 136, 156, 176, 196, 216, 236, 256, 276, 296, 314, 332, 349, 363, 377, 391, 405, 419, 433, 447, 461, 475 and 489. The amino acid sequences of the VL CDR2s of the antibodies are shown in SEQ ID NOs 17, 37, 57, 77, 97, 117, 137, 157, 177, 197, 217, 237, 257, 277, 297, 315, 333, 350, 364, 378, 392, 406, 420, 434, 448, 462, 476 and 490. The amino acid sequences of the VL CDR3s of the antibodies are shown in SEQ ID NOs: 18, 38, 58, 78, 98, 118, 138, 158, 178, 198, 218, 238, 258, 278, 298, 316, 334, 351, 365, 379, 393, 407, 421, 435, 449, 463, 477 and 491.

Given that each of these antibodies can bind to VP1 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody must contain a VH CDR1, 2 and 3 and a VL CDR1, 2 and 3 to create other VP1-binding binding molecules. Such "mixed and matched" VP1-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present disclosure.

Accordingly, the present disclosure provides an isolated monoclonal antibody or antigen binding region thereof comprising a heavy chain CDR1 comprising an amino acid sequence selected from the group consisting of SEQ ID NOs: 6, 26, 46, 66, 86, 106, 126, 146, 166, 186, 206, 226, 246, 266, 286, 306, 322, 342, 356, 370, 384, 398, 412, 426, 440, 454, 468, and 482; a heavy chain CDR2 comprising an amino acid sequence selected from the group consisting of SEQ ID NOs: 7, 27, 47, 67, 87, 107, 127, 147, 167, 187, 207, 227, 247, 267, 287, 307, 323, 343, 357, 371, 385, 399, 413, 427, 441, 455, 469, and 483; a heavy chain CDR3 comprising an amino acid sequence selected from the group consisting of SEQ ID NOs: 8, 28, 48, 68, 88, 108, 128, 148, 168, 188, 208, 228, 248, 268, 288, 308, 324, 344, 358, 372, 386, 400, 414, 428, 442, 456, 470, and 484; a light chain CDR1 comprising an amino acid sequence selected from the group consisting of SEQ ID NOs: 16, 36, 56, 76, 96, 116, 136, 156, 176, 196, 216, 236, 256, 276, 296, 314, 332, 349, 363, 377, 391, 405, 419, 433, 447, 461, 475 and 489; a light chain CDR2 comprising an amino acid sequence selected from the group consisting of SEQ ID NOs: 17, 37, 57, 77, 97, 117, 137, 157, 177, 197, 217, 237, 257, 277, 297, 315, 333, 350, 364, 378, 392, 406, 420, 434, 448, 462, 476 and 490; and a light chain CDR3 comprising an amino acid sequence selected from the group consisting of SEQ ID NOs: 18, 38, 58, 78, 98, 118, 138, 158, 178, 198, 218, 238, 258, 278, 298, 316, 334, 351, 365, 379, 393, 407, 421, 435, 449, 463, 477 and 491; wherein the antibody specifically binds to VP1.

In certain aspects, an antibody that specifically binds to VP1 is an antibody or antibody fragment (e.g., antigen binding fragment) that is described in Table 2.

1. Identification of Epitopes and Antibodies that Bind to the Same Epitope

The present disclosure provides antibodies and antibody fragments (e.g., antigen binding fragments) that bind to an epitope of VP1. In certain aspects the antibodies and antibody fragments can bind to the same epitope within all four BKV serotypes and/or JCV.

The present disclosure also provides antibodies and antibody fragments (e.g., antigen binding fragments) that bind to the same epitope as do the anti-VP1 antibodies described in Table 2. Additional antibodies and antibody fragments (e.g., antigen binding fragments) can therefore be identified based on their ability to cross-compete (e.g., to competitively inhibit the binding of, in a statistically significant manner) with other antibodies in binding assays. The ability of a test antibody to inhibit the binding of antibodies and antibody fragments (e.g., antigen binding fragments) of the present disclosure to VP1 (e.g., human BKV or JCV VP1) demonstrates that the test antibody can compete with that antibody or antibody fragment (e.g., antigen binding fragments) for binding to VP1; such an antibody may, according to non-limiting theory, bind to the same or a related (e.g., a structurally similar or spatially proximal) epitope on VP1 as the antibody or antibody fragment (e.g., antigen binding fragments) with which it competes. In a certain aspect, the antibody that binds to the same epitope on VP1 as the antibodies or antibody fragments (e.g., antigen binding fragments) of the present disclosure is a human or humanized monoclonal antibody. Such human or humanized monoclonal antibodies can be prepared and isolated as described herein.

2. Further Alteration of the Framework of Fc Region

The present disclosure disclosed specific anti-VP1 antibodies. These antibodies comprise modified antibodies or antigen binding fragments thereof that further comprise modifications to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies can be engineered to include modifications within the Fc region, typically to alter one or more functional properties of the antibody, such as serum half-life, complement fixation, Fc receptor binding, and/or antigen-dependent cellular cytotoxicity. Furthermore, an antibody can be chemically modified (e.g., one or more chemical moieties can be attached to the antibody) or be modified to alter its glycosylation, again to alter one or more functional properties of the antibody. Each of these aspects is described in further detail below.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another aspect, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another aspect, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another aspect, one or more amino acid residues are altered to thereby alter the ability of the antibody to fix complement. This approach is described in, e.g., the PCT Publication WO 94/29351 by Bodmer et al. In a specific aspect, one or more amino acids of an antibody or antigen binding fragment thereof of the present disclosure are replaced by one or more allotypic amino acid residues, for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγR1, FcγRII, FcγRIII and FcRn have been mapped and variants with improved binding have been described (see Shields et al., J. Biol. Chem. 276:6591-6604, 2001).

In still another aspect, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another aspect, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In order to minimize the ADCC activity of an antibody, specific mutations in the Fc region result in "Fc silent" antibodies that have minimal interaction with effector cells. In general, the "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody.

Silenced effector functions can be obtained by mutation in the Fc region of the antibodies and have been described in the art: LALA and N297A (Strohl, W., 2009, Curr. Opin. Biotechnol. vol. 20(6):685-691); and D265A (Baudino et al., 2008, J. Immunol. 181: 6664-69) see also Heusser et al., WO2012065950. Examples of silent Fc IgG1 antibodies are the LALA mutant comprising L234A and L235A mutation in the IgG1 Fc amino acid sequence. Another example of a silent IgG1 antibody is the DAPA (D265A, P329A) mutation (U.S. Pat. No. 6,737,056). Another silent IgG1 antibody comprises the N297A mutation, which results in aglycosylated/non-glycosylated antibodies.

Fc silent antibodies result in no or low ADCC activity, meaning that an Fc silent antibody exhibits an ADCC activity that is below 50% specific cell lysis (low ADCC activity), or that is below 1% specific cell lysis (no ADCC activity).

3. Production of the Anti-VP1 Antibodies

Anti-VP1 antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The disclosure further provides polynucleotides encoding the antibodies described herein, e.g., polynucleotides encoding heavy or light chain variable regions or segments comprising the complementarity determining regions as described herein. In some aspects, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 13, 33, 53, 73, 93, 113, 133, 153, 173, 193, 213, 233, 253, 273 and 293. In some aspects, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs:23, 43, 63, 83, 103, 123, 143, 163, 183, 203, 223, 243, 263, 283 and 303.

In some aspects, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 15, 35, 55, 75, 95, 115, 135, 155, 175, 195, 215, 235, 255, 275 and 295. In some aspects, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 25, 45, 65, 85, 105, 125, 145, 165, 185, 205, 225, 245, 265, 285 and 305.

The polynucleotides of the present disclosure can encode only the variable region sequence of an anti-VP1 antibody. They can also encode both a variable region and a constant region of the antibody. Some of the polynucleotide sequences encode a polypeptide that comprises variable regions of both the heavy chain and the light chain of one of an exemplified anti-VP1 antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-VP1 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, C A, 1990; Mattila et al., Nucleic Acids Res. 19:967, 1991; and Eckert et al., PCR Methods and Applications 1:17, 1991.

Also provided in the present disclosure are expression vectors and host cells for producing the anti-VP1 antibodies described above. Various expression vectors can be employed to express the polynucleotides encoding the anti-VP1 antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-VP1 polynucleotides and polypeptides in mammalian (e.g., human) cells include pThioHis A, B & C, pcDNA3.1/His, pEBVHis A, B & C (Invitrogen, San Diego, CA), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-VP1 antibody chain or fragment. In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements may also be required or desired for efficient expression of an anti-VP1 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-VP1 antibody sequences. More often, the inserted anti-VP1 antibody sequences are linked to a signal sequences before inclusion in the vector. Vectors to be used to receive sequences encoding anti-VP1 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-VP1 antibody chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-VP1 polypeptides. Insect cells in combination with baculovirus vectors can also be used.

In other aspects, mammalian host cells are used to express and produce the anti-VP1 polypeptides of the present disclosure. For example, they can be either a hybridoma cell line expressing endogenous immunoglobulin genes (e.g., the myeloma hybridoma clones as described in the Examples) or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-VP1 antibody chains or binding fragments can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic and Diagnostic Uses

The antibodies, antibody fragments (e.g., antigen binding fragments) of the present disclosure are useful in a variety of applications including, but not limited to, polyoma viral infection and disease. In certain aspects, the antibodies, antibody fragments (e.g., antigen binding fragments), and are useful for neutralizing BKV or JCV infection and the prevention or treatment of BK virus nephropathy, for example, BKVAN). The methods of use can be in vitro, ex vivo, or in vivo methods.

In one aspect, the antibodies, antibody fragments (e.g., antigen binding fragments), are useful for detecting the presence of BKV in a biological sample. The term "detecting" as used herein encompasses quantitative or qualitative detection. In certain aspects, a biological sample comprises a cell or tissue. In certain aspects, such tissues include normal and/or cancerous tissues that express BKV at higher levels relative to other tissues.

In one aspect, the present disclosure provides a method of detecting the presence of BKV in a biological sample. In certain aspects, the method comprises contacting the biological sample with an anti-VP1 antibody under conditions permissive for binding of the antibody to the antigen, and detecting whether a complex is formed between the antibody and the antigen. The biological sample can include, without limitation, urine or blood samples.

Also included is a method of diagnosing a disorder associated with expression of BKV or JCV virus. In certain aspects, the method comprises contacting a test cell with an anti-VP1 antibody; determining the level of expression (either quantitatively or qualitatively) of BK virus in the test cell by detecting binding of the anti-VP1 antibody to the BK virus; and comparing the level of infection in the test cell with the level of infection of BK virus in a control cell (e.g., a normal cell of the same tissue origin as the test cell or a non-BK virus infected cell), wherein a higher level of presence of BK virus in the test cell as compared to the control cell indicates the presence of a disorder associated with infection with BK virus. In certain aspects, the test cell is obtained from an individual suspected of having a BK virus infection.

In certain aspects, a method of diagnosis or detection, such as those described above, comprises detecting binding of an anti-VP1 antibody to a BKV infected cell. An exemplary assay for detecting binding of an anti-VP1 antibody to a BKV infected cell is a "FACS" assay.

Certain other methods can be used to detect binding of anti-VP1 antibodies. Such methods include, but are not limited to, antigen-binding assays that are well known in the art, such as Western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain aspects, anti-VP1 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain aspects, anti-VP1 antibodies are immobilized on an insoluble matrix. Immobilization entails separating the anti-VP1 antibody from any BKV or JCV proteins that remains free in solution. This conventionally is accomplished by either insolubilizing the anti-VP1 antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-VP1 antibody after formation of a complex between the anti-VP1 antibody and BKV or JCV protein, e.g., by immunoprecipitation.

Any of the above aspects of diagnosis or detection can be carried out using an anti-VP1 antibody of the present disclosure in place of or in addition to another anti-VP1 antibody.

In one aspect, the disclosure provides for a method of treating, reducing the likelihood of or ameliorating a disease comprising administering the antibodies, antibody fragments (e.g., antigen binding fragments), to a patient, thereby treating the disease. In certain aspects, the disease treated with the antibodies, antibody fragments (e.g., antigen binding fragments), is BK viral or JC viral infection. Examples of BKV and JCV diseases which can be treated and/or prevented include, but are not limited to, nephropathy, hemorrhagic cystitis, Progressive Multifocal Leukoencephalopathy (PML), interstitial kidney disease, ureteral stenosis, granule cell neuronopathy (GCN), vasculitis, colitis, retinitis, meningitis, and immune reconstitution inflammatory syndrome (IRIS). In certain aspects, the infection is characterized by BKV or JCV expressing cells to which the anti-VP1 antibodies, antibody fragments (e.g., antigen binding fragments) can specifically bind.

The present disclosure provides for methods of treating BK viral infection and BKVAN comprising administering a therapeutically effective amount of the antibodies, antibody fragments (e.g., antigen binding fragments). In certain aspects, the subject is a human.

In certain aspects, the method of reducing BK viral infection comprises administering to a subject a therapeutically effective amount of antibodies or antibody fragments (e.g., antigen binding fragments). In certain aspects, the subject is a human. In certain aspects, the subject is immunosuppressed. For immunosuppressed subjects, the amount of immunosuppression can be increased or decreased due to the therapeutic effects of the anti-VP1 antibodies.

In certain aspects, the transplanted tissue is infected with BK virus to which the anti-VP1 antibody binds. As the incidence of BK infection in the general population is high, there is a high probability that in the case of kidney transplantation, the patient accepting the kidney is BK virus positive or the donor providing the kidney is BK virus positive or both are BK virus positive. In order to prevent BKVAN, anti-VP1 antibodies can be administered to the kidney transplant recipient, before and/or after the kidney transplant procedure, depending on the seropositivity of the kidney donor or transplant recipient. In another aspect, the anti-VP1 antibodies can be administered to the patient when virus is detected in the urine (viruria), or when virus is detected in the blood (viremia).

For the treatment of BK or JCV viral infection, the appropriate dosage of the antibodies, or antibody fragments (e.g., antigen binding fragments), depend on various factors, such as the type of infection to be treated, the severity and course of the infection, the responsiveness of the infection, the generation of viral resistance to therapy, previous therapy, patient's clinical history, and so on. The antibody can be administered one time or over a series of treatments lasting from several days to several months, or until a cure is effected or a diminution of the infection is achieved (e.g., reduction in viruria or viral damage to the kidney). Optimal dosing schedules can be calculated from measurements of drug accumulation in the body of the patient and will vary depending on the relative potency of an individual antibody or antibody fragment (e.g., antigen binding fragment). In certain aspects, dosage is from 0.01 mg to 10 mg (e.g., 0.01 mg, 0.05 mg, 0.1 mg, 0.5 mg, 1 mg, 2 mg, 3 mg, 4 mg, 5 mg, 7 mg, 8 mg, 9 mg, or 10 mg) per kg of body weight, and can be given once or more daily, weekly, monthly or yearly. In certain aspects, the antibody or antibody fragment (e.g., antigen binding fragment), of the present disclosure is given once every two weeks or once every three weeks. The treating physician can estimate repetition rates for dosing based on measured half-life and concentrations of the antibody in bodily fluids or tissues.

Combination Therapy

In certain instances, the antibody or antibody fragment (e.g., antigen binding fragment), of the present disclosure is combined with other therapeutic agents, such as other antiviral agents, anti-allergic agents, anti-nausea agents (or anti-emetics), pain relievers, cytoprotective agents, immunosuppressants and combinations thereof.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or infection described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating BKV or JCV infection by administering to a subject in need thereof an antibody in together with immunosuppressant therapies. The anti-VP1 antibodies will act prophylactically to neutralize BKV or JCV primary infection or viral reactivation resulting from the immunosuppressant therapy prior to or post-transplantation. Examples of immunosuppressant therapy include, but are not limited to; a monophosphate dehydrogenase inhibitor, a purine synthesis inhibitor, a calcineurin inhibitor or an mTOR inhibitor. Specific examples of immunosuppressive therapeutics include but are not limited to; mycophenolate mofetil (MMF), mycophenolate sodium, azathioprine, tacrolimus, sirolimus and cyclosporine.

Pharmaceutical Compositions

To prepare pharmaceutical or sterile compositions including anti-VP1 antibodies, the antibodies of the present disclosure are mixed with a pharmaceutically acceptable carrier or excipient. The compositions can additionally contain one or more other therapeutic agents that are suitable for neutralizing BKV or JCV infection.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: Tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

In a specific aspect, the anti-VP1 antibody is a lyophilisate in a vial containing the antibody. The lyophilisate can be reconstituted with water or a pharmaceutical carrier suitable for injection. For subsequent intravenous administration, the obtained solution will usually be further diluted into a carrier solution.

The antibodies disclosed herein are useful in the neutralization of BKV or JCV in tissue transplant patients who can be immunosuppressed, so a pharmaceutical carrier of sucrose and human albumin as used previously in bone marrow transplant patients receiving CytoGam® can be used (DeRienzo et al. Pharmacotherapy 2000; 20:1175-8). Alternatively, the anti-VP1 antibodies can be introduced into transplant patients via a pharmaceutical carrier as described for another anti-viral antibody, Synagis®, as described in WO2003/105894. In this publication, the pharmaceutical carrier was comprised of histidine and/or glycine, a saccharide (e.g. sucrose) and a polyol (e.g. polysorbate).

Selecting an administration regimen for a therapeutic depends on several factors, including the severity of the infection, the level of symptoms, and the accessibility of the target cells in the biological matrix. In certain aspects, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., infusion reactions.

Actual dosage levels of the active ingredients in the pharmaceutical compositions with the anti-VP1 antibodies can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the neutralizing activity of the antibodies, the route of administration, the time of administration, the half-life of the antibody in the patient, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof can be provided by continuous infusion, or by doses at intervals of, e.g., one day, one week, or 1-7 times per week. Doses can be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the antibodies described herein, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof can be calculated using the patient's weight in kilograms (kg) multiplied by the dose to be administered in mg/kg.

Doses of the antibodies then can be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present disclosure can also be administered via one or more routes of administration using one or more of a variety of methods known in the art. As will be appreciated by the skilled artisan, the route and/or mode of administration will vary depending upon the desired results. Selected routes of administration for the antibodies include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually or topically. In one aspect, the antibodies of the present disclosure are administered by infusion. In another aspect, the antibodies are administered subcutaneously.

If the antibodies of the present disclosure are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the antibodies (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann.

Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly (methyl methacrylate), poly(acrylic acid), poly(ethylene-covinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one aspect, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more antibodies of the present disclosure. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the antibodies of the disclosure are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the antibodies are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., an immunosuppressant, a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the anti-VP1 antibodies may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the anti-VP1 antibodies of the present disclosure. The two or more therapies may be administered within one same patient visit.

In certain aspects, anti-VP1 antibodies can be formulated to ensure proper distribution in vivo. For example, the blood-brain barrier (BBB) excludes many highly hydrophilic compounds. To ensure that the anti-VP1 antibodies cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The present disclosure provides protocols for the administration of pharmaceutical composition comprising antibodies alone or in combination with other therapies to a subject in need thereof. The combination therapies (e.g., prophylactic or therapeutic agents) can be administered concomitantly or sequentially to a subject. The therapy (e.g., prophylactic or therapeutic agents) of the combination therapies can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof are administered to a subject in a sequence and within a time interval such that the antibodies can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various aspects, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other aspects, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Generation of Anti-VP1 Antibodies

B cells expressing anti-VP1 antibodies were lysed and the VH (heavy) and VL (light) chains were sequenced by RT-PCR and analyzed to identify critical post translational modification (PTM) sites. Plasmids of the VH and VL chains were then transfected in a CHO mammalian cell line in an IgG1 back bone vector for expression of the full IgG1 antibodies.

Methods for generation of monoclonal antibodies using hybridoma technology are known in the art (Antibody Methods and Protocols, Methods in Molecular Biology vol. 901, 2012, Chapter 7: 117). Briefly, female Balb/c mice were immunized with VLPs from BKV serotype I, serotype IV, and JCV (either individually or in combination) using various prime-boost strategies, doses of immunogen, and adjuvants (including but not limited to Freund's adjuvant and MF59 adjuvant). Supernatant of successfully fused (growing) hybridomas were screened for the presence of anti-VP1 antibodies by ELISA, then for functional activity in neutralization assays. CDRs from select murine IgGs were humanized by grafting onto human framework acceptor templates, cloned into mammalian IgG1 backbone expression vectors and transfected in a CHO mammalian cell line for expression of the full IgG1 antibodies.

Methods for generation of monoclonal antibodies using phage display technology are known in the art (Antibody Methods and Protocols, Methods in Molecular Biology vol. 901, 2012, Chapter 3: 33). Briefly, a human B-cell antibody library in scFv format with Vi was screened for anti-VP1 antibodies by solution panning with streptavidin-coupled magnetic beads complexed with biotinylated BKV serotype IV VLPs over 3 rounds of selection with increasing stringency. Isolates were first expressed as scFv and screened for binding to both BKV serotype IV VLPs and pentamers by ELISA. Select isolates were then cloned and expressed as IgG1, reanalyzed for binding to VP1 (serotype I and IV) by ELISA and for functional activity in neutralization assays, and transfected in a CHO mammalian cell line for expression of the full IgG1 antibodies.

A summary of the anti-VP1 antibodies is provided in Table 3.

TABLE 3

| anti-VP1 antibodies | |
| --- | --- |
| Antibody | |
| P165E2 | |
| NEG447 | P165E2 changes: germlined/affinity matured for serotype IV; VH (T35S, E43A, A73T, S74N), VL (R17K, G61D, A86V) resulted in no significant change in affinity or activity. |
| NEG447A | P165E2 changes: germlined NEG447; VL (L10V, V86D) resulted in ~3-fold greater affinity and ~8-fold more potent activity (EC90) on serotype II, ~10-fold greater affinity for serotype IV |
| P7G11 | |
| P7G11A | P7G11 variant: germlined P7G11; VH (A12V, S23T, I69V, M71I, T85S) resulted in ~150-fold greater affinity for serotype II, ~14-fold greater affinity for serotype IV |
| P8D11 | |
| P8D11A | P8D11 change to remove post-translational modification: N30S in HCDR1 resulted in no significant change in affinity or activity |
| P8D11B | P8D11 change to remove post-translational modification: N30K in HCDR1 resulted in no significant change in affinity or activity |
| P8D11C | P8D11 change to remove post-translational modification: N30Q in HCDR1 resulted in no significant change in affinity or activity |
| P8D11D | P8D11 change in Heavy Chain framework 1 region to fix proteolysis/clipping liability (V5Q, G9P, T10G) resulted in no significant change in affinity or activity |
| P8D11E | P8D11 change in Heavy Chain framework 1 region to fix proteolysis/clipping liability (T10G) resulted in no significant change in affinity or activity |
| P46F4 | |
| EBB-C1975-B5 | phage display |
| EBB-C1975-A3 | phage display |

TABLE 3-continued anti-VP1 antibodies

| Antibody | |
|---|---|
| EBB-C1975-A7 | phage display |
| EBB-C1975-E7 | phage display |
| 2081-20-8 | mouse hybridoma |
| 2075-16-1 | mouse hybridoma |
| 2075-456-4 | mouse hybridoma |
| 2081-36-8 | mouse hybridoma |
| 2081-66-5 | mouse hybridoma |
| 2081-38-5 | mouse hybridoma |
| 2081-25-6 | mouse hybridoma |
| 2077-4-1 | mouse hybridoma |
| 2077-7-5 | mouse hybridoma |
| 2077-10 1 | mouse hybridoma |
| 2077-26-1 | mouse hybridoma |
| 2077-28-2 | mouse hybridoma |

Example 2: Affinity Maturation of Anti-VP Antibodies

The anti-VP1 antibodies were affinity matured in yeast by error-prone PCR or CDR-directed mutagenesis. VP1 proteins from each of the four serotypes of BKV (as shown in Table 4) were used as the antigen in up to three rounds of selection by FACS analysis. VH (heavy) and/or VL (light) chains with enhanced binding affinity to VP1 by FACS analysis were then cloned into mammalian IgG1 backbone expression vectors and transfected in a CHO mammalian cell line for expression of the full IgG1 antibodies.

TABLE 4

| Name | VP1 protein | SEQ ID NO |
|---|---|---|
| Serotype 1, amino acids 66-145 | FSLKLSAENDFSSDSPERKMLPCYSTARIPLP NLNEDLTCGNLLMWEAVTVQTEVIGITSML NLHAGSQKVHEHGGGKPI | (SEQ ID NO: 496) |
| Serotype II, amino acids 66-145 | YSLKLTAENAFDSDSPDKKMLPCYSTARIPL PNLNEDLTCGNLLMWEAVTVKTEVIGITSM LNLHAGSQKVHENGGGKPV | (SEQ ID NO: 497) |
| Serotype III, amino acids 66-145 | YSQHLSAENAFDSDSPDKKMLPCYSTARIPL PNLNEDLTCGNLLMWEAVTVKTEVIGITSM LNLHAGSQKVHENGGGKPV | (SEQ ID NO: 498) |
| Serotype IV, amino acids 66-145 | YSLRLTAETAFDSDSPDRKMLPCYSTARIPLP NLNEDLTCGNLLMWEAVTVKTEVIGITSML NLHAGSQKVHENGGGKPI | (SEQ ID NO: 499) |

Example 3: BK Virus and Virus-Like Particle (VLP) Generation

Genomic clones of BKV serotype I were obtained from ATCC (pBR322-BKV MM, cat #45026; pBR322-BKV Dunlop, cat #45025). Infectious genomic clones of chimeric viruses for serotype II, III and IV were generated using the cloning strategy described previously (Broekema et al, Virology 2010 407:368-373). Briefly, unique restriction sites (SacII, PmlI) were introduced into BKV serotype I genomes flanking the VP1-VP2-VP3 coding region using site-directed mutagenesis. The coding region for VP1 from serotype II isolate SB (GenBank Accession CAA79596.1), serotype III isolate AS (GenBank Accession AAA46882.1) and serotype IV strain ITA-4 (GenBank Accession BAF75132) were synthesized in the context of VP2/VP3 coding region from the serotype I isolates (Genewiz, La Jolla, CA), such that the synthesized fragments encompassed the SacII-PmlI region to be used for swap combinations as described in Broekema et al., supra. The resulting chimeric genomic clones were then used to generate high titer infectious viral stocks in primary renal proximal tubule epithelial (RPTE) cells (ATCC, cat #PCS-400-010) as previously described (Abend et al, J. Virology 2007 81:272-279).

VLPs representing each of the four BKV serotypes were generated by expression of VP1 in Sf9 insect cells and extracted from frozen cell pellets from 1 L cultures by microtip sonication (3×45 second pulses, rest 5 min between pulses on ice), isolation by pelleting VLPs through a 20% sucrose cushion (116,000 g for 2.5 hours), and purification by anion exchange with a 5 ml GE HiTrap Q HP column (GE Healthcare, Pittsburgh, PA) followed by purification using a 10 ml Capto™ Core700 (GE Healthcare, Pittsburgh, PA) resin-based size exclusion column, and finally purification on a GE Sephacryl S500 26/60 (GE Healthcare, Pittsburgh, PA) size exclusion column. The prepared VLPs were used in ELISA and SPR based binding assays in Examples 6 and 7.

Example 4: Purification of BKV VP1 Pentamers

VP1 proteins from each of the four serotypes of BKV (sequences shown in Table 5 below) were cloned with N terminal GST-6×His-TEV sequences and subcloned into pGEX destination vector (GE Healthcare, Pittsburgh, PA). GST fusion proteins were expressed in E. coli, extracted from cell pellets using a microfluidizer (15,000 PSI), and purified by immobilized metal ion affinity chromatography (IMAC) using a 20 ml nickel sepharose 6 Fast Flow column (GE Healthcare, Pittsburgh, PA). The GST-6×His-TEV tag was cleaved by overnight incubation with TEV protease and final purification was performed using a 5 ml His-Trap Fast Flow column (GE Heathcare, Pittsburgh, PA), followed by Superdex 200 26/60 size exclusion column (GE Heathcare, Pittsburgh, PA).

TABLE 5

| BKV Serotype | VP1 Sequence | SEQ ID NO. |
|---|---|---|
| Serotype I, amino acids 30-297 | KGGVEVLEVKTGVDAITEVECFLNPEMGDPDENLRGFSLKLSAENDF SSDSPERKMLPCYSTARIPLPNLNEDLTCGNLLMWEAVTVQTEVIGIT SMLNLHAGSQKVHEHGGGKPIQGSNFHFFAVGGDPLEMQGVLMNYR TKYPEGTITPKNPTAQSQVMNTDHKAYLDKNNAYPVECWIPDPSRNE NTRYFGTFTGGENVPPVLHVTNTATTVLLDEQGVGPLCKADSLYVSA ADICGLFTNSSGTQQWRGLARYFKIRLRKRSVK | SEQ ID NO: 502 |
| Serotype II, amino acids 30-297 | KGGVEVLEVKTGVDAITEVECFLNPEMGDPDDNLRGYSLKLTAENAF DSDSPDKKMLPCYSTARIPLPNLNEDLTCGNLLMWEAVTVKTEVIGIT SMLNLHAGSQKVHENGGGKPVQGSNFHFFAVGGDPLEMQGVLMNY RTKYPQGTITPKNPTAQSQVMNTDHKAYLDKNNAYPVECWIPDPSRN ENTRYFGTYTGGENVPPVLHVTNTATTVLLDEQGVGPLCKADSLYVS AADICGLFTNSSGTQQWRGLARYFKIRLRKRSVK | SEQ ID NO: 503 |
| Serotype III, amino acids 30-297 | KGGVEVLEVKTGVDAITEVECFLNPEMGDPDDHLRGYSQHLSAENAF DSDSPDKKMLPCYSTARIPLPNLNEDLTCGNLLMWEAVTVKTEVIGIT SMLNLHAGSQKVHENGGGKPVQGSNFHFFAVGGDPLEMQGVLMNY RTKYPQGTITPKNPTAQSQVMNTDHKAYLDKNNAYPVECWIPDPSKN ENTRYFGTYTGGENVPPVLHVTNTATTVLLDEQGVGPLCKADSLYVS AADICGLFTNSSGTQQWRGLARYFKIRLRKRSVK | SEQ ID NO: 504 |
| Serotype IV, amino acids 30-297 | KGGVEVLEVKTGVDAITEVECFLNPEMGDPDNDLRGYSLRLTAETAF DSDSPDRKMLPCYSTARIPLPNLNEDLTCGNLLMWEAVTVKTEVIGIT SMLNLHAGSQKVHENGGGKPIQGSNFHFFAVGGDPLEMQGVLMNYR TKYPEGTVTPKNPTAQSQVMNTDHKAYLDKNNAYPVECWIPDPSRN ENTRYFGTYTGGENVPPVLHVTNTATTVLLDEQGVGPLCKADSLYVS AADICGLFTNSSGTQQWRGLPRYFKIRLRKRSVK | SEQ ID NO: 505 |

Example 5: Affinity Measurements of Anti-VP1 Antibodies (SET Assay)

Solution equilibration titration (SET) assay was used to determine the interaction affinities ($K_D$) of antibodies with BKV VP1 pentamers from all four serotypes. Antibodies were assayed at 1 pM concentration (constant), VP1 pentamers were serially diluted from a starting concentration of 10 nM. Antibody:VP1 pentamer solution was incubated overnight, then assayed for unbound antibody using an MSD array plate (Meso Scale Discovery Cat #L21XA, Rockville MD) coated with VP1 pentamer. The $K_D$ was determined by fitting the plot with a 1:1 fit model (according to Piehler et al. J. Immunol. Methods. 1997; 201(2):189-206).

In SET assays, $K_D$ values were similar for anti-VP1 antibodies binding to BKV serotype I pentamers, ranging from 0.9 to 5.0 pM. P8D11 and derivatives of P8D11 had comparable $K_D$ values for binding to BKV serotype II, III, and IV pentamers, and when compared to the other antibodies, had at least 3.5-fold greater affinity on serotype II pentamers and 47-fold greater affinity on serotype IV pentamers. This is shown in FIG. 1A-1D. In addition, P8D11 and derivatives of P8D11 demonstrated binding affinity ranging from 2.5 to 6.0 pM on serotype III pentamers, whereas the other antibodies had no detectable binding to serotype III pentamers within the tested conditions. A summary of SET affinity data for these anti-VP1 antibodies is found in FIG. 2.

Example 6: Binding of Anti-VP1 Antibodies to VP1 Pentamers and VLPs (ELISA)

The binding of anti-VP1 antibodies to VP1 pentamers and VLPs were analyzed by ELISA. Briefly, Immulon 2HB plates (VWR, 62402-972) were coated with 100 ng/well BKV VLPs or VP1 pentamers overnight. Antibodies were serially diluted in PBS with 0.5% BSA and allowed to bind antigen-coated plates for 2 h. Plates were washed with PBS and then incubated with secondary antibody (HRP-conjugated rabbit anti-human IgG, Southern Biotech #6140-05) diluted 1:6000 in 0.5% BSA in PBS for 1 h. Plates were washed with PBS and tetramethylbenzidine (TMIB) microwell peroxidase substrate (KPL, 52-00-03 IL) was used to develop the reactions.

Figure 4:
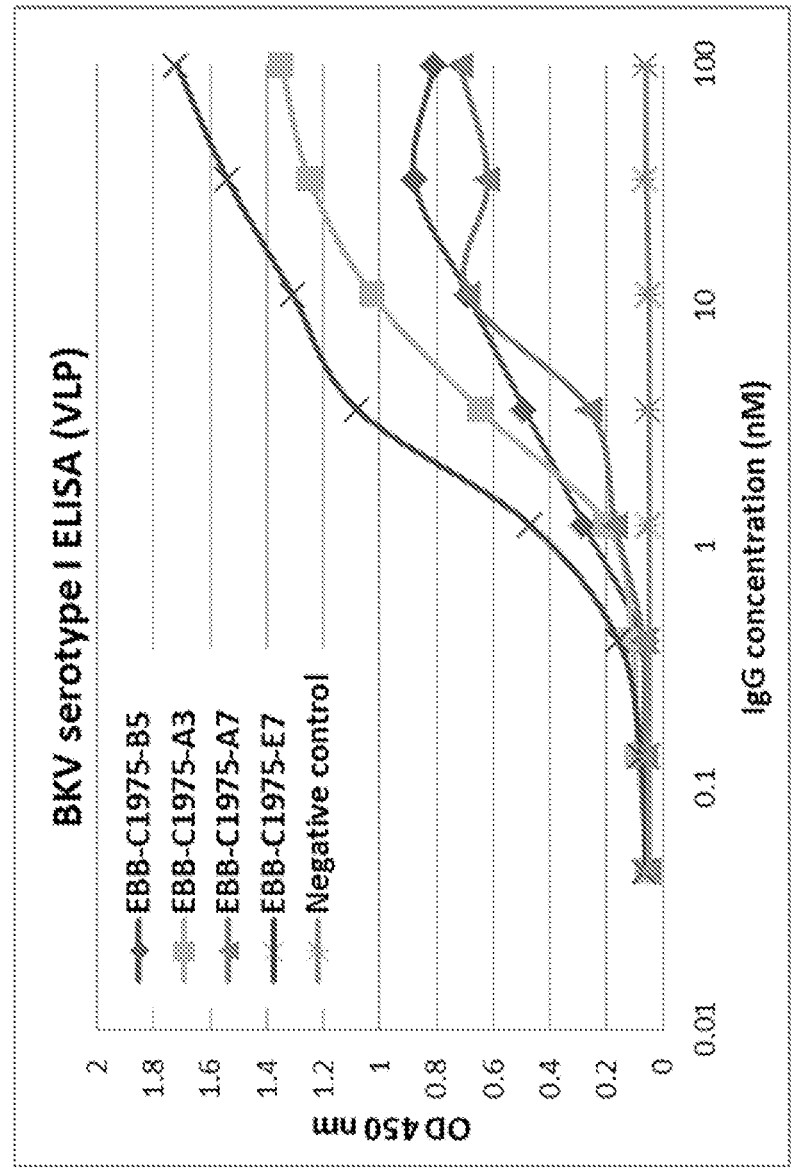
FIG. 4 is a graph of anti-VP1 antibodies binding to BKV serotype I VLPs as measured by ELISA.
Figure 5:
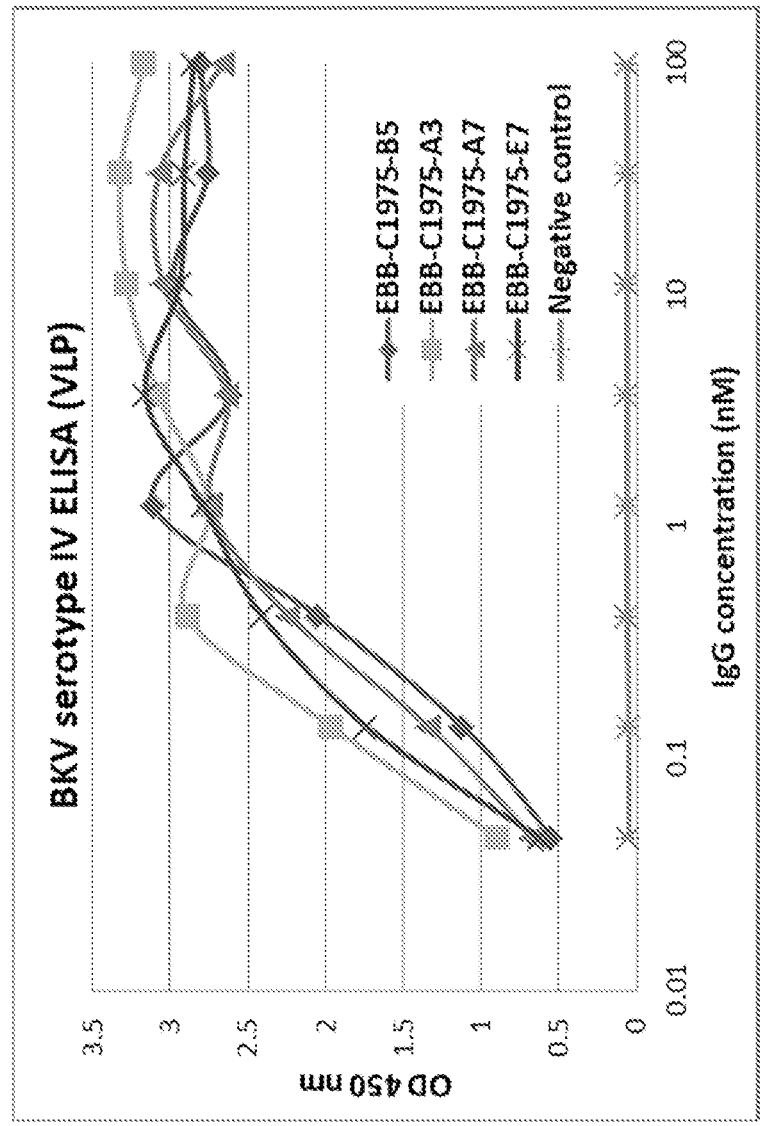
FIG. 5 is a graph of anti-VP1 antibodies binding to BKV serotype IV VLPs as measured by ELISA.
Figure 6:
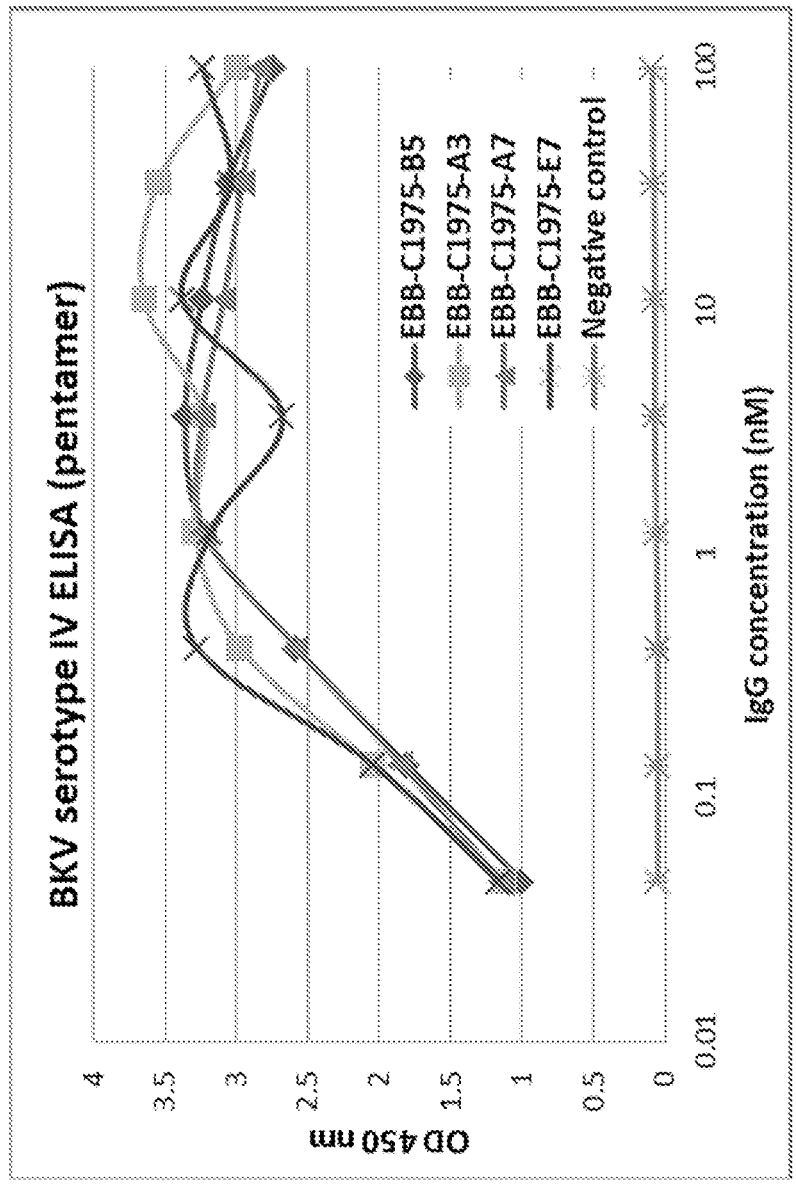
FIG. 6 is a graph of anti-VP1 antibodies binding to BKV serotype IV VP1 pentamers as measured by ELISA.
Figure 8:
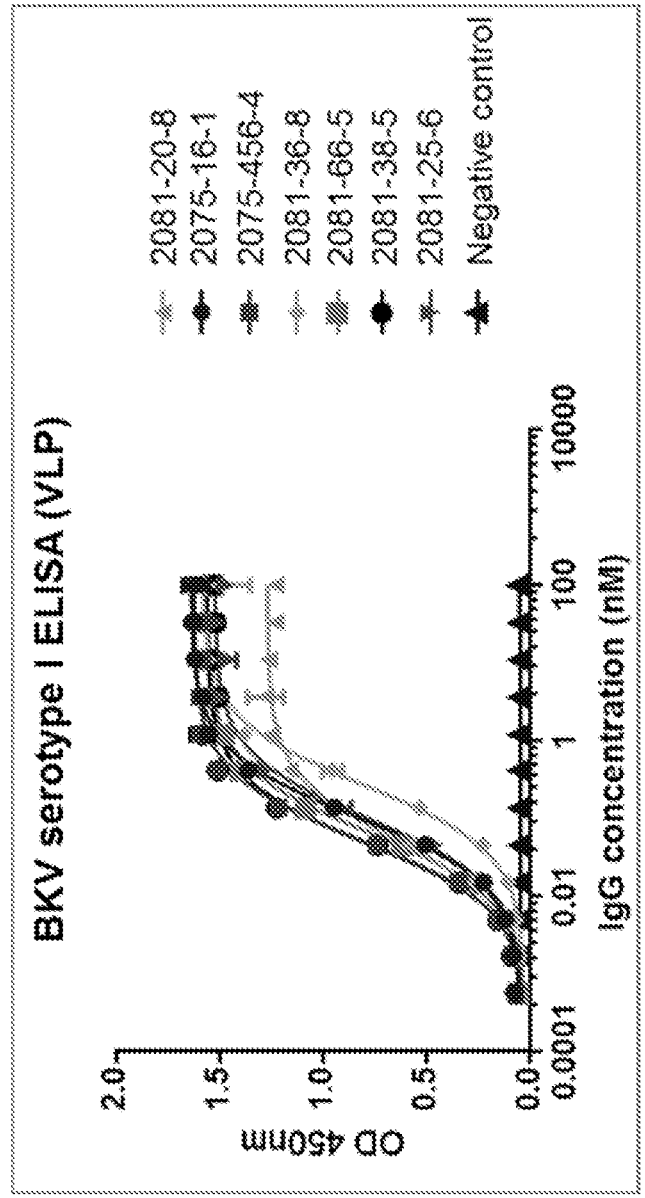
FIG. 8 is a graph of anti-VP1 antibodies binding to BKV serotype I VLPs as measured by ELISA.
Figure 10:
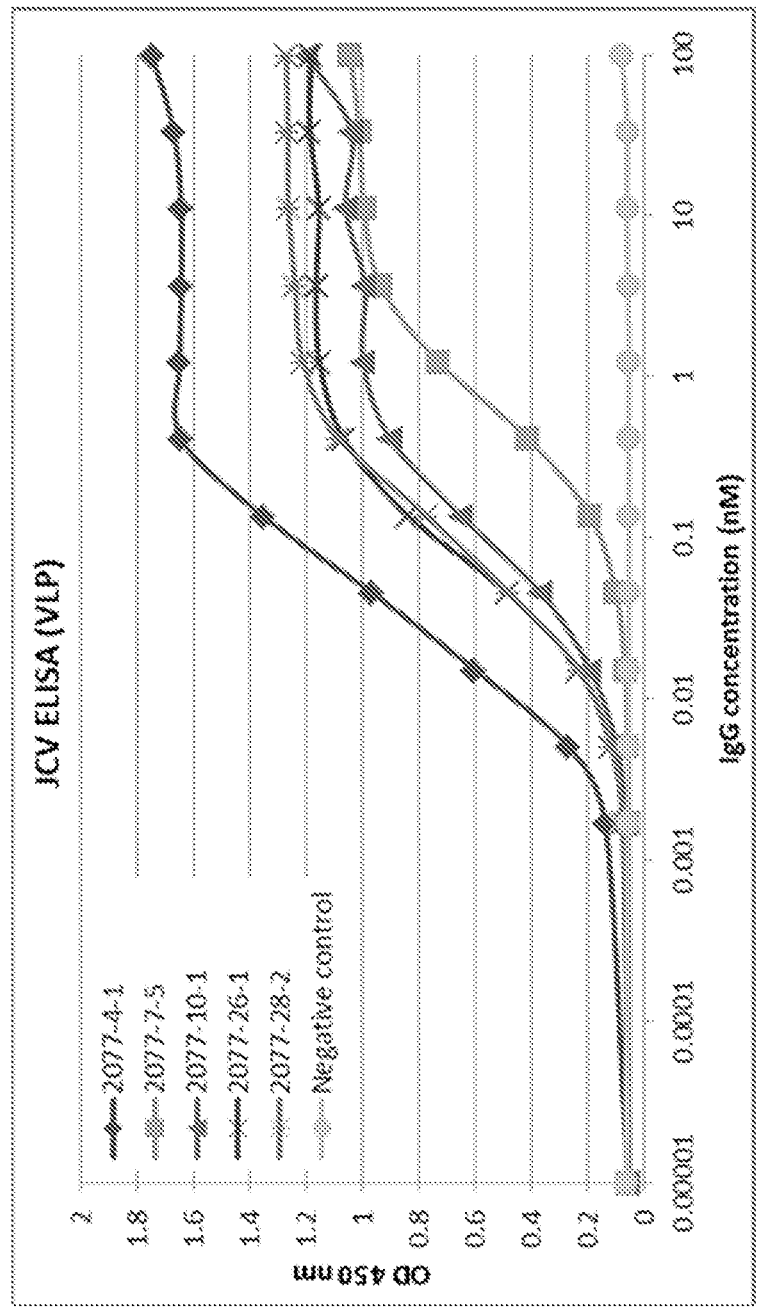
FIG. 10 is a graph of anti-VP1 antibodies binding to JC virus VLPs as measured by ELISA.

The anti-VP1 antibodies EBB-C1975-A3, A7, E7, and B5 showed similar binding to VLPs (IC50s ranging from 0.044 to 0.1 nM) or VP1 pentamers (IC50s ranging from 0.026 to 0.078 nM) from BKV serotype IV, but reduced and more variable binding activity to serotype I VLPs (IC50s ranging from 4.32 to 85.7 nM). This data is shown graphically in FIGS. 4-6 and summarized in FIG. 7. In contrast, anti-VP1 antibodies from the 2081 and 2075 series showed enhanced binding activity to serotype I VLPs, with IC50s ranging from 0.046 to 0.267 nM and this data is shown in FIGS. 8 and 9. The JCV-specific anti-VP1 antibodies of the 2077 series demonstrated binding activity to JCV VLPs ranging from 0.034 to 0.651 nM and this data is provided in FIGS. 10 and 11.

Example 7: Binding of Anti-VP Antibodies to VP1 Pentamers and VLPs by SPR

The binding of anti-VP1 antibodies to VP1 pentamers and VLPs were analyzed by surface plasmon resonance (SPR). Briefly, biotinylated Protein A is immobilized on a streptavidin-coated SPR chip surface, and anti-VP1 antibodies are captured on the resulting surface by binding to Protein A. BKV VP1 pentamers or VLPs are then flowed over the surface and allowed to bind anti-VP1 antibodies during the association phase, followed by a buffer wash during the dissociation phase.

Figure 3A:
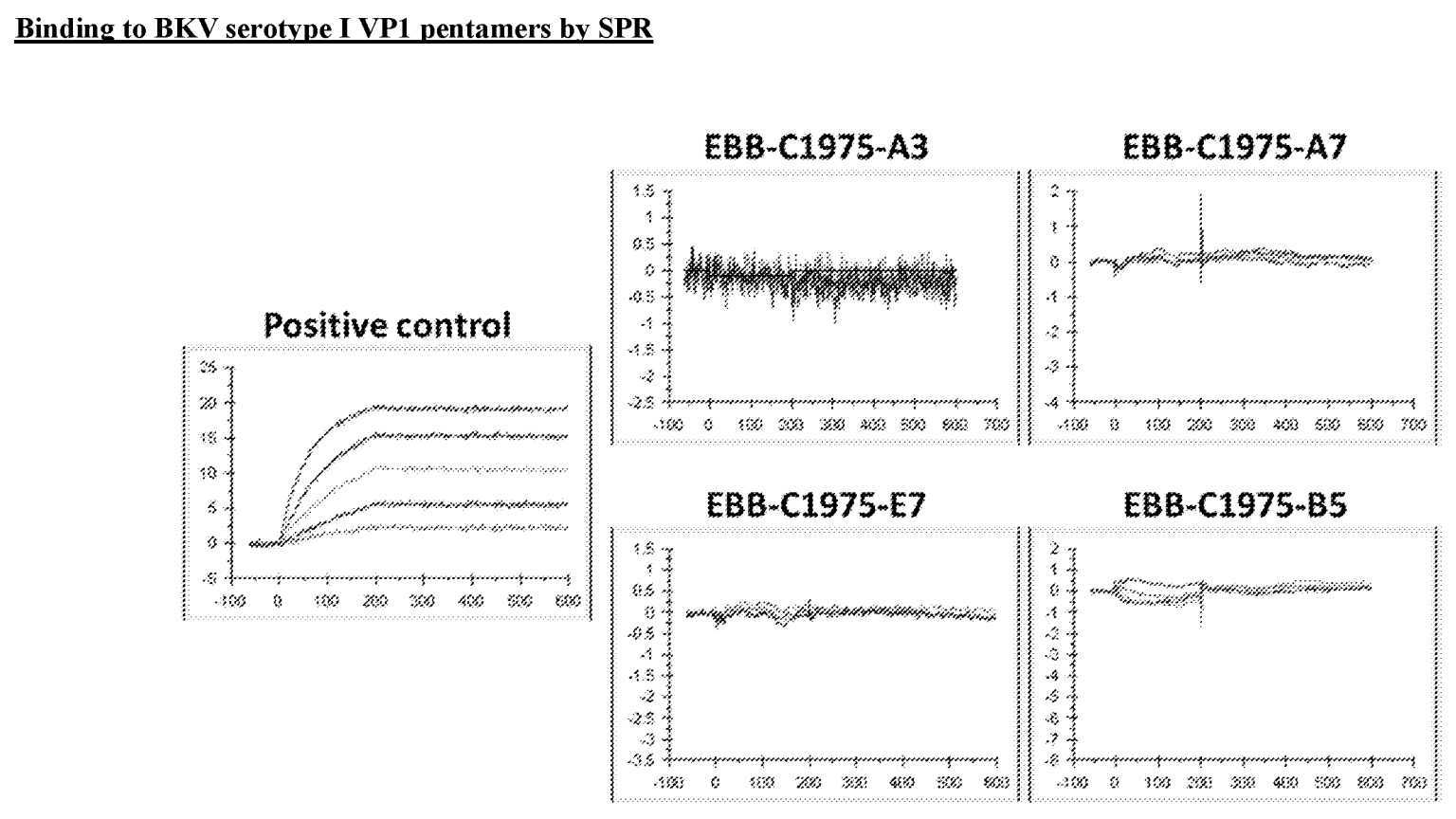
Figure 3B:
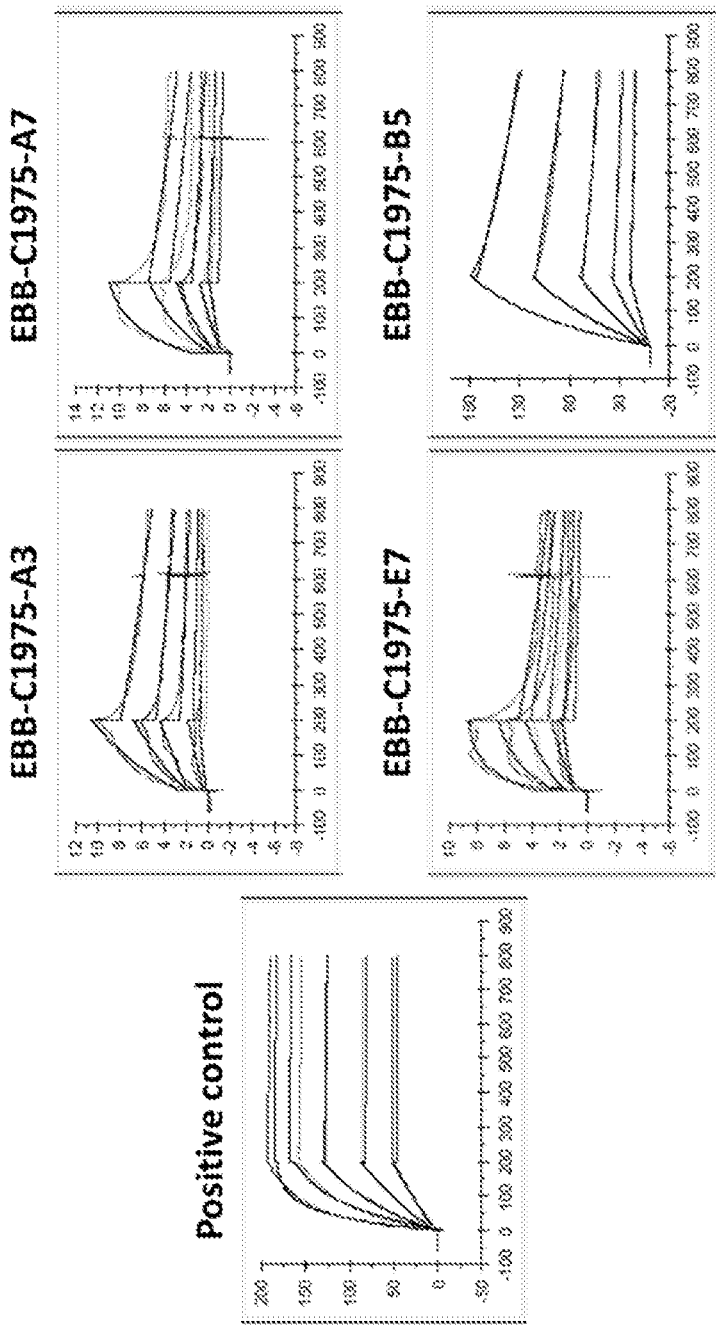
Figure 3C:
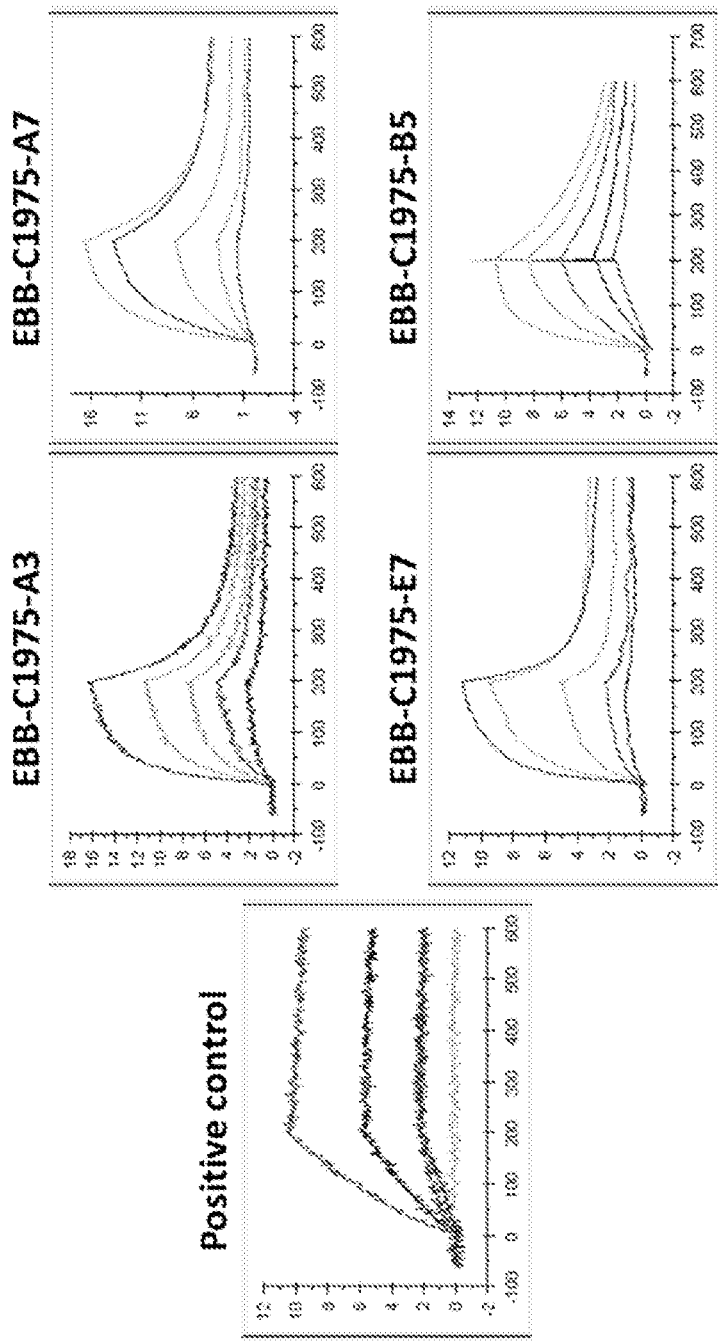
Figure 3D:
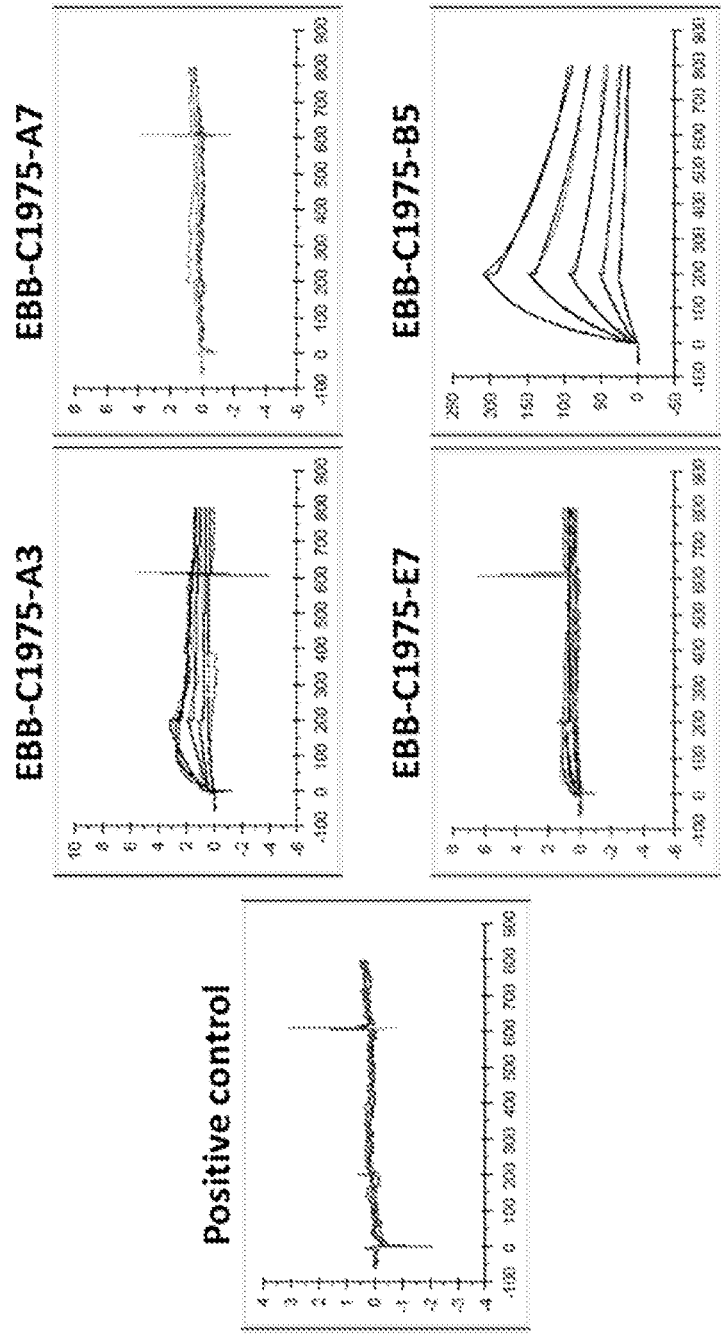
Figure 3E:
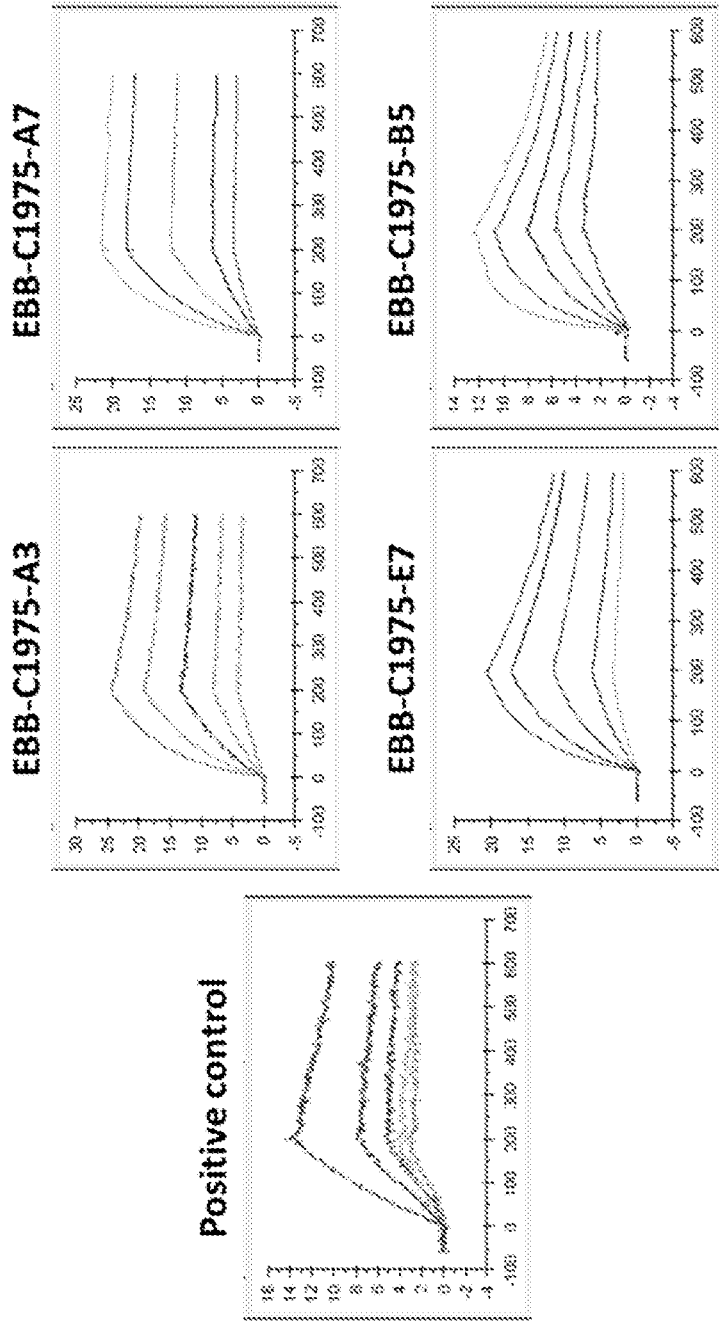

SPR was used to evaluate binding of anti-VP1 antibodies EBB-C1975-A3, A7, E7, and B5 to the four serotypes of BKV, relative to a positive control (P165E2). All four antibodies had very similar binding profiles to VP1 pentamers: no binding to serotype I and III pentamers, atypical binding to serotype II pentamers (large bulk shift and no return to baseline), and binding to serotype IV pentamers similar to P165E2 but with lower affinity (FIGS. 3A, 3C and 3E). For VLPs, EBB-C1975-A3, A7, and E7 shared similar binding profiles: atypical binding to serotype I VLPs and no binding to serotype III VLPs. However, EBB-C1975-B5 binding profile was distinct with significant binding to serotype I and III VLPs, demonstrating binding to a different epitope on VP1 (FIGS. 3B and 3D).

Figure 13A:
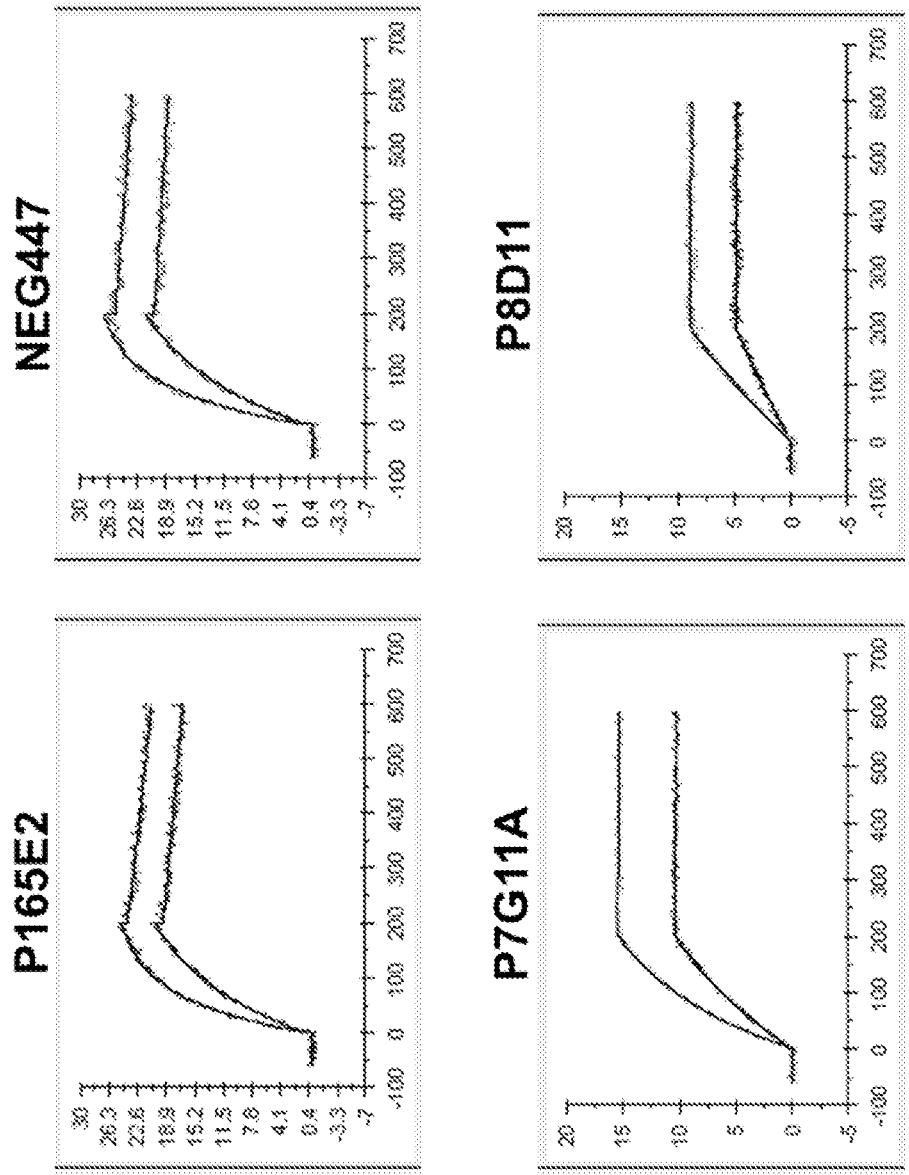
FIG. 13A-13F graphically represents binding of anti-VP1 antibodies to wild type BKV serotype I VP1 pentamers by Biacore, but that point mutations in the VP1 can disrupt binding.
Figure 13B:
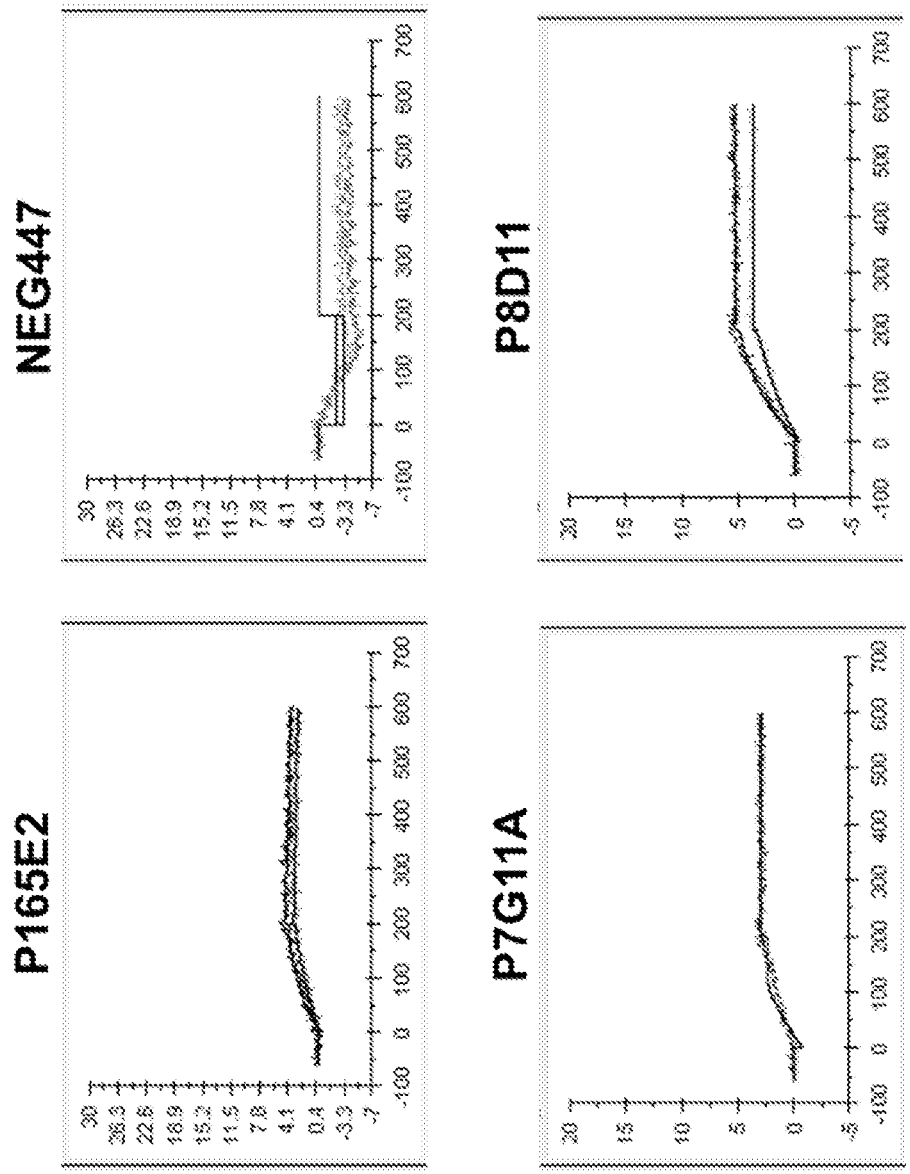
Figure 13C:
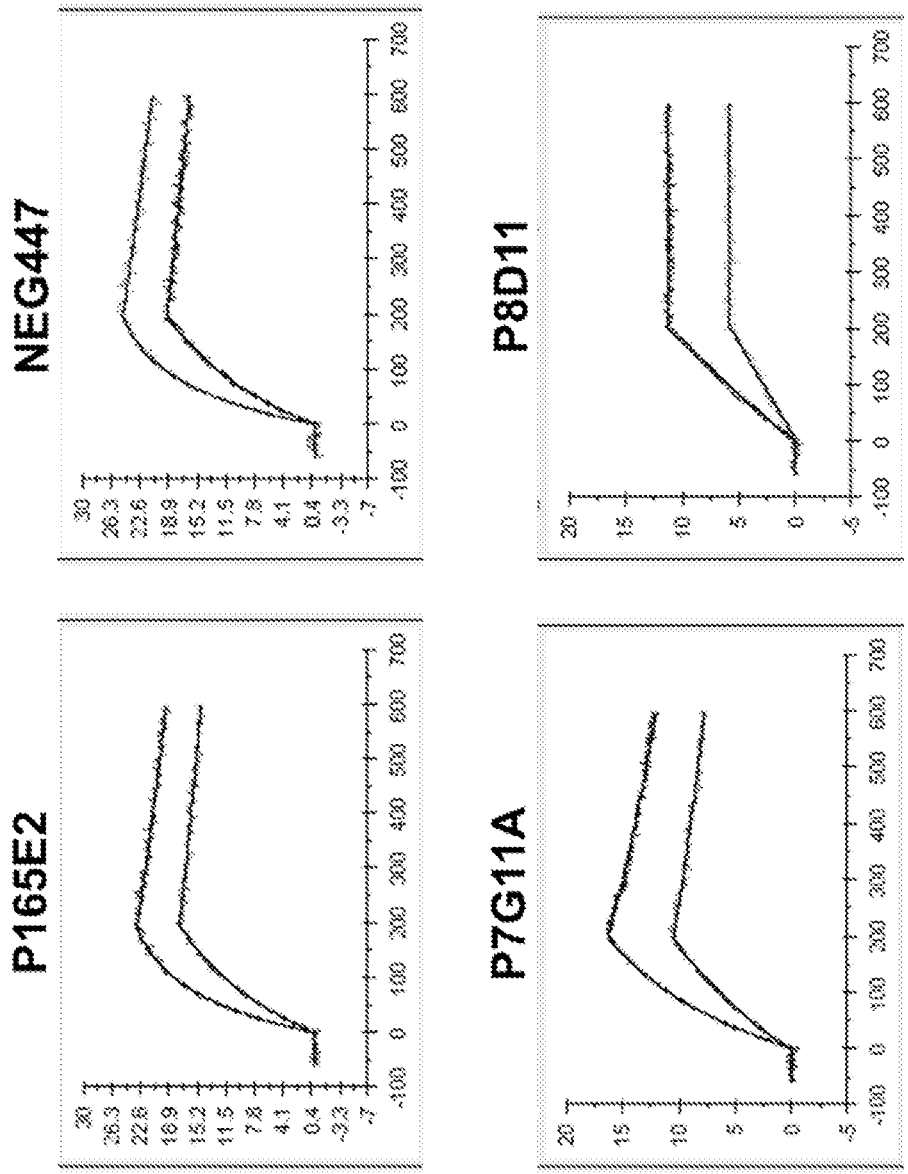
Figure 13D:
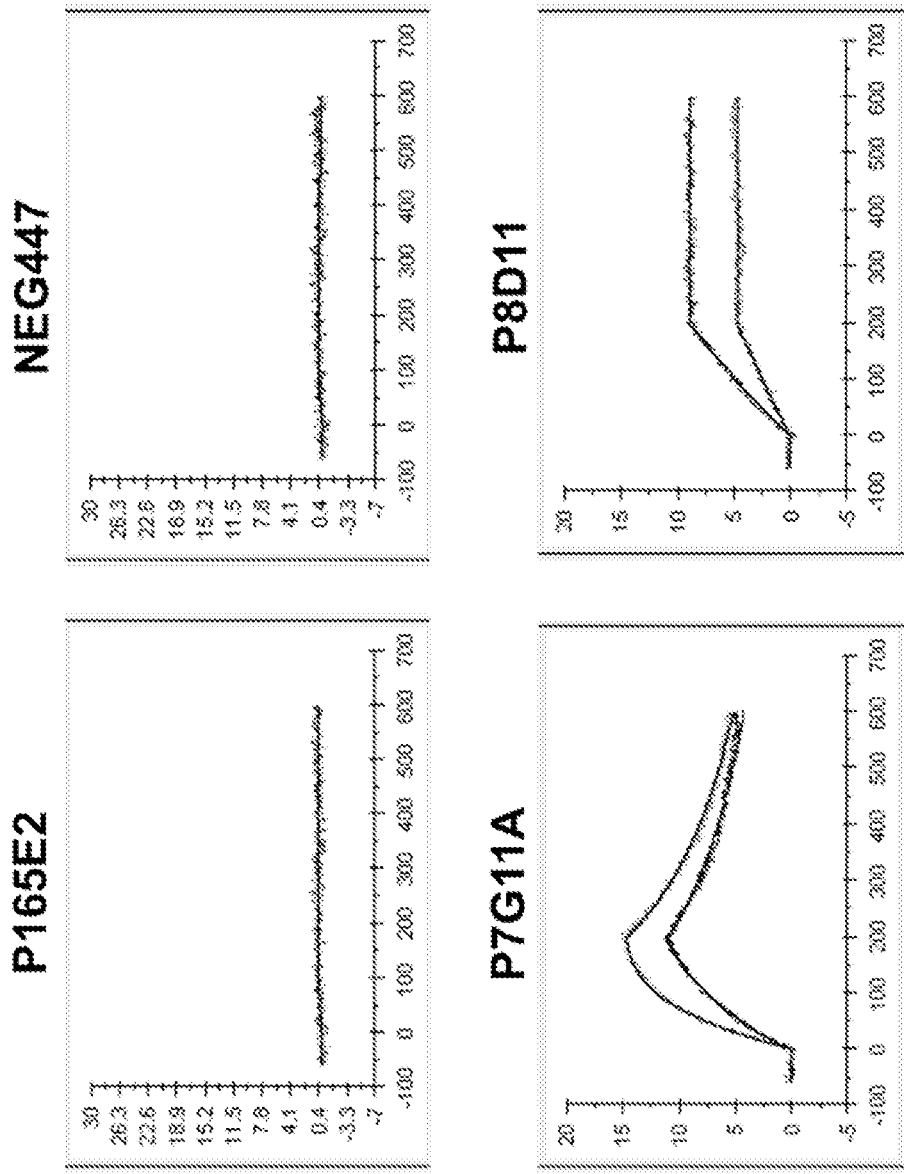
Figure 13E:
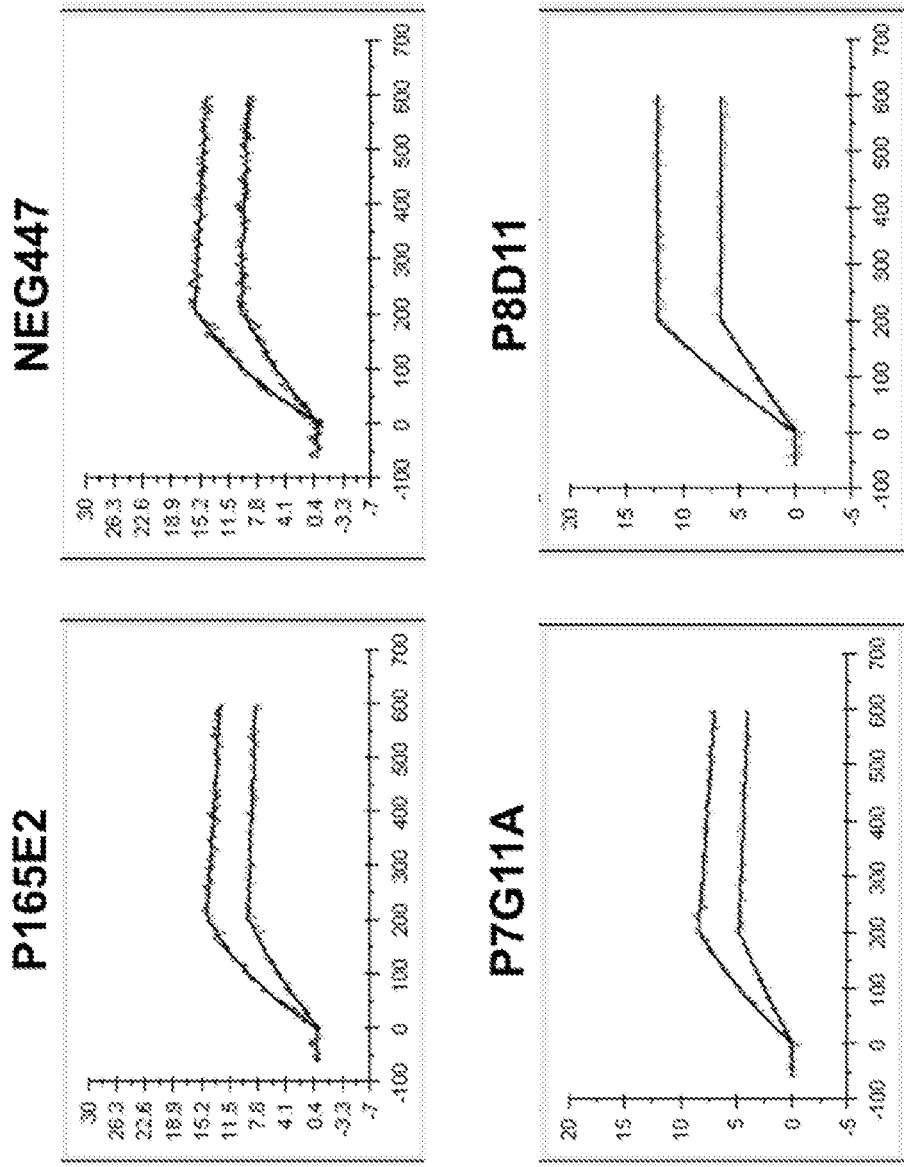
Figure 13F:
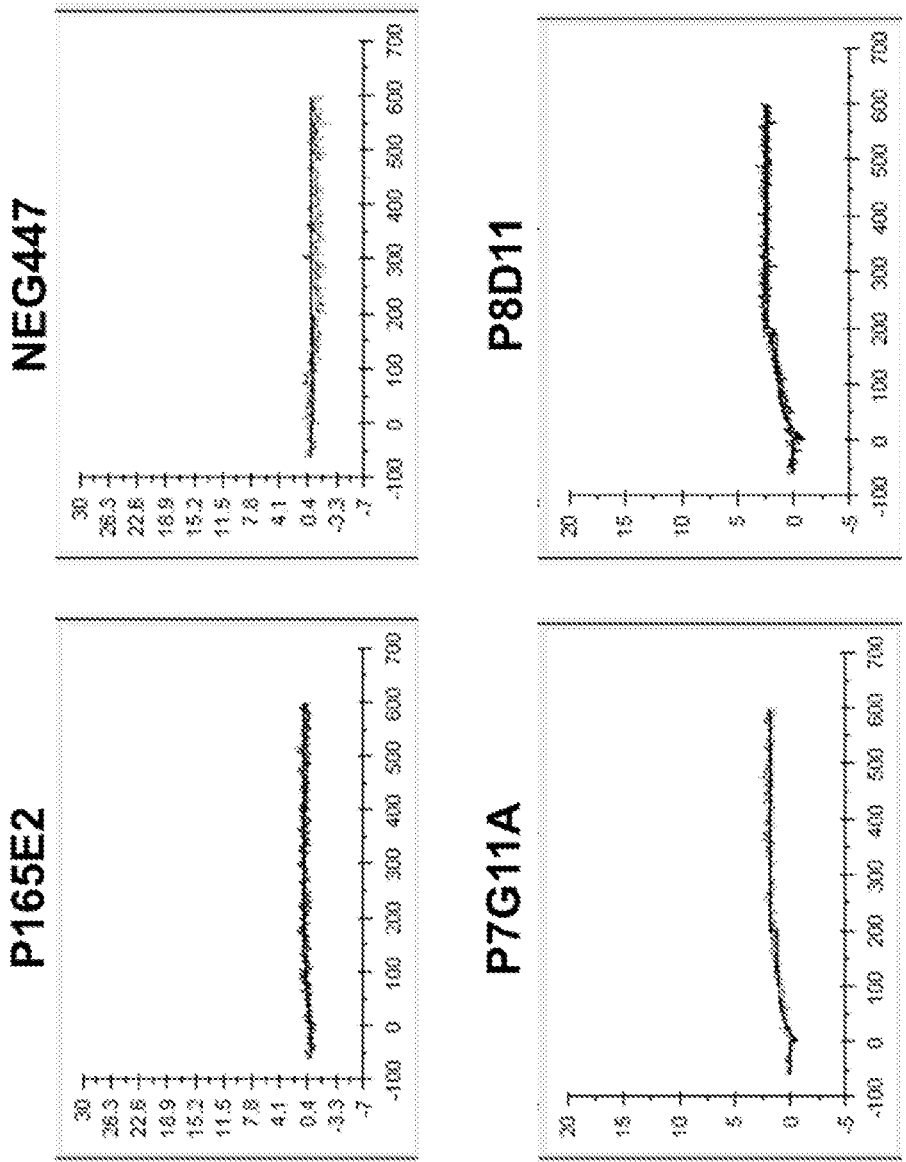
Figure 15:
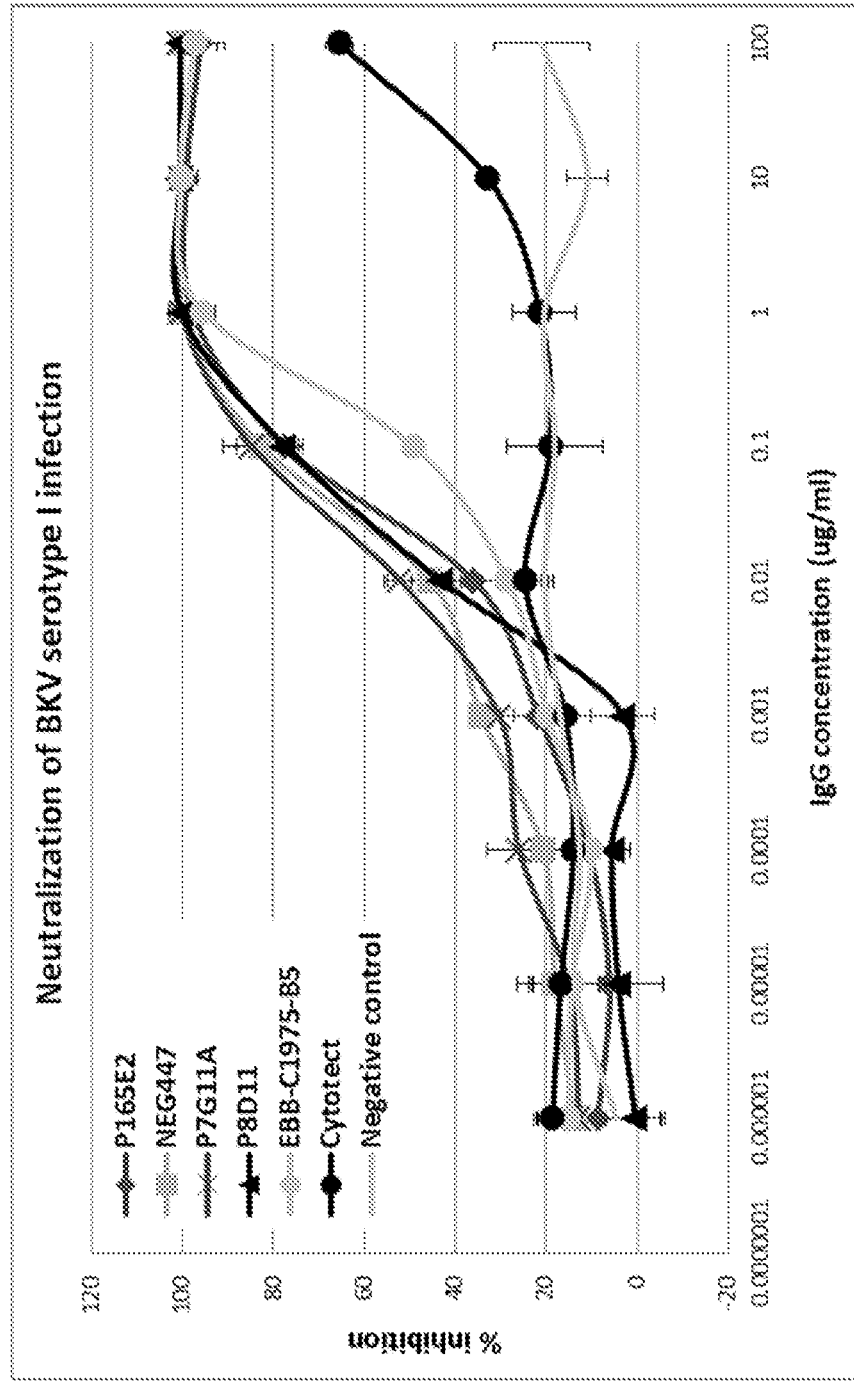
FIG. 15 is a graph of anti-VP1 antibodies neutralizing BKV serotype I infection.
Figure 16:
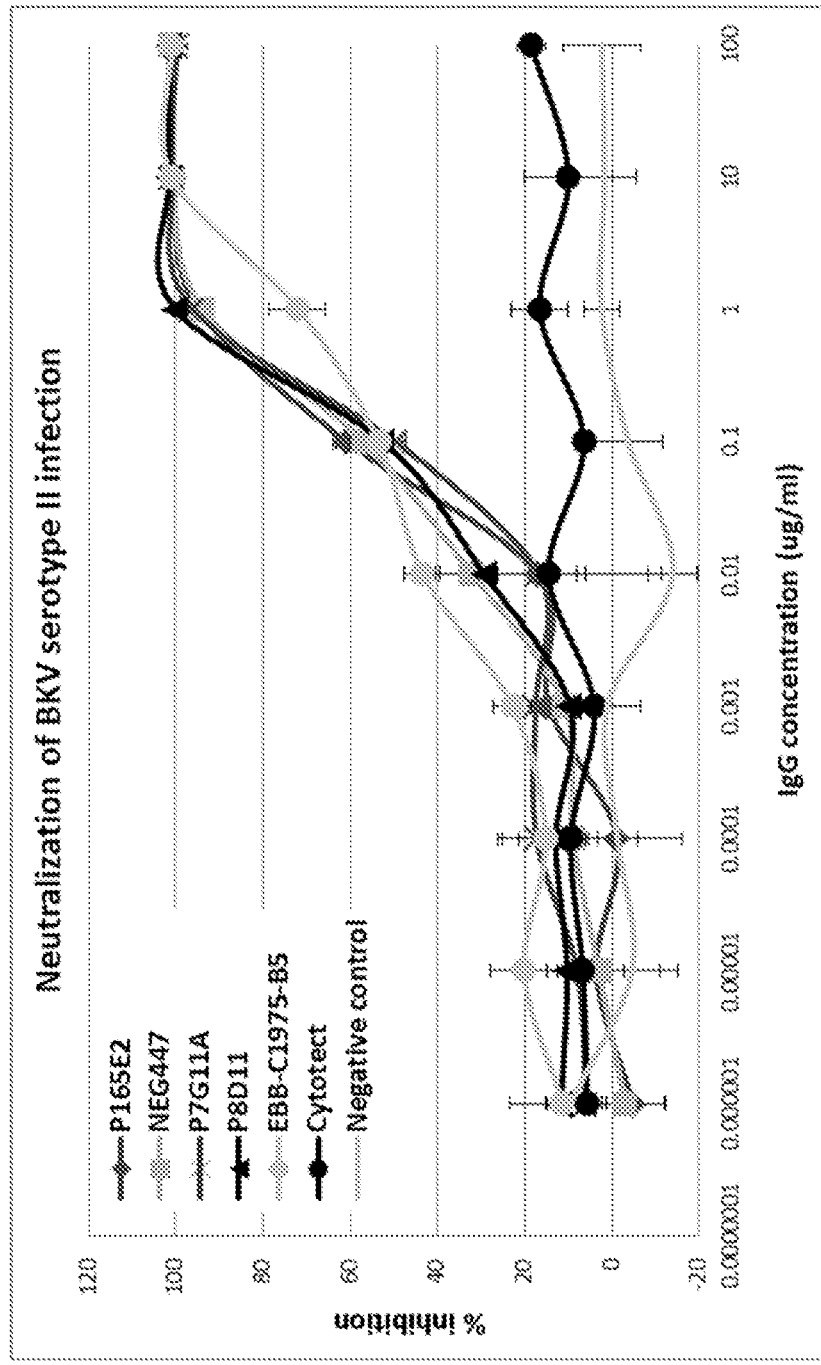
FIG. 16 is a graph of anti-VP1 antibodies neutralizing BKV serotype II infection.
Figure 17:
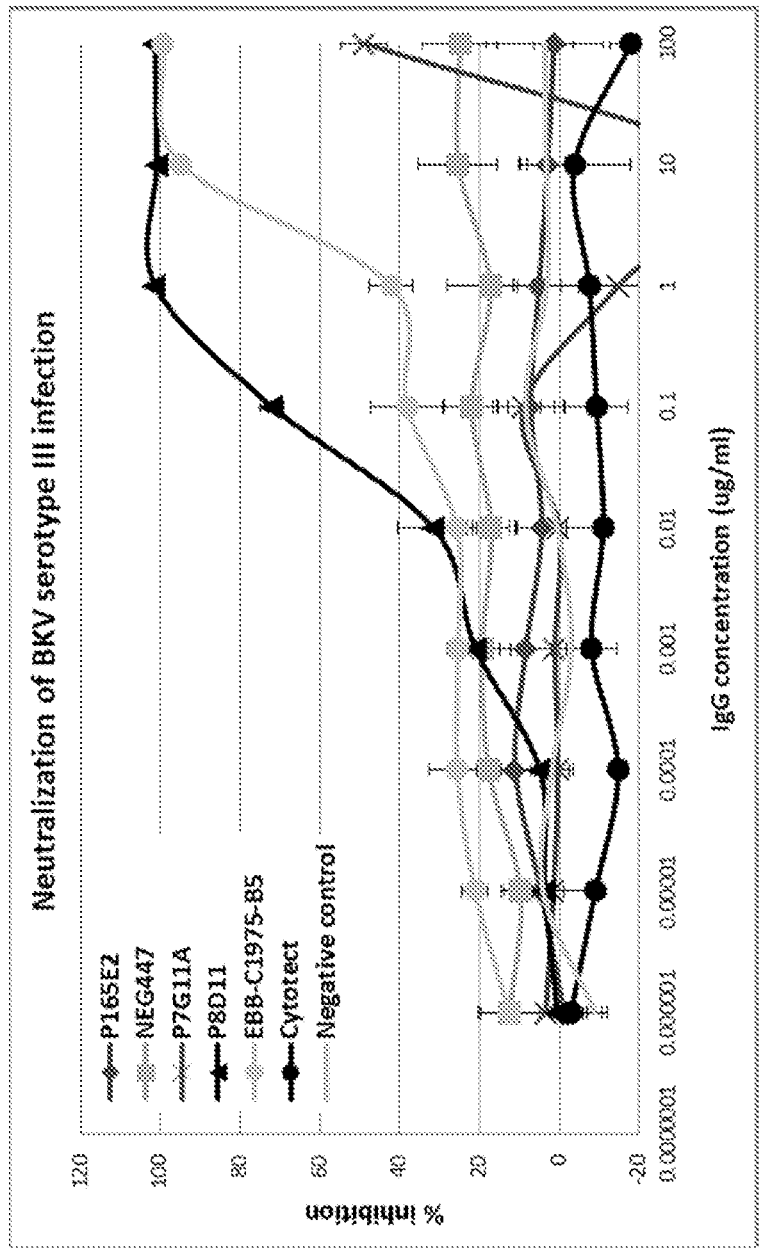
FIG. 17 is a graph of anti-VP1 antibodies neutralizing BKV serotype III infection.
Figure 18:
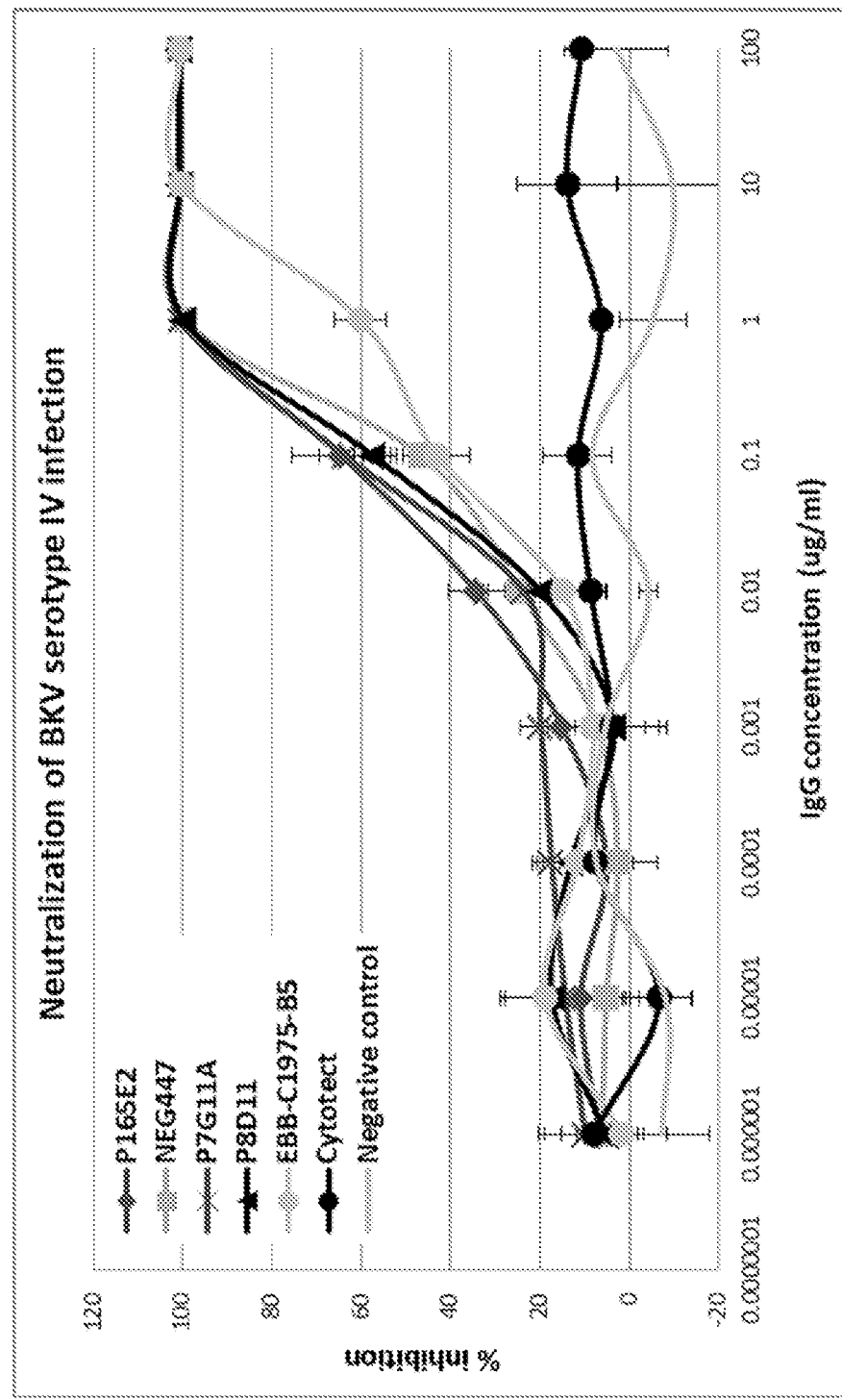
FIG. 18 is a graph of anti-VP1 antibodies neutralizing BKV serotype IV infection.
Figure 20:
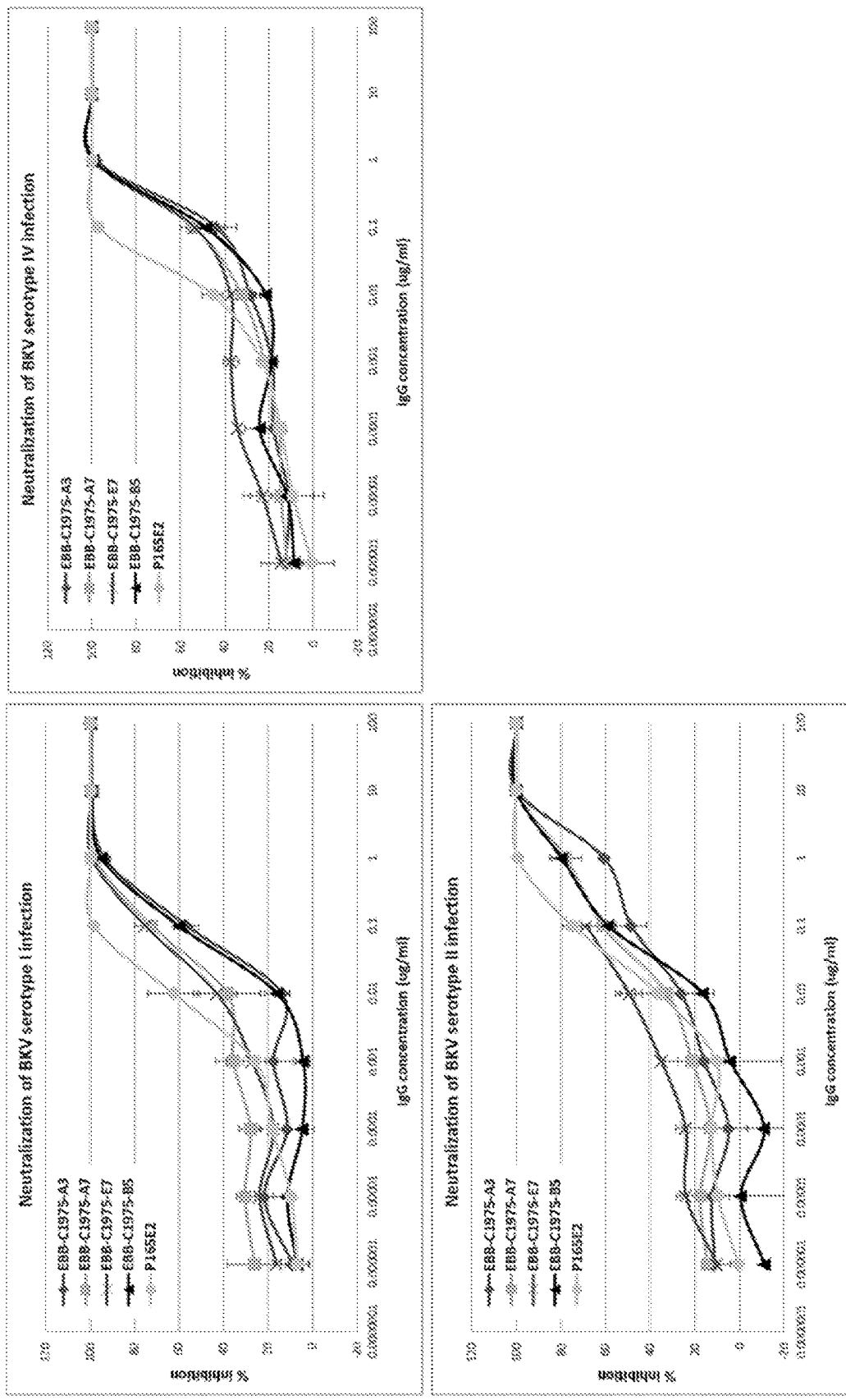
FIG. 20 is a graph of anti-VP1 antibodies neutralizing infection with BKV serotypes I, II, and IV.
Figure 22:
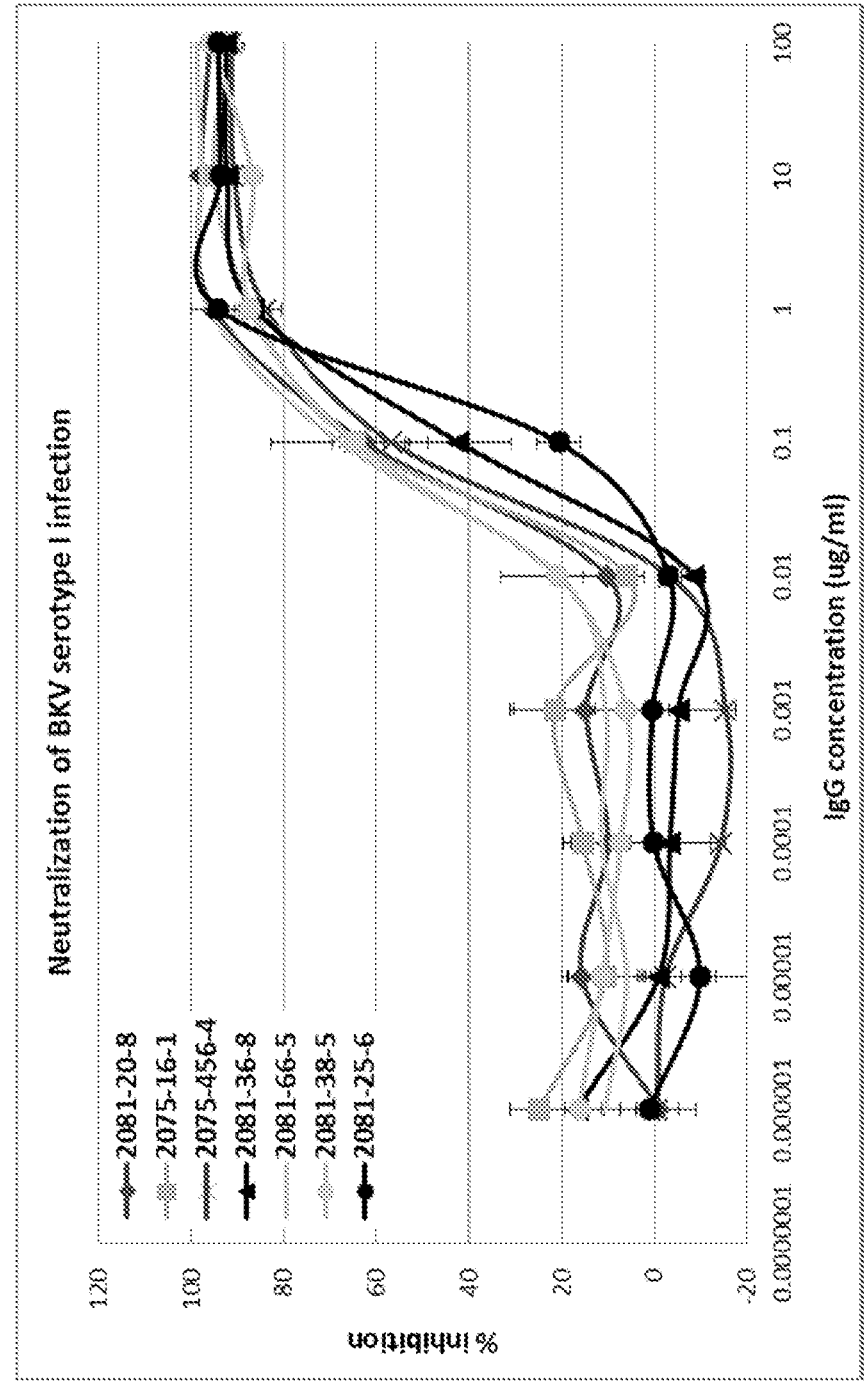
FIG. 22 is a graph of anti-VP1 antibodies neutralizing infection with BKV serotype I.

SPR was also used to characterize binding of anti-VP1 antibodies P165E2, NEG447, P7G11A, and P8D11 to VP1 pentamers by scanning alanine mutagenesis (FIGS. 13A-F and FIG. 14). All anti-VP1 antibodies showed reduced binding to F66A and I145A VP1 mutants, due to an overall impact of the mutation on VP1 pentamer structure (FIGS. 13B and 13F). In addition, K69A and E82A impacted binding of P165E2, NEG447, and P7G11A (FIGS. 13D and 13E).

Example 8: Anti-VP1 Antibodies Bind to a Conformational Epitope

To determine if the anti-VP1 antibodies bind a conformational epitope, Western blots of denatured protein by SDS-PAGE and dot blots of protein in native conformation were used. Briefly, BKV serotype I or IV VP1-pentamer were run on SDS-PAGE and transferred to nitrocellulose membrane (Western blot) or spotted directly onto nitrocellulose membrane (dot blot). Both membranes were incubated with anti-VP1 antibodies followed by anti-human IgG secondary antibody conjugated to infrared fluorescing dyes for detection using the Licor Odyssey system.

Commercially available positive control antibody (Abcam 53977) known to recognize a linear epitope detected both the denatured and non-denatured VP1. However, P165E2, P7G11 and P8D11 failed to detect denatured VP1 on the Western blot and only recognized native VP1 on the dot blot, indicating that these antibodies bind to a conformational (non-linear) epitope of VP1 (FIGS. 12A and 12B).

To further characterize the epitope of anti-VP1 antibodies, scanning alanine mutagenesis was performed for residues, primarily in the VP1 BC loop, known to be exposed on the virion surface and within a major interaction site for cell surface receptors. These mutant VP1 pentamers were assayed for binding to P8D11 and P7G11A in surface plasmon resonance (SPR) studies as described above in Example 7. Mutations at several positions impacted binding of P7G11A (F66A, K69A, E82A, I145A) (FIGS. 13A-F and FIG. 14). However, mutations at only two sites resulted in reduction of P8D11 binding (F66A, I145A) (FIG. 14). As the mutations at F66 and I145 resulted in a loss of binding of all antibodies tested, without being bound by any one theory, it is likely that these mutations result in a general disruption of the VP1 pentamer structure. All other VP1 pentamers with BC loop mutations tested retained P8D11 binding. In contrast, hydrogen-deuterium exchange studies have identified a protected region within the EF loop of VP1 upon binding of P8D11 Fab fragment. Follow-up scanning alanine mutagenesis studies confirm that key contact residues for P8D11 binding within this region include Y169, R170 and K172, with D/E175, K181, N182, T184 and Q186 to M190 being important residues as determined by deuterium exchange ((YRXKXX(D/E)XXXXXKNXTXQ) (SEQ ID NO: 500)). This is further described in Example 14 through Example 17.

Example 9: Neutralization of BK Virus by Anti-VP1 Antibodies

Infectious BKV serotype I and chimeric viruses representing serotype II, III, and IV were pre-incubated with purified antibodies for 1 hour to allow for binding and neutralization. Primary renal proximal tubule epithelial (RPTE) cells (ATCC, cat #PCS-400-010) were then exposed to the virus-antibody mixture for 4 hours, replaced with fresh medium, and incubated for 48 hours to allow for viral entry and gene expression. Cells were fixed with 4% paraformaldehyde and analyzed by immunofluorescence to detect TAg expression (Calbiochem DP02, pAb416 mouse anti-SV40 TAg antibody). The immunofluorescence was analyzed by high content image analysis using the Cellomics ArrayScan®VTI HCS Reader to quantify the percent of BKV-infected cells (TAg-positive, DAP1-positive), with data presented as percent inhibition of infection relative to untreated control wells.

As shown in FIGS. 15-23, anti-VP1 antibodies neutralized infection by BKV, including the subset of antibodies that neutralize infection by all four serotypes of BKV (I-IV). These anti-VP1 antibodies specifically include P8D11, the modifications of P8D11, and EBB-C1975-B5.

Example 10: Neutralization of JC Virus by Anti-VP1 Virus Antibodies

Figure 24:
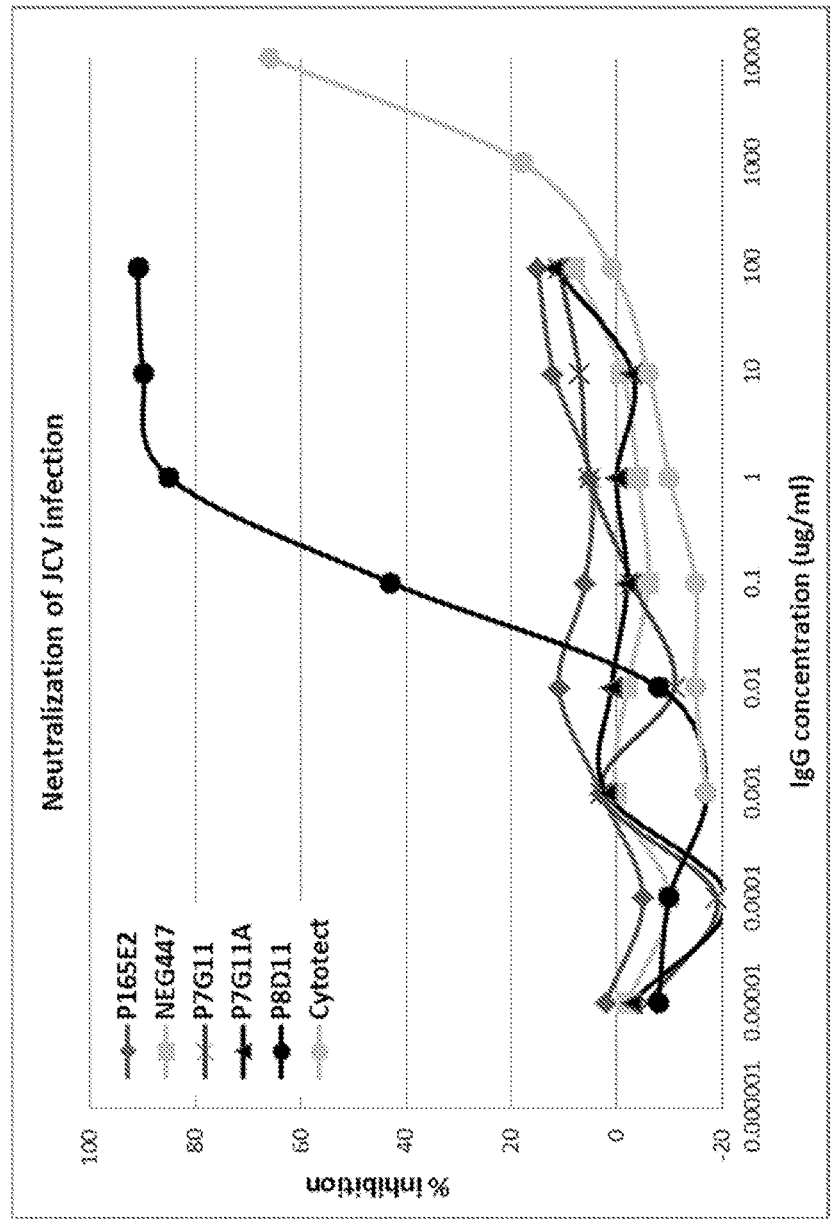
FIG. 24 is a graph of anti-VP1 antibodies neutralizing infection with JCV.
Figure 25:
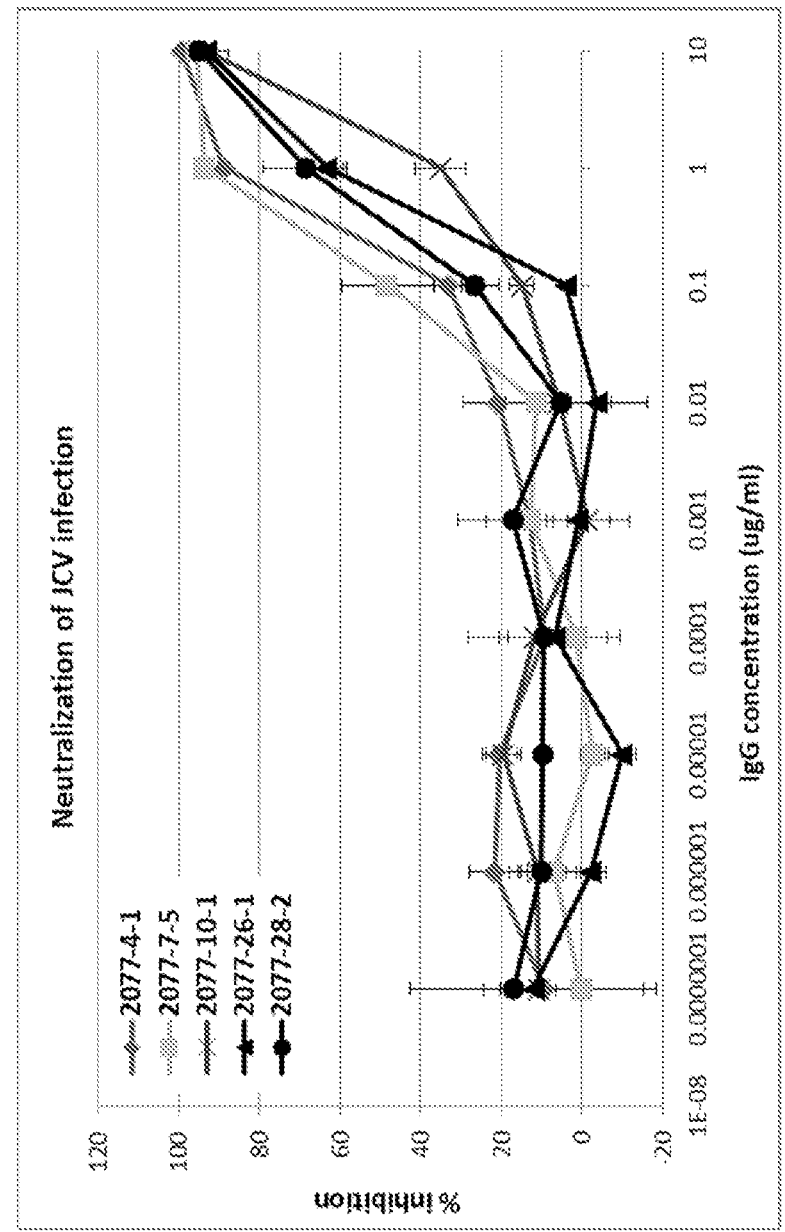
FIG. 25 is a graph of anti-VP1 antibodies neutralizing infection with JCV.

The infectious JCV isolates Mad-1 and Mad-4, have identical VP1 sequences (GenBank Accession NP_043511). These JCV isolates were pre-incubated with purified antibodies for 1 hour to allow for binding and neutralization. COS7 cells (African green monkey kidney fibroblast-like cell line expressing SV40 TAg, ATCC cat #CRL-1651) were then exposed to the virus-antibody mixture for 4 hours, replaced with fresh medium, and incubated for 72 hours to allow for viral entry and gene expression. Cells were fixed with 4% paraformaldehyde and analyzed by immunofluorescence to detect JCV VP1 expression (Abcam 53977, rabbit polyclonal anti-SV40 VP1 antibody). The assay was analyzed by high content image analysis using the Cellomics ArrayScan®VTI HCS Reader (Thermo Fisher, Waltham MA) to quantify the percent of JCV-infected cells (VP1-positive, DAP1-positive), with data presented as percent inhibition of infection relative to untreated control wells. As shown in FIGS. 24-26, a subset of anti-VP1 antibodies neutralize infection by JCV, including P8D11 and the 2077-series of antibodies.

Example 11: Viral Resistance

Resistance selection experiments with P8D11 antibodies were carried out in renal proximal tubular epithelial (RPTE) cell cultures infected with BKV serotype I or serotype IV. In serotype I studies, no viral breakthrough was observed in cultures with P8D11 out to 6 passages (84 days) and thus no resistance-associated variants (RAVs) were identified. No further passaging past this point was done, as no virus could be detected. In contrast, viral breakthrough was detected at passage 3 (day 42) with another antibody. Sequencing of BKV VP1 from these cultures identified a resistance-associated variant (RAV) with 20 amino acid changes throughout VP1, with no changes clustering around specific amino acids in the VP1 sequence. Subsequent phenotypic characterization of this pooled RAV virus showed a complete loss of neutralization activity (>7,692-fold shift in EC50) when compared to wild-type virus, but little change (3.9 fold) in the EC50 of P8D11. In addition, the VP1 mutant E82K was identified as a RAV during selection with another anti-VP1 antibody (see Example 8), and characterization of a cloned E82K mutant virus showed this variant conferred a 15,880-fold shift in EC50 when compared to wild-type virus, but showed no cross-resistance to P8D11.

Similarly, in BKV serotype IV cultures, resistance was not detected with P8D11 after 6 passages (84 days). Again, No further passaging past this point was done, as no virus could be detected. However, resistance to a different anti-BK antibody was selected as early as passage 1 (day 14). Changes in amino acids L68R and E73K were identified as change-from-reference mutations and conferred 600- and 227-fold shifts in EC50 values respectively, but displayed no cross-resistance to P8D11. In summary, P8D11 has a high barrier-to-resistance and maintains neutralizing activity against resistant variants for both serotypes I and IV.

Example 12: Toxicity

Because VP1 is an exogenous, non-human target that is not expressed on the cell surface, the anti-VP1 antibodies disclosed herein constitute a low risk for toxicity in human. A TCR study demonstrated there was no staining of 42 human tissues and blood smears by P8D11, supporting the absence of anti-VP1 antibody cross-reactivity with human proteins. The anti-VP1 antibodies have shown no antibody-dependent cell-mediated cytotoxicity (ADCC) in vitro, consistent with the fact that VP1 protein is not expressed on the host cell surface.

Example 13: SET Affinity Assay of P8D11 on JCV VLPs

Progressive Multifocal Leukoencephalopathy (PML) is a rare, but frequently fatal infection of the brain of immunocompromised patients by JC virus. The major capsid protein (VP1) of JC virus, is involved in binding sialic acid receptors on the surface of host cells. Certain mutations in the VP1, such as at amino acids L55 and S269, abolish sialic acid recognition and play a role in PML pathogenesis (Chen et al., mAbs 2015; 7(4), 681-692). These two mutations occur frequently in PML patients (Gorelik et al., J. Infect. Dis. 2011 204:103-114 and Reid et al., J. Infect. Dis. 2011; 204:237-244). The antibodies of the disclosure were tested to see if they bound to the mutated JCV VLPs with mutations at those positions. Binding of the anti-VP1 antibodies to these VLPs would indicate that JC virus carrying these common VP1 mutations would not be resistant to therapy.

Two series of twenty-two serial dilution of VLP were prepared in sample buffer. Two constant concentrations of the P8D11 antibody were added. The concentration of P8D11 antibody used was either 9 nM or 1 pM. The concentration range of JCV consensus ranged from 105 pg/ml-72 pg/ml. The concentration range of JCV L55F mutant was 300 pg/ml-143 pg/ml. The concentration range of JCV S269F mutant was 300 pg/ml-143 pg/ml. A volume of 60 µl of each VLP:antibody mix was distributed in duplicates to a 384-well polypropylene microtiter plate (PP MTP). Sample buffer served as negative control and a sample containing no antigen as positive control (Bmax). The plate was sealed and incubated over night (o/n) at room temperature (RT). A 384-well standard MSD array plate was coated o/n with 2 and 0.002 pg/ml of BKV-VP1 serotype I pentameric protein. After three times washing with 50 µl/well washing buffer, the plate was blocked with 50 µl/well blocking buffer for 1 hour at RT. After washing, a volume of 30 µl/well of each VLP:antibody mix was transferred from the PP MTP to the coated MSD plate and incubated for 20 min at RT. After an additional wash step, 30 µl of detection antibody (diluted 1:2000) in sample buffer was added to each well and incubated for 30 min at RT. The MSD plate was washed and 35 µl/well of read buffer was added and incubated for 5 min. ECL signals were measured with the MSD SECTOR Imager 6000.

The reagents used were: Bovine serum albumin (BSA), (VWR Cat #422351S), Phosphate-buffered saline (PBS) 10x, (Teknova Cat #P0195), MSD Read Buffer T 4x, (Meso Scale Discovery Cat #R92TC-1), Tris-buffered saline (TBS) 20x, (Teknova Cat #T1680), Tween-20, (VWR Cat #437082Q). The buffers used were; Blocking buffer: 1x PBS+5% (w/v) BSA, Coating buffer: 1x PBS, Sample buffer: 1x PBS+0.5% (w/v) BSA+0.02% (v/v) Tween-20, Wash buffer: 1x TBS+0.05% (v/v) Tween-20 and Read buffer: 1x MSD Read Buffer.

A solution equilibrium titration (SET) assay was used to determine the interaction affinities ($K_D$) of P8D11 with JCV VLPs as described in Example 5. P8D11 antibody was assayed at either 9 nM or 1 pM concentrations (constant) and JCV VLPs were serially diluted as follows: consensus VLPs ranged from 105 pg/ml-72 pg/ml, and L55F and S269F mutant VLPs both ranged from 300 pg/ml-143 pg/ml. Antibody:VP1 pentamer solution was incubated overnight, then assayed for unbound antibody using an MSD array plate (Meso Scale Discovery, Cat #L21XA, Rockville MD) coated with VP1 pentamer. The $K_D$ was determined by fitting the plot with a 1:1 fit model (according to Piehler et al. J. Immunol. Methods. 1997; 201(2):189-206). The analysis was performed by using KinExA® Pro and n-Curve Analysis softwares from Sapidyne (Boise ID).

FIG. 27 depicts the results of the SET assay in tabular form. This data provides the affinity determination ($K_D$) of P8D11 antibody to consensus JCV VLPs and VLPs containing VP1 mutations commonly associated with PML. P8D11 showed binding affinities to all JCV VLPs in the low nanomolar range. However, the binding affinity to the L55F mutant was approximately 2-fold lower than the affinity for wild type (consensus) and S269F mutant VLPs. Therefore, this indicates that the P8D11 antibody would still be an effective therapy against either wild type JC virus or JC virus with mutations commonly associated with PML.

Example 14: Deuterium Exchange Study (P8D11 Fab in Complex with BKV VP1 Pentamers) for Epitope Mapping Deuterium exchange mass spectrometry (HDx-MS) measures the deuterium uptake on the amide backbone of a protein. These measurements are sensitive to the amide's solvent accessibility and to changes in the hydrogen bonding network of the backbone amides. HDx-MS is often used to compare proteins in two different states, such as apo and ligand-bound, and coupled with rapid digestion with pepsin. In such experiments one can locate regions, typically of 10 to 15 amino acids, that show differential deuterium uptake between two different states. Regions that are protected are either directly involved in ligand binding or allosterically affected by binding of the antibody to the ligand.

In these experiments, the deuterium uptake of BKV VP1 protein (SEQ ID NO:502), was measured in the absence and presence of P8D11 Fab fragment. Regions in VP1 that show a decrease in deuterium uptake upon binding of the Fab fragment are likely to be involved in the epitope; however, due to the nature of the measurement it is also possible to detect changes remote from the direct binding site (allosteric effects). In general, the regions that have the greatest amount of protection are involved in direct binding.

The epitope mapping experiments are performed on a Waters Synapt® G2 HDx-MS platform, which includes LEAP® robot system, nanoACQUITY® UPLC System, and Synapt® G2 mass spectrometer. In this method, triplicate control experiments are carried out as follows. BKV serotype I VP1 pentamer is diluted into 110 µl of 95% deuterated PBS buffer (pH 7.4) and incubated at room temperature on a bench rotator for 25 minutes (% D=85.5%). Deuterium exchange is quenched by 1:1 dilution with cold quench buffer (6M Urea and 1M TCEP pH=2.5) on ice for 5 min. After quenching the tube is transferred onto a LEAP system (Thermo box is set at 2° C.) and the quenched sample is injected by the LEAP system onto the UPLC system for analysis. The UPLC system incorporates an immobilized pepsin column 2.1 mm×30 mm (Life Technologies 2-3131-00) that is maintained at 12° C. An 8-minute 2 to 35% acetonitrile gradient and Waters UPLC CSH C18 1.0×100 mm column is used for separation. Next, triplicate experiments are carried out using the antibody. The P8D11 Fab fragment is immobilized on Protein G agarose beads (Thermo Scientific Cat #22851) using standard techniques. Briefly, the antibody is centrifuged to remove a storage buffer. Then 200 µl of PBS buffer (pH 7.4) and a concentration of VP1 pentamers are added to the immobilized P8D11 Fab fragment and incubated for 30 min at room temperature. After incubation, the complex is centrifuged and washed with 200 µl PBS buffer and centrifuged again. For deuterium exchange, 200 µl of deuterated PBS is added to the antigen-antibody complex for incubation at room temperature for 25 minutes (% D=85.5%). Deuterium buffer is then removed, and immediately, 125 µl ice cold quench buffer is added. After quenching for 5 minutes, the column is centrifuged and the flow-through is transferred into a prechilled HPLC vial. The sample is analyzed using the same on-line pepsin digestion/LC-MS setup as the control experiment.

The results of these measurements are summarized in FIG. 28. FIG. 28 shows the baseline corrected differences between the control and P8D11 antibody bound sample divided by the standard error in the measurement. In this plot the more negative value indicates a greater amount of protection in a given region upon binding of P8D11 Fab fragment to BKV serotype I VP1 pentamer. We observe the most significant amounts of protection in amino acids 168-190 of the VP1 protein upon binding of P8D11 Fab fragment. This region of the EF loop is highly conserved across all four serotypes of BK virus and JC virus, as can be seen with the sequences bolded and underlined in Table 1 ((NYRTKYPXGTXXPKNXTXQSQVM) (SEQ ID NO:501)).

In conclusion, the deuterium mapping data indicate that P8D11 antibody binds to an epitope within the EF loop of BKV VP1. This region is highly conserved across all four BKV serotypes and JC virus, and thus supports the result that P8D11 has neutralizing activity across all four BKV serotypes and JC virus.

Example 15: Targeted Alanine Scanning and SPR for Epitope Mapping of P8D11

Biacore surface plasmon resonance (SPR) was used to characterize the binding of anti-VP1 antibodies to VP1 pentamers generated for epitope mapping by scanning alanine mutagenesis. Experiments were performed at 25° C. in phosphate buffered saline (PBS) supplemented with 0.005% Tween 20 detergent (Calbiochem #655206) and run on a Biacore T-200 instrument (GE Healthcare Life Sciences). Biotinylated protein A (Sigma #P2165) was immobilized onto a Series S streptavidin sensor chip to approximately 1200 response units (RUs) and remaining free streptavidin sites were blocked with biotin-PEG (Pierce EZ-Link #PI21346). Antibodies were captured onto the prepared protein A sensor chip with a 4 second injection at a flow rate of 30 µl/minute. Antibodies were immobilized at 20-40 RUs on flowcells 2, 3 and 4, leaving flowcell 1 as a reference cell without any antibody. VP1 pentamers were then injected over the chip for 200 seconds at 100 µl/min followed by injections of buffer to monitor dissociation. Between each pentamer and pentamer concentration, the sensor chip surface was regenerated with an injection of 25 mM NaOH for 60 seconds at 30 µl/minute to remove antibodies before re-capture of antibodies onto the protein A surfaces for the next cycle. Data analysis was done in the GE BiaEvaluation software where double reference subtraction was applied. Assessment of the effect of alanine mutagenesis on VP1 pentamer binding was achieved by comparison of the binding RU levels and shapes of the binding curves compared to those of the wildtype pentamer.

Figure 29B:
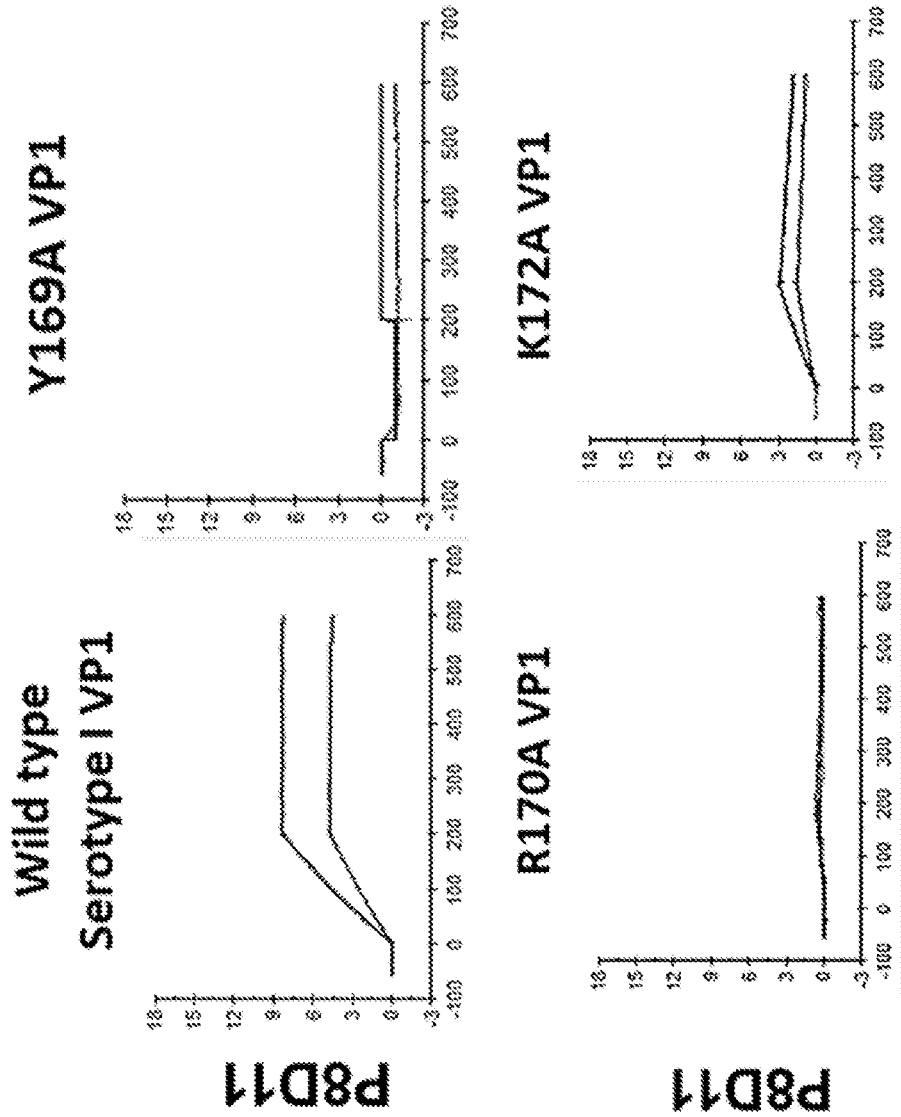

As discussed previously, the epitopes for antibodies P8D11 and P7G11A are conformational and non-contiguous (FIGS. 12A-B). Here, single mutations to alanine at Y169, R170 and K172 in the EF loop of BKV VP1 abolishes binding of P8D11 (FIGS. 29A and 29B). Mutations at Y169 and R170 also abolish binding of the P7G11A antibody, however binding of this antibody is not affected by changes at position K172 of the EF loop of BKV VP1 (FIGS. 29A and 29C).

Example 16: Epitope Mapping by X-Ray Crystallography

The crystal structure of the scFv chain of the antibody P8D11 bound to the BKV major capsid protein VP1 in its pentameric form was determined. As detailed below, a 5.5:1 solution of scFv:BKV-VP1 pentamer was used to produce a crystallographically suitable complex composed of five scFv chains bound to each pentamer. Protein crystallography was then employed to generate an atomic resolution structure and define the epitope.

Crystallization and Structure Determination

The P8D11 scFv/BKV-VP1 complex was concentrated to 5.2 mg/ml and screened for crystallization. Crystals for data collection were grown by hanging drop vapor diffusion at 18° C. Crystals were grown by mixing 1.0 µl of the complex with 1.0 µl of reservoir solution containing 25% (w/v) PEG3350, 0.2 M magnesium chloride and 0.1M Bis-Tris pH 7.0, and equilibrating the drop against 350 µl of the same reservoir solution. Crystals grew overnight and continued to grow for a few days. Before data collection, the crystals were transferred to 75% of reservoir solutions plus 25% glycerol and flash cooled in liquid nitrogen.

Diffraction data were collected in-house on a Rigaku FRE+ copper source and an R-axis X-ray detector. Data was processed and scaled using Autoproc (Global Phasing, LTD). The data of BKV-VP1 was processed to 2.66 Å in space group P42212 with cell dimensions a=224.4 Å, b=224.4 Å, c=144.04 Å, alpha=90°, beta=90°, gamma=90°. The structure of the complex was solved by molecular replacement using Phaser (McCoy et al., (2007) J. Appl. Cryst. 40:658-674) with a BKV-VP1 pentamer as the search model. The final model was built in COOT (Emsley &

Cowtan (2004) Acta Cryst. D60:2126-2132) and refined with Buster (Global Phasing, LTD, Cambridge, UK). The Rwork and Rfree values are 17.1% and 21.4%, respectively; and root-mean-square (r.m.s) deviation values of bond lengths and bond angles are 0.010 Å and 1.18°, respectively.

Figure 31B:
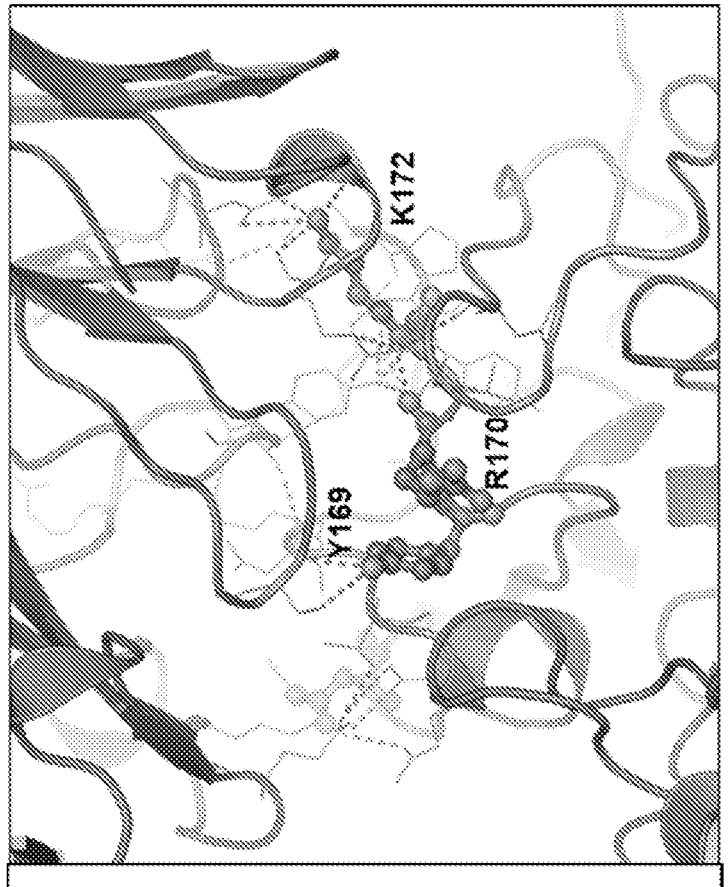
FIG. 31A-B is a graphical representation of how P8D11 contacts the residues of the VP1 pentamer.
Figure 31A:
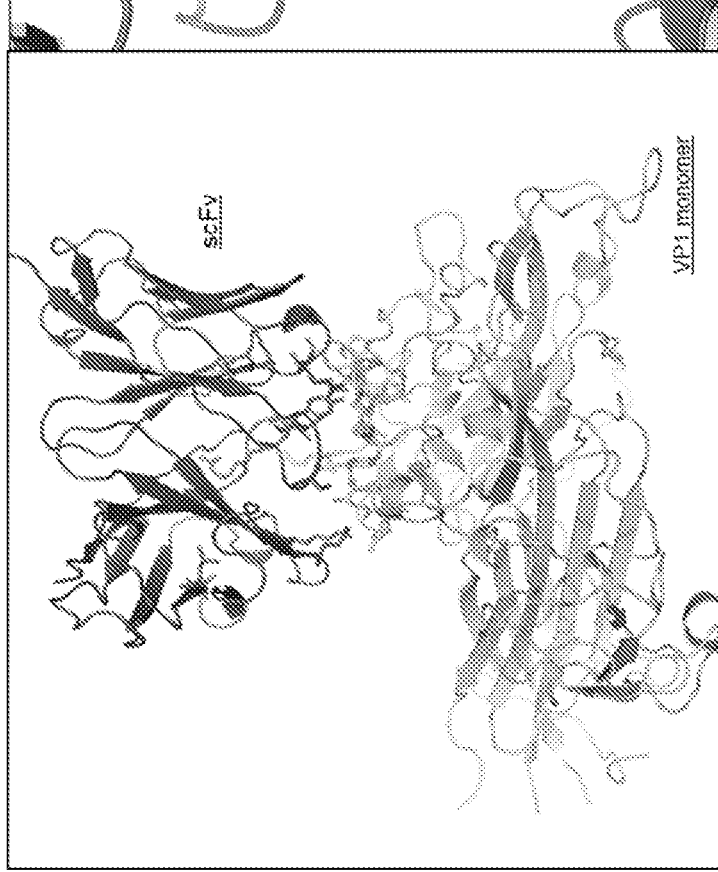

Residues of BKV-VP1-Pentamer that are in contact with the P8D11 scFv, the types of interactions, and the buried surface areas are all identified by PISA (Krissinel et al., (2007) J Mol Biol. 372:774-97) and listed in Table 6 below. It was found the each monomer of the VP1-pentamer contains a single isolated epitope for the P8D11 antibody. Thus five scFv domains bind to each pentamer at five chemically and sterically equivalent positions. Details for the interactions at each epitope are essentially identical so that only one scFv/VP1-epitope interface is analyzed here.

detailed in Table 6. These residues form the three-dimensional conformational epitope that is recognized by the P8D11-scFv (FIG. 31A-B). This epitope defined by crystallography is in good agreement with that defined by hydrogen deuterium exchange mass spectrometry (HDx-MS), in which residues 168-190 are substantially protected by P8D11-Fab (FIG. 28). There is also good agreement with the Alanine scan that was done on the key amino acids of the epitope (FIG. 29A-C) which showed that TYR169, ARG170 and LYS172 are contact residues which are part of the epitope of the P8D11 antibody.

P8D11-scFv epitope on BKV-VP1. All residues of BKV-VP1 that are in contact with P8D11-scFv in the crystal structure are identified by PISA, listed and sorted by their buried surface area by P8D11-scFv. Types of interaction are also listed where applicable.

TABLE 6

| Anti-VP1 scFv residue | Hydrogen bond | Salt Bridge | ASA* | BSA* | VP1 Pentamer residue | Hydrogen bond | Salt Bridge | ASA* | BSA* |
|---|---|---|---|---|---|---|---|---|---|
| ASN31 | 0 | 0 | 72.36 | 1.11 | SER77 | 1 | 0 | 74.90 | 25.99 |
| TYR32 | 0 | 0 | 60.89 | 6.59 | SER78 | 0 | 0 | 73.45 | 46.46 |
| TRP33 | 0 | 0 | 42.56 | 39.19 | ASP79 | 1 | 0 | 36.90 | 2.33 |
| LYS52 | 2 | 0 | 66.84 | 59.49 | SER80 | 0 | 0 | 63.82 | 20.03 |
| LYS53 | 0 | 1 | 89.76 | 40.27 | TYR169 | 2 | 0 | 66.99 | 44.33 |
| ASP54 | 0 | 0 | 100.58 | 3.42 | ARG170 | 1 | 0 | 117.97 | 54.91 |
| SER56 | 0 | 0 | 78.38 | 5.60 | THR171 | 1 | 0 | 12.44 | 9.58 |
| GLU57 | 2 | 0 | 63.29 | 46.19 | LYS172 | 2 | 2 | 142.87 | 121.15 |
| TRY59 | 0 | 0 | 55.86 | 13.29 | TYR173 | 3 | 0 | 33.81 | 24.25 |
| VAL99 | 0 | 0 | 19.54 | 17.42 | PRO174 | 1 | 0 | 27.18 | 4.61 |
| ARG100 | 1 | 0 | 97.42 | 14.49 | GLU175 | 1 | 0 | 165.93 | 61.70 |
| GLY102 | 1 | 0 | 45.24 | 23.46 | GLY176 | 0 | 0 | 30.62 | 0.58 |
| ARG103 | 5 | 0 | 190.68 | 157.62 | THR177 | 1 | 0 | 21.14 | 13.74 |
| TYR104 | 4 | 0 | 68.25 | 63.79 | ILE178 | 0 | 0 | 63.25 | 0.67 |
| PHE105 | 0 | 0 | 37.94 | 32.69 | THR179 | 2 | 0 | 29.52 | 22.67 |
| ASN526 | 0 | 0 | 84.174 | 16.28 | PRO180 | 0 | 0 | 11.34 | 7.66 |
| GLY528 | 1 | 0 | 27.52 | 11.48 | LYS181 | 2 | 0 | 164.73 | 85.21 |
| SER529 | 0 | 0 | 62.31 | 55.68 | ASN182 | 1 | 0 | 111.76 | 104.95 |
| ARG530 | 4 | 0 | 83.56 | 70.86 | PRO183 | 0 | 0 | 50.84 | 49.34 |
| PRO531 | 0 | 0 | 14.77 | 13.77 | THR184 | 1 | 0 | 67.62 | 67.45 |
| ASP549 | 0 | 0 | 21.15 | 4.11 | ALA185 | 0 | 0 | 61.12 | 6.85 |
| ASP550 | 0 | 2 | 37.36 | 16.62 | GLN186 | 1 | 0 | 103.62 | 42.67 |
| SER551 | 0 | 0 | 68.46 | 11.52 | ASN191 | 2 | 0 | 13.15 | 12.56 |
| ASN552 | 1 | 0 | 65.13 | 28.37 | THR192 | 0 | 0 | 89.19 | 1.87 |
| TRP590 | 0 | 0 | 51.46 | 50.45 | ASP193 | 0 | 1 | 123.11 | 71.49 |
| SER591 | 0 | 0 | 40.49 | 16.66 | | | | | |
| SER592 | 0 | 0 | 51.90 | 25.61 | | | | | |
| SER593 | 2 | 0 | 45.01 | 33.37 | | | | | |

*ASA: Accessible Surface Area
*BSA: Buried Surface Area

Epitopes of P8D11-scFv on BKV-VP1
Overall Structure

Figure 30:
FIG. 30 is an X-ray crystal structure of P8D11 in complex with BKV VP1 pentamer.

The overall folding of each polyomavirus VP1-pentmer structure is highly homologous at the level of tertiary structure. Primary sequences are well conserved with identity as at 69-85%. Each pentamer is composed of five monomers, each of which is composed by a three-strand β sheet stacking against another five-strand β sheet and then a four-strand β sheet. The P8D11 scFv is a VH-VL fusion protein with a 20 amino acid linker between VH and VL domains. As shown in FIG. 30, the VH-VL fusion protein binds to an epitope located on the lateral, exterior surface of the BKV-VP1-pentamer.

Epitope of P8D11

The crystal structure of the BKV-VP1/P8D11 complex is used to identify the P8D11 epitope on BKV-VP1. The interaction surface on VP1 by P8D11-scFv is formed by several continuous and discontinuous (i.e. noncontiguous) sequences: namely residues 77-80, 169-186, and 191-192, as Example 18: Formulation The anti-VP1 antibodies described herein are monoclonal antibodies, IgG1 isotype with lambda light chain, and can be lyophilized. These antibodies are soluble and stable in a histidine-sucrose formulation buffer for 4 weeks. In addition, anti-VP1 antibodies were soluble at >200 mg/ml as minimally formulated drug substance (e.g., in histidine buffer in the absence of stabilizers).

For subsequent intravenous administration, the obtained solution will usually be further diluted into a carrier solution to the ready-to-use antibody solution for infusion.

Important stability-indicating analytical methods to select the most stable formulation encompassed, amongst others, size-exclusion chromatography to determine aggregation levels, subvisible particulate matter testing, and potency testing.

It is understood that the examples and aspects described herein are for illustrative purposes only and that various

```
                                SEQUENCE LISTING

Sequence total quantity: 543
SEQ ID NO: 1            moltype = AA  length = 362
FEATURE                 Location/Qualifiers
source                  1..362
                        mol_type = protein
                        note = Polyomavirus sp.
                        organism = unidentified
SEQUENCE: 1
MAPTKRKGEC PGAAPKKPKE PVQVPKLLIK GGVEVLEVKT GVDAITEVEC FLNPEMGDPD  60
ENLRGFSLKL SAENDFSSDS PERKMLPCYS TARIPLPNLN EDLTCGNLLM WEAVTVQTEV 120
IGITSMLNLH AGSQKVHEHG GGKPIQGSNF HFFAVGGDPL EMQGVLMNYR TKYPEGTITP 180
KNPTAQSQVM NTDHKAYLDK NNAYPVECWI PDPSRNENTR YFGTFTGGEN VPPVLHVTNT 240
ATTVLLDEQG VGPLCKADSL YVSAADICGL FTNSSGTQQW RGLARYFKIR LRKRSVKNPY 300
PISFLLSDLI NRRTQRVDGQ PMYGMESQVE EVRVFDGTER LPGDPDMIRY IDKQGQLQTK 360
ML                                                                362

SEQ ID NO: 2            moltype = AA  length = 362
FEATURE                 Location/Qualifiers
source                  1..362
                        mol_type = protein
                        note = Polyomavirus sp.
                        organism = unidentified
SEQUENCE: 2
MAPTKRKGEC PGAAPKKPKE PVQVPKLLIK GGVEVLEVKT GVDAITEVEC FLNPEMGDPD  60
DNLRGYSLKL TAENAFDSDS PDKKMLPCYS TARIPLPNLN EDLTCGNLLM WEAVTVKTEV 120
IGITSMLNLH AGSQKVHENG GGKPVQGSNF HFFAVGGDPL EMQGVLMNYR TKYPQGTITP 180
KNPTAQSQVM NTDHKAYLDK NNAYPVECWI PDPSRNENTR YFGTYTGGEN VPPVLHVTNT 240
ATTVLLDEQG VGPLCKADSL YVSAADICGL FTNSSGTQQW RGLARYFKIR LRKRSVKNPY 300
PISFLLSDLI NRRTQKVDGQ PMYGMESQVE EVRVFDGTEQ LPGDPDMIRY IDRQGQLQTK 360
MV                                                                362

SEQ ID NO: 3            moltype = AA  length = 362
FEATURE                 Location/Qualifiers
source                  1..362
                        mol_type = protein
                        note = Polyomavirus sp.
                        organism = unidentified
SEQUENCE: 3
MAPTKRKGEC PGAAPKKPKE PVQVPKLLIK GGVEVLEVKT GVDAITEVEC FLNPEMGDPD  60
DHLRGYSQHL SAENAFDSDS PDKKMLPCYS TARIPLPNLN EDLTCGNLLM WEAVTVKTEV 120
IGITSMLNLH AGSQKVHENG GGKPVQGSNF HFFAVGGDPL EMQGVLMNYR TKYPQGTITP 180
KNPTAQSQVM NTDHKAYLDK NNAYPVECWI PDPSKNENTR YFGTYTGGEN VPPVLHVTNT 240
ATTVLLDEQG VGPLCKADSL YVSAADICGL FTNSSGTQQW RGLARYFKIR LRKRSVKNPY 300
PISFLLSDLI NRRTQKVDGQ PMYGMESQVE EVRVFDGTEQ LPGDPDMIRY IDRQGQLQTK 360
MV                                                                362

SEQ ID NO: 4            moltype = AA  length = 362
FEATURE                 Location/Qualifiers
source                  1..362
                        mol_type = protein
                        note = Polyomavirus sp.
                        organism = unidentified
SEQUENCE: 4
MAPTKRKGEC PGAAPKKPKE PVQVPKLLIK GGVEVLEVKT GVDAITEVEC FLNPEMGDPD  60
NDLRGYSLRL TAETAFDSDS PDRKMLPCYS TARIPLPNLN EDLTCGNLLM WEAVTVKTEV 120
IGITSMLNLH AGSQKVHENG GGKPIQGSNF HFFAVGGDPL EMQGVLMNYR TKYPEGTVTP 180
KNPTAQSQVM NTDHKAYLDK NNAYPVECWI PDPSRNENTR YFGTYTGGEN VPPVLHVTNT 240
ATTVLLDEQG VGPLCKADSL YVSAADICGL FTNSSGTQQW RGLPRYFKIR LRKRSVKNPY 300
PISFLLSDLI NRRTQRVDGQ PMYGMESQVE EVRVFDGTEQ LPGDPDMIRY IDRQGQLQTK 360
MV                                                                362

SEQ ID NO: 5            moltype = AA  length = 354
FEATURE                 Location/Qualifiers
source                  1..354
                        mol_type = protein
                        note = Orthopolyomavirus sp.
                        organism = unidentified
SEQUENCE: 5
MAPTKRKGER KDPVQVPKLL IRGGVEVLEV KTGVDSITEV ECFLTPEMGD PDEHLRGFSK  60
SISISDTFES DSPNKDMLPC YSVARIPLPN LNEDLTCGNI LMWEAVTLKT EVIGVTTLMN 120
VHSNGQATHD NGAGKPVQGT SFHFFSVGGE ALELQGVVFN YRTKYPDGTI FPKNATVQSQ 180
VMNTEHKAYL DKNKAYPVEC WVPDPTRNEN TRYFGTLTGG ENVPPVLHIT NTATTVLLDE 240
```

```
FGVGPLCKGD NLYLSAVDVC GMFTNRSGSQ QWRGLSRYFK VQLRKRRVKN PYPISFLLTD   300
LINRRTPRVD GQPMYGMDAQ VEEVRVFEGT EELPGDPDMM RYVDRYGQLQ TKML         354

SEQ ID NO: 6           moltype = AA  length = 5
FEATURE                Location/Qualifiers
source                 1..5
                       mol_type = protein
                       organism = synthetic construct
SEQUENCE: 6
NYWMT                                                               5

SEQ ID NO: 7           moltype = AA  length = 17
FEATURE                Location/Qualifiers
source                 1..17
                       mol_type = protein
                       organism = synthetic construct
SEQUENCE: 7
NIKKDGSEKY YVDSVRG                                                  17

SEQ ID NO: 8           moltype = AA  length = 11
FEATURE                Location/Qualifiers
source                 1..11
                       mol_type = protein
                       organism = synthetic construct
SEQUENCE: 8
VRSGRYFALD D                                                        11

SEQ ID NO: 9           moltype = AA  length = 7
FEATURE                Location/Qualifiers
source                 1..7
                       mol_type = protein
                       organism = synthetic construct
SEQUENCE: 9
GFTFNNY                                                             7

SEQ ID NO: 10          moltype = AA  length = 6
FEATURE                Location/Qualifiers
source                 1..6
                       mol_type = protein
                       organism = synthetic construct
SEQUENCE: 10
KKDGSE                                                              6

SEQ ID NO: 11          moltype = AA  length = 11
FEATURE                Location/Qualifiers
source                 1..11
                       mol_type = protein
                       organism = synthetic construct
SEQUENCE: 11
VRSGRYFALD D                                                        11

SEQ ID NO: 12          moltype = AA  length = 120
FEATURE                Location/Qualifiers
source                 1..120
                       mol_type = protein
                       organism = synthetic construct
SEQUENCE: 12
QVQLVESGGT LVQPGGSLRL SCAASGFTFN NYWMTWVRQA PGKGLEWVAN IKKDGSEKYY   60
VDSVRGRFTI SRDNAKNSLF LQMNSLRPED TAVYFCATVR SGRYFALDDW GQGTLVTVSS  120

SEQ ID NO: 13          moltype = DNA  length = 360
FEATURE                Location/Qualifiers
misc_feature           1..360
                       note = source = /note=Description of synthetic construct:
                        Synthetic polynucleotide
source                 1..360
                       mol_type = other DNA
                       organism = synthetic construct
SEQUENCE: 13
caggtgcagc tggtggaatc aggcggcaca ctggtgcagc ctggcggtag cctgagactg   60
agctgcgctg ctagtggctt cacctttaac aactactgga tgacctgggt taggcaggcc  120
cctggtaaag gcctcgagtg ggtggcaaat atcaagaagg acgtagcga aagtactac    180
gtggactcag tcagaggccg gttcactatc tctaggata acgctaagaa tagcctgttc   240
ctgcagatga actcactgag ccccgaggat accgccgtct acttctgtgc taccgtcaga  300
tcaggccgct acttcgccct ggacgactgg ggtcaaggca cactggtcac cgtgtctagc  360

SEQ ID NO: 14          moltype = AA  length = 450
FEATURE                Location/Qualifiers
source                 1..450
```

```
                        mol_type = protein
                        organism = synthetic construct
SEQUENCE: 14
QVQLVESGGT LVQPGGSLRL SCAASGFTFN NYWMTWVRQA PGKGLEWVAN IKKDGSEKYY    60
VDSVRGRFTI SRDNAKNSLF LQMNSLRPED TAVYFCATVR SGRYFALDDW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKRVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 15           moltype = DNA   length = 1350
FEATURE                 Location/Qualifiers
misc_feature            1..1350
                        note = source = /note=Description of synthetic construct:
                         Synthetic polynucleotide
source                  1..1350
                        mol_type = other DNA
                        organism = synthetic construct
SEQUENCE: 15
caggtgcagc tggtggaatc aggcggcaca ctggtgcagc ctggcggtag cctgagactg    60
agctgcgctg ctagtggctt caccttaac aactactgga tgacctgggt taggcaggcc   120
cctggtaaag gcctcgagtg ggtggcaaat atcaagaagg acgtagcga gaagtactac   180
gtggactcag tcagaggccg gttcactatc tctagggata cgctaagaa tagcctgttc   240
ctgcagatga actcactgag gcccgaggat accgccgtct acttctgtgc taccgtcaga   300
tcaggccgct acttcgccct ggacgactgg ggtcaaggca cactggtcac cgtgtctagc   360
gctagcacta agggcccaag tgtgtttccc ctggccccca gcagcaagtc tacttccggc   420
ggaactgctg ccctgggttg cctggtgaag gactacttcc ccgagcccgt gacagtgtcc   480
tggaactgtg gggctctgac ttccggcgtg cacaccttcc ccgccgtgct gcagagcagc   540
ggcctgtaca gcctgagcag cgtggtgaca gtgccctcca gctctctggg aacccagacc   600
tatatctgca acgtgaacca caagcccagc aacaccaagg tggacaagag agtggagccc   660
aagagctgcg acaagaccca cacctgcccc cctgcccag ctccagaact gctgggaggg   720
cctccgtgt tcctgttccc ccccaagccc aaggacaccc tgatgatcag caggaccccc   780
gaggtgacct gcgtggtggt ggacgtgtcc cacgaggacc cagaggtgaa gttcaactgg   840
tacgtggacg gcgtggaggt gcacaacgcc aagaccaagc ccagagagga gcagtacaac   900
agcacctaca gggtggtgtc cgtgctgacc gtgctgcacc aggactggct gaacggcaaa   960
gaatacaagt gcaaagtctc caacaaggcc ctgccagccc caatcgaaaa gacaatcagc  1020
aaggccaagg gccagccacg ggagccccag gtgtacaccc tgcccccag ccggagggag  1080
atgaccaaga accaggtgtc cctgacctgt ctggtgaagg gcttctaccc cagcgatatc  1140
gccgtggagt gggagagcaa cggccagccc gagaacaact acaagaccac ccccccagtg  1200
ctggacagca cgcagcttt cttcctgtac agcaagctga ccgtggacaa gtccaggtgg  1260
cagcagggca acgtgttcag ctgcagcgtg atgcacgagg ccctgcacaa ccactacacc  1320
cagaagtccc tgagcctgag ccccggcaag                                  1350

SEQ ID NO: 16           moltype = AA   length = 11
FEATURE                 Location/Qualifiers
source                  1..11
                        mol_type = protein
                        organism = synthetic construct
SEQUENCE: 16
GGDNIGSRPV H                                                        11

SEQ ID NO: 17           moltype = AA   length = 7
FEATURE                 Location/Qualifiers
source                  1..7
                        mol_type = protein
                        organism = synthetic construct
SEQUENCE: 17
DDSNRPS                                                              7

SEQ ID NO: 18           moltype = AA   length = 10
FEATURE                 Location/Qualifiers
source                  1..10
                        mol_type = protein
                        organism = synthetic construct
SEQUENCE: 18
QVWSSSTDHP                                                          10

SEQ ID NO: 19           moltype = AA   length = 7
FEATURE                 Location/Qualifiers
source                  1..7
                        mol_type = protein
                        organism = synthetic construct
SEQUENCE: 19
DNIGSRP                                                              7

SEQ ID NO: 20           moltype =    length =
SEQUENCE: 20
```

```
SEQ ID NO: 21            moltype = AA   length = 7
FEATURE                  Location/Qualifiers
source                   1..7
                         mol_type = protein
                         organism = synthetic construct
SEQUENCE: 21
WSSSTDH                                                                  7

SEQ ID NO: 22            moltype = AA   length = 107
FEATURE                  Location/Qualifiers
source                   1..107
                         mol_type = protein
                         organism = synthetic construct
SEQUENCE: 22
QSVLTQPPSV SVAPGKTARI TCGGDNIGSR PVHWYQQKPG QAPILVVYDD SNRPSGIPER         60
FSGSNSGNTA TLTISRVEAG DEADYYCQVW SSSTDHPFGG GTKVTVL                     107

SEQ ID NO: 23            moltype = DNA   length = 321
FEATURE                  Location/Qualifiers
misc_feature             1..321
                         note = source = /note=Description of synthetic construct:
                         Synthetic polynucleotide
source                   1..321
                         mol_type = other DNA
                         organism = synthetic construct
SEQUENCE: 23
cagtcagtcc tgactcagcc ccctagcgtc agcgtggccc ctggtaaaac cgctagaatc         60
acctgtggcg gcgataatat cggctctagg cccgtgcact ggtatcagca gaagcccggt        120
caagccccta tcctggtggt ctacgacgac tctaatagac ctagcggaat ccccgagcgg        180
tttagcggct ctaattctgg taataccgct accctgacta tctctagggt ggaagccggc        240
gacgaggccg actactactg tcaagtctgg tctagctcta ccgatcaccc cttcggcgga        300
ggcactaagg ttacagtgct g                                                  321

SEQ ID NO: 24            moltype = AA   length = 213
FEATURE                  Location/Qualifiers
source                   1..213
                         mol_type = protein
                         organism = synthetic construct
SEQUENCE: 24
QSVLTQPPSV SVAPGKTARI TCGGDNIGSR PVHWYQQKPG QAPILVVYDD SNRPSGIPER         60
FSGSNSGNTA TLTISRVEAG DEADYYCQVW SSSTDHPFGG GTKVTVLGQP KAAPSVTLFP        120
PSSEELQANK ATLVCLISDF YPGAVTVAWK ADSSPVKAGV ETTTPSKQSN NKYAASSYLS        180
LTPEQWKSHR SYSCQVTHEG STVEKTVAPT ECS                                    213

SEQ ID NO: 25            moltype = DNA   length = 639
FEATURE                  Location/Qualifiers
misc_feature             1..639
                         note = source = /note=Description of synthetic construct:
                         Synthetic polynucleotide
source                   1..639
                         mol_type = other DNA
                         organism = synthetic construct
SEQUENCE: 25
cagtcagtcc tgactcagcc ccctagcgtc agcgtggccc ctggtaaaac cgctagaatc         60
acctgtggcg gcgataatat cggctctagg cccgtgcact ggtatcagca gaagcccggt        120
caagccccta tcctggtggt ctacgacgac tctaatagac ctagcggaat ccccgagcgg        180
tttagcggct ctaattctgg taataccgct accctgacta tctctagggt ggaagccggc        240
gacgaggccg actactactg tcaagtctgg tctagctcta ccgatcaccc cttcggcgga        300
ggcactaagg ttacagtgct gggtcaacct aaggctgccc cagcgtgac cctgttcccc         360
ccagcagcg aggagctgca ggccaacaag gccaccctgg tgtgcctgat cagcgacttc        420
tacccaggcg ccgtgaccgt ggcctggaag gccgacagca gccccgtgaa ggccggcgtg       480
gagaccacca ccccccagcaa gcagaccaac aacaagtacg ccgccagcag ctacctgagc      540
ctgacccccg agcagtggaa gagccacagg tcctacagct gccaggtgac ccacgagggc      600
agcaccgtgg aaaagaccgt ggccccaacc gagtgcagc                             639

SEQ ID NO: 26            moltype = AA   length = 5
FEATURE                  Location/Qualifiers
REGION                   1..5
                         note = source = /note=Description of synthetic construct:
                         Synthetic peptide
source                   1..5
                         mol_type = protein
                         organism = synthetic construct
SEQUENCE: 26
NYWMT                                                                    5

SEQ ID NO: 27            moltype = AA   length = 17
```

```
FEATURE                 Location/Qualifiers
source                  1..17
                        mol_type = protein
                        organism = synthetic construct
SEQUENCE: 27
NIKKDGSEKY YVDSVRG                                                           17

SEQ ID NO: 28           moltype = AA   length = 11
FEATURE                 Location/Qualifiers
source                  1..11
                        mol_type = protein
                        organism = synthetic construct
SEQUENCE: 28
VRSGRYFALD D                                                                 11

SEQ ID NO: 29           moltype = AA   length = 7
FEATURE                 Location/Qualifiers
source                  1..7
                        mol_type = protein
                        organism = synthetic construct
SEQUENCE: 29
GFTFSNY                                                                       7

SEQ ID NO: 30           moltype = AA   length = 6
FEATURE                 Location/Qualifiers
source                  1..6
                        mol_type = protein
                        organism = synthetic construct
SEQUENCE: 30
KKDGSE                                                                        6

SEQ ID NO: 31           moltype = AA   length = 11
FEATURE                 Location/Qualifiers
source                  1..11
                        mol_type = protein
                        organism = synthetic construct
SEQUENCE: 31
VRSGRYFALD D                                                                 11

SEQ ID NO: 32           moltype = AA   length = 120
FEATURE                 Location/Qualifiers
source                  1..120
                        mol_type = protein
                        organism = synthetic construct
SEQUENCE: 32
QVQLVESGGT LVQPGGSLRL SCAASGFTFS NYWMTWVRQA PGKGLEWVAN IKKDGSEKYY             60
VDSVRGRFTI SRDNAKNSLF LQMNSLRPED TAVYFCATVR SGRYFALDDW GQGTLVTVSS            120

SEQ ID NO: 33           moltype = DNA   length = 360
FEATURE                 Location/Qualifiers
misc_feature            1..360
                        note = source = /note=Description of synthetic construct:
                            Synthetic polynucleotide
source                  1..360
                        mol_type = other DNA
                        organism = synthetic construct
SEQUENCE: 33
caggtgcagc tggtggaatc aggcggcaca ctggtgcagc ctggcggtag cctgagactg             60
agctgcgctg ctagtggctt caccttctct aactactgga tgacctgggt caggcaggcc           120
cctggtaaag gcctcgagtg ggttggcaaat atcaagaagg acggtagcga agtactac            180
gtggactcag tcagaggccg gttcactatc tctagggata cgctaagaa tagcctgttc            240
ctgcagatga actcactgag gcccgaggat accgccgtct acttctgtgc taccgtcaga           300
tcaggccgct acttcgccct ggacgactgg ggtcaaggca cactggtcac cgtgtctagc           360

SEQ ID NO: 34           moltype = AA   length = 450
FEATURE                 Location/Qualifiers
source                  1..450
                        mol_type = protein
                        organism = synthetic construct
SEQUENCE: 34
QVQLVESGGT LVQPGGSLRL SCAASGFTFS NYWMTWVRQA PGKGLEWVAN IKKDGSEKYY             60
VDSVRGRFTI SRDNAKNSLF LQMNSLRPED TAVYFCATVR SGRYFALDDW GQGTLVTVSS            120
ASTKGPSVFP LAPSSKSTSG GTAALGCLVK DYFPEPVTVS WNSGALTSGV HTFPAVLQSS            180
GLYSLSSVVT VPSSSLGTQT YICNVNHKPS NTKVDKRVEP KSCDKTHTCP PCPAPELLGG            240
PSVFLFPPKP KDTLMISRTP EVTCVVVDVS HEDPEVKFNW YVDGVEVHNA KTKPREEQYN            300
STYRVVSVLT VLHQDWLNGK EYKCKVSNKA LPAPIEKTIS KAKGQPREPQ VYTLPPSREE            360
MTKNQVSLTC LVKGFYPSDI AVEWESNGQP ENNYKTTPPV LDSDGSFFLY SKLTVDKSRW            420
QQGNVFSCSV MHEALHNHYT QKSLSLSPGK                                             450
```

-continued

```
SEQ ID NO: 35          moltype = DNA  length = 1350
FEATURE                Location/Qualifiers
misc_feature           1..1350
                       note = source = /note=Description of synthetic construct:
                       Synthetic polynucleotide
source                 1..1350
                       mol_type = other DNA
                       organism = synthetic construct
SEQUENCE: 35
caggtgcagc tggtggaatc aggcggcaca ctggtgcagc ctggcggtag cctgagactg   60
agctgcgctg ctagtggctt caccttctct aactactgga tgacctgggt caggcaggcc  120
cctggtaaag gcctcgagtg ggtggcaaat atcaagaagg acgtagcga aagtactac    180
gtggactcag tcagaggccg gttcactatc tctaggata acgctaagaa tagcctgttc   240
ctgcagatga actcactgag gcccgaggat accgccgtct acttctgtgc taccgtcaga  300
tcaggccgct acttcgccct ggacgactgg ggtcaaggca cactggtcac cgtgtctagc  360
gctagcacta agggcccaag tgtgtttccc ctggccccca gcagcaagtc tacttccggc  420
ggaactgctg ccctgggttg cctggtgaag gactacttcc ccgagcccgt gacagtgtcc  480
tggaactctg gggctctgac ttccggcgtg cacaccttcc ccgccgtgct gcagagcagc  540
ggcctgtaca gcctgagcag cgtggtgaca gtgccctcca gctctctggg aacccagacc  600
tatatctgca acgtgaacca caagcccagc aacaccaagg tggacaagag agtggagccc  660
aagagctgcg acaagaccca cacctgcccc cctgcccag  ctccagaact gctgggaggg  720
ccttccgtgt tcctgttccc ccccaagccc aaggacaccc tgatgatcag caggaccccc  780
gaggtgacct gcgtggtggt ggacgtgtcc cacgaggacc cagaggtgaa gttcaactgg  840
tacgtggacg gcgtggaggt gcacaacgcc aagaccaagc cagagagga gcagtacaac  900
agcacctaca gggtggtgtc cgtgctgacc gtgctgcacc aggactggct gaacggcaaa  960
gaatacaagt gcaaagtctc caacaaggcc ctgccagccc aatcgaaaa gacaatcagc 1020
aaggccaagg gccagccacg ggagcccag  gtgtacaccc tgcccccag  ccggaggag  1080
atgaccaaga accaggtgtc cctgacctgt ctggtgaagg gcttctaccc cagcgatatc 1140
gccgtggagt gggagagcaa cggccagccc gagaacaact acaagaccac cccccagtg  1200
ctggacagcg acggcagctt cttcctgtac agcaagctga ccgtggacaa gtccaggtgg 1260
cagcagggca acgtgttcag ctgcagcgtg atgcacgagg ccctgcacaa ccactacacc 1320
cagaagtccc tgagcctgag ccccggcaag                                  1350

SEQ ID NO: 36          moltype = AA  length = 11
FEATURE                Location/Qualifiers
source                 1..11
                       mol_type = protein
                       organism = synthetic construct
SEQUENCE: 36
GGDNIGSRPV H                                                       11

SEQ ID NO: 37          moltype = AA  length = 7
FEATURE                Location/Qualifiers
source                 1..7
                       mol_type = protein
                       organism = synthetic construct
SEQUENCE: 37
DDSNRPS                                                             7

SEQ ID NO: 38          moltype = AA  length = 10
FEATURE                Location/Qualifiers
source                 1..10
                       mol_type = protein
                       organism = synthetic construct
SEQUENCE: 38
QVWSSSTDHP                                                         10

SEQ ID NO: 39          moltype = AA  length = 7
FEATURE                Location/Qualifiers
source                 1..7
                       mol_type = protein
                       organism = synthetic construct
SEQUENCE: 39
DNIGSRP                                                             7

SEQ ID NO: 40          moltype =   length =
SEQUENCE: 40
000

SEQ ID NO: 41          moltype = AA  length = 7
FEATURE                Location/Qualifiers
source                 1..7
                       mol_type = protein
                       organism = synthetic construct
SEQUENCE: 41
WSSSTDH                                                             7

SEQ ID NO: 42          moltype = AA  length = 107
FEATURE                Location/Qualifiers
```

```
source                          1..107
                                mol_type = protein
                                organism = synthetic construct
SEQUENCE: 42
QSVLTQPPSV SVAPGKTARI TCGGDNIGSR PVHWYQQKPG QAPILVVYDD SNRPSGIPER    60
FSGSNSGNTA TLTISRVEAG DEADYYCQVW SSSTDHPFGG GTKVTVL                 107

SEQ ID NO: 43                   moltype = DNA  length = 321
FEATURE                         Location/Qualifiers
misc_feature                    1..321
                                note = source = /note=Description of synthetic construct:
                                   Synthetic polynucleotide
source                          1..321
                                mol_type = other DNA
                                organism = synthetic construct
SEQUENCE: 43
cagtcagtcc tgactcagcc ccctagcgtc agcgtggccc ctggtaaaac cgctagaatc    60
acctgtggcg gcgataatat cggctctagg cccgtgcact ggtatcagca gaagcccggt   120
caagccccta tcctggtggt ctacgacgac tctaatagac ctagcggaat ccccgagcgg   180
tttagcggct ctaattctgg taataccgct accctgacta tctctagggt ggaagccggc   240
gacgaggccg actactactg tcaagtctgg tctagctcta ccgatcaccc cttcggcgga   300
ggcactaagg ttacagtgct g                                             321

SEQ ID NO: 44                   moltype = AA  length = 213
FEATURE                         Location/Qualifiers
source                          1..213
                                mol_type = protein
                                organism = synthetic construct
SEQUENCE: 44
QSVLTQPPSV SVAPGKTARI TCGGDNIGSR PVHWYQQKPG QAPILVVYDD SNRPSGIPER    60
FSGSNSGNTA TLTISRVEAG DEADYYCQVW SSSTDHPFGG GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                                213

SEQ ID NO: 45                   moltype = DNA  length = 639
FEATURE                         Location/Qualifiers
misc_feature                    1..639
                                note = source = /note=Description of synthetic construct:
                                   Synthetic polynucleotide
source                          1..639
                                mol_type = other DNA
                                organism = synthetic construct
SEQUENCE: 45
cagtcagtcc tgactcagcc ccctagcgtc agcgtggccc ctggtaaaac cgctagaatc    60
acctgtggcg gcgataatat cggctctagg cccgtgcact ggtatcagca gaagcccggt   120
caagccccta tcctggtggt ctacgacgac tctaatagac ctagcggaat ccccgagcgg   180
tttagcggct ctaattctgg taataccgct accctgacta tctctagggt ggaagccggc   240
gacgaggccg actactactg tcaagtctgg tctagctcta ccgatcaccc cttcggcgga   300
ggcactaagg ttacagtgct gggtcaacct aaggctgccc cagcgtgac cctgttcccc    360
cccagcagcg aggagctgca ggccaacaag gccaccctgg tgtgcctgat cagcgacttc   420
tacccaggcg ccgtgaccgt ggcctggaag gccgacagca gccccgtgaa ggccggcgtg   480
gagaccacca cccccagcaa gcagagcaac aacaagtacg ccgccagcag ctacctgagc   540
ctgacccccg agcagtggaa gagccacagg tcctacagct gccaggtgac ccacgagggc   600
agcaccgtgg aaaagaccgt ggccccaacc gagtgcagc                          639

SEQ ID NO: 46                   moltype = AA  length = 5
FEATURE                         Location/Qualifiers
source                          1..5
                                mol_type = protein
                                organism = synthetic construct
SEQUENCE: 46
NYWMT                                                                 5

SEQ ID NO: 47                   moltype = AA  length = 17
FEATURE                         Location/Qualifiers
source                          1..17
                                mol_type = protein
                                organism = synthetic construct
SEQUENCE: 47
NIKKDGSEKY YVDSVRG                                                   17

SEQ ID NO: 48                   moltype = AA  length = 11
FEATURE                         Location/Qualifiers
source                          1..11
                                mol_type = protein
                                organism = synthetic construct
SEQUENCE: 48
VRSGRYFALD D                                                         11
```

```
SEQ ID NO: 49            moltype = AA   length = 7
FEATURE                  Location/Qualifiers
source                   1..7
                         mol_type = protein
                         organism = synthetic construct
SEQUENCE: 49
GFTFKNY                                                                  7

SEQ ID NO: 50            moltype = AA   length = 6
FEATURE                  Location/Qualifiers
source                   1..6
                         mol_type = protein
                         organism = synthetic construct
SEQUENCE: 50
KKDGSE                                                                   6

SEQ ID NO: 51            moltype = AA   length = 11
FEATURE                  Location/Qualifiers
source                   1..11
                         mol_type = protein
                         organism = synthetic construct
SEQUENCE: 51
VRSGRYFALD D                                                             11

SEQ ID NO: 52            moltype = AA   length = 120
FEATURE                  Location/Qualifiers
source                   1..120
                         mol_type = protein
                         organism = synthetic construct
SEQUENCE: 52
QVQLVESGGT LVQPGGSLRL SCAASGFTFK NYWMTWVRQA PGKGLEWVAN IKKDGSEKYY         60
VDSVRGRFTI SRDNAKNSLF LQMNSLRPED TAVYFCATVR SGRYFALDDW GQGTLVTVSS         120

SEQ ID NO: 53            moltype = DNA   length = 360
FEATURE                  Location/Qualifiers
misc_feature             1..360
                         note = source = /note=Description of synthetic construct:
                         Synthetic polynucleotide
source                   1..360
                         mol_type = other DNA
                         organism = synthetic construct
SEQUENCE: 53
caggtgcagc tggtggaatc aggcggcaca ctggtgcagc ctggcggtag cctgagactg         60
agctgcgctg ctagtggctt cacctttaag aactactgga tgacctgggt caggcaggcc         120
cctggtaaag gctcgagtg gtggcaaat atcaagaagg acggtagcga gaagtactac           180
gtggactcag tcagaggccg gttcactatc tctagggata cgctaagaa tagcctgttc          240
ctgcagatga actcactgag gcccgaggat accgccgtct acttctgtgc taccgtcaga         300
tcaggccgct acttcgccct ggacgactgg ggtcaaggca cactggtcac cgtgtctagc        360

SEQ ID NO: 54            moltype = AA   length = 450
FEATURE                  Location/Qualifiers
source                   1..450
                         mol_type = protein
                         organism = synthetic construct
SEQUENCE: 54
QVQLVESGGT LVQPGGSLRL SCAASGFTFK NYWMTWVRQA PGKGLEWVAN IKKDGSEKYY         60
VDSVRGRFTI SRDNAKNSLF LQMNSLRPED TAVYFCATVR SGRYFALDDW GQGTLVTVSS         120
ASTKGPSVFP LAPSSKSTSG GTAALGCLVK DYFPEPVTVS WNSGALTSGV HTFPAVLQSS         180
GLYSLSSVVT VPSSSLGTQT YICNVNHKPS NTKVDKRVEP KSCDKTHTCP PCPAPELLGG         240
PSVFLFPPKP KDTLMISRTP EVTCVVVDVS HEDPEVKFNW YVDGVEVHNA KTKPREEQYN         300
STYRVVSVLT VLHQDWLNGK EYKCKVSNKA LPAPIEKTIS KAKGQPREPQ VYTLPPSREE         360
MTKNQVSLTC LVKGFYPSDI AVEWESNGQP ENNYKTTPPV LDSDGSFFLY SKLTVDKSRW         420
QQGNVFSCSV MHEALHNHYT QKSLSLSPGK                                         450

SEQ ID NO: 55            moltype = DNA   length = 1350
FEATURE                  Location/Qualifiers
misc_feature             1..1350
                         note = source = /note=Description of synthetic construct:
                         Synthetic polynucleotide
source                   1..1350
                         mol_type = other DNA
                         organism = synthetic construct
SEQUENCE: 55
caggtgcagc tggtggaatc aggcggcaca ctggtgcagc ctggcggtag cctgagactg         60
agctgcgctg ctagtggctt cacctttaag aactactgga tgacctgggt caggcaggcc         120
cctggtaaag gctcgagtg gtggcaaat atcaagaagg acggtagcga gaagtactac           180
gtggactcag tcagaggccg gttcactatc tctagggata cgctaagaa tagcctgttc          240
ctgcagatga actcactgag gcccgaggat accgccgtct acttctgtgc taccgtcaga         300
tcaggccgct acttcgccct ggacgactgg ggtcaaggca cactggtcac cgtgtctagc        360
```

```
gctagcacta agggcccaag tgtgtttccc ctggccccca gcagcaagtc tacttccggc    420
ggaactgctg ccctgggttg cctggtgaag gactacttcc ccgagcccgt gacagtgtcc    480
tggaactctg ggctctgac  ttccggcgtg cacaccttcc ccgccgtgct gcagagcagc    540
ggcctgtaca gcctgagcag cgtggtgaca gtgccctcca gctctctggg aacccagacc    600
tatatctgca acgtgaacca caagcccagc aacaccaagg tggacaagag agtggagccc    660
aagagctgcg acaagaccca cacctgcccc ccctgcccag ctccagaact gctgggaggg    720
ccttccgtgt tcctgttccc ccccaagccc aaggacaccc tgatgatcag caggaccccc    780
gaggtgacct gcgtggtggt ggacgtgtcc cacgaggacc cagaggtgaa gttcaactgg    840
tacgtggacg gcgtggaggt gcacaacgcc aagaccaagc cagagagga  gcagtacaac    900
agcacctaca gggtggtgtc cgtgctgacc gtgctgcacc aggactggct gaacggcaaa    960
gaatacaagt gcaaagtctc caacaaggcc ctgccagccc aatcgaaaa  gacaatcagc   1020
aaggccaagg gccagccacg ggagcccag  gtgtacaccc tgccccccag ccggaggag   1080
atgaccaaga accaggtgtc cctgacctgt ctggtgaagg gcttctaccc cagcgatatc   1140
gccgtggagt gggagagcaa cggccagccc gagaacaact acaagaccac ccccccagtg   1200
ctggacagcg acggcagctt cttcctgtac agcaagctga ccgtggacaa gtccaggtgg   1260
cagcagggca acgtgttcag ctgcagcgtg atgcacgagg ccctgcacaa ccactacacc   1320
cagaagtccc tgagcctgag ccccggcaag                                    1350

SEQ ID NO: 56          moltype = AA  length = 11
FEATURE                Location/Qualifiers
source                 1..11
                       mol_type = protein
                       organism = synthetic construct
SEQUENCE: 56
GGDNIGSRPV H                                                        11

SEQ ID NO: 57          moltype = AA  length = 7
FEATURE                Location/Qualifiers
source                 1..7
                       mol_type = protein
                       organism = synthetic construct
SEQUENCE: 57
DDSNRPS                                                             7

SEQ ID NO: 58          moltype = AA  length = 10
FEATURE                Location/Qualifiers
source                 1..10
                       mol_type = protein
                       organism = synthetic construct
SEQUENCE: 58
QVWSSSTDHP                                                          10

SEQ ID NO: 59          moltype = AA  length = 7
FEATURE                Location/Qualifiers
source                 1..7
                       mol_type = protein
                       organism = synthetic construct
SEQUENCE: 59
DNIGSRP                                                             7

SEQ ID NO: 60          moltype =     length =
SEQUENCE: 60
000

SEQ ID NO: 61          moltype = AA  length = 7
FEATURE                Location/Qualifiers
source                 1..7
                       mol_type = protein
                       organism = synthetic construct
SEQUENCE: 61
WSSSTDH                                                             7

SEQ ID NO: 62          moltype = AA  length = 107
FEATURE                Location/Qualifiers
source                 1..107
                       mol_type = protein
                       organism = synthetic construct
SEQUENCE: 62
QSVLTQPPSV SVAPGKTARI TCGGDNIGSR PVHWYQQKPG QAPILVVYDD SNRPSGIPER    60
FSGSNSGNTA TLTISRVEAG DEADYYCQVW SSSTDHPFGG GTKVTVL                 107

SEQ ID NO: 63          moltype = DNA  length = 321
FEATURE                Location/Qualifiers
misc_feature           1..321
                       note = source = /note=Description of synthetic construct:
                       Synthetic polynucleotide
source                 1..321
                       mol_type = other DNA
                       organism = synthetic construct
```

```
SEQUENCE: 63
cagtcagtcc tgactcagcc ccctagcgtc agcgtggccc ctggtaaaac cgctagaatc    60
acctgtggcg gcgataatat cggctctagg cccgtgcact ggtatcagca gaagcccggt   120
caagccccta tcctggtggt ctacgacgac tctaatagac ctagcggaat ccccgagcgg   180
tttagcggct ctaattctgg taataccgct accctgacta tctctagggt ggaagccggc   240
gacgaggccg actactactg tcaagtctgg tctagctcta ccgatcaccc cttcggcgga   300
ggcactaagg ttacagtgct g                                             321

SEQ ID NO: 64              moltype = AA  length = 213
FEATURE                    Location/Qualifiers
source                     1..213
                           mol_type = protein
                           organism = synthetic construct
SEQUENCE: 64
QSVLTQPPSV SVAPGKTARI TCGGDNIGSR PVHWYQQKPG QAPILVVYDD SNRPSGIPER    60
FSGSNSGNTA TLTISRVEAG DEADYYCQVW SSSTDHPFGG GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                                213

SEQ ID NO: 65              moltype = DNA  length = 639
FEATURE                    Location/Qualifiers
misc_feature               1..639
                           note = source = /note=Description of synthetic construct:
                             Synthetic polynucleotide
source                     1..639
                           mol_type = other DNA
                           organism = synthetic construct
SEQUENCE: 65
cagtcagtcc tgactcagcc ccctagcgtc agcgtggccc ctggtaaaac cgctagaatc    60
acctgtggcg gcgataatat cggctctagg cccgtgcact ggtatcagca gaagcccggt   120
caagccccta tcctggtggt ctacgacgac tctaatagac ctagcggaat ccccgagcgg   180
tttagcggct ctaattctgg taataccgct accctgacta tctctagggt ggaagccggc   240
gacgaggccg actactactg tcaagtctgg tctagctcta ccgatcaccc cttcggcgga   300
ggcactaagg ttacagtgct gggtcaacct aaggctcccg tcagcgtgac cctgttcccc   360
cccagcagcg aggagctgca ggccaacaag gccaccctgg tgtgcctgat cagcgacttc   420
tacccaggcg ccgtgaccgt ggcctggaag gccgacagca gccccgtgaa ggccggcgtg   480
gagaccacca cccccagcaa gcagagcaac aacaagtacg ccgccagcag ctacctgagc   540
ctgacccccg agcagtggaa gagccacagg tcctacagct gccaggtgac ccacgagggc   600
agcaccgtgg aaaagaccgt ggccccaacc gagtgcagc                          639

SEQ ID NO: 66              moltype = AA  length = 5
FEATURE                    Location/Qualifiers
source                     1..5
                           mol_type = protein
                           organism = synthetic construct
SEQUENCE: 66
NYWMT                                                                 5

SEQ ID NO: 67              moltype = AA  length = 17
FEATURE                    Location/Qualifiers
source                     1..17
                           mol_type = protein
                           organism = synthetic construct
SEQUENCE: 67
NIKKDGSEKY YVDSVRG                                                   17

SEQ ID NO: 68              moltype = AA  length = 11
FEATURE                    Location/Qualifiers
source                     1..11
                           mol_type = protein
                           organism = synthetic construct
SEQUENCE: 68
VRSGRYFALD D                                                         11

SEQ ID NO: 69              moltype = AA  length = 7
FEATURE                    Location/Qualifiers
source                     1..7
                           mol_type = protein
                           organism = synthetic construct
SEQUENCE: 69
GFTFQNY                                                               7

SEQ ID NO: 70              moltype = AA  length = 6
FEATURE                    Location/Qualifiers
source                     1..6
                           mol_type = protein
                           organism = synthetic construct
SEQUENCE: 70
KKDGSE                                                                6
```

```
SEQ ID NO: 71             moltype = AA   length = 11
FEATURE                   Location/Qualifiers
source                    1..11
                          mol_type = protein
                          organism = synthetic construct
SEQUENCE: 71
VRSGRYFALD D                                                               11

SEQ ID NO: 72             moltype = AA   length = 120
FEATURE                   Location/Qualifiers
source                    1..120
                          mol_type = protein
                          organism = synthetic construct
SEQUENCE: 72
QVQLVESGGT LVQPGGSLRL SCAASGFTFQ NYWMTWVRQA PGKGLEWVAN IKKDGSEKYY  60
VDSVRGRFTI SRDNAKNSLF LQMNSLRPED TAVYFCATVR SGRYFALDDW GQGTLVTVSS 120

SEQ ID NO: 73             moltype = DNA   length = 360
FEATURE                   Location/Qualifiers
misc_feature              1..360
                          note = source = /note=Description of synthetic construct:
                          Synthetic polynucleotide
source                    1..360
                          mol_type = other DNA
                          organism = synthetic construct
SEQUENCE: 73
caggtgcagc tggtggaatc aggcggcaca ctggtgcagc ctggcggtag cctgagactg  60
agctgcgccg ctagtggatt cacctttcag aactactgga tgacctgggt cagacaggcc 120
cctggtaaag gcctcgagtg ggtggcaaat atcaagaagg acggtagcga agtactac   180
gtggactcag tcagaggccg gttcactatc tctagggata cgctaagaa tagcctgttc  240
ctgcagatga actcactgag gcccgaggat accgccgtct acttctgtgc taccgtcaga 300
tcaggccgct acttcgccct ggacgactgg ggtcaaggca cactggtcac cgtgtctagc 360

SEQ ID NO: 74             moltype = AA   length = 450
FEATURE                   Location/Qualifiers
source                    1..450
                          mol_type = protein
                          organism = synthetic construct
SEQUENCE: 74
QVQLVESGGT LVQPGGSLRL SCAASGFTFQ NYWMTWVRQA PGKGLEWVAN IKKDGSEKYY  60
VDSVRGRFTI SRDNAKNSLF LQMNSLRPED TAVYFCATVR SGRYFALDDW GQGTLVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKRVEP KSCDKTHTCP PCPAPELLGG 240
PSVFLFPPKP KDTLMISRTP EVTCVVVDVS HEDPEVKFNW YVDGVEVHNA KTKPREEQYN 300
STYRVVSVLT VLHQDWLNGK EYKCKVSNKA LPAPIEKTIS KAKGQPREPQ VYTLPPSREE 360
MTKNQVSLTC LVKGFYPSDI AVEWESNGQP ENNYKTTPPV LDSDGSFFLY SKLTVDKSRW 420
QQGNVFSCSV MHEALHNHYT QKSLSLSPGK                                  450

SEQ ID NO: 75             moltype = DNA   length = 1350
FEATURE                   Location/Qualifiers
misc_feature              1..1350
                          note = source = /note=Description of synthetic construct:
                          Synthetic polynucleotide
source                    1..1350
                          mol_type = other DNA
                          organism = synthetic construct
SEQUENCE: 75
caggtgcagc tggtggaatc aggcggcaca ctggtgcagc ctggcggtag cctgagactg  60
agctgcgccg ctagtggatt cacctttcag aactactgga tgacctgggt cagacaggcc 120
cctggtaaag gcctcgagtg ggtggcaaat atcaagaagg acggtagcga agtactac   180
gtggactcag tcagaggccg gttcactatc tctagggata cgctaagaa tagcctgttc  240
ctgcagatga actcactgag gcccgaggat accgccgtct acttctgtgc taccgtcaga 300
tcaggccgct acttcgccct ggacgactgg ggtcaaggca cactggtcac cgtgtctagc 360
gctagcacta agggcccaag tgtgtttccc ctggccccca gcagcaagtc tacttccggc 420
ggaactgctg ccctgggttg cctggtgaag gactacttcc ccgagcccgt gacagtgtcc 480
tggaactctg ggctctgac ttccggcgtg cacaccttcc ccgccgtgct gcagagcagc  540
ggcctgtaca gcctgagcag cgtggtgaca gtgccctcca gctctctggg aacccagacc 600
tatatctgca acgtgaacca caagcccagc aacaccaagg tggacaagag agtggagccc 660
aagagctgcg acaagaccca cacctgcccc cctgcccag ctccagaact gctgggaggg  720
ccttccgtgt tcctgttccc ccccaagccc aaggacaccc tgatgatcag caggaccccc 780
gaggtgacct gcgtggtggt ggacgtgtcc cacgaggacc cagaggtgaa gttcaactgg 840
tacgtggacg gcgtggaggt gcacaacgcc aagaccaagc cagagagga gcagtacaac  900
agcacctaca gggtggtgtc cgtcctgacc gtgctgcacc aggactggct gaacggcaaa 960
gaatacaagt gcaaagtctc caacaaggcc ctgccagccc caatcgaaaa gacaatcagc 1020
aaggccaagg gccagccacg ggagcccag gtgtacaccc tgcccccag ccgggaggag  1080
atgaccaaga accaggtgtc cctgacctgt ctggtgaagg gcttctaccc cagcgatatc 1140
gccgtggagt gggagagcaa cggccagccc gagaacaact acaagaccac ccccccagtg 1200
ctggacagcg acggcagctt cttcctgtac agcaagctga ccgtggacaa gtccaggtgg 1260
```

```
cagcagggca acgtgttcag ctgcagcgtg atgcacgagg ccctgcacaa ccactacacc   1320
cagaagtccc tgagcctgag ccccggcaag                                    1350
```

SEQ ID NO: 76            moltype = AA   length = 11
FEATURE                  Location/Qualifiers
source                   1..11
                         mol_type = protein
                         organism = synthetic construct
SEQUENCE: 76
GGDNIGSRPV H                                                        11

SEQ ID NO: 77            moltype = AA   length = 7
FEATURE                  Location/Qualifiers
source                   1..7
                         mol_type = protein
                         organism = synthetic construct
SEQUENCE: 77
DDSNRPS                                                             7

SEQ ID NO: 78            moltype = AA   length = 10
FEATURE                  Location/Qualifiers
source                   1..10
                         mol_type = protein
                         organism = synthetic construct
SEQUENCE: 78
QVWSSSTDHP                                                          10

SEQ ID NO: 79            moltype = AA   length = 7
FEATURE                  Location/Qualifiers
source                   1..7
                         mol_type = protein
                         organism = synthetic construct
SEQUENCE: 79
DNIGSRP                                                             7

SEQ ID NO: 80            moltype =      length =
SEQUENCE: 80
000

SEQ ID NO: 81            moltype = AA   length = 7
FEATURE                  Location/Qualifiers
source                   1..7
                         mol_type = protein
                         organism = synthetic construct
SEQUENCE: 81
WSSSTDH                                                             7

SEQ ID NO: 82            moltype = AA   length = 107
FEATURE                  Location/Qualifiers
source                   1..107
                         mol_type = protein
                         organism = synthetic construct
SEQUENCE: 82
QSVLTQPPSV SVAPGKTARI TCGGDNIGSR PVHWYQQKPG QAPILVVYDD SNRPSGIPER   60
FSGSNSGNTA TLTISRVEAG DEADYYCQVW SSSTDHPFGG GTKVTVL                 107

SEQ ID NO: 83            moltype = DNA   length = 321
FEATURE                  Location/Qualifiers
misc_feature             1..321
                         note = source = /note=Description of synthetic construct:
                         Synthetic polynucleotide
source                   1..321
                         mol_type = other DNA
                         organism = synthetic construct
SEQUENCE: 83
```
cagtcagtcc tgactcagcc ccctagcgtc agcgtggccc ctggtaaaac cgctagaatc   60
acctgtggcg gcgataatat cggctctagg cccgtgcact ggtatcagca gaagcccggt   120
caagccccta tcctggtggt ctacgacgac tctaatagac tagcggaatc cccgagcgg   180
tttagcggct ctaattctgg taataccgct accctgacta tctctagggt ggaagccggc   240
gacgaggccg actactactg tcaagtctgg tctagctcta ccgatcaccc cttcggcgga   300
ggcactaagg ttacagtgct g                                             321
```

SEQ ID NO: 84            moltype = AA   length = 213
FEATURE                  Location/Qualifiers
source                   1..213
                         mol_type = protein
                         organism = synthetic construct
SEQUENCE: 84
QSVLTQPPSV SVAPGKTARI TCGGDNIGSR PVHWYQQKPG QAPILVVYDD SNRPSGIPER   60

```
FSGSNSGNTA TLTISRVEAG DEADYYCQVW SSSTDHPFGG GTKVTVLGQP KAAPSVTLFP    120
PSSEELQANK ATLVCLISDF YPGAVTVAWK ADSSPVKAGV ETTTPSKQSN NKYAASSYLS    180
LTPEQWKSHR SYSCQVTHEG STVEKTVAPT ECS                                 213

SEQ ID NO: 85           moltype = DNA  length = 639
FEATURE                 Location/Qualifiers
misc_feature            1..639
                        note = source = /note=Description of synthetic construct:
                         Synthetic polynucleotide
source                  1..639
                        mol_type = other DNA
                        organism = synthetic construct
SEQUENCE: 85
cagtcagtcc tgactcagcc ccctagcgtc agcgtggccc ctggtaaaac cgctagaatc     60
acctgtggcg gcgataatat cggctctagg cccgtgcact ggtatcagca gaagcccggt    120
caagccccta tcctggtggt ctacgacgac tctaatagac ctagcggaat ccccgagcgg    180
tttagcggct ctaattctgg taataccgct accctgacta tctctagggt ggaagccggc    240
gacgaggccg actactactg tcaagtctgg tctagctcta ccgatcaccc cttcggcgga    300
ggcactaagg ttacagtgct gggtcaacct aaggctgccc ccagcgtgac cctgttcccc    360
cccagcagcg aggagctgca ggccaacaag gccaccctgg tgtgcctgat cagcgacttc    420
tacccaggcg ccgtgaccgt ggcctggaag gccgacagca ccccgtgaa ggccggcgtg     480
gagaccacca cccccagcaa gcagagcaac aacaagtacg cgccagcag ctacctgagc     540
ctgacccccg agcagtggaa gagccacagg tcctacagct gccaggtgac ccacgagggc    600
agcaccgtgg aaaagaccgt ggccccaacc gagtgcagc                           639

SEQ ID NO: 86           moltype = AA  length = 5
FEATURE                 Location/Qualifiers
source                  1..5
                        mol_type = protein
                        organism = synthetic construct
SEQUENCE: 86
NYWMT                                                                  5

SEQ ID NO: 87           moltype = AA  length = 17
FEATURE                 Location/Qualifiers
source                  1..17
                        mol_type = protein
                        organism = synthetic construct
SEQUENCE: 87
NIKKDGSEKY YVDSVRG                                                    17

SEQ ID NO: 88           moltype = AA  length = 11
FEATURE                 Location/Qualifiers
source                  1..11
                        mol_type = protein
                        organism = synthetic construct
SEQUENCE: 88
VRSGRYFALD D                                                          11

SEQ ID NO: 89           moltype = AA  length = 7
FEATURE                 Location/Qualifiers
source                  1..7
                        mol_type = protein
                        organism = synthetic construct
SEQUENCE: 89
GFTFNNY                                                                7

SEQ ID NO: 90           moltype = AA  length = 6
FEATURE                 Location/Qualifiers
source                  1..6
                        mol_type = protein
                        organism = synthetic construct
SEQUENCE: 90
KKDGSE                                                                 6

SEQ ID NO: 91           moltype = AA  length = 11
FEATURE                 Location/Qualifiers
source                  1..11
                        mol_type = protein
                        organism = synthetic construct
SEQUENCE: 91
VRSGRYFALD D                                                          11

SEQ ID NO: 92           moltype = AA  length = 120
FEATURE                 Location/Qualifiers
source                  1..120
                        mol_type = protein
                        organism = synthetic construct
SEQUENCE: 92
```

```
QVQLQESGPG LVQPGGSLRL SCAASGFTFN NYWMTWVRQA PGKGLEWVAN IKKDGSEKYY   60
VDSVRGRFTI SRDNAKNSLF LQMNSLRPED TAVYFCATVR SGRYFALDDW GQGTLVTVSS  120
```

SEQ ID NO: 93           moltype = DNA   length = 360
FEATURE                 Location/Qualifiers
misc_feature            1..360
                        note = source = /note=Description of synthetic construct:
                         Synthetic polynucleotide
source                  1..360
                        mol_type = other DNA
                        organism = synthetic construct
SEQUENCE: 93
```
caggtgcagc tgcaggaatc aggcccagga ctggtgcagc ctggcggtag cctgagactg   60
agctgcgctg ctagtggctt cacctttaac aactactgga tgacctgggt ccgccaggcc  120
cctggcaaag gcctggagtg ggtggcaaat atcaagaagg acggtagcga agtactactac 180
gtggactcag tcagaggccg gttcactatc tctagggata acgctaagaa tagcctgttc  240
ctgcagatga actcactgag gcccgaggat accgccgtct acttctgtgc taccgtcaga  300
tcaggccgct acttcgccct ggacgactgg ggccagggca cctggtcac cgtgtcttcc  360
```

SEQ ID NO: 94           moltype = AA   length = 450
FEATURE                 Location/Qualifiers
source                  1..450
                        mol_type = protein
                        organism = synthetic construct
SEQUENCE: 94
```
QVQLQESGPG LVQPGGSLRL SCAASGFTFN NYWMTWVRQA PGKGLEWVAN IKKDGSEKYY   60
VDSVRGRFTI SRDNAKNSLF LQMNSLRPED TAVYFCATVR SGRYFALDDW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450
```

SEQ ID NO: 95           moltype = DNA   length = 1350
FEATURE                 Location/Qualifiers
misc_feature            1..1350
                        note = source = /note=Description of synthetic construct:
                         Synthetic polynucleotide
source                  1..1350
                        mol_type = other DNA
                        organism = synthetic construct
SEQUENCE: 95
```
caggtgcagc tgcaggaatc aggcccagga ctggtgcagc ctggcggtag cctgagactg   60
agctgcgctg ctagtggctt cacctttaac aactactgga tgacctgggt ccgccaggcc  120
cctggcaaag gcctggagtg ggtggcaaat atcaagaagg acggtagcga agtactac    180
gtggactcag tcagaggccg gttcactatc tctagggata acgctaagaa tagcctgttc  240
ctgcagatga actcactgag gcccgaggat accgccgtct acttctgtgc taccgtcaga  300
tcaggccgct acttcgccct ggacgactgg ggccagggca cctggtcac cgtgtcttcc   360
gctagcacta agggcccaag tgtgtttccc ctggccccca gcagcaagtc tacttccggc  420
ggaactgctg ccctgggttg cctggtgaag gactacttcc ccgagcccgt gacagtgtcc  480
tggaactctg ggctctgac ttccggcgtg cacaccttcc ccgccgtgct gcagagcagc  540
ggcctgtaca gcctgagcag cgtggtgaca gtgccctcca gctctctggg aacccagacc  600
tatatctgca acgtgaacca caagcccagc aacaccaagg tggacaagag agtggagccc  660
aagagctgcg acaagaccca cacctgcccc cctgcccag ctccagaact gctgggaggg  720
ccttccgtgt tcctgttccc ccccaagccc aaggacaccc tgatgatcag caggacccc   780
gaggtgacct gcgtggtggt ggacgtgtcc cacgaggacc cagaggtgaa gttcaactgg  840
tacgtggacg gcgtggaggt gcacaacgcc aagaccaagc cagagagga gcagtacaac  900
agcacctaca gggtggtgtc cgtgctgacc gtgctgcacc aggactggct gaacggcaaa  960
gaatacaagt gcaaagtctc caacaaggcc ctgccagccc caatcgaaaa gacaatcagc 1020
aaggccaagg gccagccacg ggagcccag gtgtacaccc tgcccccag ccgggaggag 1080
atgaccaaga accaggtgtc cctgacctgt ctggtgaagg gcttctaccc cagcgatatc 1140
gccgtggagt gggagagcaa cggccagccc gagaacaact acaagaccac ccccccagtg 1200
ctggacagcg acggcagctt cttcctgtac agcaagctga ccgtggacaa gtccaggtgg 1260
cagcagggca acgtgttcag ctgcagcgtg atgcacgagg ccctgcacaa ccactacacc 1320
cagaagtccc tgagcctgag ccccggcaag                                  1350
```

SEQ ID NO: 96           moltype = AA   length = 11
FEATURE                 Location/Qualifiers
source                  1..11
                        mol_type = protein
                        organism = synthetic construct
SEQUENCE: 96
```
GGDNIGSRPV H                                                       11
```

SEQ ID NO: 97           moltype = AA   length = 7
FEATURE                 Location/Qualifiers
source                  1..7
                        mol_type = protein

```
                        organism = synthetic construct
SEQUENCE: 97
DDSNRPS                                                                 7

SEQ ID NO: 98           moltype = AA   length = 10
FEATURE                 Location/Qualifiers
source                  1..10
                        mol_type = protein
                        organism = synthetic construct
SEQUENCE: 98
QVWSSSTDHP                                                             10

SEQ ID NO: 99           moltype = AA   length = 7
FEATURE                 Location/Qualifiers
source                  1..7
                        mol_type = protein
                        organism = synthetic construct
SEQUENCE: 99
DNIGSRP                                                                 7

SEQ ID NO: 100          moltype =    length =
SEQUENCE: 100
000

SEQ ID NO: 101          moltype = AA   length = 7
FEATURE                 Location/Qualifiers
source                  1..7
                        mol_type = protein
                        organism = synthetic construct
SEQUENCE: 101
WSSSTDH                                                                 7

SEQ ID NO: 102          moltype = AA   length = 107
FEATURE                 Location/Qualifiers
source                  1..107
                        mol_type = protein
                        organism = synthetic construct
SEQUENCE: 102
QSVLTQPPSV SVAPGKTARI TCGGDNIGSR PVHWYQQKPG QAPILVVYDD SNRPSGIPER        60
FSGSNSGNTA TLTISRVEAG DEADYYCQVW SSSTDHPFGG GTKVTVL                    107

SEQ ID NO: 103          moltype = DNA   length = 321
FEATURE                 Location/Qualifiers
misc_feature            1..321
                        note = source = /note=Description of synthetic construct:
                          Synthetic polynucleotide
source                  1..321
                        mol_type = other DNA
                        organism = synthetic construct
SEQUENCE: 103
cagtcagtcc tgactcagcc ccctagcgtc agcgtggccc ctggtaaaac cgctagaatc        60
acctgtggcg gcgataatat cggctctagg cccgtgcact ggtatcagca gaagcccggt       120
caagccccta tcctggtggt ctacgacgac tctaatagac ctagcggaat ccccgagcgg       180
tttagcggct ctaattctgg taataccgct accctgacta tctctagggt ggaagccggc       240
gacgaggccg actactactg tcaagtctgg tctagctcta ccgatcaccc cttcggcgga       300
ggcactaagg ttacagtgct g                                                321

SEQ ID NO: 104          moltype = AA   length = 213
FEATURE                 Location/Qualifiers
source                  1..213
                        mol_type = protein
                        organism = synthetic construct
SEQUENCE: 104
QSVLTQPPSV SVAPGKTARI TCGGDNIGSR PVHWYQQKPG QAPILVVYDD SNRPSGIPER        60
FSGSNSGNTA TLTISRVEAG DEADYYCQVW SSSTDHPFGG GTKVTVLGQP KAAPSVTLFP       120
PSSEELQANK ATLVCLISDF YPGAVTVAWK ADSSPVKAGV ETTTPSKQSN NKYAASSYLS       180
LTPEQWKSHR SYSCQVTHEG STVEKTVAPT ECS                                   213

SEQ ID NO: 105          moltype = DNA   length = 639
FEATURE                 Location/Qualifiers
misc_feature            1..639
                        note = source = /note=Description of synthetic construct:
                          Synthetic polynucleotide
source                  1..639
                        mol_type = other DNA
                        organism = synthetic construct
SEQUENCE: 105
cagtcagtcc tgactcagcc ccctagcgtc agcgtggccc ctggtaaaac cgctagaatc        60
acctgtggcg gcgataatat cggctctagg cccgtgcact ggtatcagca gaagcccggt       120
```

```
caagccccta tcctggtggt ctacgacgac tctaatagac ctagcggaat ccccgagcgg    180
tttagcggct ctaattctgg taataccgct accctgacta tctctagggt ggaagccggc    240
gacgaggccg actactactg tcaagtctgg tctagctcta ccgatcaccc cttcggcgga    300
ggcactaagg ttacagtgct gggtcaacct aaggctgccc ccagcgtgac cctgttcccc    360
cccagcagcg aggagctgca ggccaacaag gccaccctgg tgtgcctgat cagcgacttc    420
tacccaggcg ccgtgaccgt ggcctggaag gccgacagca gccccgtgaa ggccggcgtg    480
gagaccacca cccccagcaa gcagagcaac aacaagtacg ccgccagcag ctacctgagc    540
ctgacccccg agcagtggaa gagccacagg tcctacagct gccaggtgac ccacgagggc    600
agcaccgtgg aaaagaccgt ggccccaacc gagtgcagc                           639
```

| | | |
|---|---|---|
| SEQ ID NO: 106 | moltype = AA   length = 5 | |
| FEATURE | Location/Qualifiers | |
| source | 1..5 | |
| | mol_type = protein | |
| | organism = synthetic construct | |
| SEQUENCE: 106 | | |
| NYWMT | | 5 |

| | | |
|---|---|---|
| SEQ ID NO: 107 | moltype = AA   length = 17 | |
| FEATURE | Location/Qualifiers | |
| source | 1..17 | |
| | mol_type = protein | |
| | organism = synthetic construct | |
| SEQUENCE: 107 | | |
| NIKKDGSEKY YVDSVRG | | 17 |

| | | |
|---|---|---|
| SEQ ID NO: 108 | moltype = AA   length = 11 | |
| FEATURE | Location/Qualifiers | |
| source | 1..11 | |
| | mol_type = protein | |
| | organism = synthetic construct | |
| SEQUENCE: 108 | | |
| VRSGRYFALD D | | 11 |

| | | |
|---|---|---|
| SEQ ID NO: 109 | moltype = AA   length = 7 | |
| FEATURE | Location/Qualifiers | |
| source | 1..7 | |
| | mol_type = protein | |
| | organism = synthetic construct | |
| SEQUENCE: 109 | | |
| GFTFNNY | | 7 |

| | | |
|---|---|---|
| SEQ ID NO: 110 | moltype = AA   length = 6 | |
| FEATURE | Location/Qualifiers | |
| source | 1..6 | |
| | mol_type = protein | |
| | organism = synthetic construct | |
| SEQUENCE: 110 | | |
| KKDGSE | | 6 |

| | | |
|---|---|---|
| SEQ ID NO: 111 | moltype = AA   length = 11 | |
| FEATURE | Location/Qualifiers | |
| source | 1..11 | |
| | mol_type = protein | |
| | organism = synthetic construct | |
| SEQUENCE: 111 | | |
| VRSGRYFALD D | | 11 |

| | | |
|---|---|---|
| SEQ ID NO: 112 | moltype = AA   length = 120 | |
| FEATURE | Location/Qualifiers | |
| REGION | 1..120 | |
| | note = source = /note=Description of synthetic construct: Synthetic polypeptide | |
| source | 1..120 | |
| | mol_type = protein | |
| | organism = synthetic construct | |
| SEQUENCE: 112 | | |
| QVQLVESGGG LVQPGGSLRL SCAASGFTFN NYWMTWVRQA PGKGLEWVAN IKKDGSEKYY | | 60 |
| VDSVRGRFTI SRDNAKNSLF LQMNSLRPED TAVYFCATVR SGRYFALDDW GQGTLVTVSS | | 120 |

| | | |
|---|---|---|
| SEQ ID NO: 113 | moltype = DNA   length = 360 | |
| FEATURE | Location/Qualifiers | |
| misc_feature | 1..360 | |
| | note = source = /note=Description of synthetic construct: Synthetic polynucleotide | |
| source | 1..360 | |
| | mol_type = other DNA | |
| | organism = synthetic construct | |
| SEQUENCE: 113 | | |

```
caggtgcagc tggtggaatc aggcggcgga ctggtgcagc ctggcggtag cctgagactg    60
agctgcgctg ctagtggctt cacctttaac aactactgga tgacctgggt taggcaggcc   120
cctggtaaag gcctcgagtg ggtggcaaat atcaagaagg acgtagcga gaagtactac   180
gtggactcag tcagaggccg gttcactatc tctagggata cgctaagaa tagcctgttc   240
ctgcagatga actcactgag gcccgaggat accgccgtct acttctgtgc taccgtcaga   300
tcaggccgct acttcgccct ggacgactgg ggtcaaggca cactggtcac cgtgtctagc   360
```

| SEQ ID NO: 114 | moltype = AA   length = 450 |
|---|---|
| FEATURE | Location/Qualifiers |
| source | 1..450 |
| | mol_type = protein |
| | organism = synthetic construct |

SEQUENCE: 114
```
QVQLVESGGG LVQPGGSLRL SCAASGFTFN NYWMTWVRQA PGKGLEWVAN IKKDGSEKYY    60
VDSVRGRFTI SRDNAKNSLF LQMNSLRPED TAVYFCATVR SGRYFALDDW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKRVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450
```

| SEQ ID NO: 115 | moltype = DNA   length = 1350 |
|---|---|
| FEATURE | Location/Qualifiers |
| misc_feature | 1..1350 |
| | note = source = /note=Description of synthetic construct: Synthetic polynucleotide |
| source | 1..1350 |
| | mol_type = other DNA |
| | organism = synthetic construct |

SEQUENCE: 115
```
caggtgcagc tggtggaatc aggcggcgga ctggtgcagc ctggcggtag cctgagactg    60
agctgcgctg ctagtggctt cacctttaac aactactgga tgacctgggt taggcaggcc   120
cctggtaaag gcctcgagtg ggtggcaaat atcaagaagg acgtagcga gaagtactac   180
gtggactcag tcagaggccg gttcactatc tctagggata cgctaagaa tagcctgttc   240
ctgcagatga actcactgag gcccgaggat accgccgtct acttctgtgc taccgtcaga   300
tcaggccgct acttcgccct ggacgactgg ggtcaaggca cactggtcac cgtgtctagc   360
gctagcacta aagggcccaag tgtgtttccc ctggccccca gcagcaagtc tacttccggc   420
ggaactgctg ccctgggttg cctggtgaag gactacttcc ccgagcccgt gacagtgtcc   480
tggaactctg ggctctgac ttccggcgtg cacaccttcc ccgccgtgct gcagagcagc   540
ggcctgtaca gcctgagcag cgtggtgaca gtgccctcca gctctctggg aacccagacc   600
tatatctgca acgtgaacca caagcccagc aacaccaagg tggacaagag agtggagccc   660
aagagctgtg acaagaccca cacctgcccc cctgcccag ctccagaact gctgggaggg   720
ccttccgtgt tcctgttccc ccccaagccc aaggacaccc tgatgatcag caggacccc   780
gaggtgacct gcgtggtggt ggacgtgtcc cacgaggacc cagaggtgaa gttcaactgg   840
tacgtggacg gcgtggaggt gcacaacgcc aagaccaagc cagagagga gcagtacaac   900
agcacctaca gggtggtgtc cgtgctgacc gtgctgcaac aggactggct gaacggcaaa   960
gaatacaagt gcaaagtctc caacaaggcc ctgccagccc caatcgaaaa gacaatcagc   1020
aaggccaagg gccagccacg ggagcccag gtgtacaccc tgcccccag ccgggaggag   1080
atgaccaaga accaggtgtc cctgacctgt ctggtgaagg gcttctaccc cagcgatatc   1140
gccgtggagt gggagagcaa cggccagccc gagaacaact acaagaccac ccccccagtg   1200
ctggacagcg acggcagctt cttcctgtac agcaagctga ccgtggacaa gtccaggtgg   1260
cagcagggca acgtgttcag ctgcagcgtg atgcacgagg ccctgcacaa ccactacacc   1320
cagaagtccc tgagcctgag ccccggcaag                                   1350
```

| SEQ ID NO: 116 | moltype = AA   length = 11 |
|---|---|
| FEATURE | Location/Qualifiers |
| source | 1..11 |
| | mol_type = protein |
| | organism = synthetic construct |

SEQUENCE: 116
```
GGDNIGSRPV H                                                        11
```

| SEQ ID NO: 117 | moltype = AA   length = 7 |
|---|---|
| FEATURE | Location/Qualifiers |
| source | 1..7 |
| | mol_type = protein |
| | organism = synthetic construct |

SEQUENCE: 117
```
DDSNRPS                                                              7
```

| SEQ ID NO: 118 | moltype = AA   length = 10 |
|---|---|
| FEATURE | Location/Qualifiers |
| source | 1..10 |
| | mol_type = protein |
| | organism = synthetic construct |

SEQUENCE: 118
```
QVWSSSTDHP                                                          10
```

```
SEQ ID NO: 119          moltype = AA   length = 7
FEATURE                 Location/Qualifiers
source                  1..7
                        mol_type = protein
                        organism = synthetic construct
SEQUENCE: 119
DNIGSRP                                                                 7

SEQ ID NO: 120          moltype =     length =
SEQUENCE: 120
000

SEQ ID NO: 121          moltype = AA   length = 7
FEATURE                 Location/Qualifiers
source                  1..7
                        mol_type = protein
                        organism = synthetic construct
SEQUENCE: 121
WSSSTDH                                                                 7

SEQ ID NO: 122          moltype = AA   length = 107
FEATURE                 Location/Qualifiers
source                  1..107
                        mol_type = protein
                        organism = synthetic construct
SEQUENCE: 122
QSVLTQPPSV SVAPGKTARI TCGGDNIGSR PVHWYQQKPG QAPILVVYDD SNRPSGIPER        60
FSGSNSGNTA TLTISRVEAG DEADYYCQVW SSSTDHPFGG GTKVTVL                    107

SEQ ID NO: 123          moltype = DNA   length = 321
FEATURE                 Location/Qualifiers
misc_feature            1..321
                        note = source = /note=Description of synthetic construct:
                         Synthetic polynucleotide
source                  1..321
                        mol_type = other DNA
                        organism = synthetic construct
SEQUENCE: 123
cagtcagtcc tgactcagcc ccctagcgtc agcgtggccc ctggtaaaac cgctagaatc        60
acctgtggcg gcgataatat cggctctagg cccgtgcact ggtatcagca gaagcccggt       120
caagccccta tcctggtggt ctacgacgac tctaatagac ctagcggaat ccccgagcgg       180
tttagcggct ctaattctgg taataccgct accctgacta tctctagggt ggaagccggc       240
gacgaggccg actactactg tcaagtctgg tctagctcta ccgatcaccc cttcggcgga       300
ggcactaagg ttacagtgct g                                                 321

SEQ ID NO: 124          moltype = AA   length = 213
FEATURE                 Location/Qualifiers
source                  1..213
                        mol_type = protein
                        organism = synthetic construct
SEQUENCE: 124
QSVLTQPPSV SVAPGKTARI TCGGDNIGSR PVHWYQQKPG QAPILVVYDD SNRPSGIPER        60
FSGSNSGNTA TLTISRVEAG DEADYYCQVW SSSTDHPFGG GTKVTVLGQP KAAPSVTLFP       120
PSSEELQANK ATLVCLISDF YPGAVTVAWK ADSSPVKAGV ETTTPSKQSN NKYAASSYLS       180
LTPEQWKSHR SYSCQVTHEG STVEKTVAPT ECS                                   213

SEQ ID NO: 125          moltype = DNA   length = 639
FEATURE                 Location/Qualifiers
misc_feature            1..639
                        note = source = /note=Description of synthetic construct:
                         Synthetic polynucleotide
source                  1..639
                        mol_type = other DNA
                        organism = synthetic construct
SEQUENCE: 125
cagtcagtcc tgactcagcc ccctagcgtc agcgtggccc ctggtaaaac cgctagaatc        60
acctgtggcg gcgataatat cggctctagg cccgtgcact ggtatcagca gaagcccggt       120
caagccccta tcctggtggt ctacgacgac tctaatagac ctagcggaat ccccgagcgg       180
tttagcggct ctaattctgg taataccgct accctgacta tctctagggt ggaagccggc       240
gacgaggccg actactactg tcaagtctgg tctagctcta ccgatcaccc cttcggcgga       300
ggcactaagg ttacagtgct gggtcaacct aaggctgccc ccagcgtgac cctgttcccc       360
cccagcagcg aggagctgca ggccaacaag gccaccctgg tgtgcctgat cagcgacttc       420
tacccaggcg ccgtgaccgt ggcctggaag gccgacagca gccccgtgaa ggccggcgtg       480
gagaccacca cccccagcaa gcagagcaac aacaagtacg ccgccagcag ctacctgagc       540
ctgaccccca gcagtggaa gagccacagg tcctacagct gccaggtgac ccacgagggc       600
agcaccgtgg aaaagaccgt ggccccaacc gagtgcagc                             639

SEQ ID NO: 126          moltype = AA   length = 5
FEATURE                 Location/Qualifiers
```

```
source                    1..5
                          mol_type = protein
                          organism = synthetic construct
SEQUENCE: 126
RDYWT                                                                 5

SEQ ID NO: 127            moltype = AA  length = 16
FEATURE                   Location/Qualifiers
source                    1..16
                          mol_type = protein
                          organism = synthetic construct
SEQUENCE: 127
NIYYSGSTNY NPSLKS                                                    16

SEQ ID NO: 128            moltype = AA  length = 16
FEATURE                   Location/Qualifiers
source                    1..16
                          mol_type = protein
                          organism = synthetic construct
SEQUENCE: 128
VPGCSSTSCI DGWFDP                                                    16

SEQ ID NO: 129            moltype = AA  length = 7
FEATURE                   Location/Qualifiers
source                    1..7
                          mol_type = protein
                          organism = synthetic construct
SEQUENCE: 129
GGSISRD                                                               7

SEQ ID NO: 130            moltype = AA  length = 5
FEATURE                   Location/Qualifiers
source                    1..5
                          mol_type = protein
                          organism = synthetic construct
SEQUENCE: 130
YYSGS                                                                 5

SEQ ID NO: 131            moltype = AA  length = 16
FEATURE                   Location/Qualifiers
source                    1..16
                          mol_type = protein
                          organism = synthetic construct
SEQUENCE: 131
VPGCSSTSCI DGWFDP                                                    16

SEQ ID NO: 132            moltype = AA  length = 124
FEATURE                   Location/Qualifiers
source                    1..124
                          mol_type = protein
                          organism = synthetic construct
SEQUENCE: 132
QVQLQESGPG LVKPSETLSL TCTVSGGSIS RDYWTWVRQP PGEGLEWIGN IYYSGSTNYN     60
PSLKSRVTIS VAASKKQFSL KLTSVTAADT AVYYCARVPG CSSTSCIDGW FDPWGQGILV    120
TVSS                                                                124

SEQ ID NO: 133            moltype = DNA  length = 372
FEATURE                   Location/Qualifiers
misc_feature              1..372
                          note = source = /note=Description of synthetic construct:
                          Synthetic polynucleotide
source                    1..372
                          mol_type = other DNA
                          organism = synthetic construct
SEQUENCE: 133
caggtgcagc tgcaagaatc aggccctggc ctggtcaagc ctagcgagac actgagcctg     60
acctgcaccg tcagcggcgg ctctatctct agggactact ggacctgggt ccgacagcct    120
cctggcgagg gcctcgagtg gatcggtaat atctactata gcggctctac taactataac    180
cctagcctga gtctagggt cacaattagc gtggccgcct ctaagaagca gtttagcctg    240
aagctgacta gcgtgaccgc cgctgacacc gccgtctact actgcgctag agtgcccggc    300
tgctctagca ctagctgtat cgacggctgg tttgacccct ggggtcaagg gatcctggtc    360
accgtgtcta gc                                                       372

SEQ ID NO: 134            moltype = AA  length = 454
FEATURE                   Location/Qualifiers
source                    1..454
                          mol_type = protein
                          organism = synthetic construct
SEQUENCE: 134
```

```
QVQLQESGPG LVKPSETLSL TCTVSGGSIS RDYWTWVRQP PGEGLEWIGN IYYSGSTNYN    60
PSLKSRVTIS VAASKKQFSL KLTSVTAADT AVYYCARVPG CSSTSCIDGW FDPWGQGILV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK RVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SREEMTKNQV SLTCLVKGFY PSDIAVEWES NGQPENNYKT TPPVLDSDGS FFLYSKLTVD   420
KSRWQQGNVF SCSVMHEALH NHYTQKSLSL SPGK                              454

SEQ ID NO: 135           moltype = DNA   length = 1362
FEATURE                  Location/Qualifiers
misc_feature             1..1362
                         note = source = /note=Description of synthetic construct:
                          Synthetic polynucleotide
source                   1..1362
                         mol_type = other DNA
                         organism = synthetic construct
SEQUENCE: 135
caggtgcagc tgcaagaatc aggccctggc ctggtcaagc ctagcgagac actgagcctg    60
acctgcaccg tcagcggcgg ctctatctct agggactact ggacctgggt ccgacagcct   120
cctggcgagg gcctcgagtg gatcggtaat atctactata gcggtctcta taactataac   180
cctagcctga agtctagggt cacaattagc gtggccagcc ctaagaagca gtttagcctg   240
aagctgacta gcgtgaccgc cgctgacacc gccgtctact actgcgctag agtgcccggc   300
tgctctagca ctagctgtat cgacggctgg tttgaccctt ggggtcaagg gatcctggtc   360
accgtgtcta gcgctagcac taagggccca agtgtgtttc cctggcccc agcagcaag    420
tctacttccg gcgaactgc tgccctgggt tgcctggtga aggactactt ccccgagccc   480
gtgacagtgt cctggaactc tggggctctg acttccggcg tgcacacctt ccccgccgtg   540
ctgcagagca gcgcctgta cagcctgagc agcgtggtga cagtgccctc cagctctctg   600
ggaacccaga cctatatctg caacgtgaac cacaagccca gcaacaccaa ggtggacaag   660
agagtggagc ccaagagctg cgacaagacc cacacctgcc cccctgccc agctccagaa   720
ctgctgggag gccttccgt gttcctgttc cccccaagc ccaaggacac cctgatgatc    780
agcaggaccc ccgaggtgac ctgcgtggtg gtggacgtgt cccacgagga cccagaggtg   840
aagttcaact ggtacgtgga cggcgtggag gtgcacaacg ccaagaccaa gcccagagag   900
gagcagtaca acagcaccta cagggtgtg tccgtgctga ccgtgctgca ccaggactgg   960
ctgaacggca agaatacaa gtgcaaagtc tccaacaagg ccctgccagc cccaatcgaa  1020
aagacaatca gcaaggccaa gggccagcca cgggagcccc aggtgtacac cctgcccccc  1080
agccgggagg agatgaccaa gaaccaggtg tccctgacct gtctggtgaa gggcttctac  1140
cccagcgata tcgccgtgga gtgggagagc aacggccagc cgagaacaa ctacaagacc   1200
acccccccag tgctggacag cgacggcagc ttcttcctgt acagcaagct gaccgtggac  1260
aagtccaggt ggcagcaggg caacgtgttc agctgcagcg tgatgcacga ggcccacac    1320
aaccactaca cccagaagtc cctgagcctg agccccggca ag                     1362

SEQ ID NO: 136           moltype = AA   length = 13
FEATURE                  Location/Qualifiers
source                   1..13
                         mol_type = protein
                         organism = synthetic construct
SEQUENCE: 136
SGSSSNIGNT YVS                                                     13

SEQ ID NO: 137           moltype = AA   length = 7
FEATURE                  Location/Qualifiers
source                   1..7
                         mol_type = protein
                         organism = synthetic construct
SEQUENCE: 137
DNNKRPS                                                            7

SEQ ID NO: 138           moltype = AA   length = 11
FEATURE                  Location/Qualifiers
source                   1..11
                         mol_type = protein
                         organism = synthetic construct
SEQUENCE: 138
GTWDSSLSAW V                                                       11

SEQ ID NO: 139           moltype = AA   length = 9
FEATURE                  Location/Qualifiers
source                   1..9
                         mol_type = protein
                         organism = synthetic construct
SEQUENCE: 139
SSSNIGNTY                                                          9

SEQ ID NO: 140           moltype =   length =
SEQUENCE: 140
000

SEQ ID NO: 141           moltype = AA   length = 8
```

```
FEATURE                 Location/Qualifiers
source                  1..8
                        mol_type = protein
                        organism = synthetic construct
SEQUENCE: 141
WDSSLSAW                                                                    8

SEQ ID NO: 142          moltype = AA  length = 110
FEATURE                 Location/Qualifiers
source                  1..110
                        mol_type = protein
                        organism = synthetic construct
SEQUENCE: 142
QSVLTQPPSL SAAPGQRVTI SCSGSSSNIG NTYVSWYQQL PGTAPKLLIY DNNKRPSGIP    60
GRFSGSKSGT SATLGITGLQ TGDEAAYYCG TWDSSLSAWV FGGGTRLTVL              110

SEQ ID NO: 143          moltype = DNA  length = 330
FEATURE                 Location/Qualifiers
misc_feature            1..330
                        note = source = /note=Description of synthetic construct:
                        Synthetic polynucleotide
source                  1..330
                        mol_type = other DNA
                        organism = synthetic construct
SEQUENCE: 143
cagtcagtcc tgactcagcc ccctagcctg agcgccgctc ccggtcaaag agtgactatt    60
agctgtagcg gctctagctc taatatcggt aataccctacg tcagctggta tcagcagctg   120
cccggcaccg cccctaagct gctgatctac gataacaaca gcggcctag cggaatccct    180
ggtcgcttta gcggatctaa atcaggcact agcgctaccc tgggaatcac cggcctgcag   240
accggcgacg aagccgccta ctactgcggc acctgggact ctagtctgag cgcctgggtg   300
ttcggcggag gcactagact gaccgtgctg                                    330

SEQ ID NO: 144          moltype = AA  length = 216
FEATURE                 Location/Qualifiers
source                  1..216
                        mol_type = protein
                        organism = synthetic construct
SEQUENCE: 144
QSVLTQPPSL SAAPGQRVTI SCSGSSSNIG NTYVSWYQQL PGTAPKLLIY DNNKRPSGIP    60
GRFSGSKSGT SATLGITGLQ TGDEAAYYCG TWDSSLSAWV FGGGTRLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 145          moltype = DNA  length = 648
FEATURE                 Location/Qualifiers
misc_feature            1..648
                        note = source = /note=Description of synthetic construct:
                        Synthetic polynucleotide
source                  1..648
                        mol_type = other DNA
                        organism = synthetic construct
SEQUENCE: 145
cagtcagtcc tgactcagcc ccctagcctg agcgccgctc ccggtcaaag agtgactatt    60
agctgtagcg gctctagctc taatatcggt aataccctacg tcagctggta tcagcagctg   120
cccggcaccg cccctaagct gctgatctac gataacaaca gcggcctag cggaatccct    180
ggtcgcttta gcggatctaa atcaggcact agcgctaccc tgggaatcac cggcctgcag   240
accggcgacg aagccgccta ctactgcggc acctgggact ctagtctgag cgcctgggtg   300
ttcggcggag gcactagact gaccgtgctg ggtcaaccta aggctgcccc cagcgtgacc   360
ctgttccccc ccagcagcga ggagctgcag gccaacaagg ccaccctggt gtgcctgatc   420
agcgacttct acccaggcgc cgtgaccgtg gcctggaagg ccgacagcag cccccgtgaag   480
gccggcgtgg agaccaccac ccccagcaag cagagcaaca acaagtacgc cgccagcagc   540
tacctgagcc tgaccccccga cagtggaaga gccacaggt cctacagctg ccaggtgacc   600
cacgagggca gcaccgtgga aaagaccgtg gccccaaccg agtgcagc                648

SEQ ID NO: 146          moltype = AA  length = 5
FEATURE                 Location/Qualifiers
source                  1..5
                        mol_type = protein
                        organism = synthetic construct
SEQUENCE: 146
RDYWS                                                                5

SEQ ID NO: 147          moltype = AA  length = 16
FEATURE                 Location/Qualifiers
source                  1..16
                        mol_type = protein
                        organism = synthetic construct
SEQUENCE: 147
NIYYSGSTNY NPSLKS                                                   16
```

```
SEQ ID NO: 148            moltype = AA  length = 16
FEATURE                   Location/Qualifiers
source                    1..16
                          mol_type = protein
                          organism = synthetic construct
SEQUENCE: 148
VPGCSSTSCI DGWFDP                                                      16

SEQ ID NO: 149            moltype = AA  length = 7
FEATURE                   Location/Qualifiers
source                    1..7
                          mol_type = protein
                          organism = synthetic construct
SEQUENCE: 149
GGSISRD                                                                7

SEQ ID NO: 150            moltype = AA  length = 5
FEATURE                   Location/Qualifiers
source                    1..5
                          mol_type = protein
                          organism = synthetic construct
SEQUENCE: 150
YYSGS                                                                  5

SEQ ID NO: 151            moltype = AA  length = 16
FEATURE                   Location/Qualifiers
source                    1..16
                          mol_type = protein
                          organism = synthetic construct
SEQUENCE: 151
VPGCSSTSCI DGWFDP                                                      16

SEQ ID NO: 152            moltype = AA  length = 124
FEATURE                   Location/Qualifiers
source                    1..124
                          mol_type = protein
                          organism = synthetic construct
SEQUENCE: 152
QVQLQESGPG LVKPSETLSL TCTVSGGSIS RDYWSWVRQP PGAGLEWIGN IYYSGSTNYN      60
PSLKSRVTIS VATNKKQFSL KLTSVTAADT AVYYCARVPG CSSTSCIDGW FDPWGQGILV     120
TVSS                                                                  124

SEQ ID NO: 153            moltype = DNA  length = 372
FEATURE                   Location/Qualifiers
misc_feature              1..372
                          note = source = /note=Description of synthetic construct:
                           Synthetic polynucleotide
source                    1..372
                          mol_type = other DNA
                          organism = synthetic construct
SEQUENCE: 153
caggtgcagc tgcaagaatc aggccctggc ctggtcaagc ctagcgagac actgagcctg      60
acctgcaccg tcagcggcgg ctctatctct agggactact ggtcctgggt ccgacaacct     120
cctggcgctg gcctcgagtg gatcggtaat atctactata gcggctctac taactataac     180
cctagcctga agtctagggt cacaattagt gtggcactac acaagaagca gtttagcctg     240
aagctgacta gcgtgaccgc cgctgacacc gccgtctact actgcgctag agtgcccggc     300
tgctctagca ctagctgtat cgacggttgg tttgacccct ggggtcaagg gatcctggtc     360
accgtgtcta gc                                                         372

SEQ ID NO: 154            moltype = AA  length = 454
FEATURE                   Location/Qualifiers
source                    1..454
                          mol_type = protein
                          organism = synthetic construct
SEQUENCE: 154
QVQLQESGPG LVKPSETLSL TCTVSGGSIS RDYWSWVRQP PGAGLEWIGN IYYSGSTNYN      60
PSLKSRVTIS VATNKKQFSL KLTSVTAADT AVYYCARVPG CSSTSCIDGW FDPWGQGILV     120
TVSSASTKGP SVFPLAPSSK STSGGTAALG CLVKDYFPEP VTVSWNSGAL TSGVHTFPAV     180
LQSSGLYSLS SVVTVPSSSL GTQTYICNVN HKPSNTKVDK RVEPKSCDKT HTCPPCPAPE     240
LLGGPSVFLF PPKPKDTLMI SRTPEVTCVV VDVSHEDPEV KFNWYVDGVE VHNAKTKPRE     300
EQYNSTYRVV SVLTVLHQDW LNGKEYKCKV SNKALPAPIE KTISKAKGQP REPQVYTLPP     360
SREEMTKNQV SLTCLVKGFY PSDIAVEWES NGQPENNYKT TPPVLDSDGS FFLYSKLTVD     420
KSRWQQGNVF SCSVMHEALH NHYTQKSLSL SPGK                                 454

SEQ ID NO: 155            moltype = DNA  length = 1362
FEATURE                   Location/Qualifiers
misc_feature              1..1362
                          note = source = /note=Description of synthetic construct:
```

```
                        Synthetic polynucleotide
source                  1..1362
                        mol_type = other DNA
                        organism = synthetic construct
SEQUENCE: 155
caggtgcagc tgcaagaatc aggccctggc ctggtcaagc ctagcgagac actgagcctg    60
acctgcaccg tcagcggcgg ctctatctct agggactact ggtcctgggt ccgacaacct   120
cctggcgctg gcctcgagtg gatcggtaat atctactata gcggctctac taactataac   180
cctagcctga agtctagggt cacaattagt gtggctacta caagaagca gtttagcctg   240
aagctgacta gcgtgaccgc cgctgacacc gccgtctact actgcgctag agtgcccggc   300
tgctctagca ctagctgtat cgacggttgg tttgacccct ggggtcaagg gatcctggtc   360
accgtgtcta gcgctagcac taagggccca agtgtgtttc ccctggcccc cagcagcaag   420
tctacttccg gcggaactgc tgccctgggt tgccctggtga aggactactt ccccgagccc   480
gtgacagtgt cctggaactc tggggctctg acttccggcg tgcacacctt ccccgccgtg   540
ctgcagagca gcggcctgta cagcctgagc agcgtggtga cagtgccctc cagctctctg   600
ggaacccaga cctatatctg caacgtgaac cacaagccca gcaacaccaa ggtggacaag   660
agagtggagc ccaagagctg cgacaagacc cacacctgcc ccccctgccc agctccagaa   720
ctgctgggag ggccttccgt gttcctgttc ccccccaagc ccaaggacac cctgatgatc   780
agcaggaccc ccgaggtgac ctgcgtggtg gtggacgtgt cccacgagga cccagaggtg   840
aagttcaact ggtacgtgga cggcgtggag gtgcacaacg ccaagaccaa gcccagagag   900
gagcagtaca acagcaccta cagggtggtg tccgtgctga ccgtgctgca ccaggactgg   960
ctgaacggca agaataccaa gtgcaaagtc tccaacaagg ccctgccagc cccaatcgaa  1020
aagacaatca gcaaggccaa gggccagcca cgggagcccc aggtgtacac cctgccccc   1080
agccgggagg agatgaccaa gaaccaggtg tccctgacct gtctggtgaa gggcttctac  1140
cccagcgata tcgccgtgga gtgggagagc aacggccagc ccgagaacaa ctacaagacc  1200
acccccccag tgctggacag cgacggcagc ttcttcctgt acagcaagct gaccgtggac  1260
aagtccaggt ggcagcaggg caacgtgttc agctgcacgc tgatgcacga ggccctgcac  1320
aaccactaca cccagaagtc cctgagcctg agccccggca ag                     1362

SEQ ID NO: 156          moltype = AA   length = 13
FEATURE                 Location/Qualifiers
source                  1..13
                        mol_type = protein
                        organism = synthetic construct
SEQUENCE: 156
SGSSSNIGNT YVS                                                       13

SEQ ID NO: 157          moltype = AA   length = 7
FEATURE                 Location/Qualifiers
source                  1..7
                        mol_type = protein
                        organism = synthetic construct
SEQUENCE: 157
DNNKRPS                                                              7

SEQ ID NO: 158          moltype = AA   length = 11
FEATURE                 Location/Qualifiers
source                  1..11
                        mol_type = protein
                        organism = synthetic construct
SEQUENCE: 158
GTWDSSLSAW V                                                         11

SEQ ID NO: 159          moltype = AA   length = 9
FEATURE                 Location/Qualifiers
source                  1..9
                        mol_type = protein
                        organism = synthetic construct
SEQUENCE: 159
SSSNIGNTY                                                            9

SEQ ID NO: 160          moltype =      length =
SEQUENCE: 160
000

SEQ ID NO: 161          moltype = AA   length = 8
FEATURE                 Location/Qualifiers
source                  1..8
                        mol_type = protein
                        organism = synthetic construct
SEQUENCE: 161
WDSSLSAW                                                             8

SEQ ID NO: 162          moltype = AA   length = 110
FEATURE                 Location/Qualifiers
source                  1..110
                        mol_type = protein
                        organism = synthetic construct
SEQUENCE: 162
```

```
QSVLTQPPSL SAAPGQKVTI SCSGSSSNIG NTYVSWYQQL PGTAPKLLIY DNNKRPSGIP    60
DRFSGSKSGT SATLGITGLQ TGDEAVYYCG TWDSSLSAWV FGGGTRLTVL             110
```

| SEQ ID NO: 163 | moltype = DNA  length = 330 |
|---|---|
| FEATURE | Location/Qualifiers |
| misc_feature | 1..330 |
| | note = source = /note=Description of synthetic construct: Synthetic polynucleotide |
| source | 1..330 |
| | mol_type = other DNA |
| | organism = synthetic construct |

```
SEQUENCE: 163
cagtcagtcc tgactcagcc ccctagcctg agcgccgctc ccggtcaaaa agtgactatt    60
agctgtagcg gctctagctc taatatcggt aataccacg tcagctggta tcagcagctg   120
cccggcaccg cccctaagct gctgatctac gataacaaca agcggcctag cggaatcccc   180
gataggttta gcggatctaa gtcaggcact agcgctaccc tgggaatcac cggcctgcag   240
accggcgacg aggccgtcta ctactgcggc acctgggact ctagtctgag cgcctgggtg   300
ttcggcggag gcactagact gaccgtgctg                                   330
```

| SEQ ID NO: 164 | moltype = AA  length = 216 |
|---|---|
| FEATURE | Location/Qualifiers |
| source | 1..216 |
| | mol_type = protein |
| | organism = synthetic construct |

```
SEQUENCE: 164
QSVLTQPPSL SAAPGQKVTI SCSGSSSNIG NTYVSWYQQL PGTAPKLLIY DNNKRPSGIP    60
DRFSGSKSGT SATLGITGLQ TGDEAVYYCG TWDSSLSAWV FGGGTRLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216
```

| SEQ ID NO: 165 | moltype = DNA  length = 648 |
|---|---|
| FEATURE | Location/Qualifiers |
| misc_feature | 1..648 |
| | note = source = /note=Description of synthetic construct: Synthetic polynucleotide |
| source | 1..648 |
| | mol_type = other DNA |
| | organism = synthetic construct |

```
SEQUENCE: 165
cagtcagtcc tgactcagcc ccctagcctg agcgccgctc ccggtcaaaa agtgactatt    60
agctgtagcg gctctagctc taatatcggt aataccacg tcagctggta tcagcagctg   120
cccggcaccg cccctaagct gctgatctac gataacaaca agcggcctag cggaatcccc   180
gataggttta gcggatctaa gtcaggcact agcgctaccc tgggaatcac cggcctgcag   240
accggcgacg aggccgtcta ctactgcggc acctgggact ctagtctgag cgcctgggtg   300
ttcggcggag gcactagact gaccgtgctg ggtcaaccta aggctgcccc cagcgtgacc   360
ctgttccccc ccagcagcga ggagctgcag gccaacaagg ccaccctggt gtgcctgatc   420
agcgacttct acccaggcgc cgtgaccgtg gcctggaagg ccgacagcag ccccgtgaag   480
gccggcgtgg agaccaccac ccccagcaag cagagcaaca acaagtacgc cgccagcagc   540
tacctgagcc tgacccccga gcagtggaag agccacaggt cctacagctg ccaggtgacc   600
cacgagggca gcaccgtgga aaagaccgtg gccccaaccg agtgcagc                648
```

| SEQ ID NO: 166 | moltype = AA  length = 5 |
|---|---|
| FEATURE | Location/Qualifiers |
| source | 1..5 |
| | mol_type = protein |
| | organism = synthetic construct |

```
SEQUENCE: 166
RDYWS                                                                5
```

| SEQ ID NO: 167 | moltype = AA  length = 16 |
|---|---|
| FEATURE | Location/Qualifiers |
| source | 1..16 |
| | mol_type = protein |
| | organism = synthetic construct |

```
SEQUENCE: 167
NIYYSGSTNY NPSLKS                                                   16
```

| SEQ ID NO: 168 | moltype = AA  length = 16 |
|---|---|
| FEATURE | Location/Qualifiers |
| source | 1..16 |
| | mol_type = protein |
| | organism = synthetic construct |

```
SEQUENCE: 168
VPGCSSTSCI DGWFDP                                                   16
```

| SEQ ID NO: 169 | moltype = AA  length = 7 |
|---|---|
| FEATURE | Location/Qualifiers |
| source | 1..7 |
| | mol_type = protein |

```
                        organism = synthetic construct
SEQUENCE: 169
GGSISRD                                                                  7

SEQ ID NO: 170          moltype = AA   length = 5
FEATURE                 Location/Qualifiers
source                  1..5
                        mol_type = protein
                        organism = synthetic construct
SEQUENCE: 170
YYSGS                                                                    5

SEQ ID NO: 171          moltype = AA   length = 16
FEATURE                 Location/Qualifiers
source                  1..16
                        mol_type = protein
                        organism = synthetic construct
SEQUENCE: 171
VPGCSSTSCI DGWFDP                                                       16

SEQ ID NO: 172          moltype = AA   length = 124
FEATURE                 Location/Qualifiers
source                  1..124
                        mol_type = protein
                        organism = synthetic construct
SEQUENCE: 172
QVQLQESGPG LVKPSETLSL TCTVSGGSIS RDYWSWVRQP PGAGLEWIGN IYYSGSTNYN        60
PSLKSRVTIS VATNKKQFSL KLTSVTAADT AVYYCARVPG CSSTSCIDGW FDPWGQGILV       120
TVSS                                                                   124

SEQ ID NO: 173          moltype = DNA   length = 372
FEATURE                 Location/Qualifiers
misc_feature            1..372
                        note = source = /note=Description of synthetic construct:
                         Synthetic polynucleotide
source                  1..372
                        mol_type = other DNA
                        organism = synthetic construct
SEQUENCE: 173
caggtgcaat tgcaggaaag cggccctggc ctcgtgaagc ccagcgagac actgagcctg        60
acctgtaccg tgtccggcgg cagcatcagc agagactact ggagctgggt tcgccagcct      120
ccaggcgcag gactggaatg gatcggcaac atctactaca gcggcagcac caactacaac      180
cccagcctga agtccagagt gaccatcagc gtggccacaa acaagaaaca gttctccctg      240
aagctgacca gcgtgacagc cgccgatacc gccgtgtact actgcgccag agtgcctggc      300
tgtagcagca ccagctgcat cgacggatgg ttcgaccctt ggggccaggg cattctcgtg      360
accgtcagct ca                                                          372

SEQ ID NO: 174          moltype = AA   length = 454
FEATURE                 Location/Qualifiers
source                  1..454
                        mol_type = protein
                        organism = synthetic construct
SEQUENCE: 174
QVQLQESGPG LVKPSETLSL TCTVSGGSIS RDYWSWVRQP PGAGLEWIGN IYYSGSTNYN        60
PSLKSRVTIS VATNKKQFSL KLTSVTAADT AVYYCARVPG CSSTSCIDGW FDPWGQGILV       120
TVSSASTKGP SVFPLAPSSK STSGGTAALG CLVKDYFPEP VTVSWNSGAL TSGVHTFPAV       180
LQSSGLYSLS SVVTVPSSSL GTQTYICNVN HKPSNTKVDK RVEPKSCDKT HTCPPCPAPE       240
LLGGPSVFLF PPKPKDTLMI SRTPEVTCVV VDVSHEDPEV KFNWYVDGVE VHNAKTKPRE       300
EQYNSTYRVV SVLTVLHQDW LNGKEYKCKV SNKALPAPIE KTISKAKGQP REPQVYTLPP       360
SREEMTKNQV SLTCLVKGFY PSDIAVEWES NGQPENNYKT TPPVLDSDGS FFLYSKLTVD       420
KSRWQQGNVF SCSVMHEALH NHYTQKSLSL SPGK                                   454

SEQ ID NO: 175          moltype = DNA   length = 1362
FEATURE                 Location/Qualifiers
misc_feature            1..1362
                        note = source = /note=Description of synthetic construct:
                         Synthetic polynucleotide
source                  1..1362
                        mol_type = other DNA
                        organism = synthetic construct
SEQUENCE: 175
caggtgcaat tgcaggaaag cggccctggc ctcgtgaagc ccagcgagac actgagcctg        60
acctgtaccg tgtccggcgg cagcatcagc agagactact ggagctgggt tcgccagcct      120
ccaggcgcag gactggaatg gatcggcaac atctactaca gcggcagcac caactacaac      180
cccagcctga agtccagagt gaccatcagc gtggccacaa acaagaaaca gttctccctg      240
aagctgacca gcgtgacagc cgccgatacc gccgtgtact actgcgccag agtgcctggc      300
tgtagcagca ccagctgcat cgacggatgg ttcgaccctt ggggccaggg cattctcgtg      360
accgtcagct cagctagcac caagggcccc agcgtgttcc ccctggcccc cagcagcaag      420
agcaccagcg gcggcacagc cgccctgggc tgcctggtga aggactactt ccccgagccc      480
```

```
gtgaccgtgt cctggaacag cggagccctg acctccggcg tgcacacctt ccccgccgtg    540
ctgcagagca gcggcctgta cagcctgtcc agcgtggtga cagtgcccag cagcagcctg    600
ggcacccaga cctacatctg caacgtgaac cacaagccca gcaacaccaa ggtggacaag    660
agagtggagc ccaagagctg cgacaagacc cacacctgcc ccccctgccc agccccagag    720
ctgctgggcg gaccctccgt gttcctgttc ccccccaagc caaggacacc cctgatgatc    780
agcaggaccc ccgaggtgac ctgcgtggtg gtggacgtga gccacgagga cccagaggtg    840
aagttcaact ggtacgtgga cggcgtggag gtgcacaacg ccaagaccaa gcccagagag    900
gagcagtaca acagcaccta cagggtggtg tccgtgctga ccgtgctgca ccaggactgg    960
ctgaacggca aggaatacaa gtgcaaggtc tccaacaagg ccctgccagc ccccatcgaa   1020
aagaccatca gcaaggccaa gggccagcca cgggagcccc aggtgtacac cctgcccccc   1080
tcccgggagg agatgaccaa gaaccaggtg tccctgacct gtctggtgaa gggcttctac   1140
cccagcgaca tcgccgtgga gtgggagagc aacggccagc ccgagaacaa ctacaagacc   1200
accccccag tgctggacag cgacggcagc ttcttcctgt acagcaagct gaccgtggac    1260
aagtccaggt ggcagcaggg caacgtgttc agctgcagcg tgatgcacga ggccctgcac   1320
aaccactaca cccagaagag cctgagcctg tcccccggca ag                      1362

SEQ ID NO: 176              moltype = AA  length = 13
FEATURE                     Location/Qualifiers
source                      1..13
                            mol_type = protein
                            organism = synthetic construct
SEQUENCE: 176
SGSSSNIGNT YVS                                                       13

SEQ ID NO: 177              moltype = AA  length = 7
FEATURE                     Location/Qualifiers
source                      1..7
                            mol_type = protein
                            organism = synthetic construct
SEQUENCE: 177
DNNKRPS                                                               7

SEQ ID NO: 178              moltype = AA  length = 11
FEATURE                     Location/Qualifiers
source                      1..11
                            mol_type = protein
                            organism = synthetic construct
SEQUENCE: 178
GTWDSSLSAW V                                                         11

SEQ ID NO: 179              moltype = AA  length = 9
FEATURE                     Location/Qualifiers
source                      1..9
                            mol_type = protein
                            organism = synthetic construct
SEQUENCE: 179
SSSNIGNTY                                                             9

SEQ ID NO: 180              moltype =     length =
SEQUENCE: 180
000

SEQ ID NO: 181              moltype = AA  length = 8
FEATURE                     Location/Qualifiers
source                      1..8
                            mol_type = protein
                            organism = synthetic construct
SEQUENCE: 181
WDSSLSAW                                                              8

SEQ ID NO: 182              moltype = AA  length = 110
FEATURE                     Location/Qualifiers
source                      1..110
                            mol_type = protein
                            organism = synthetic construct
SEQUENCE: 182
QSVLTQPPSV SAAPGQKVTI SCSGSSSNIG NTYVSWYQQL PGTAPKLLIY DNNKRPSGIP    60
DRFSGSKSGT SATLGITGLQ TGDEADYYCG TWDSSLSAWV FGGGTRLTVL              110

SEQ ID NO: 183              moltype = DNA  length = 330
FEATURE                     Location/Qualifiers
misc_feature                1..330
                            note = source = /note=Description of synthetic construct:
                             Synthetic polynucleotide
source                      1..330
                            mol_type = other DNA
                            organism = synthetic construct
SEQUENCE: 183
caaagcgtgc tgacccagcc tcctagcgtg tctgctgccc ctggccagaa ggtgaccatc     60
```

```
agctgtagcg gcagcagctc aacatcggc aacacctacg tgtcctggta tcagcagctg    120
cccggcaccg cccccaaact gctgatctac gacaacaaca agcggcccag cggcatcccc    180
gatagatttt ctggcagcaa gagcggcacc agcgccaccc tgggaatcac aggactgcag    240
acaggggacg aggccgatta ctactgtggc acctgggatt ctagcctgag cgcctgggtg    300
ttcggcggag gcacaagact gacagtgctg                                    330

SEQ ID NO: 184           moltype = AA   length = 216
FEATURE                  Location/Qualifiers
source                   1..216
                         mol_type = protein
                         organism = synthetic construct
SEQUENCE: 184
QSVLTQPPSV SAAPGQKVTI SCSGSSSNIG NTYVSWYQQL PGTAPKLLIY DNNKRPSGIP     60
DRFSGSKSGT SATLGITGLQ TGDEADYYCG TWDSSLSAWV FGGGTRLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 185           moltype = DNA   length = 648
FEATURE                  Location/Qualifiers
misc_feature             1..648
                         note = source = /note=Description of synthetic construct:
                          Synthetic polynucleotide
source                   1..648
                         mol_type = other DNA
                         organism = synthetic construct
SEQUENCE: 185
caaagcgtgc tgacccagcc tcctagcgtg tctgctgccc ctggccagaa ggtgaccatc     60
agctgtagcg gcagcagctc aacatcggc aacacctacg tgtcctggta tcagcagctg    120
cccggcaccg cccccaaact gctgatctac gacaacaaca agcggcccag cggcatcccc    180
gatagatttt ctggcagcaa gagcggcacc agcgccaccc tgggaatcac aggactgcag    240
acaggggacg aggccgatta ctactgtggc acctgggatt ctagcctgag cgcctgggtg    300
ttcggcggag gcacaagact gacagtgctg ggtcagccta aggccgctcc ctccgtgacc    360
ctgttccccc ccagctccga ggaactgcag gccaacaagg ccaccctggt gtgcctgatc    420
agcgacttct accctggcgc cgtgaccgtg gcctggaagg ccgacagcag ccccgtgaag    480
gccggcgtgg agacaaccac ccccagcaag cagagcaaca acaagtacgc cgccagcagc    540
tacctgagcc tgacccccga gcagtggaag agccacagaa gctacagctg ccaggtcacc    600
cacgagggca gcaccgtgga gaaaaccgtg gcccccaccg agtgcagc                 648

SEQ ID NO: 186           moltype = AA   length = 7
FEATURE                  Location/Qualifiers
source                   1..7
                         mol_type = protein
                         organism = synthetic construct
SEQUENCE: 186
SGGYSWS                                                                7

SEQ ID NO: 187           moltype = AA   length = 16
FEATURE                  Location/Qualifiers
source                   1..16
                         mol_type = protein
                         organism = synthetic construct
SEQUENCE: 187
YIYYRGTTYY NPSLKS                                                     16

SEQ ID NO: 188           moltype = AA   length = 13
FEATURE                  Location/Qualifiers
source                   1..13
                         mol_type = protein
                         organism = synthetic construct
SEQUENCE: 188
ALTHLVGVGW FDP                                                        13

SEQ ID NO: 189           moltype = AA   length = 9
FEATURE                  Location/Qualifiers
source                   1..9
                         mol_type = protein
                         organism = synthetic construct
SEQUENCE: 189
GGSISSGGY                                                              9

SEQ ID NO: 190           moltype = AA   length = 5
FEATURE                  Location/Qualifiers
source                   1..5
                         mol_type = protein
                         organism = synthetic construct
SEQUENCE: 190
YYRGT                                                                  5

SEQ ID NO: 191           moltype = AA   length = 13
```

```
FEATURE                 Location/Qualifiers
source                  1..13
                        mol_type = protein
                        organism = synthetic construct
SEQUENCE: 191
ALTHLVGVGW FDP                                                          13

SEQ ID NO: 192          moltype = AA  length = 123
FEATURE                 Location/Qualifiers
source                  1..123
                        mol_type = protein
                        organism = synthetic construct
SEQUENCE: 192
QVQLQESGPG LAKPSQTLSL TCSVSGGSIS SGGYSWSWIR QPPGKGLEYI GYIYYRGTTY        60
YNPSLKSRIT MSVDTSNNQI SLKLTSVTAA DTAVYYCARA LTHLVGVGWF DPWGQGTMVT       120
VSS                                                                    123

SEQ ID NO: 193          moltype = DNA  length = 369
FEATURE                 Location/Qualifiers
misc_feature            1..369
                        note = source = /note=Description of synthetic construct:
                        Synthetic polynucleotide
source                  1..369
                        mol_type = other DNA
                        organism = synthetic construct
SEQUENCE: 193
caggtgcagc tgcaagaatc aggccctggc ctggctaagc ctagtcagac cctgagcctg        60
acctgtagcg tcagcggagg ctctatctct agcggcggct atagctggtc ctggattaga       120
cagcccccag gtaaaggcct cgagtatatc ggctatatct actataggg cactacctac        180
tataacccta gcctgaagtc taggatcact atgagcgtgg acacctctaa caatcagatt       240
agcctgaagc tgactagcgt gaccgccgct gacaccgccg tctactactg cgctagagcc       300
ctgactcacc tcgttggagt gggctggttt gacccttggg gtcaaggcac tatggtcacc       360
gtgtctagc                                                              369

SEQ ID NO: 194          moltype = AA  length = 453
FEATURE                 Location/Qualifiers
source                  1..453
                        mol_type = protein
                        organism = synthetic construct
SEQUENCE: 194
QVQLQESGPG LAKPSQTLSL TCSVSGGSIS SGGYSWSWIR QPPGKGLEYI GYIYYRGTTY        60
YNPSLKSRIT MSVDTSNNQI SLKLTSVTAA DTAVYYCARA LTHLVGVGWF DPWGQGTMVT       120
VSSASTKGPS VFPLAPSSKS TSGGTAALGC LVKDYFPEPV TVSWNSGALT SGVHTFPAVL       180
QSSGLYSLSS VVTVPSSSLG TQTYICNVNH KPSNTKVDKR VEPKSCDKTH TCPPCPAPEL       240
LGGPSVFLFP PKPKDTLMIS RTPEVTCVVV DVSHEDPEVK FNWYVDGVEV HNAKTKPREE       300
QYNSTYRVVS VLTVLHQDWL NGKEYKCKVS NKALPAPIEK TISKAKGQPR EPQVYTLPPS       360
REEMTKNQVS LTCLVKGFYP SDIAVEWESN GQPENNYKTT PPVLDSDGSF FLYSKLTVDK       420
SRWQQGNVFS CSVMHEALHN HYTQKSLSLS PGK                                    453

SEQ ID NO: 195          moltype = DNA  length = 1359
FEATURE                 Location/Qualifiers
misc_feature            1..1359
                        note = source = /note=Description of synthetic construct:
                        Synthetic polynucleotide
source                  1..1359
                        mol_type = other DNA
                        organism = synthetic construct
SEQUENCE: 195
caggtgcagc tgcaagaatc aggccctggc ctggctaagc ctagtcagac cctgagcctg        60
acctgtagcg tcagcggagg ctctatctct agcggcggct atagctggtc ctggattaga       120
cagcccccag gtaaaggcct cgagtatatc ggctatatct actataggg cactacctac        180
tataacccta gcctgaagtc taggatcact atgagcgtgg acacctctaa caatcagatt       240
agcctgaagc tgactagcgt gaccgccgct gacaccgccg tctactactg cgctagagcc       300
ctgactcacc tcgttggagt gggctggttt gacccttggg gtcaaggcac tatggtcacc       360
gtgtctagcg ctagcactaa gggcccaagt gtgtttcccc tggccccag cagcaagtct        420
acttccggcg aactgctgc cctgggttgc ctggtgaagg actactttcc cgagcccgtg        480
acagtgtcct ggaactctgg ggctctgact tccggcgtgc acaccttccc cgccgtgctg       540
cagagcagcg gcctgtacag cctgagcagc gtggtgacag tgccctccag ctctctggga       600
acccagacct atatctgcaa cgtgaaccac aagcccagca acaccaaggt ggacaagaga       660
gtggagccca gagctgcga caagacccac acctgccccc cctgcccagc tccagaactg       720
ctgggagggc cttccgtgtt cctgttcccc ccaagcccaa ggacaccct gatgatcagc        780
aggaccccg aggtgacctg cgtggtggtg gacgtgtccc acgaggaccc agaggtgaag       840
ttcaactggt acgtggacgg cgtggaggtg cacaacgcca agaccaagcc cagagaggag      900
cagtacaaca gcacctacag ggtggtgtcc gtgctgcacca ggactggctg                960
aacggcaaag aatacaagtg caaagtctcc aacaaggccc tgccagcccc aatcgaaaag     1020
acaatcagca aggccaaggg ccagccacgg gagcccagg tgtacaccct gccccccagc     1080
cgggaggaga tgaccaagaa ccaggtgtcc ctgacctgtc tggtgaaggg cttctacccc     1140
agcgatatcc ccgtggagtg ggagagcaac ggccagcccg agaacaacta caagaccacc     1200
ccccagtgc tggacagcga cggcagcttc ttcctgtaca gcaagctgac cgtggacaag     1260
```

```
tccaggtggc agcagggcaa cgtgttcagc tgcagcgtga tgcacgaggc cctgcacaac    1320
cactacaccc agaagtccct gagcctgagc cccggcaag                           1359

SEQ ID NO: 196          moltype = AA  length = 13
FEATURE                 Location/Qualifiers
source                  1..13
                        mol_type = protein
                        organism = synthetic construct
SEQUENCE: 196
SGGSSNLGSN YVS                                                       13

SEQ ID NO: 197          moltype = AA  length = 7
FEATURE                 Location/Qualifiers
source                  1..7
                        mol_type = protein
                        organism = synthetic construct
SEQUENCE: 197
DNNKRPS                                                              7

SEQ ID NO: 198          moltype = AA  length = 11
FEATURE                 Location/Qualifiers
source                  1..11
                        mol_type = protein
                        organism = synthetic construct
SEQUENCE: 198
GTWDGSLSAW V                                                         11

SEQ ID NO: 199          moltype = AA  length = 9
FEATURE                 Location/Qualifiers
source                  1..9
                        mol_type = protein
                        organism = synthetic construct
SEQUENCE: 199
GSSNLGSNY                                                            9

SEQ ID NO: 200          moltype =     length =
SEQUENCE: 200
000

SEQ ID NO: 201          moltype = AA  length = 8
FEATURE                 Location/Qualifiers
source                  1..8
                        mol_type = protein
                        organism = synthetic construct
SEQUENCE: 201
WDGSLSAW                                                             8

SEQ ID NO: 202          moltype = AA  length = 110
FEATURE                 Location/Qualifiers
source                  1..110
                        mol_type = protein
                        organism = synthetic construct
SEQUENCE: 202
QSVLTQPPSV SAAPGQKVTI SCSGGSSNLG SNYVSWYQQL PGTAPKLLIY DNNKRPSGIP    60
DRFSGSKSGT SATLGITGLQ TGDEADYYCG TWDGSLSAWV FGGGTKVTVL               110

SEQ ID NO: 203          moltype = DNA  length = 330
FEATURE                 Location/Qualifiers
misc_feature            1..330
                        note = source = /note=Description of synthetic construct:
                        Synthetic polynucleotide
source                  1..330
                        mol_type = other DNA
                        organism = synthetic construct
SEQUENCE: 203
cagtcagtcc tgactcagcc ccctagcgtc agcgccgctc ccggtcaaaa agtgactatt    60
agctgtagcg gcggctcctc taacctgggc tctaactacg tcagctggta tcagcagctg   120
cccggcaccg cccctaagct gctgatctac gataacaaca gcggcctag cggaatcccc    180
gataggttta gcggctctaa gtcaggcact agcgctaccc tgggaatcac cggcctgcag   240
accggcgacg aggccgacta ctactgtggc acctgggacg gtagcctgag cgcctgggtg   300
ttcggcggag gcactaaagt cacagtgctg                                    330

SEQ ID NO: 204          moltype = AA  length = 216
FEATURE                 Location/Qualifiers
source                  1..216
                        mol_type = protein
                        organism = synthetic construct
SEQUENCE: 204
QSVLTQPPSV SAAPGQKVTI SCSGGSSNLG SNYVSWYQQL PGTAPKLLIY DNNKRPSGIP    60
```

```
DRFSGSKSGT SATLGITGLQ TGDEADYYCG TWDGSLSAWV FGGGTKVTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 205              moltype = DNA   length = 648
FEATURE                     Location/Qualifiers
misc_feature                1..648
                            note = source = /note=Description of synthetic construct:
                             Synthetic polynucleotide
source                      1..648
                            mol_type = other DNA
                            organism = synthetic construct
SEQUENCE: 205
cagtcagtcc tgactcagcc ccctagcgtc agcgccgctc ccggtcaaaa agtgactatt     60
agctgtagcg gcggtcctc taacctgggc tctaactacg tcagctggta tcagcagctg    120
cccggcaccg cccctaagct gctgatctac gataacaaca gcggcctag cggaatcccc    180
gataggttta gcggctctaa gtcaggcact agcgctaccc tgggaatcac cggcctgcag    240
accggcgacg aggccgacta ctactgtggc acctgggcc gtagcctgag cgcctgggtg    300
ttcggcggag gcactaaagt cacagtgctg ggtcaaccta aggctgcccc cagcgtgacc    360
ctgttccccc ccagcagcga ggagctgcag gccaacaagg ccaccctggt gtgcctgatc    420
agcgacttct acccaggcgc cgtgaccgtg gcctggaagg ccgacagcag ccccgtgaag    480
gccggcgtgg agaccaccac cccagcaag cagagcaaca acaagtacgc cgccagcagc    540
tacctgagcc tgacccccga gcagtggaag agccacaggt cctacagctg ccaggtgacc    600
cacgagggca gcaccgtgga aaagaccgtg gccccaaccg agtgcagc                 648

SEQ ID NO: 206              moltype = AA    length = 7
FEATURE                     Location/Qualifiers
source                      1..7
                            mol_type = protein
                            organism = synthetic construct
SEQUENCE: 206
SGGYSWS                                                                7

SEQ ID NO: 207              moltype = AA    length = 16
FEATURE                     Location/Qualifiers
source                      1..16
                            mol_type = protein
                            organism = synthetic construct
SEQUENCE: 207
YIYYRGTTYY NPSLKS                                                     16

SEQ ID NO: 208              moltype = AA    length = 13
FEATURE                     Location/Qualifiers
source                      1..13
                            mol_type = protein
                            organism = synthetic construct
SEQUENCE: 208
ALTHLVGVGW FDP                                                        13

SEQ ID NO: 209              moltype = AA    length = 9
FEATURE                     Location/Qualifiers
source                      1..9
                            mol_type = protein
                            organism = synthetic construct
SEQUENCE: 209
GGSISSGGY                                                              9

SEQ ID NO: 210              moltype = AA    length = 5
FEATURE                     Location/Qualifiers
source                      1..5
                            mol_type = protein
                            organism = synthetic construct
SEQUENCE: 210
YYRGT                                                                  5

SEQ ID NO: 211              moltype = AA    length = 13
FEATURE                     Location/Qualifiers
source                      1..13
                            mol_type = protein
                            organism = synthetic construct
SEQUENCE: 211
ALTHLVGVGW FDP                                                        13

SEQ ID NO: 212              moltype = AA    length = 123
FEATURE                     Location/Qualifiers
source                      1..123
                            mol_type = protein
                            organism = synthetic construct
SEQUENCE: 212
```

```
QVQLQESGPG LVKPSQTLSL TCTVSGGSIS SGGYSWSWIR QPPGKGLEYI GYIYYRGTTY    60
YNPSLKSRVT ISVDTSNNQI SLKLSSVTAA DTAVYYCARA LTHLVGVGWF DPWGQGTMVT   120
VSS                                                                 123

SEQ ID NO: 213          moltype = DNA   length = 369
FEATURE                 Location/Qualifiers
misc_feature            1..369
                        note = source = /note=Description of synthetic construct:
                         Synthetic polynucleotide
source                  1..369
                        mol_type = other DNA
                        organism = synthetic construct
SEQUENCE: 213
caggtgcagc tgcaagaatc aggccctggc ctggtcaagc ctagtcagac cctgagcctg    60
acctgcaccg tcagcggagg ctctatctct agcggcggct atagctggtc ctggattaga   120
cagcccccag gtaaaggcct cgagtatatc ggctatatct actataggg cactacctac    180
tataacccta gcctgaagtc tagggtcaca attagcgtgg acacctctaa caatcagatt   240
agcctgaagc tgtctagcgt gaccgccgct gacaccgccg tctactactg cgctagagcc   300
ctgactcacc tcgtcggagt gggctggttt gacccttggg gtcaaggcac tatggtcacc   360
gtgtctagc                                                           369

SEQ ID NO: 214          moltype = AA   length = 453
FEATURE                 Location/Qualifiers
source                  1..453
                        mol_type = protein
                        organism = synthetic construct
SEQUENCE: 214
QVQLQESGPG LVKPSQTLSL TCTVSGGSIS SGGYSWSWIR QPPGKGLEYI GYIYYRGTTY    60
YNPSLKSRVT ISVDTSNNQI SLKLSSVTAA DTAVYYCARA LTHLVGVGWF DPWGQGTMVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKR VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 215          moltype = DNA   length = 1359
FEATURE                 Location/Qualifiers
misc_feature            1..1359
                        note = source = /note=Description of synthetic construct:
                         Synthetic polynucleotide
source                  1..1359
                        mol_type = other DNA
                        organism = synthetic construct
SEQUENCE: 215
caggtgcagc tgcaagaatc aggccctggc ctggtcaagc ctagtcagac cctgagcctg    60
acctgcaccg tcagcggagg ctctatctct agcggcggct atagctggtc ctggattaga   120
cagcccccag gtaaaggcct cgagtatatc ggctatatct actataggg cactacctac    180
tataacccta gcctgaagtc tagggtcaca attagcgtgg acacctctaa caatcagatt   240
agcctgaagc tgtctagcgt gaccgccgct gacaccgccg tctactactg cgctagagcc   300
ctgactcacc tcgtcggagt gggctggttt gacccttggg gtcaaggcac tatggtcacc   360
gtgtctagcg ctagcactaa gggcccaagt gtgtttcccc tggccccag cagcaagtct    420
acttccggcg gaactgctgc cctgggttgc ctggtgaagg actactttcc cgagcccgtg   480
acagtgtcct ggaactctgg ggctctgact tccggcgtgc acaccttccc cgccgtgctg   540
cagagcagcg gcctgtacag cctgagcagc gtggtgacag tgccctccag ctctctggga   600
acccagacct atatctgcaa cgtgaaccac aagcccagca acaccaaggt ggacaagaga   660
gtggagccca gagctgcga caagacccac acctgccccc cctgcccagc tccagaactg   720
ctgggagggc cttccgtgtt cctgttcccc ccaagccca aggacaccct gatgatcagc    780
aggacccccg aggtgacctg cgtggtggtg gacgtgtccc acgaggaccc agaggtgaag   840
ttcaactggt acgtggacgg cgtggaggtg cacaacgcca agaccaagcc cagagaggag   900
cagtacaaca gcacctacag ggtggtgtcc gtgctgaccg tgctgcacca ggactggctg   960
aacggcaaaa aatacaagtg caaagtctcc aacaaggccc tgccagcccc aatcgaaaag  1020
acaatcagca aggccaaggg ccagccacgg gagcccagg tgtacaccct gccccccagc   1080
cgggaggaga tgaccaagaa ccaggtgtcc ctgacctgtc tggtgaaggg cttctaccca  1140
agcgatatcg ccgtggagtg ggagagcaac ggccagcccg agaacaacta caagaccacc  1200
ccccagtgc tggacagcga cggcagcttc ttcctgtaca gcaagctgac cgtggacaag   1260
tccaggtggc agcagggcaa cgtgttcagc tgcagcgtga tgcacgaggc cctgcacaac  1320
cactacaccc agaagtccct gagcctgagc ccggcaag                          1359

SEQ ID NO: 216          moltype = AA   length = 13
FEATURE                 Location/Qualifiers
source                  1..13
                        mol_type = protein
                        organism = synthetic construct
SEQUENCE: 216
SGGSSNLGSN YVS                                                      13

SEQ ID NO: 217          moltype = AA   length = 7
FEATURE                 Location/Qualifiers
```

```
source                       1..7
                             mol_type = protein
                             organism = synthetic construct
SEQUENCE: 217
DNNKRPS                                                                  7

SEQ ID NO: 218               moltype = AA   length = 11
FEATURE                      Location/Qualifiers
source                       1..11
                             mol_type = protein
                             organism = synthetic construct
SEQUENCE: 218
GTWDGSLSAW V                                                            11

SEQ ID NO: 219               moltype = AA   length = 9
FEATURE                      Location/Qualifiers
source                       1..9
                             mol_type = protein
                             organism = synthetic construct
SEQUENCE: 219
GSSNLGSNY                                                                9

SEQ ID NO: 220               moltype =      length =
SEQUENCE: 220
000

SEQ ID NO: 221               moltype = AA   length = 8
FEATURE                      Location/Qualifiers
source                       1..8
                             mol_type = protein
                             organism = synthetic construct
SEQUENCE: 221
WDGSLSAW                                                                 8

SEQ ID NO: 222               moltype = AA   length = 110
FEATURE                      Location/Qualifiers
source                       1..110
                             mol_type = protein
                             organism = synthetic construct
SEQUENCE: 222
QSVLTQPPSV SAAPGQKVTI SCSGGSSNLG SNYVSWYQQL PGTAPKLLIY DNNKRPSGIP        60
DRFSGSKSGT SATLGITGLQ TGDEADYYCG TWDGSLSAWV FGGGTKVTVL                  110

SEQ ID NO: 223               moltype = DNA   length = 330
FEATURE                      Location/Qualifiers
misc_feature                 1..330
                             note = source = /note=Description of synthetic construct:
                              Synthetic polynucleotide
source                       1..330
                             mol_type = other DNA
                             organism = synthetic construct
SEQUENCE: 223
cagtcagtcc tgactcagcc ccctagcgtc agcgccgctc ccggtcaaaa agtgactatt        60
agctgtagcg gcggctcctc taacctgggc tctaactacg tcagctggta tcagcagctg      120
cccggcaccg cccctaagct gctgatctac gataacaacc agcggcctag cggaatcccc      180
gataggttta gcggctctaa gtcaggcact agcgctaccc tgggaatcac cggcctgcag      240
accggcgacg aggccgacta ctactgtggc acctgggacg gtagcctgag cgcctgggtg      300
ttcggcggag gcactaaagt cacagtgctg                                       330

SEQ ID NO: 224               moltype = AA   length = 216
FEATURE                      Location/Qualifiers
source                       1..216
                             mol_type = protein
                             organism = synthetic construct
SEQUENCE: 224
QSVLTQPPSV SAAPGQKVTI SCSGGSSNLG SNYVSWYQQL PGTAPKLLIY DNNKRPSGIP        60
DRFSGSKSGT SATLGITGLQ TGDEADYYCG TWDGSLSAWV FGGGTKVTVL GQPKAAPSVT       120
LFPPSSEELQ ANKATLVCLI SDFYPGAVTV AWKADSSPVK AGVETTTPSK QSNNKYAASS       180
YLSLTPEQWK SHRSYSCQVT HEGSTVEKTV APTECS                                216

SEQ ID NO: 225               moltype = DNA   length = 648
FEATURE                      Location/Qualifiers
misc_feature                 1..648
                             note = source = /note=Description of synthetic construct:
                              Synthetic polynucleotide
source                       1..648
                             mol_type = other DNA
                             organism = synthetic construct
SEQUENCE: 225
```

```
cagtcagtcc tgactcagcc ccctagcgtc agcgccgctc ccggtcaaaa agtgactatt    60
agctgtagcg gcggctcctc taacctgggc tctaactacg tcagctggta tcagcagctg   120
cccggcaccg cccctaagct gctgatctac gataacaaca agcggcctag cggaatcccc   180
gataggttta gcggctctaa gtcaggcact agcgctaccc tgggaatcac cggcctgcag   240
accggcgacg aggccgacta ctactgtggc acctgggacg gtagcctgag cgcctgggtg   300
ttcggcggag gcactaaagt cacagtgctg ggtcaaccta aggctgcccc cagcgtgacc   360
ctgttccccc ccagcagcga ggagctgcag gccaacaagg ccaccctggt gtgcctgatc   420
agcgacttct acccaggcgc cgtgaccgtg gcctggaagg ccgacagcag ccccgtgaag   480
gccggcgtgg agaccaccac ccccagcaag cagagcaaca acaagtacgc cgccagcagc   540
tacctgagcc tgaccccgga gcagtggaag agccacaggt cctacagctg ccaggtgacc   600
cacgagggca gcaccgtgga aaagaccgtg gccccaaccg agtgcagc                648
```

SEQ ID NO: 226                moltype = AA   length = 5
FEATURE                       Location/Qualifiers
source                        1..5
                              mol_type = protein
                              organism = synthetic construct
SEQUENCE: 226
AYYWT                                                                 5

SEQ ID NO: 227                moltype = AA   length = 16
FEATURE                       Location/Qualifiers
source                        1..16
                              mol_type = protein
                              organism = synthetic construct
SEQUENCE: 227
YISHSGSTNY NPSLKS                                                    16

SEQ ID NO: 228                moltype = AA   length = 16
FEATURE                       Location/Qualifiers
source                        1..16
                              mol_type = protein
                              organism = synthetic construct
SEQUENCE: 228
LGDTASLSRF YYYIDV                                                    16

SEQ ID NO: 229                moltype = AA   length = 7
FEATURE                       Location/Qualifiers
source                        1..7
                              mol_type = protein
                              organism = synthetic construct
SEQUENCE: 229
GGSTSAY                                                               7

SEQ ID NO: 230                moltype = AA   length = 5
FEATURE                       Location/Qualifiers
source                        1..5
                              mol_type = protein
                              organism = synthetic construct
SEQUENCE: 230
SHSGS                                                                 5

SEQ ID NO: 231                moltype = AA   length = 16
FEATURE                       Location/Qualifiers
source                        1..16
                              mol_type = protein
                              organism = synthetic construct
SEQUENCE: 231
LGDTASLSRF YYYIDV                                                    16

SEQ ID NO: 232                moltype = AA   length = 124
FEATURE                       Location/Qualifiers
source                        1..124
                              mol_type = protein
                              organism = synthetic construct
SEQUENCE: 232
QVQLVQSGPG LVKPSETLSL TCTVSGGSTS AYYWTWIRQP PGKGLEWIGY ISHSGSTNYN    60
PSLKSRVTIS ADTSKNQLSL KVNSVTAADT AVYYCARLGD TASLSRFYYY IDVWGKGTTV   120
TVSS                                                                124

SEQ ID NO: 233                moltype = DNA   length = 372
FEATURE                       Location/Qualifiers
misc_feature                  1..372
                              note = source = /note=Description of synthetic construct:
                              Synthetic polynucleotide
source                        1..372
                              mol_type = other DNA
                              organism = synthetic construct
SEQUENCE: 233

```
caggtgcagc tggtgcagtc tggcccagga ctggtgaagc cttcggagac cctgtccctc    60
acctgcactg tctctggtgg ctccaccagt gcttactact ggacctggat tcggcagccc   120
ccagggaagg gactggagtg gattgggtat atctctcaca gtgggagcac caactacaac   180
ccctcccctca agagtcgagt caccatatca gcagacacgt ccaagaacca gctctccctg   240
aaggtgaact ctgtgaccgc cgcagacacg gccgtgtatt actgtgcgag acttggggat   300
acagcttcac ttagccgctt ctactactac attgacgtct ggggcaaagg gaccacggtc   360
accgtctcct ca                                                       372

SEQ ID NO: 234          moltype = AA   length = 454
FEATURE                 Location/Qualifiers
source                  1..454
                        mol_type = protein
                        organism = synthetic construct
SEQUENCE: 234
QVQLVQSGPG LVKPSETLSL TCTVSGGSTS AYYWTWIRQP PGKGLEWIGY ISHSGSTNYN    60
PSLKSRVTIS ADTSKNQLSL KVNSVTAADT AVYYCARLGD TASLSRFYYY IDVWGKGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK RVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SREEMTKNQV SLTCLVKGFY PSDIAVEWES NGQPENNYKT TPPVLDSDGS FFLYSKLTVD   420
KSRWQQGNVF SCSVMHEALH NHYTQKSLSL SPGK                              454

SEQ ID NO: 235          moltype = DNA   length = 1362
FEATURE                 Location/Qualifiers
misc_feature            1..1362
                        note = source = /note=Description of synthetic construct:
                        Synthetic polynucleotide
source                  1..1362
                        mol_type = other DNA
                        organism = synthetic construct
SEQUENCE: 235
caggtgcagc tggtgcagtc tggcccagga ctggtgaagc cttcggagac cctgtccctc    60
acctgcactg tctctggtgg ctccaccagt gcttactact ggacctggat tcggcagccc   120
ccagggaagg gactggagtg gattgggtat atctctcaca gtgggagcac caactacaac   180
ccctcccctca agagtcgagt caccatatca gcagacacgt ccaagaacca gctctccctg   240
aaggtgaact ctgtgaccgc cgcagacacg gccgtgtatt actgtgcgag acttggggat   300
acagcttcac ttagccgctt ctactactac attgacgtct ggggcaaagg gaccacggtc   360
accgtctcct cagctagcac caagggccca tcggtcttcc cctggcacc tcctccaag    420
agcacctctg ggggcacagc ggccctgggc tgcctggtca aggactactt ccccgaaccg   480
gtgacggtgt cgtggaactc aggcgccctg accagcggcg tgcacacctt cccggctgtc   540
ctacagtcct caggactcta ctccctcagc agcgtggtga ccgtgccctc cagcagcttg   600
ggcacccaga cctacatctg caacgtgaat cacaagccca gcaacaccaa ggtggacaag   660
agagttgagc ccaaatcttg tgacaaaact cacacatgcc caccgtgccc agcacctgaa   720
ctcctggggg gaccgtcagt cttcctcttc cccccaaaac ccaaggacac cctcatgatc   780
tcccggaccc ctgaggtcac atgcgtggtg gtggacgtga gccacgaaga ccctgaggtc   840
aagttcaact ggtacgtgga cggcgtggag gtgcataatg ccaagacaaa gccgcgggag   900
gagcagtaca acagcacgta ccgtgtggtc agcgtcctca ccgtcctgca ccaggactgg   960
ctgaatggca aggagtacaa gtgcaaggtc tccaacaaag cccctcccagc ccccatcgag  1020
aaaaccatct ccaaagccaa agggcagccc cgagaaccac aggtgtacac cctgcccca   1080
tcccgggagg agatgaccaa gaaccaggtc agcctgacct gcctggtcaa aggcttctat   1140
cccagcgaca tcgccgtgga gtgggagagc aatgggcagc cggagaacaa ctacaagacc   1200
acgcctcccg tgctggactc cgacggctcc ttcttcctct acagcaagct caccgtggac   1260
aagagcaggt ggcagcaggg gaacgtcttc tcatgctccg tgatgcatga ggctctgcac   1320
aaccactaca cgcagaagag cctctccctg tctccgggta aa                     1362

SEQ ID NO: 236          moltype = AA   length = 12
FEATURE                 Location/Qualifiers
source                  1..12
                        mol_type = protein
                        organism = synthetic construct
SEQUENCE: 236
RASQSVSSNY LA                                                       12

SEQ ID NO: 237          moltype = AA   length = 7
FEATURE                 Location/Qualifiers
source                  1..7
                        mol_type = protein
                        organism = synthetic construct
SEQUENCE: 237
GASSRAT                                                              7

SEQ ID NO: 238          moltype = AA   length = 10
FEATURE                 Location/Qualifiers
source                  1..10
                        mol_type = protein
                        organism = synthetic construct
SEQUENCE: 238
QQYGSSPPYT                                                          10
```

```
SEQ ID NO: 239          moltype = AA   length = 8
FEATURE                 Location/Qualifiers
source                  1..8
                        mol_type = protein
                        organism = synthetic construct
SEQUENCE: 239
SQSVSSNY                                                            8

SEQ ID NO: 240          moltype =    length =
SEQUENCE: 240
000

SEQ ID NO: 241          moltype = AA   length = 7
FEATURE                 Location/Qualifiers
source                  1..7
                        mol_type = protein
                        organism = synthetic construct
SEQUENCE: 241
YGSSPPY                                                             7

SEQ ID NO: 242          moltype = AA   length = 109
FEATURE                 Location/Qualifiers
source                  1..109
                        mol_type = protein
                        organism = synthetic construct
SEQUENCE: 242
EIVMTQSPDT LSLSPGERAT LSCRASQSVS SNYLAWYQQK PGEAPRLLIY GASSRATGIP   60
DRFSGSGSGT DFTLTISRLE PEDFAVYYCQ QYGSSPPYTF GQGTRLEIK              109

SEQ ID NO: 243          moltype = DNA   length = 328
FEATURE                 Location/Qualifiers
misc_feature            1..328
                        note = source = /note=Description of synthetic construct:
                         Synthetic polynucleotide
source                  1..328
                        mol_type = other DNA
                        organism = synthetic construct
SEQUENCE: 243
gaaattgtaa tgacgcagtc tccagacacc ctgtctttgt ctccagggga aagagccacc   60
ctctcctgca gggccagtca gagtgttagc agcaactact tagcctggta ccagcagaaa  120
cctggcgagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcacctcc gtacactttt  300
ggccagggga cacgactgga gattaaac                                    328

SEQ ID NO: 244          moltype = AA   length = 216
FEATURE                 Location/Qualifiers
source                  1..216
                        mol_type = protein
                        organism = synthetic construct
SEQUENCE: 244
EIVMTQSPDT LSLSPGERAT LSCRASQSVS SNYLAWYQQK PGEAPRLLIY GASSRATGIP   60
DRFSGSGSGT DFTLTISRLE PEDFAVYYCQ QYGSSPPYTF GQGTRLEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 245          moltype = DNA   length = 648
FEATURE                 Location/Qualifiers
misc_feature            1..648
                        note = source = /note=Description of synthetic construct:
                         Synthetic polynucleotide
source                  1..648
                        mol_type = other DNA
                        organism = synthetic construct
SEQUENCE: 245
gaaattgtaa tgacgcagtc tccagacacc ctgtctttgt ctccagggga aagagccacc   60
ctctcctgca gggccagtca gagtgttagc agcaactact tagcctggta ccagcagaaa  120
cctggcgagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcacctcc gtacactttt  300
ggccagggga cacgactgga gattaaacgt acggtggctg caccatctgt cttcatcttc  360
ccgccatctg atgagcagtt gaaatctgga actgcctctg ttgtgtgcct gctgaataac  420
ttctatcccc gcgaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaaccgcg gagagtgt             648

SEQ ID NO: 246          moltype = AA   length = 5
```

| | | |
|---|---|---|
| FEATURE | Location/Qualifiers | |
| source | 1..5 | |
| | mol_type = protein | |
| | organism = synthetic construct | |
| SEQUENCE: 246 | | |
| RNYMS | | 5 |
| | | |
| SEQ ID NO: 247 | moltype = AA length = 16 | |
| FEATURE | Location/Qualifiers | |
| source | 1..16 | |
| | mol_type = protein | |
| | organism = synthetic construct | |
| SEQUENCE: 247 | | |
| GIYSGGSTYY ADSVKG | | 16 |
| | | |
| SEQ ID NO: 248 | moltype = AA length = 13 | |
| FEATURE | Location/Qualifiers | |
| source | 1..13 | |
| | mol_type = protein | |
| | organism = synthetic construct | |
| SEQUENCE: 248 | | |
| EDEFWSGYSA GVD | | 13 |
| | | |
| SEQ ID NO: 249 | moltype = AA length = 7 | |
| FEATURE | Location/Qualifiers | |
| source | 1..7 | |
| | mol_type = protein | |
| | organism = synthetic construct | |
| SEQUENCE: 249 | | |
| GFTVRRN | | 7 |
| | | |
| SEQ ID NO: 250 | moltype = AA length = 5 | |
| FEATURE | Location/Qualifiers | |
| source | 1..5 | |
| | mol_type = protein | |
| | organism = synthetic construct | |
| SEQUENCE: 250 | | |
| YSGGS | | 5 |
| | | |
| SEQ ID NO: 251 | moltype = AA length = 13 | |
| FEATURE | Location/Qualifiers | |
| source | 1..13 | |
| | mol_type = protein | |
| | organism = synthetic construct | |
| SEQUENCE: 251 | | |
| EDEFWSGYSA GVD | | 13 |
| | | |
| SEQ ID NO: 252 | moltype = AA length = 121 | |
| FEATURE | Location/Qualifiers | |
| source | 1..121 | |
| | mol_type = protein | |
| | organism = synthetic construct | |
| SEQUENCE: 252 | | |
| EVQLVETGGG LVQPGGSLRL SCAASGFTVR RNYMSWVRQA PGKGLEWVSG IYSGGSTYYA | | 60 |
| DSVKGRFTIS RDYSKNTLSL QMNTLRVEDT AVYFCAREDE FWSGYSAGVD WGQGTLVTVS | | 120 |
| S | | 121 |
| | | |
| SEQ ID NO: 253 | moltype = DNA length = 364 | |
| FEATURE | Location/Qualifiers | |
| misc_feature | 1..364 | |
| | note = source = /note=Description of synthetic construct: | |
| | Synthetic polynucleotide | |
| source | 1..364 | |
| | mol_type = other DNA | |
| | organism = synthetic construct | |
| SEQUENCE: 253 | | |
| gaggtgcagc tggtggagac tgaggaggc ttggtccagc cggggggtc cctgagactc | | 60 |
| tcatgtgcag cctctggatt caccgtcaga cgcaattaca tgagttgggt ccgccaggct | | 120 |
| ccggggaagg gactggagtg gtctcaggg atctacagtg gtggtagcac atactacgca | | 180 |
| gactccgtga aggccgatt caccatctcc agagactatt ccaagaacac actgtctctt | | 240 |
| caaatgaaca ccctgagagt cgaggacacg gccgtgtatt tctgtgcgag agaagacgaa | | 300 |
| ttttggagcg gtattccgc tggggtcgac tggggccagg gaaccctggt caccgtctcc | | 360 |
| tcag | | 364 |
| | | |
| SEQ ID NO: 254 | moltype = AA length = 451 | |
| FEATURE | Location/Qualifiers | |
| source | 1..451 | |
| | mol_type = protein | |
| | organism = synthetic construct | |

| SEQUENCE: 254 | | | | | |
|---|---|---|---|---|---|
| EVQLVETGGG | LVQPGGSLRL | SCAASGFTVR | RNYMSWVRQA | PGKGLEWVSG | IYSGGSTYYA | 60
| DSVKGRFTIS | RDYSKNTLSL | QMNTLRVEDT | AVYFCAREDE | FWSGYSAGVD | WGQGTLVTVS | 120
| SASTKGPSVF | PLAPSSKSTS | GGTAALGCLV | KDYFPEPVTV | SWNSGALTSG | VHTFPAVLQS | 180
| SGLYSLSSVV | TVPSSSLGTQ | TYICNVNHKP | SNTKVDKRVE | PKSCDKTHTC | PPCPAPELLG | 240
| GPSVFLFPPK | PKDTLMISRT | PEVTCVVVDV | SHEDPEVKFN | WYVDGVEVHN | AKTKPREEQY | 300
| NSTYRVVSVL | TVLHQDWLNG | KEYKCKVSNK | ALPAPIEKTI | SKAKGQPREP | QVYTLPPSRE | 360
| EMTKNQVSLT | CLVKGFYPSD | IAVEWESNGQ | PENNYKTTPP | VLDSDGSFFL | YSKLTVDKSR | 420
| WQQGNVFSCS | VMHEALHNHY | TQKSLSLSPG | K | | | 451

```
SEQ ID NO: 255          moltype = DNA   length = 1353
FEATURE                 Location/Qualifiers
misc_feature            1..1353
                        note = source = /note=Description of synthetic construct:
                        Synthetic polynucleotide
source                  1..1353
                        mol_type = other DNA
                        organism = synthetic construct
SEQUENCE: 255
gaggtgcagc tggtggagac tggaggaggc ttggtccagc cggggggggtc cctgagactc   60
tcatgtgcag cctctggatt caccgtcaga cgcaattaca tgagttgggt ccgccaggct  120
ccggggaagg gactggagtg ggtctcaggg atctacatgt gtggtagcac atactacgca  180
gactccgtga agggccgatt caccatctcc agagactatt ccaagaacac actgtctctt  240
caaatgaaca ccctgagagt cgaggacacg gccgtgtatt tctgtgcgag agaagacgaa  300
tttttggagcg ggtattccgc tggggtcgac tgggccagg gaaccctggt caccgtctcc  360
tcagctagca ccaagggccc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacaccc tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gagagttgag  660
cccaaatctt gtgacaaaac tcacacatgc ccaccgtgcc cagcacctga actcctgggg  720
ggaccgtcag tcttcctctt ccccccaaaa cccaaggaca cctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc 1020
tccaaagcca aagggcagcc ccgagaacca caggtgtaca ccctgccccc atcccggag 1080
gagatgacca agaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tacagcaagc tcaccgtgga caagagcagg 1260
tggcagcagg ggaacgtctt ctcatgctcc gtgatgcatg aggctctgca caaccactac 1320
acgcagaaga gcctctccct gtctccgggt aaa                              1353

SEQ ID NO: 256          moltype = AA   length = 11
FEATURE                 Location/Qualifiers
source                  1..11
                        mol_type = protein
                        organism = synthetic construct
SEQUENCE: 256
RASQSISSYL N                                                        11

SEQ ID NO: 257          moltype = AA   length = 7
FEATURE                 Location/Qualifiers
source                  1..7
                        mol_type = protein
                        organism = synthetic construct
SEQUENCE: 257
AASSLQS                                                              7

SEQ ID NO: 258          moltype = AA   length = 9
FEATURE                 Location/Qualifiers
source                  1..9
                        mol_type = protein
                        organism = synthetic construct
SEQUENCE: 258
QQSYNTPRT                                                            9

SEQ ID NO: 259          moltype = AA   length = 7
FEATURE                 Location/Qualifiers
source                  1..7
                        mol_type = protein
                        organism = synthetic construct
SEQUENCE: 259
SQSISSY                                                              7

SEQ ID NO: 260          moltype =   length =
SEQUENCE: 260
000
```

-continued

```
SEQ ID NO: 261            moltype = AA  length = 6
FEATURE                   Location/Qualifiers
source                    1..6
                          mol_type = protein
                          organism = synthetic construct
SEQUENCE: 261
SYNTPR                                                                    6

SEQ ID NO: 262            moltype = AA  length = 107
FEATURE                   Location/Qualifiers
source                    1..107
                          mol_type = protein
                          organism = synthetic construct
SEQUENCE: 262
DIRLTQSPSS LSASVGDRVT ITCRASQSIS SYLNWYQQKP GKAPKLLIYA ASSLQSGVPS         60
RFSGSGSGTD FTLTISSLQP EDFATYYCQQ SYNTPRTFGQ GTKVEIK                      107

SEQ ID NO: 263            moltype = DNA  length = 323
FEATURE                   Location/Qualifiers
misc_feature              1..323
                          note = source = /note=Description of synthetic construct:
                          Synthetic polynucleotide
source                    1..323
                          mol_type = other DNA
                          organism = synthetic construct
SEQUENCE: 263
gacatccggt tgacccagtc tccatcctcc ctgtctgcat ctgtaggaga cagagtcacc         60
atcacttgcc gggcaagtca gagcattagc agctatttga attggtatca gcagaaacca        120
gggaaagccc ctaagctcct gatctatgct gcatccagtt tgcaaagtgg ggtcccatca        180
aggttcagtg gcagtggatc tgggacagat ttcactctca ccatcagcag tctgcaacct        240
gaagattttg caacttacta ctgtcaacag agttacaata cccctcgaac gttcggccaa        300
gggaccaagg tggagatcaa acg                                                323

SEQ ID NO: 264            moltype = AA  length = 214
FEATURE                   Location/Qualifiers
source                    1..214
                          mol_type = protein
                          organism = synthetic construct
SEQUENCE: 264
DIRLTQSPSS LSASVGDRVT ITCRASQSIS SYLNWYQQKP GKAPKLLIYA ASSLQSGVPS         60
RFSGSGSGTD FTLTISSLQP EDFATYYCQQ SYNTPRTFGQ GTKVEIKRTV AAPSVFIFPP        120
SDEQLKSGTA SVVCLLNNFY PREAKVQWKV DNALQSGNSQ ESVTEQDSKD STYSLSSTLT        180
LSKADYEKHK VYACEVTHQG LSSPVTKSFN RGEC                                    214

SEQ ID NO: 265            moltype = DNA  length = 642
FEATURE                   Location/Qualifiers
misc_feature              1..642
                          note = source = /note=Description of synthetic construct:
                          Synthetic polynucleotide
source                    1..642
                          mol_type = other DNA
                          organism = synthetic construct
SEQUENCE: 265
gacatccggt tgacccagtc tccatcctcc ctgtctgcat ctgtaggaga cagagtcacc         60
atcacttgcc gggcaagtca gagcattagc agctatttga attggtatca gcagaaacca        120
gggaaagccc ctaagctcct gatctatgct gcatccagtt tgcaaagtgg ggtcccatca        180
aggttcagtg gcagtggatc tgggacagat ttcactctca ccatcagcag tctgcaacct        240
gaagattttg caacttacta ctgtcaacag agttacaata cccctcgaac gttcggccaa        300
gggaccaagg tggagatcaa acgtacggtg gctgcaccat ctgtcttcat cttcccgcca        360
tctgatgagc agttgaaatc tggaactgcc tctgttgtgt gcctgctgaa taacttctat        420
ccccgcgagg ccaaagtaca gtggaaggtg gataacgccc tccaatcggg taactcccag        480
gagagtgtca cagagcagga cagcaaggac agcacctaca gcctcagcag caccctgacg        540
ctgagcaaag cagactacga gaaacacaaa gtctacgcct gcgaagtcac ccatcagggc        600
ctgagctcgc ccgtcacaaa gagcttcaac cgcggagagt gt                          642

SEQ ID NO: 266            moltype = AA  length = 5
FEATURE                   Location/Qualifiers
source                    1..5
                          mol_type = protein
                          organism = synthetic construct
SEQUENCE: 266
RNYMS                                                                     5

SEQ ID NO: 267            moltype = AA  length = 16
FEATURE                   Location/Qualifiers
source                    1..16
                          mol_type = protein
                          organism = synthetic construct
SEQUENCE: 267
```

```
GIYSGGSTYY ADSVKG                                                    16

SEQ ID NO: 268          moltype = AA   length = 13
FEATURE                 Location/Qualifiers
source                  1..13
                        mol_type = protein
                        organism = synthetic construct
SEQUENCE: 268
EDEFWSGYSA GVD                                                       13

SEQ ID NO: 269          moltype = AA   length = 7
FEATURE                 Location/Qualifiers
source                  1..7
                        mol_type = protein
                        organism = synthetic construct
SEQUENCE: 269
GFTVSRN                                                               7

SEQ ID NO: 270          moltype = AA   length = 5
FEATURE                 Location/Qualifiers
source                  1..5
                        mol_type = protein
                        organism = synthetic construct
SEQUENCE: 270
YSGGS                                                                 5

SEQ ID NO: 271          moltype = AA   length = 13
FEATURE                 Location/Qualifiers
source                  1..13
                        mol_type = protein
                        organism = synthetic construct
SEQUENCE: 271
EDEFWSGYSA GVD                                                       13

SEQ ID NO: 272          moltype = AA   length = 121
FEATURE                 Location/Qualifiers
source                  1..121
                        mol_type = protein
                        organism = synthetic construct
SEQUENCE: 272
QVQLVESGGG LVQPGGSLRL SCAASGFTVS RNYMSWVRQA PGKGLEWVSG IYSGGSTYYA     60
DSVKGRFTIS RDYSKNTLSL QMNTLRVEDT AVYFCAREDE FWSGYSAGVD WGQGTLVTVS    120
S                                                                   121

SEQ ID NO: 273          moltype = DNA   length = 365
FEATURE                 Location/Qualifiers
misc_feature            1..365
                        note = source = /note=Description of synthetic construct:
                        Synthetic polynucleotide
source                  1..365
                        mol_type = other DNA
                        organism = synthetic construct
SEQUENCE: 273
caggtgcagc tggtggaatc tggaggaggc ttggtccagc ctgggggtc cctgagactc      60
tcatgtgcag cctctggatt caccgtcagt cgcaattaca tgagttgggt ccgccaggct    120
ccggggaagg gactggagtg ggtctcaggg atttacagtg gtggtagcac atactacgca    180
gactccgtga agggccgatt caccatctcc agagactatt ccaagaacac actgtctctt    240
caaatgaaca ccctgagagt cgaggacacg gccgtgtatt tctgtgcgag agaagacgaa    300
ttttggagtg gtattccgc tggggtcgac tggggccagg gaaccctggt caccgtctcc     360
tcagc                                                                365

SEQ ID NO: 274          moltype = AA   length = 451
FEATURE                 Location/Qualifiers
source                  1..451
                        mol_type = protein
                        organism = synthetic construct
SEQUENCE: 274
QVQLVESGGG LVQPGGSLRL SCAASGFTVS RNYMSWVRQA PGKGLEWVSG IYSGGSTYYA     60
DSVKGRFTIS RDYSKNTLSL QMNTLRVEDT AVYFCAREDE FWSGYSAGVD WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKRVE PKSCDKTHTC PPCPAPELLG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRE    360
EMTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 275          moltype = DNA   length = 1353
FEATURE                 Location/Qualifiers
misc_feature            1..1353
```

|  | note = source = /note=Description of synthetic construct: Synthetic polynucleotide |
|---|---|
| source | 1..1353 |
|  | mol_type = other DNA |
|  | organism = synthetic construct |

SEQUENCE: 275

```
caggtgcagc tggtggaatc tggaggaggc ttggtccagc ctgggggtc cctgagactc      60
tcatgtgcag cctctggatt caccgtcagt cgcaattaca tgagttgggt ccgccaggct    120
ccggggaagg gactggagtg ggtctcaggg atttacagtg gtggtagcac atactacgca    180
gactccgtga agggccgatt caccatctcc agagactact ccaagaacac actgtctctt    240
caaatgaaca ccctgagagt cgaggacacg gccgtgtatt tctgtgcgag agaagacgaa    300
ttttggagtg ggtattccgc tggggtcgac tggggccagg gaaccctggt caccgtctcc    360
tcagctagca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggag   1080
gagatgacca gaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

| SEQ ID NO: 276 | moltype = AA length = 11 |
|---|---|
| FEATURE | Location/Qualifiers |
| source | 1..11 |
|  | mol_type = protein |
|  | organism = synthetic construct |

SEQUENCE: 276
RASQSISSYL N　　　　　　　　　　　　　　　　　　　　　　　　　　11

| SEQ ID NO: 277 | moltype = AA length = 7 |
|---|---|
| FEATURE | Location/Qualifiers |
| source | 1..7 |
|  | mol_type = protein |
|  | organism = synthetic construct |

SEQUENCE: 277
AASSLQS　　　　　　　　　　　　　　　　　　　　　　　　　　　　7

| SEQ ID NO: 278 | moltype = AA length = 9 |
|---|---|
| FEATURE | Location/Qualifiers |
| source | 1..9 |
|  | mol_type = protein |
|  | organism = synthetic construct |

SEQUENCE: 278
QQSYSTPRT　　　　　　　　　　　　　　　　　　　　　　　　　　9

| SEQ ID NO: 279 | moltype = AA length = 7 |
|---|---|
| FEATURE | Location/Qualifiers |
| source | 1..7 |
|  | mol_type = protein |
|  | organism = synthetic construct |

SEQUENCE: 279
SQSISSY　　　　　　　　　　　　　　　　　　　　　　　　　　　　7

| SEQ ID NO: 280 | moltype = length = |
|---|---|
| SEQUENCE: 280 |  |
| 000 |  |

| SEQ ID NO: 281 | moltype = AA length = 6 |
|---|---|
| FEATURE | Location/Qualifiers |
| source | 1..6 |
|  | mol_type = protein |
|  | organism = synthetic construct |

SEQUENCE: 281
SYSTPR　　　　　　　　　　　　　　　　　　　　　　　　　　　　6

| SEQ ID NO: 282 | moltype = AA length = 107 |
|---|---|
| FEATURE | Location/Qualifiers |
| source | 1..107 |
|  | mol_type = protein |
|  | organism = synthetic construct |

```
SEQUENCE: 282
DIRMTQSPSS LSASVGDRVT ITCRASQSIS SYLNWYQQKP GKAPTLLIYA ASSLQSGVPS    60
RFSGSGSGTD FTLTISSLQP EDFATYYCQQ SYSTPRTFGQ GTKVEIK                 107

SEQ ID NO: 283           moltype = DNA   length = 322
FEATURE                  Location/Qualifiers
misc_feature             1..322
                         note = source = /note=Description of synthetic construct:
                         Synthetic polynucleotide
source                   1..322
                         mol_type = other DNA
                         organism = synthetic construct
SEQUENCE: 283
gacatccgga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctacgctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctcggac gttcggccaa   300
gggaccaagg tggagatcaa ac                                            322

SEQ ID NO: 284           moltype = AA   length = 214
FEATURE                  Location/Qualifiers
source                   1..214
                         mol_type = protein
                         organism = synthetic construct
SEQUENCE: 284
DIRMTQSPSS LSASVGDRVT ITCRASQSIS SYLNWYQQKP GKAPTLLIYA ASSLQSGVPS    60
RFSGSGSGTD FTLTISSLQP EDFATYYCQQ SYSTPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 285           moltype = DNA   length = 642
FEATURE                  Location/Qualifiers
misc_feature             1..642
                         note = source = /note=Description of synthetic construct:
                         Synthetic polynucleotide
source                   1..642
                         mol_type = other DNA
                         organism = synthetic construct
SEQUENCE: 285
gacatccgga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctacgctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctcggac gttcggccaa   300
gggaccaagg tggagatcaa acgtacggtg gctgcaccat ctgtcttcat cttcccgcca   360
tctgatgagc agttgaaatc tggaactgcc tctgttgtgt gcctgctgaa taacttctat   420
cccgcgagg ccaaagtaca gtggaaggtg gataacgccc tccaatcggg taactcccag   480
gagagtgtca cagagcagga cagcaaggac agcacctaca gcctcagcag cacccctgacg   540
ctgagcaaag cagactacga gaaacacaaa gtctacgcct gcgaagtcac ccatcagggc   600
ctgagctcgc ccgtcacaaa gagcttcaac cgcggagagt gt                     642

SEQ ID NO: 286           moltype = AA   length = 5
FEATURE                  Location/Qualifiers
source                   1..5
                         mol_type = protein
                         organism = synthetic construct
SEQUENCE: 286
RNYMS                                                                 5

SEQ ID NO: 287           moltype = AA   length = 16
FEATURE                  Location/Qualifiers
source                   1..16
                         mol_type = protein
                         organism = synthetic construct
SEQUENCE: 287
GIYGGGRTYY AESVKG                                                    16

SEQ ID NO: 288           moltype = AA   length = 13
FEATURE                  Location/Qualifiers
source                   1..13
                         mol_type = protein
                         organism = synthetic construct
SEQUENCE: 288
EDEFWSGYSA GVD                                                       13

SEQ ID NO: 289           moltype = AA   length = 7
FEATURE                  Location/Qualifiers
source                   1..7
```

```
                            mol_type = protein
                            organism = synthetic construct
SEQUENCE: 289
GFTVSRN                                                                 7

SEQ ID NO: 290              moltype = AA   length = 5
FEATURE                     Location/Qualifiers
source                      1..5
                            mol_type = protein
                            organism = synthetic construct
SEQUENCE: 290
YGGGR                                                                   5

SEQ ID NO: 291              moltype = AA   length = 13
FEATURE                     Location/Qualifiers
source                      1..13
                            mol_type = protein
                            organism = synthetic construct
SEQUENCE: 291
EDEFWSGYSA GVD                                                         13

SEQ ID NO: 292              moltype = AA   length = 121
FEATURE                     Location/Qualifiers
source                      1..121
                            mol_type = protein
                            organism = synthetic construct
SEQUENCE: 292
EVQLLESGGG LVRPGGSLRV SCAASGFTVS RNYMSWVRQA PGKGLEWVSG IYGGGRTYYA       60
ESVKGRFTIS RDYSKNTLFL QMNTLRVEDT ALYFCAREDE FWSGYSAGVD WGQGTLVTVS      120
S                                                                     121

SEQ ID NO: 293              moltype = DNA   length = 363
FEATURE                     Location/Qualifiers
misc_feature                1..363
                            note = source = /note=Description of synthetic construct:
                              Synthetic polynucleotide
source                      1..363
                            mol_type = other DNA
                            organism = synthetic construct
SEQUENCE: 293
gaggtgcagc tgttggagtc cgggggaggc ttggtccggc ctgggggtc cctgagagtc        60
tcatgtgcag cctctggatt caccgtcagt cgcaattaca tgagttgggt ccgccaggct     120
ccggggaagg gactggagtg ggtctcaggg atttacggtg gtggtaggac ttactacgca     180
gagtccgtga agggccgatt caccatctcc agagactatt ccaagaacac actgtttctt     240
caaatgaaca ccctgagagt cgaggacacg gccctgtatt tctgtgcgag agaagacgaa     300
ttttggagtg gtattctgc tggggtcgac tggggccagg gaaccctggt cactgtctcc     360
tca                                                                   363

SEQ ID NO: 294              moltype = AA   length = 451
FEATURE                     Location/Qualifiers
source                      1..451
                            mol_type = protein
                            organism = synthetic construct
SEQUENCE: 294
EVQLLESGGG LVRPGGSLRV SCAASGFTVS RNYMSWVRQA PGKGLEWVSG IYGGGRTYYA       60
ESVKGRFTIS RDYSKNTLFL QMNTLRVEDT ALYFCAREDE FWSGYSAGVD WGQGTLVTVS      120
SASTKGPSVF PLAPSSKSTS GGTAALGCLV KDYFPEPVTV SWNSGALTSG VHTFPAVLQS      180
SGLYSLSSVV TVPSSSLGTQ TYICNVNHKP SNTKVDKRVE PKSCDKTHTC PPCPAPELLG      240
GPSVFLFPPK PKDTLMISRT PEVTCVVVDV SHEDPEVKFN WYVDGVEVHN AKTKPREEQY      300
NSTYRVVSVL TVLHQDWLNG KEYKCKVSNK ALPAPIEKTI SKAKGQPREP QVYTLPPSRE      360
EMTKNQVSLT CLVKGFYPSD IAVEWESNGQ PENNYKTTPP VLDSDGSFFL YSKLTVDKSR      420
WQQGNVFSCS VMHEALHNHY TQKSLSLSPG K                                    451

SEQ ID NO: 295              moltype = DNA   length = 1353
FEATURE                     Location/Qualifiers
misc_feature                1..1353
                            note = source = /note=Description of synthetic construct:
                              Synthetic polynucleotide
source                      1..1353
                            mol_type = other DNA
                            organism = synthetic construct
SEQUENCE: 295
gaggtgcagc tgttggagtc cgggggaggc ttggtccggc ctgggggtc cctgagagtc        60
tcatgtgcag cctctggatt caccgtcagt cgcaattaca tgagttgggt ccgccaggct     120
ccggggaagg gactggagtg ggtctcaggg atttacggtg gtggtaggac ttactacgca     180
gagtccgtga agggccgatt caccatctcc agagactatt ccaagaacac actgtttctt     240
caaatgaaca ccctgagagt cgaggacacg gccctgtatt tctgtgcgag agaagacgaa     300
ttttggagtg gtattctgc tggggtcgac tggggccagg gaaccctggt cactgtctcc     360
tcagctagca ccaaggggcc atcggtcttc ccctggcac cctcctccaa gagcacctct     420
```

```
gggggcacag cggccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcaccag    600
acctacatct gcaacgtgaa tcacaagccc agcaacacca aggtggacaa gagagttgag   660
cccaaatctt gtgacaaaac tcacacatgc ccaccgtgcc cagcacctga actcctgggg   720
ggaccgtcag tcttcctctt ccccccaaaa cccaaggaca ccctcatgat ctcccggacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgtgtggt cagcgtcctc accgtcctgc accaggactg gctgaatggc   960
aaggagtaca agtgcaaggt ctccaacaaa gccctcccag cccccatcga gaaaaccatc  1020
tccaaagcca aagggcagcc ccgagaacca caggtgtaca ccctgccccc atcccgggag  1080
gagatgacca gaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                               1353

SEQ ID NO: 296        moltype = AA   length = 11
FEATURE               Location/Qualifiers
source                1..11
                      mol_type = protein
                      organism = synthetic construct
SEQUENCE: 296
RASQSISSYL N                                                         11

SEQ ID NO: 297        moltype = AA   length = 7
FEATURE               Location/Qualifiers
source                1..7
                      mol_type = protein
                      organism = synthetic construct
SEQUENCE: 297
AASTLQT                                                              7

SEQ ID NO: 298        moltype = AA   length = 9
FEATURE               Location/Qualifiers
source                1..9
                      mol_type = protein
                      organism = synthetic construct
SEQUENCE: 298
QQSYNTPRT                                                            9

SEQ ID NO: 299        moltype = AA   length = 7
FEATURE               Location/Qualifiers
source                1..7
                      mol_type = protein
                      organism = synthetic construct
SEQUENCE: 299
SQSISSY                                                              7

SEQ ID NO: 300        moltype =   length =
SEQUENCE: 300
000

SEQ ID NO: 301        moltype = AA   length = 6
FEATURE               Location/Qualifiers
source                1..6
                      mol_type = protein
                      organism = synthetic construct
SEQUENCE: 301
SYNTPR                                                               6

SEQ ID NO: 302        moltype = AA   length = 107
FEATURE               Location/Qualifiers
source                1..107
                      mol_type = protein
                      organism = synthetic construct
SEQUENCE: 302
DIQVTQSPSS LSASVGDRVT ITCRASQSIS SYLNWYQQEP GKAPKLLIYA ASTLQTGVPS    60
RFSGSGSGTD FTLTISSLQP EDFATYYCQQ SYNTPRTFGQ GTKVEIK                 107

SEQ ID NO: 303        moltype = DNA   length = 323
FEATURE               Location/Qualifiers
misc_feature          1..323
                      note = source = /note=Description of synthetic construct:
                      Synthetic polynucleotide
source                1..323
                      mol_type = other DNA
                      organism = synthetic construct
SEQUENCE: 303
```

```
gacatccagg tgacccagtc tccatcctcc ctgtctgcat ctgtaggaga cagagtcacc    60
atcacttgcc gggcaagtca gagcattagc agctatttaa attggtatca gcaggaacca   120
gggaaagccc ctaaactcct gatctacgct gcatccactt tgcaaactgg ggtcccatca   180
cggttcagtg gtagtggatc tgggacagat ttcactctca ccatcagcag tctgcaacct   240
gaagattttg caacttatta ctgtcaacag agttacaata cccctcgaac cttcggccaa   300
gggaccaagg tggaaatcaa acg                                           323

SEQ ID NO: 304          moltype = AA  length = 214
FEATURE                 Location/Qualifiers
source                  1..214
                        mol_type = protein
                        organism = synthetic construct
SEQUENCE: 304
DIQVTQSPSS LSASVGDRVT ITCRASQSIS SYLNWYQQEP GKAPKLLIYA ASTLQTGVPS    60
RFSGSGSGTD FTLTISSLQP EDFATYYCQQ SYNTPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 305          moltype = DNA  length = 642
FEATURE                 Location/Qualifiers
misc_feature            1..642
                        note = source = /note=Description of synthetic construct:
                        Synthetic polynucleotide
source                  1..642
                        mol_type = other DNA
                        organism = synthetic construct
SEQUENCE: 305
gacatccagg tgacccagtc tccatcctcc ctgtctgcat ctgtaggaga cagagtcacc    60
atcacttgcc gggcaagtca gagcattagc agctatttaa attggtatca gcaggaacca   120
gggaaagccc ctaaactcct gatctacgct gcatccactt tgcaaactgg ggtcccatca   180
cggttcagtg gtagtggatc tgggacagat ttcactctca ccatcagcag tctgcaacct   240
gaagattttg caacttatta ctgtcaacag agttacaata cccctcgaac cttcggccaa   300
gggaccaagg tggaaatcaa acgtacggtg gctgcaccat ctgtcttcat cttcccgcca   360
tctgatgagc agttgaaatc tggaactgcc tctgttgtgt gcctgctgaa taacttctat   420
cccgcgagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgccc gcgaagtcac ccatcagggc   600
ctgagctcgc ccgtcacaaa gagcttcaac cgcggagagt gt                     642

SEQ ID NO: 306          moltype = AA  length = 7
FEATURE                 Location/Qualifiers
source                  1..7
                        mol_type = protein
                        organism = synthetic construct
SEQUENCE: 306
NGGYYWS                                                               7

SEQ ID NO: 307          moltype = AA  length = 16
FEATURE                 Location/Qualifiers
source                  1..16
                        mol_type = protein
                        organism = synthetic construct
SEQUENCE: 307
CIHYSGGTYY NPSLKS                                                    16

SEQ ID NO: 308          moltype = AA  length = 14
FEATURE                 Location/Qualifiers
source                  1..14
                        mol_type = protein
                        organism = synthetic construct
SEQUENCE: 308
ALIAAPGISD WFDP                                                      14

SEQ ID NO: 309          moltype = AA  length = 9
FEATURE                 Location/Qualifiers
source                  1..9
                        mol_type = protein
                        organism = synthetic construct
SEQUENCE: 309
GGSISNGGY                                                             9

SEQ ID NO: 310          moltype = AA  length = 5
FEATURE                 Location/Qualifiers
source                  1..5
                        mol_type = protein
                        organism = synthetic construct
SEQUENCE: 310
HYSGG                                                                 5
```

```
SEQ ID NO: 311          moltype = AA  length = 14
FEATURE                 Location/Qualifiers
source                  1..14
                        mol_type = protein
                        organism = synthetic construct
SEQUENCE: 311
ALIAAPGISD WFDP                                                              14

SEQ ID NO: 312          moltype = AA  length = 124
FEATURE                 Location/Qualifiers
source                  1..124
                        mol_type = protein
                        organism = synthetic construct
SEQUENCE: 312
QVQLQESGPG LVKPSQTLSL TCTVSGGSIS NGGYYWSWIR LHPGKGLEWI GCIHYSGGTY            60
YNPSLKSRVT VSLDTSKNQF SLNLISVTAA DTAIYFCARA LIAAPGISDW FDPWGQGTLV           120
TVSS                                                                       124

SEQ ID NO: 313          moltype = AA  length = 454
FEATURE                 Location/Qualifiers
source                  1..454
                        mol_type = protein
                        organism = synthetic construct
SEQUENCE: 313
QVQLQESGPG LVKPSQTLSL TCTVSGGSIS NGGYYWSWIR LHPGKGLEWI GCIHYSGGTY            60
YNPSLKSRVT VSLDTSKNQF SLNLISVTAA DTAIYFCARA LIAAPGISDW FDPWGQGTLV           120
TVSSASTKGP SVFPLAPSSK STSGGTAALG CLVKDYFPEP VTVSWNSGAL TSGVHTFPAV           180
LQSSGLYSLS SVVTVPSSSL GTQTYICNVN HKPSNTKVDK KVEPKSCDKT HTCPPCPAPE           240
LLGGPSVFLF PPKPKDTLMI SRTPEVTCVV VDVSHEDPEV KFNWYVDGVE VHNAKTKPRE           300
EQYNSTYRVV SVLTVLHQDW LNGKEYKCKV SNKALPAPIE KTISKAKGQP REPQVYTLPP           360
SREEMTKNQV SLTCLVKGFY PSDIAVEWES NGQPENNYKT TPPVLDSDGS FFLYSKLTVD           420
KSRWQQGNVF SCSVMHEALH NHYTQKSLSL SPGK                                      454

SEQ ID NO: 314          moltype = AA  length = 13
FEATURE                 Location/Qualifiers
source                  1..13
                        mol_type = protein
                        organism = synthetic construct
SEQUENCE: 314
SGSNSNVGHN YVS                                                              13

SEQ ID NO: 315          moltype = AA  length = 7
FEATURE                 Location/Qualifiers
source                  1..7
                        mol_type = protein
                        organism = synthetic construct
SEQUENCE: 315
DNNKRPS                                                                      7

SEQ ID NO: 316          moltype = AA  length = 11
FEATURE                 Location/Qualifiers
source                  1..11
                        mol_type = protein
                        organism = synthetic construct
SEQUENCE: 316
GTWDSSLSAG V                                                                11

SEQ ID NO: 317          moltype = AA  length = 9
FEATURE                 Location/Qualifiers
source                  1..9
                        mol_type = protein
                        organism = synthetic construct
SEQUENCE: 317
SNSNVGHNY                                                                    9

SEQ ID NO: 318          moltype =     length =
SEQUENCE: 318
000

SEQ ID NO: 319          moltype = AA  length = 8
FEATURE                 Location/Qualifiers
source                  1..8
                        mol_type = protein
                        organism = synthetic construct
SEQUENCE: 319
WDSSLSAG                                                                     8

SEQ ID NO: 320          moltype = AA  length = 110
FEATURE                 Location/Qualifiers
```

```
source                          1..110
                                mol_type = protein
                                organism = synthetic construct
SEQUENCE: 320
QSVLTQPPSV SAAPGQKVTI SCSGSNSNVG HNYVSWYQQL PGTAPKLLIY DNNKRPSGIP    60
DRFSGSKSGT SATLGITGLQ TGDEADYYCG TWDSSLSAGV FGGGTKVTVL              110

SEQ ID NO: 321                  moltype = AA  length = 216
FEATURE                         Location/Qualifiers
source                          1..216
                                mol_type = protein
                                organism = synthetic construct
SEQUENCE: 321
QSVLTQPPSV SAAPGQKVTI SCSGSNSNVG HNYVSWYQQL PGTAPKLLIY DNNKRPSGIP    60
DRFSGSKSGT SATLGITGLQ TGDEADYYCG TWDSSLSAGV FGGGTKVTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 322                  moltype = AA  length = 5
FEATURE                         Location/Qualifiers
source                          1..5
                                mol_type = protein
                                organism = synthetic construct
SEQUENCE: 322
SSWMN                                                                5

SEQ ID NO: 323                  moltype = AA  length = 17
FEATURE                         Location/Qualifiers
source                          1..17
                                mol_type = protein
                                organism = synthetic construct
SEQUENCE: 323
RIYPGDADTY YSGKFKG                                                  17

SEQ ID NO: 324                  moltype = AA  length = 7
FEATURE                         Location/Qualifiers
source                          1..7
                                mol_type = protein
                                organism = synthetic construct
SEQUENCE: 324
HSSGFTY                                                              7

SEQ ID NO: 325                  moltype = AA  length = 7
FEATURE                         Location/Qualifiers
source                          1..7
                                mol_type = protein
                                organism = synthetic construct
SEQUENCE: 325
GYTFSSS                                                              7

SEQ ID NO: 326                  moltype = AA  length = 6
FEATURE                         Location/Qualifiers
source                          1..6
                                mol_type = protein
                                organism = synthetic construct
SEQUENCE: 326
YPGDAD                                                               6

SEQ ID NO: 327                  moltype = AA  length = 7
FEATURE                         Location/Qualifiers
source                          1..7
                                mol_type = protein
                                organism = synthetic construct
SEQUENCE: 327
HSSGFTY                                                              7

SEQ ID NO: 328                  moltype = AA  length = 116
FEATURE                         Location/Qualifiers
source                          1..116
                                mol_type = protein
                                organism = synthetic construct
SEQUENCE: 328
QVQLVQSGAE VKKPGASVKV SCKASGYTFS SSWMNWVRQA PGQRLEWMGR IYPGDADTYY    60
SGKFKGRVTI TADSSARTAY MELSSLRSED TAVYYCAIHS SGFTYWGQGT LVTVSS       116

SEQ ID NO: 329                  moltype = DNA  length = 350
FEATURE                         Location/Qualifiers
misc_feature                    1..350
                                note = source = /note=Description of synthetic construct:
```

```
                        Synthetic polynucleotide
source                  1..350
                        mol_type = other DNA
                        organism = synthetic construct
SEQUENCE: 329
caggtccagc ttgtgcagtc tggggctgag gtgaagaagc ctggggcctc agtgaaggtt    60
tcctgcaagg cttctggcta tacattcagc agctcttgga tgaactgggt gcgccaggcc   120
cccggacaaa ggcttgagtg gatgggacgg atctatccag agacgccga tacttactac    180
agtgggaaat tcaagggcag agtcaccatt accgccgaca gctccgcgag aacagcctac   240
atggagctga gcagcctgag atctgaagac acggctgtgt attactgtgc gatccacagc   300
tcgggctttta cttactgggg ccagggcacc ctggtcaccg tctcctcagc              350

SEQ ID NO: 330          moltype = AA  length = 446
FEATURE                 Location/Qualifiers
source                  1..446
                        mol_type = protein
                        organism = synthetic construct
SEQUENCE: 330
QVQLVQSGAE VKKPGASVKV SCKASGYTFS SSWMNWVRQA PGQRLEWMGR IYPGDADTYY    60
SGKFKGRVTI TADSSARTAY MELSSLRSED TAVYYCAIHS SGFTYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 331          moltype = DNA  length = 1338
FEATURE                 Location/Qualifiers
misc_feature            1..1338
                        note = source = /note=Description of synthetic construct:
                        Synthetic polynucleotide
source                  1..1338
                        mol_type = other DNA
                        organism = synthetic construct
SEQUENCE: 331
caggtccagc ttgtgcagtc tggggctgag gtgaagaagc ctggggcctc agtgaaggtt    60
tcctgcaagg cttctggcta tacattcagc agctcttgga tgaactgggt gcgccaggcc   120
cccggacaaa ggcttgagtg gatgggacgg atctatccag agacgccga tacttactac    180
agtgggaaat tcaagggcag agtcaccatt accgccgaca gctccgcgag aacagcctac   240
atggagctga gcagcctgag atctgaagac acggctgtgt attactgtgc gatccacagc   300
tcgggctttta cttactgggg ccagggcacc ctggtcaccg tctcctcagc tagcaccaag   360
ggcccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca cacctteccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagagag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggaccctga ggtcacatgc    780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
aaggtctccca acaaagccct cccagccccc atcgagaaaa ccatctccaa agccaaaggg  1020
cagccccgag aaccacaggt gtacaccctg cccccatccc gggaggagat gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaa                                                1338

SEQ ID NO: 332          moltype = AA  length = 11
FEATURE                 Location/Qualifiers
source                  1..11
                        mol_type = protein
                        organism = synthetic construct
SEQUENCE: 332
RASQDISDYL N                                                        11

SEQ ID NO: 333          moltype = AA  length = 7
FEATURE                 Location/Qualifiers
source                  1..7
                        mol_type = protein
                        organism = synthetic construct
SEQUENCE: 333
YTSRLHS                                                              7

SEQ ID NO: 334          moltype = AA  length = 9
FEATURE                 Location/Qualifiers
source                  1..9
```

```
                    mol_type = protein
                    organism = synthetic construct
SEQUENCE: 334
QQTHTLPFT                                                           9

SEQ ID NO: 335      moltype = AA  length = 7
FEATURE             Location/Qualifiers
source              1..7
                    mol_type = protein
                    organism = synthetic construct
SEQUENCE: 335
SQDISDY                                                             7

SEQ ID NO: 336      moltype =   length =
SEQUENCE: 336
000

SEQ ID NO: 337      moltype = AA  length = 6
FEATURE             Location/Qualifiers
source              1..6
                    mol_type = protein
                    organism = synthetic construct
SEQUENCE: 337
THTLPF                                                              6

SEQ ID NO: 338      moltype = AA  length = 107
FEATURE             Location/Qualifiers
REGION              1..107
                    note = source = /note=Description of synthetic construct:
                    Synthetic polypeptide
source              1..107
                    mol_type = protein
                    organism = synthetic construct
SEQUENCE: 338
DIQMTQSPSS LSASVGDRVT ITCRASQDIS DYLNWYQQKP GKAPKLLIYY TSRLHSGVPS   60
RFSGSGSGTD YTLTISSLQP EDFATYFCQQ THTLPFTFGG GTKVEIK                107

SEQ ID NO: 339      moltype = DNA  length = 323
FEATURE             Location/Qualifiers
misc_feature        1..323
                    note = source = /note=Description of synthetic construct:
                    Synthetic polynucleotide
source              1..323
                    mol_type = other DNA
                    organism = synthetic construct
SEQUENCE: 339
gacatccaga tgacccagtc tccatcctcc ctgtctgcat ctgtaggaga cagagtcacc   60
atcacttgca gggcaagtca ggacattagc gattatttaa actggtatca gcagaaacca  120
gggaaagccc ctaagctcct gatctattat acatcaagat acactcagg gtcccatca   180
aggttcagtg gcagtggatc tgggacagat tacactctca ccatcagcag tctgcaacct  240
gaagattttg caacttactt ctgtcaacag actcatacgc ttcctttcac gttcggcgga  300
gggaccaagg tggagatcaa acg                                          323

SEQ ID NO: 340      moltype = AA  length = 214
FEATURE             Location/Qualifiers
source              1..214
                    mol_type = protein
                    organism = synthetic construct
SEQUENCE: 340
DIQMTQSPSS LSASVGDRVT ITCRASQDIS DYLNWYQQKP GKAPKLLIYY TSRLHSGVPS   60
RFSGSGSGTD YTLTISSLQP EDFATYFCQQ THTLPFTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 341      moltype = DNA  length = 642
FEATURE             Location/Qualifiers
misc_feature        1..642
                    note = source = /note=Description of synthetic construct:
                    Synthetic polynucleotide
source              1..642
                    mol_type = other DNA
                    organism = synthetic construct
SEQUENCE: 341
gacatccaga tgacccagtc tccatcctcc ctgtctgcat ctgtaggaga cagagtcacc   60
atcacttgca gggcaagtca ggacattagc gattatttaa actggtatca gcagaaacca  120
gggaaagccc ctaagctcct gatctattat acatcaagat acactcagg gtcccatca   180
aggttcagtg gcagtggatc tgggacagat tacactctca ccatcagcag tctgcaacct  240
gaagattttg caacttactt ctgtcaacag actcatacgc ttcctttcac gttcggcgga  300
gggaccaagg tggagatcaa acgtacggtg gctgcaccat ctgtcttcat cttcccgcca  360
```

```
tctgatgagc agttgaaatc tggaactgcc tctgttgtgt gcctgctgaa taacttctat    420
ccccgcgagg ccaaagtaca gtggaaggtg gataacgccc tccaatcggg taactcccag    480
gagagtgtca cagagcagga cagcaaggac agcacctaca gcctcagcag cacccctgacg   540
ctgagcaaag cagactacga gaaacacaaa gtctacgcct gcgaagtcac ccatcagggc    600
ctgagctcgc ccgtcacaaa gagcttcaac cgcggagagt gt                       642
```

```
SEQ ID NO: 342         moltype = AA  length = 5
FEATURE                Location/Qualifiers
source                 1..5
                       mol_type = protein
                       organism = synthetic construct
SEQUENCE: 342
NYWMH                                                                 5

SEQ ID NO: 343         moltype = AA  length = 17
FEATURE                Location/Qualifiers
source                 1..17
                       mol_type = protein
                       organism = synthetic construct
SEQUENCE: 343
NIYPGSGNTN YGENFKS                                                    17

SEQ ID NO: 344         moltype = AA  length = 16
FEATURE                Location/Qualifiers
REGION                 1..16
                       note = source = /note=Description of synthetic construct:
                        Synthetic peptide
source                 1..16
                       mol_type = protein
                       organism = synthetic construct
SEQUENCE: 344
SAIYYGYDGH YFAMDY                                                     16

SEQ ID NO: 345         moltype = AA  length = 7
FEATURE                Location/Qualifiers
source                 1..7
                       mol_type = protein
                       organism = synthetic construct
SEQUENCE: 345
GYTFTNY                                                               7

SEQ ID NO: 346         moltype = AA  length = 6
FEATURE                Location/Qualifiers
source                 1..6
                       mol_type = protein
                       organism = synthetic construct
SEQUENCE: 346
YPGSGN                                                                6

SEQ ID NO: 347         moltype = AA  length = 16
FEATURE                Location/Qualifiers
source                 1..16
                       mol_type = protein
                       organism = synthetic construct
SEQUENCE: 347
SAIYYGYDGH YFAMDY                                                     16

SEQ ID NO: 348         moltype = AA  length = 125
FEATURE                Location/Qualifiers
source                 1..125
                       mol_type = protein
                       organism = synthetic construct
SEQUENCE: 348
QVQLQQPGSE LVRPGASVKL SCKASGYTFT NYWMHWVKQG HGQGLEWIGN IYPGSGNTNY     60
GENFKSKGTL TVDTSSSTAY MHLSRLTSED SAVYYCSRSA IYYGYDGHYF AMDYWGQGTS     120
VTVSS                                                                 125

SEQ ID NO: 349         moltype = AA  length = 11
FEATURE                Location/Qualifiers
source                 1..11
                       mol_type = protein
                       organism = synthetic construct
SEQUENCE: 349
KASQDIRKYI A                                                          11

SEQ ID NO: 350         moltype = AA  length = 7
FEATURE                Location/Qualifiers
source                 1..7
                       mol_type = protein
```

```
                            organism = synthetic construct
SEQUENCE: 350
YTSTLQS                                                                      7

SEQ ID NO: 351              moltype = AA  length = 9
FEATURE                     Location/Qualifiers
source                      1..9
                            mol_type = protein
                            organism = synthetic construct
SEQUENCE: 351
LQYDNILFT                                                                    9

SEQ ID NO: 352              moltype = AA  length = 7
FEATURE                     Location/Qualifiers
source                      1..7
                            mol_type = protein
                            organism = synthetic construct
SEQUENCE: 352
SQDIRKY                                                                      7

SEQ ID NO: 353              moltype =     length =
SEQUENCE: 353
000

SEQ ID NO: 354              moltype = AA  length = 6
FEATURE                     Location/Qualifiers
source                      1..6
                            mol_type = protein
                            organism = synthetic construct
SEQUENCE: 354
YDNILF                                                                       6

SEQ ID NO: 355              moltype = AA  length = 107
FEATURE                     Location/Qualifiers
source                      1..107
                            mol_type = protein
                            organism = synthetic construct
SEQUENCE: 355
DIQMTQSPSS LSASLGGKVT ITCKASQDIR KYIAWYQHKP GKGPRLLINY TSTLQSGIPS            60
RFRGSGSGRD YSFSISNLEP EDIATYYCLQ YDNILFTFGT GTKLEIK                         107

SEQ ID NO: 356              moltype = AA  length = 5
FEATURE                     Location/Qualifiers
source                      1..5
                            mol_type = protein
                            organism = synthetic construct
SEQUENCE: 356
SCWMN                                                                        5

SEQ ID NO: 357              moltype = AA  length = 17
FEATURE                     Location/Qualifiers
source                      1..17
                            mol_type = protein
                            organism = synthetic construct
SEQUENCE: 357
RIYPGDGDTK YTEKFKD                                                          17

SEQ ID NO: 358              moltype = AA  length = 7
FEATURE                     Location/Qualifiers
source                      1..7
                            mol_type = protein
                            organism = synthetic construct
SEQUENCE: 358
SGSGLPY                                                                      7

SEQ ID NO: 359              moltype = AA  length = 7
FEATURE                     Location/Qualifiers
source                      1..7
                            mol_type = protein
                            organism = synthetic construct
SEQUENCE: 359
GYSFSSC                                                                      7

SEQ ID NO: 360              moltype = AA  length = 6
FEATURE                     Location/Qualifiers
source                      1..6
                            mol_type = protein
                            organism = synthetic construct
SEQUENCE: 360
```

```
SEQ ID NO: 361          moltype = AA  length = 7
FEATURE                 Location/Qualifiers
source                  1..7
                        mol_type = protein
                        organism = synthetic construct
SEQUENCE: 361
SGSGLPY                                                                 7

SEQ ID NO: 362          moltype = AA  length = 116
FEATURE                 Location/Qualifiers
source                  1..116
                        mol_type = protein
                        organism = synthetic construct
SEQUENCE: 362
QVHLQQSGPE LVKPGASVTI SCKTSGYSFS SCWMNWVKQR PGQGLEWIGR IYPGDGDTKY   60
TEKFKDKATL TADKSSSTAY MQLSSLTSVD SALYFCAISG SGLPYWGQGT LVTVSE      116

SEQ ID NO: 363          moltype = AA  length = 11
FEATURE                 Location/Qualifiers
source                  1..11
                        mol_type = protein
                        organism = synthetic construct
SEQUENCE: 363
RASQDIHNYL N                                                           11

SEQ ID NO: 364          moltype = AA  length = 7
FEATURE                 Location/Qualifiers
source                  1..7
                        mol_type = protein
                        organism = synthetic construct
SEQUENCE: 364
STSRLHS                                                                 7

SEQ ID NO: 365          moltype = AA  length = 9
FEATURE                 Location/Qualifiers
source                  1..9
                        mol_type = protein
                        organism = synthetic construct
SEQUENCE: 365
QQTHTLPLT                                                               9

SEQ ID NO: 366          moltype = AA  length = 7
FEATURE                 Location/Qualifiers
source                  1..7
                        mol_type = protein
                        organism = synthetic construct
SEQUENCE: 366
SQDIHNY                                                                 7

SEQ ID NO: 367          moltype =    length =
SEQUENCE: 367
000

SEQ ID NO: 368          moltype = AA  length = 6
FEATURE                 Location/Qualifiers
source                  1..6
                        mol_type = protein
                        organism = synthetic construct
SEQUENCE: 368
THTLPL                                                                  6

SEQ ID NO: 369          moltype = AA  length = 107
FEATURE                 Location/Qualifiers
source                  1..107
                        mol_type = protein
                        organism = synthetic construct
SEQUENCE: 369
DIQMTQTTSS LSASLGDRVT ISCRASQDIH NYLNWYQQKP DGTIKLLIYS TSRLHSGVPS   60
RFSGSGSGTH YSLTINNLEQ EDIATYFCQQ THTLPLTFGA GTKLELK                107

SEQ ID NO: 370          moltype = AA  length = 5
FEATURE                 Location/Qualifiers
source                  1..5
                        mol_type = protein
                        organism = synthetic construct
SEQUENCE: 370
SYWMN                                                                   5
```

```
SEQ ID NO: 371          moltype = AA   length = 17
FEATURE                 Location/Qualifiers
source                  1..17
                        mol_type = protein
                        organism = synthetic construct
SEQUENCE: 371
QIYPGNGDTN YNGKFKG                                                      17

SEQ ID NO: 372          moltype = AA   length = 12
FEATURE                 Location/Qualifiers
source                  1..12
                        mol_type = protein
                        organism = synthetic construct
SEQUENCE: 372
EARQGYHYAM DY                                                           12

SEQ ID NO: 373          moltype = AA   length = 7
FEATURE                 Location/Qualifiers
source                  1..7
                        mol_type = protein
                        organism = synthetic construct
SEQUENCE: 373
GYAFSSY                                                                 7

SEQ ID NO: 374          moltype = AA   length = 6
FEATURE                 Location/Qualifiers
source                  1..6
                        mol_type = protein
                        organism = synthetic construct
SEQUENCE: 374
YPGNGD                                                                  6

SEQ ID NO: 375          moltype = AA   length = 12
FEATURE                 Location/Qualifiers
source                  1..12
                        mol_type = protein
                        organism = synthetic construct
SEQUENCE: 375
EARQGYHYAM DY                                                           12

SEQ ID NO: 376          moltype = AA   length = 121
FEATURE                 Location/Qualifiers
source                  1..121
                        mol_type = protein
                        organism = synthetic construct
SEQUENCE: 376
QVQLQQSGAG LVRPGSSVKI SCKTSGYAFS SYWMNWVKQR PGQGLEWIGQ IYPGNGDTNY        60
NGKFKGKATL TADKSSNTAY IQLNSLTSED SAVYFCAREA RQGYHYAMDY WGQGTSVTVS       120
L                                                                      121

SEQ ID NO: 377          moltype = AA   length = 12
FEATURE                 Location/Qualifiers
source                  1..12
                        mol_type = protein
                        organism = synthetic construct
SEQUENCE: 377
SASSSMINSNY LH                                                          12

SEQ ID NO: 378          moltype = AA   length = 7
FEATURE                 Location/Qualifiers
source                  1..7
                        mol_type = protein
                        organism = synthetic construct
SEQUENCE: 378
RTSNLAS                                                                 7

SEQ ID NO: 379          moltype = AA   length = 8
FEATURE                 Location/Qualifiers
source                  1..8
                        mol_type = protein
                        organism = synthetic construct
SEQUENCE: 379
QQGSNIFT                                                                8

SEQ ID NO: 380          moltype = AA   length = 8
FEATURE                 Location/Qualifiers
source                  1..8
                        mol_type = protein
```

```
                        organism = synthetic construct
SEQUENCE: 380
SSMINSNY                                                                        8

SEQ ID NO: 381          moltype =    length =
SEQUENCE: 381
000

SEQ ID NO: 382          moltype = AA   length = 5
FEATURE                 Location/Qualifiers
source                  1..5
                        mol_type = protein
                        organism = synthetic construct
SEQUENCE: 382
GSNIF                                                                           5

SEQ ID NO: 383          moltype = AA   length = 107
FEATURE                 Location/Qualifiers
source                  1..107
                        mol_type = protein
                        organism = synthetic construct
SEQUENCE: 383
EIVFTQSPTT MAAFPGEKIT ITCSASSMIN SNYLHWYQQK PGFSPKVLIY RTSNLASGVP        60
ARFSGTGSGT SFSLTIGTME AEDVATYYCQ QGSNIFTFGS GTKLEIK                     107

SEQ ID NO: 384          moltype = AA   length = 5
FEATURE                 Location/Qualifiers
source                  1..5
                        mol_type = protein
                        organism = synthetic construct
SEQUENCE: 384
NSWMN                                                                           5

SEQ ID NO: 385          moltype = AA   length = 17
FEATURE                 Location/Qualifiers
source                  1..17
                        mol_type = protein
                        organism = synthetic construct
SEQUENCE: 385
RIYPGDGDTQ YNEKFKG                                                             17

SEQ ID NO: 386          moltype = AA   length = 7
FEATURE                 Location/Qualifiers
source                  1..7
                        mol_type = protein
                        organism = synthetic construct
SEQUENCE: 386
SRSGLDY                                                                         7

SEQ ID NO: 387          moltype = AA   length = 7
FEATURE                 Location/Qualifiers
source                  1..7
                        mol_type = protein
                        organism = synthetic construct
SEQUENCE: 387
GFTFSNS                                                                         7

SEQ ID NO: 388          moltype = AA   length = 6
FEATURE                 Location/Qualifiers
source                  1..6
                        mol_type = protein
                        organism = synthetic construct
SEQUENCE: 388
YPGDGD                                                                          6

SEQ ID NO: 389          moltype = AA   length = 7
FEATURE                 Location/Qualifiers
source                  1..7
                        mol_type = protein
                        organism = synthetic construct
SEQUENCE: 389
SRSGLDY                                                                         7

SEQ ID NO: 390          moltype = AA   length = 116
FEATURE                 Location/Qualifiers
source                  1..116
                        mol_type = protein
                        organism = synthetic construct
SEQUENCE: 390
```

```
QVQLQQSGPE LVKPGASVRI SCKVSGFTFS NSWMNWVKQR PGQGLEWIGR IYPGDGDTQY    60
NEKFKGKATL TADTSSNTAY IQLNSLTSVD SAVFFCARSR SGLDYWGQGT TLTVSS       116

SEQ ID NO: 391        moltype = AA  length = 11
FEATURE               Location/Qualifiers
source                1..11
                      mol_type = protein
                      organism = synthetic construct
SEQUENCE: 391
RASQDIYNYL N                                                        11

SEQ ID NO: 392        moltype = AA  length = 7
FEATURE               Location/Qualifiers
source                1..7
                      mol_type = protein
                      organism = synthetic construct
SEQUENCE: 392
STSRLHS                                                             7

SEQ ID NO: 393        moltype = AA  length = 9
FEATURE               Location/Qualifiers
source                1..9
                      mol_type = protein
                      organism = synthetic construct
SEQUENCE: 393
HQSHTVPFT                                                           9

SEQ ID NO: 394        moltype = AA  length = 7
FEATURE               Location/Qualifiers
source                1..7
                      mol_type = protein
                      organism = synthetic construct
SEQUENCE: 394
SQDIYNY                                                             7

SEQ ID NO: 395        moltype =     length =
SEQUENCE: 395
000

SEQ ID NO: 396        moltype = AA  length = 6
FEATURE               Location/Qualifiers
source                1..6
                      mol_type = protein
                      organism = synthetic construct
SEQUENCE: 396
SHTVPF                                                              6

SEQ ID NO: 397        moltype = AA  length = 107
FEATURE               Location/Qualifiers
source                1..107
                      mol_type = protein
                      organism = synthetic construct
SEQUENCE: 397
DIQMTQSTSS LSASLGDRVT ISCRASQDIY NYLNWFQQKP DGTVKPLIYS TSRLHSGVSS    60
RFSGSGSGTD YSLTISNLER EDIATYFCHQ SHTVPFTFGS GTKLEIK                 107

SEQ ID NO: 398        moltype = AA  length = 5
FEATURE               Location/Qualifiers
source                1..5
                      mol_type = protein
                      organism = synthetic construct
SEQUENCE: 398
SSWIN                                                               5

SEQ ID NO: 399        moltype = AA  length = 17
FEATURE               Location/Qualifiers
source                1..17
                      mol_type = protein
                      organism = synthetic construct
SEQUENCE: 399
RIYPGDGDTN YNGKFKG                                                  17

SEQ ID NO: 400        moltype = AA  length = 7
FEATURE               Location/Qualifiers
source                1..7
                      mol_type = protein
                      organism = synthetic construct
SEQUENCE: 400
HSSGFPH                                                             7
```

```
SEQ ID NO: 401          moltype = AA   length = 7
FEATURE                 Location/Qualifiers
source                  1..7
                        mol_type = protein
                        organism = synthetic construct
SEQUENCE: 401
GYTFSSS                                                                    7

SEQ ID NO: 402          moltype = AA   length = 6
FEATURE                 Location/Qualifiers
source                  1..6
                        mol_type = protein
                        organism = synthetic construct
SEQUENCE: 402
YPGDGD                                                                     6

SEQ ID NO: 403          moltype = AA   length = 7
FEATURE                 Location/Qualifiers
source                  1..7
                        mol_type = protein
                        organism = synthetic construct
SEQUENCE: 403
HSSGFPH                                                                    7

SEQ ID NO: 404          moltype = AA   length = 116
FEATURE                 Location/Qualifiers
source                  1..116
                        mol_type = protein
                        organism = synthetic construct
SEQUENCE: 404
QVQLQQSGPE LVKPGASVKI SCKASGYTFS SSWINWVKQR PGQGLEWIGR IYPGDGDTNY    60
NGKFKGKATL TADKSSSTVD MHLSSLTYVD SAVYFCAIHS SGFPHWGQGT LVTVSA        116

SEQ ID NO: 405          moltype = AA   length = 11
FEATURE                 Location/Qualifiers
source                  1..11
                        mol_type = protein
                        organism = synthetic construct
SEQUENCE: 405
RTSQDISDYL N                                                              11

SEQ ID NO: 406          moltype = AA   length = 7
FEATURE                 Location/Qualifiers
source                  1..7
                        mol_type = protein
                        organism = synthetic construct
SEQUENCE: 406
YTSRLHS                                                                    7

SEQ ID NO: 407          moltype = AA   length = 9
FEATURE                 Location/Qualifiers
source                  1..9
                        mol_type = protein
                        organism = synthetic construct
SEQUENCE: 407
QQTNTLPFT                                                                  9

SEQ ID NO: 408          moltype = AA   length = 7
FEATURE                 Location/Qualifiers
source                  1..7
                        mol_type = protein
                        organism = synthetic construct
SEQUENCE: 408
SQDISDY                                                                    7

SEQ ID NO: 409          moltype =      length =
SEQUENCE: 409
000

SEQ ID NO: 410          moltype = AA   length = 6
FEATURE                 Location/Qualifiers
source                  1..6
                        mol_type = protein
                        organism = synthetic construct
SEQUENCE: 410
TNTLPF                                                                     6

SEQ ID NO: 411          moltype = AA   length = 107
```

```
FEATURE              Location/Qualifiers
source               1..107
                     mol_type = protein
                     organism = synthetic construct
SEQUENCE: 411
DIQMTQTTSS LSASLGGRVT ISCRTSQDIS DYLNWYQQKP DGAVKLLIYY TSRLHSGVPS    60
RFSGSGSGTD YSLTISNLEQ EDIATYFCQQ TNTLPFTFGG GTKLEIK                 107

SEQ ID NO: 412       moltype = AA   length = 5
FEATURE              Location/Qualifiers
source               1..5
                     mol_type = protein
                     organism = synthetic construct
SEQUENCE: 412
RYWMN                                                                 5

SEQ ID NO: 413       moltype = AA   length = 17
FEATURE              Location/Qualifiers
source               1..17
                     mol_type = protein
                     organism = synthetic construct
SEQUENCE: 413
QIYPGDGDTK YNGKFKD                                                   17

SEQ ID NO: 414       moltype = AA   length = 8
FEATURE              Location/Qualifiers
source               1..8
                     mol_type = protein
                     organism = synthetic construct
SEQUENCE: 414
YGNYGMDY                                                              8

SEQ ID NO: 415       moltype = AA   length = 7
FEATURE              Location/Qualifiers
source               1..7
                     mol_type = protein
                     organism = synthetic construct
SEQUENCE: 415
GYAFSRY                                                               7

SEQ ID NO: 416       moltype = AA   length = 6
FEATURE              Location/Qualifiers
source               1..6
                     mol_type = protein
                     organism = synthetic construct
SEQUENCE: 416
YPGDGD                                                                6

SEQ ID NO: 417       moltype = AA   length = 8
FEATURE              Location/Qualifiers
source               1..8
                     mol_type = protein
                     organism = synthetic construct
SEQUENCE: 417
YGNYGMDY                                                              8

SEQ ID NO: 418       moltype = AA   length = 117
FEATURE              Location/Qualifiers
source               1..117
                     mol_type = protein
                     organism = synthetic construct
SEQUENCE: 418
QVQLQQSGAE LVRPGSSVKI SCKASGYAFS RYWMNWVKQR PGQGLEWIGQ IYPGDGDTKY    60
NGKFKDTATL TADKSSSTAY LQLSSLTSED SAVYFCAKYG NYGMDYWGQG TSVTVSS      117

SEQ ID NO: 419       moltype = AA   length = 16
FEATURE              Location/Qualifiers
source               1..16
                     mol_type = protein
                     organism = synthetic construct
SEQUENCE: 419
RSSQSLEYGN GNTYLN                                                    16

SEQ ID NO: 420       moltype = AA   length = 7
FEATURE              Location/Qualifiers
source               1..7
                     mol_type = protein
                     organism = synthetic construct
SEQUENCE: 420
```

-continued

```
RVSNRFS                                                              7

SEQ ID NO: 421          moltype = AA  length = 9
FEATURE                 Location/Qualifiers
source                  1..9
                        mol_type = protein
                        organism = synthetic construct
SEQUENCE: 421
LQFTHVPYT                                                            9

SEQ ID NO: 422          moltype = AA  length = 12
FEATURE                 Location/Qualifiers
source                  1..12
                        mol_type = protein
                        organism = synthetic construct
SEQUENCE: 422
SQSLEYGNGN TY                                                        12

SEQ ID NO: 423          moltype =     length =
SEQUENCE: 423
000

SEQ ID NO: 424          moltype = AA  length = 6
FEATURE                 Location/Qualifiers
source                  1..6
                        mol_type = protein
                        organism = synthetic construct
SEQUENCE: 424
FTHVPY                                                               6

SEQ ID NO: 425          moltype = AA  length = 112
FEATURE                 Location/Qualifiers
source                  1..112
                        mol_type = protein
                        organism = synthetic construct
SEQUENCE: 425
DAVMTQTPLS LPVSLGDQAS ISCRSSQSLE YGNGNTYLNW YLQKPGQSPQ LLIYRVSNRF     60
SGVLDRFSGS GSGTDFTLKI SRVEAEDLGV YFCLQFTHVP YTFGGGTKLE IK             112

SEQ ID NO: 426          moltype = AA  length = 5
FEATURE                 Location/Qualifiers
source                  1..5
                        mol_type = protein
                        organism = synthetic construct
SEQUENCE: 426
GYTMN                                                                5

SEQ ID NO: 427          moltype = AA  length = 17
FEATURE                 Location/Qualifiers
source                  1..17
                        mol_type = protein
                        organism = synthetic construct
SEQUENCE: 427
LFNPYNGGTR YNQKFKG                                                   17

SEQ ID NO: 428          moltype = AA  length = 13
FEATURE                 Location/Qualifiers
source                  1..13
                        mol_type = protein
                        organism = synthetic construct
SEQUENCE: 428
LRNYGIGDDF FDY                                                       13

SEQ ID NO: 429          moltype = AA  length = 7
FEATURE                 Location/Qualifiers
source                  1..7
                        mol_type = protein
                        organism = synthetic construct
SEQUENCE: 429
GYSFTGY                                                              7

SEQ ID NO: 430          moltype = AA  length = 6
FEATURE                 Location/Qualifiers
source                  1..6
                        mol_type = protein
                        organism = synthetic construct
SEQUENCE: 430
NPYNGG                                                               6
```

```
SEQ ID NO: 431          moltype = AA  length = 13
FEATURE                 Location/Qualifiers
source                  1..13
                        mol_type = protein
                        organism = synthetic construct
SEQUENCE: 431
LRNYGIGDDF FDY                                                         13

SEQ ID NO: 432          moltype = AA  length = 122
FEATURE                 Location/Qualifiers
source                  1..122
                        mol_type = protein
                        organism = synthetic construct
SEQUENCE: 432
EVQLQQSGPE LVKPGASMKI SCKASGYSFT GYTMNWVKQS HGENLEWIGL FNPYNGGTRY       60
NQKFKGKATL TVDKSSSTAY MELLSLTSED SAVYYCARLR NYGIGDDFFD YWGQGTTLTV      120
SS                                                                    122

SEQ ID NO: 433          moltype = AA  length = 11
FEATURE                 Location/Qualifiers
source                  1..11
                        mol_type = protein
                        organism = synthetic construct
SEQUENCE: 433
KASQDVGTAV A                                                           11

SEQ ID NO: 434          moltype = AA  length = 7
FEATURE                 Location/Qualifiers
source                  1..7
                        mol_type = protein
                        organism = synthetic construct
SEQUENCE: 434
WASTRHT                                                                 7

SEQ ID NO: 435          moltype = AA  length = 9
FEATURE                 Location/Qualifiers
source                  1..9
                        mol_type = protein
                        organism = synthetic construct
SEQUENCE: 435
QQYSNYPYT                                                               9

SEQ ID NO: 436          moltype = AA  length = 7
FEATURE                 Location/Qualifiers
source                  1..7
                        mol_type = protein
                        organism = synthetic construct
SEQUENCE: 436
SQDVGTA                                                                 7

SEQ ID NO: 437          moltype =     length =
SEQUENCE: 437
000

SEQ ID NO: 438          moltype = AA  length = 6
FEATURE                 Location/Qualifiers
source                  1..6
                        mol_type = protein
                        organism = synthetic construct
SEQUENCE: 438
YSNYPY                                                                  6

SEQ ID NO: 439          moltype = AA  length = 107
FEATURE                 Location/Qualifiers
source                  1..107
                        mol_type = protein
                        organism = synthetic construct
SEQUENCE: 439
DIVMTQSHKF MSTSVGDRVS ITCKASQDVG TAVAWYQQKP GQSPKLLIYW ASTRHTGVPD       60
RFTGSGSGTD FTLTISNVQS EDLTDYFCQQ YSNYPYTFGG GTKLEIK                   107

SEQ ID NO: 440          moltype = AA  length = 5
FEATURE                 Location/Qualifiers
source                  1..5
                        mol_type = protein
                        organism = synthetic construct
SEQUENCE: 440
GYTMN                                                                   5
```

```
SEQ ID NO: 441           moltype = AA  length = 17
FEATURE                  Location/Qualifiers
source                   1..17
                         mol_type = protein
                         organism = synthetic construct
SEQUENCE: 441
LFNPYNGGIN YNQKFKG                                                       17

SEQ ID NO: 442           moltype = AA  length = 13
FEATURE                  Location/Qualifiers
source                   1..13
                         mol_type = protein
                         organism = synthetic construct
SEQUENCE: 442
LRYYGIGDDF FDY                                                           13

SEQ ID NO: 443           moltype = AA  length = 7
FEATURE                  Location/Qualifiers
source                   1..7
                         mol_type = protein
                         organism = synthetic construct
SEQUENCE: 443
GYSFTGY                                                                   7

SEQ ID NO: 444           moltype = AA  length = 6
FEATURE                  Location/Qualifiers
source                   1..6
                         mol_type = protein
                         organism = synthetic construct
SEQUENCE: 444
NPYNGG                                                                    6

SEQ ID NO: 445           moltype = AA  length = 13
FEATURE                  Location/Qualifiers
source                   1..13
                         mol_type = protein
                         organism = synthetic construct
SEQUENCE: 445
LRYYGIGDDF FDY                                                           13

SEQ ID NO: 446           moltype = AA  length = 122
FEATURE                  Location/Qualifiers
source                   1..122
                         mol_type = protein
                         organism = synthetic construct
SEQUENCE: 446
EVQLQQSGPE LVKPGASMKI SCKASGYSFT GYTMNWVKQS HGKNLEWIGL FNPYNGGINY   60
NQKFKGKATL TVDKSSSTAY MELLSLTSED SAVYYCARLR YYGIGDDFFD YWGQGTSLTV  120
SS                                                                122

SEQ ID NO: 447           moltype = AA  length = 11
FEATURE                  Location/Qualifiers
source                   1..11
                         mol_type = protein
                         organism = synthetic construct
SEQUENCE: 447
KASRDVGTAV A                                                             11

SEQ ID NO: 448           moltype = AA  length = 7
FEATURE                  Location/Qualifiers
source                   1..7
                         mol_type = protein
                         organism = synthetic construct
SEQUENCE: 448
WASTRHT                                                                   7

SEQ ID NO: 449           moltype = AA  length = 9
FEATURE                  Location/Qualifiers
source                   1..9
                         mol_type = protein
                         organism = synthetic construct
SEQUENCE: 449
QQYSNYPYT                                                                 9

SEQ ID NO: 450           moltype = AA  length = 7
FEATURE                  Location/Qualifiers
source                   1..7
                         mol_type = protein
                         organism = synthetic construct
```

```
SEQUENCE: 450
SRDVGTA                                                                    7

SEQ ID NO: 452         moltype = AA  length = 6
FEATURE                Location/Qualifiers
source                 1..6
                       mol_type = protein
                       organism = synthetic construct
SEQUENCE: 452
YSNYPY                                                                     6

SEQ ID NO: 453         moltype = AA  length = 107
FEATURE                Location/Qualifiers
source                 1..107
                       mol_type = protein
                       organism = synthetic construct
SEQUENCE: 453
DIVMTQSHKF MSTSVGDRVS ITCKASRDVG TAVAWYQQKP GQSPKLLIYW ASTRHTGVPD          60
RFTGSGSGTD FTLTISNVQS EDLADYFCQQ YSNYPYTFGG GTKLEMK                      107

SEQ ID NO: 454         moltype = AA  length = 5
FEATURE                Location/Qualifiers
source                 1..5
                       mol_type = protein
                       organism = synthetic construct
SEQUENCE: 454
GYTMN                                                                      5

SEQ ID NO: 455         moltype = AA  length = 17
FEATURE                Location/Qualifiers
source                 1..17
                       mol_type = protein
                       organism = synthetic construct
SEQUENCE: 455
LFNPYNGGPN YNQKFKG                                                        17

SEQ ID NO: 456         moltype = AA  length = 13
FEATURE                Location/Qualifiers
source                 1..13
                       mol_type = protein
                       organism = synthetic construct
SEQUENCE: 456
LRYYGIGDDF FDY                                                            13

SEQ ID NO: 457         moltype = AA  length = 7
FEATURE                Location/Qualifiers
source                 1..7
                       mol_type = protein
                       organism = synthetic construct
SEQUENCE: 457
GYSFTGY                                                                    7

SEQ ID NO: 458         moltype = AA  length = 6
FEATURE                Location/Qualifiers
source                 1..6
                       mol_type = protein
                       organism = synthetic construct
SEQUENCE: 458
NPYNGG                                                                     6

SEQ ID NO: 459         moltype = AA  length = 13
FEATURE                Location/Qualifiers
source                 1..13
                       mol_type = protein
                       organism = synthetic construct
SEQUENCE: 459
LRYYGIGDDF FDY                                                            13

SEQ ID NO: 460         moltype = AA  length = 122
FEATURE                Location/Qualifiers
source                 1..122
                       mol_type = protein
                       organism = synthetic construct
SEQUENCE: 460
EVQLQQSGPE LVKPGASMKI SCKASGYSFT GYTMNWMKQG HGKNLEWIGL FNPYNGGPNY         60
```

```
NQKFKGKATL TVDKSSSTAY MELLSLTSED SAVYYCARLR YYGIGDDFFD YWGQGTTLTV  120
SS                                                                122

SEQ ID NO: 461         moltype = AA  length = 11
FEATURE                Location/Qualifiers
source                 1..11
                       mol_type = protein
                       organism = synthetic construct
SEQUENCE: 461
KASQDVGTAV A                                                       11

SEQ ID NO: 462         moltype = AA  length = 7
FEATURE                Location/Qualifiers
source                 1..7
                       mol_type = protein
                       organism = synthetic construct
SEQUENCE: 462
WASTRHT                                                            7

SEQ ID NO: 463         moltype = AA  length = 9
FEATURE                Location/Qualifiers
source                 1..9
                       mol_type = protein
                       organism = synthetic construct
SEQUENCE: 463
QQYSSYPYT                                                          9

SEQ ID NO: 464         moltype = AA  length = 7
FEATURE                Location/Qualifiers
source                 1..7
                       mol_type = protein
                       organism = synthetic construct
SEQUENCE: 464
SQDVGTA                                                            7

SEQ ID NO: 465         moltype =     length =
SEQUENCE: 465
000

SEQ ID NO: 466         moltype = AA  length = 6
FEATURE                Location/Qualifiers
source                 1..6
                       mol_type = protein
                       organism = synthetic construct
SEQUENCE: 466
YSSYPY                                                             6

SEQ ID NO: 467         moltype = AA  length = 107
FEATURE                Location/Qualifiers
source                 1..107
                       mol_type = protein
                       organism = synthetic construct
SEQUENCE: 467
DIVMTQSHKF MSTSVGDRVS ITCKASQDVG TAVAWYQQKP GQSPKLLIYW ASTRHTGVPD   60
RFTGSGSGTD FTLTITNVQS EDLTDYFCQQ YSSYPYTFGG GTKLEIK                107

SEQ ID NO: 468         moltype = AA  length = 5
FEATURE                Location/Qualifiers
source                 1..5
                       mol_type = protein
                       organism = synthetic construct
SEQUENCE: 468
GYTMN                                                              5

SEQ ID NO: 469         moltype = AA  length = 17
FEATURE                Location/Qualifiers
source                 1..17
                       mol_type = protein
                       organism = synthetic construct
SEQUENCE: 469
LFNPYNGGPS YNQKFKG                                                 17

SEQ ID NO: 470         moltype = AA  length = 13
FEATURE                Location/Qualifiers
source                 1..13
                       mol_type = protein
                       organism = synthetic construct
SEQUENCE: 470
LRYYGIGDDF FDY                                                     13
```

```
SEQ ID NO: 471          moltype = AA  length = 7
FEATURE                 Location/Qualifiers
source                  1..7
                        mol_type = protein
                        organism = synthetic construct
SEQUENCE: 471
GYSFTGY                                                                    7

SEQ ID NO: 472          moltype = AA  length = 6
FEATURE                 Location/Qualifiers
source                  1..6
                        mol_type = protein
                        organism = synthetic construct
SEQUENCE: 472
NPYNGG                                                                     6

SEQ ID NO: 473          moltype = AA  length = 13
FEATURE                 Location/Qualifiers
source                  1..13
                        mol_type = protein
                        organism = synthetic construct
SEQUENCE: 473
LRYYGIGDDF FDY                                                            13

SEQ ID NO: 474          moltype = AA  length = 122
FEATURE                 Location/Qualifiers
source                  1..122
                        mol_type = protein
                        organism = synthetic construct
SEQUENCE: 474
EVQLQQSGPD LVKPGASMKL SCKASGYSFT GYTMNWVKQS HGKNLEWIGL FNPYNGGPSY         60
NQKFKGKATL TVDKSSSTAY MELLSLTPED SAVYYCARLR YYGIGDDFFD YWGQGTTLTV        120
SS                                                                       122

SEQ ID NO: 475          moltype = AA  length = 11
FEATURE                 Location/Qualifiers
source                  1..11
                        mol_type = protein
                        organism = synthetic construct
SEQUENCE: 475
KASQDVGTAV A                                                              11

SEQ ID NO: 476          moltype = AA  length = 7
FEATURE                 Location/Qualifiers
source                  1..7
                        mol_type = protein
                        organism = synthetic construct
SEQUENCE: 476
WASTRHT                                                                    7

SEQ ID NO: 477          moltype = AA  length = 9
FEATURE                 Location/Qualifiers
source                  1..9
                        mol_type = protein
                        organism = synthetic construct
SEQUENCE: 477
QQYSNYPYT                                                                  9

SEQ ID NO: 478          moltype = AA  length = 7
FEATURE                 Location/Qualifiers
source                  1..7
                        mol_type = protein
                        organism = synthetic construct
SEQUENCE: 478
SQDVGTA                                                                    7

SEQ ID NO: 479          moltype =     length =
SEQUENCE: 479
000

SEQ ID NO: 480          moltype = AA  length = 6
FEATURE                 Location/Qualifiers
source                  1..6
                        mol_type = protein
                        organism = synthetic construct
SEQUENCE: 480
YSNYPY                                                                     6
```

```
SEQ ID NO: 481            moltype = AA   length = 107
FEATURE                   Location/Qualifiers
source                    1..107
                          mol_type = protein
                          organism = synthetic construct
SEQUENCE: 481
DIVMTQSHKF MSTSVGDRVS ITCKASQDVG TAVAWYQEKP GQSPKLLIYW ASTRHTGVPD    60
RFTGSGSGTD FTLTISNVQS EDLAYYFCQQ YSNYPYTFGG GTKLEIK                 107

SEQ ID NO: 482            moltype = AA   length = 5
FEATURE                   Location/Qualifiers
source                    1..5
                          mol_type = protein
                          organism = synthetic construct
SEQUENCE: 482
GYTMN                                                               5

SEQ ID NO: 483            moltype = AA   length = 17
FEATURE                   Location/Qualifiers
source                    1..17
                          mol_type = protein
                          organism = synthetic construct
SEQUENCE: 483
LFNPYNGGAT YNQRFKG                                                  17

SEQ ID NO: 484            moltype = AA   length = 13
FEATURE                   Location/Qualifiers
source                    1..13
                          mol_type = protein
                          organism = synthetic construct
SEQUENCE: 484
LRKYGIGDDF FDY                                                      13

SEQ ID NO: 485            moltype = AA   length = 7
FEATURE                   Location/Qualifiers
source                    1..7
                          mol_type = protein
                          organism = synthetic construct
SEQUENCE: 485
GYSFTGY                                                             7

SEQ ID NO: 486            moltype = AA   length = 6
FEATURE                   Location/Qualifiers
source                    1..6
                          mol_type = protein
                          organism = synthetic construct
SEQUENCE: 486
NPYNGG                                                              6

SEQ ID NO: 487            moltype = AA   length = 13
FEATURE                   Location/Qualifiers
source                    1..13
                          mol_type = protein
                          organism = synthetic construct
SEQUENCE: 487
LRKYGIGDDF FDY                                                      13

SEQ ID NO: 488            moltype = AA   length = 122
FEATURE                   Location/Qualifiers
source                    1..122
                          mol_type = protein
                          organism = synthetic construct
SEQUENCE: 488
EVQLQQSGPE LVKPGASMKI SCKASGYSFT GYTMNWVKQS HGKNLEWIGL FNPYNGGATY    60
NQRFKGKATL TVDKSSSTAY MDLLSLTSED SAVYYCTRLR KYGIGDDFFD YWGQGTTLTV    120
SS                                                                  122

SEQ ID NO: 489            moltype = AA   length = 11
FEATURE                   Location/Qualifiers
source                    1..11
                          mol_type = protein
                          organism = synthetic construct
SEQUENCE: 489
KASQDVGTAV A                                                        11

SEQ ID NO: 490            moltype = AA   length = 7
FEATURE                   Location/Qualifiers
source                    1..7
                          mol_type = protein
```

```
                          -continued organism = synthetic construct
SEQUENCE: 490
WASTRHT                                                              7

SEQ ID NO: 491      moltype = AA   length = 9
FEATURE             Location/Qualifiers
source              1..9
                    mol_type = protein
                    organism = synthetic construct
SEQUENCE: 491
QQYSTYTYT                                                            9

SEQ ID NO: 492      moltype = AA   length = 7
FEATURE             Location/Qualifiers
source              1..7
                    mol_type = protein
                    organism = synthetic construct
SEQUENCE: 492
SQDVGTA                                                              7

SEQ ID NO: 493      moltype =    length =
SEQUENCE: 493
000

SEQ ID NO: 494      moltype = AA   length = 6
FEATURE             Location/Qualifiers
source              1..6
                    mol_type = protein
                    organism = synthetic construct
SEQUENCE: 494
YSTYTY                                                               6

SEQ ID NO: 495      moltype = AA   length = 107
FEATURE             Location/Qualifiers
source              1..107
                    mol_type = protein
                    organism = synthetic construct
SEQUENCE: 495
DIVMTQSHKF MSTSVGDRVS ITCKASQDVG TAVAWYQQKP GQSPKLLIYW ASTRHTGVPD    60
RFTGSGSGTD FTLTISNVQS EDLADYFCQQ YSTYTYTFGG GTKLEIK                 107

SEQ ID NO: 496      moltype = AA   length = 80
FEATURE             Location/Qualifiers
source              1..80
                    mol_type = protein
                    organism = synthetic construct
SEQUENCE: 496
FSLKLSAEND FSSDSPERKM LPCYSTARIP LPNLNEDLTC GNLLMWEAVT VQTEVIGITS    60
MLNLHAGSQK VHEHGGGKPI                                                80

SEQ ID NO: 497      moltype = AA   length = 80
FEATURE             Location/Qualifiers
source              1..80
                    mol_type = protein
                    organism = synthetic construct
SEQUENCE: 497
YSLKLTAENA FDSDSPDKKM LPCYSTARIP LPNLNEDLTC GNLLMWEAVT VKTEVIGITS    60
MLNLHAGSQK VHENGGGKPV                                                80

SEQ ID NO: 498      moltype = AA   length = 80
FEATURE             Location/Qualifiers
source              1..80
                    mol_type = protein
                    organism = synthetic construct
SEQUENCE: 498
YSQHLSAENA FDSDSPDKKM LPCYSTARIP LPNLNEDLTC GNLLMWEAVT VKTEVIGITS    60
MLNLHAGSQK VHENGGGKPV                                                80

SEQ ID NO: 499      moltype = AA   length = 80
FEATURE             Location/Qualifiers
source              1..80
                    mol_type = protein
                    organism = synthetic construct
SEQUENCE: 499
YSLRLTAETA FDSDSPDRKM LPCYSTARIP LPNLNEDLTC GNLLMWEAVT VKTEVIGITS    60
MLNLHAGSQK VHENGGGKPI                                                80

SEQ ID NO: 500      moltype = AA   length = 18
FEATURE             Location/Qualifiers
```

```
VARIANT                 3
                        note = Any amino acid
VARIANT                 5..6
                        note = Any amino acid
VARIANT                 7
                        note = D or E
VARIANT                 7
                        note = Variant residue given in the sequence has no
                         preference with respect to that in the annotation for
                         variant position
VARIANT                 8..12
                        note = Any amino acid
VARIANT                 15
                        note = Any amino acid
VARIANT                 17
                        note = Any amino acid
source                  1..18
                        mol_type = protein
                        organism = synthetic construct
SEQUENCE: 500
YRXKXXDXXX XXKNXTXQ                                                          18

SEQ ID NO: 501          moltype = AA  length = 23
FEATURE                 Location/Qualifiers
VARIANT                 8
                        note = Any amino acid
VARIANT                 11..12
                        note = Any amino acid
VARIANT                 16
                        note = Any amino acid
VARIANT                 18
                        note = Any amino acid
REGION                  1..23
                        note = source = /note=Description of synthetic construct:
                         Synthetic peptide
source                  1..23
                        mol_type = protein
                        organism = synthetic construct
SEQUENCE: 501
NYRTKYPXGT XXPKNXTXQS QVM                                                    23

SEQ ID NO: 502          moltype = AA  length = 268
FEATURE                 Location/Qualifiers
source                  1..268
                        mol_type = protein
                        organism = synthetic construct
SEQUENCE: 502
KGGVEVLEVK TGVDAITEVE CFLNPEMGDP DENLRGFSLK LSAENDFSSD SPERKMLPCY   60
STARIPLPNL NEDLTCGNLL MWEAVTVQTE VIGITSMLNL HAGSQKVHEH GGGKPIQGSN   120
FHFFAVGGDP LEMQGVLMNY RTKYPEGTIT PKNPTAQSQV MNTDHKAYLD KNNAYPVECW   180
IPDPSRNENT RYFGTFTGGE NVPPVLHVTN TATTVLLDEQ GVGPLCKADS LYVSAADICG   240
LFTNSSGTQQ WRGLARYFKI RLRKRSVK                                     268

SEQ ID NO: 503          moltype = AA  length = 268
FEATURE                 Location/Qualifiers
source                  1..268
                        mol_type = protein
                        organism = synthetic construct
SEQUENCE: 503
KGGVEVLEVK TGVDAITEVE CFLNPEMGDP DDNLRGYSLK LTAENAFDSD SPDKKMLPCY   60
STARIPLPNL NEDLTCGNLL MWEAVTVKTE VIGITSMLNL HAGSQKVHEN GGGKPVQGSN   120
FHFFAVGGDP LEMQGVLMNY RTKYPQGTIT PKNPTAQSQV MNTDHKAYLD KNNAYPVECW   180
IPDPSRNENT RYFGTYTGGE NVPPVLHVTN TATTVLLDEQ GVGPLCKADS LYVSAADICG   240
LFTNSSGTQQ WRGLARYFKI RLRKRSVK                                     268

SEQ ID NO: 504          moltype = AA  length = 268
FEATURE                 Location/Qualifiers
source                  1..268
                        mol_type = protein
                        organism = synthetic construct
SEQUENCE: 504
KGGVEVLEVK TGVDAITEVE CFLNPEMGDP DDHLRGYSQH LSAENAFDSD SPDKKMLPCY   60
STARIPLPNL NEDLTCGNLL MWEAVTVKTE VIGITSMLNL HAGSQKVHEN GGGKPVQGSN   120
FHFFAVGGDP LEMQGVLMNY RTKYPQGTIT PKNPTAQSQV MNTDHKAYLD KNNAYPVECW   180
IPDPSKNENT RYFGTYTGGE NVPPVLHVTN TATTVLLDEQ GVGPLCKADS LYVSAADICG   240
LFTNSSGTQQ WRGLARYFKI RLRKRSVK                                     268

SEQ ID NO: 505          moltype = AA  length = 268
FEATURE                 Location/Qualifiers
```

```
source                   1..268
                         mol_type = protein
                         organism = synthetic construct
SEQUENCE: 505
KGGVEVLEVK TGVDAITEVE CFLNPEMGDP DNDLRGYSLR LTAETAFDSD SPDRKMLPCY   60
STARIPLPNL NEDLTCGNLL MWEAVTVKTE VIGITSMLNL HAGSQKVHEN GGGKPIQGSN  120
FHFFAVGGDP LEMQGVLMNY RTKYPEGTVT PKNPTAQSQV MNTDHKAYLD KNNAYPVECW  180
IPDPSRNENT RYFGTYTGGE NVPPVLHVTN TATTVLLDEQ GVGPLCKADS LYVSAADICG  240
LFTNSSGTQQ WRGLPRYFKI RLRKRSVK                                    268

SEQ ID NO: 506           moltype = AA  length = 6
FEATURE                  Location/Qualifiers
REGION                   1..6
                         note = Synthetic 6xHis tag
source                   1..6
                         mol_type = protein
                         organism = synthetic construct
SEQUENCE: 506
HHHHHH                                                              6

SEQ ID NO: 507           moltype = AA  length = 10
FEATURE                  Location/Qualifiers
VARIANT                  5
                         note = Any amino acid
source                   1..10
                         mol_type = protein
                         organism = synthetic construct
SEQUENCE: 507
GFTFXNYWMT                                                         10

SEQ ID NO: 508           moltype = AA  length = 10
FEATURE                  Location/Qualifiers
source                   1..10
                         mol_type = protein
                         organism = synthetic construct
SEQUENCE: 508
GFTFNNYWMT                                                         10

SEQ ID NO: 509           moltype = AA  length = 17
FEATURE                  Location/Qualifiers
source                   1..17
                         mol_type = protein
                         organism = synthetic construct
SEQUENCE: 509
NIKKDGSEKY YVDSVRG                                                 17

SEQ ID NO: 510           moltype = AA  length = 11
FEATURE                  Location/Qualifiers
source                   1..11
                         mol_type = protein
                         organism = synthetic construct
SEQUENCE: 510
VRSGRYFALD D                                                       11

SEQ ID NO: 511           moltype = AA  length = 11
FEATURE                  Location/Qualifiers
source                   1..11
                         mol_type = protein
                         organism = synthetic construct
SEQUENCE: 511
GGDNIGSRPV H                                                       11

SEQ ID NO: 512           moltype = AA  length = 7
FEATURE                  Location/Qualifiers
source                   1..7
                         mol_type = protein
                         organism = synthetic construct
SEQUENCE: 512
DDSNRPS                                                             7

SEQ ID NO: 513           moltype = AA  length = 10
FEATURE                  Location/Qualifiers
source                   1..10
                         mol_type = protein
                         organism = synthetic construct
SEQUENCE: 513
QVWSSSTDHP                                                         10

SEQ ID NO: 514           moltype = AA  length = 10
```

```
FEATURE               Location/Qualifiers
source                1..10
                      mol_type = protein
                      organism = synthetic construct
SEQUENCE: 514
GFTFSNYWMT                                                              10

SEQ ID NO: 515        moltype = AA  length = 17
FEATURE               Location/Qualifiers
source                1..17
                      mol_type = protein
                      organism = synthetic construct
SEQUENCE: 515
NIKKDGSEKY YVDSVRG                                                      17

SEQ ID NO: 516        moltype = AA  length = 11
FEATURE               Location/Qualifiers
source                1..11
                      mol_type = protein
                      organism = synthetic construct
SEQUENCE: 516
VRSGRYFALD D                                                            11

SEQ ID NO: 517        moltype = AA  length = 11
FEATURE               Location/Qualifiers
source                1..11
                      mol_type = protein
                      organism = synthetic construct
SEQUENCE: 517
GGDNIGSRPV H                                                            11

SEQ ID NO: 518        moltype = AA  length = 7
FEATURE               Location/Qualifiers
source                1..7
                      mol_type = protein
                      organism = synthetic construct
SEQUENCE: 518
DDSNRPS                                                                 7

SEQ ID NO: 519        moltype = AA  length = 10
FEATURE               Location/Qualifiers
source                1..10
                      mol_type = protein
                      organism = synthetic construct
SEQUENCE: 519
QVWSSSTDHP                                                              10

SEQ ID NO: 520        moltype = AA  length = 10
FEATURE               Location/Qualifiers
source                1..10
                      mol_type = protein
                      organism = synthetic construct
SEQUENCE: 520
GFTFKNYWMT                                                              10

SEQ ID NO: 521        moltype = AA  length = 17
FEATURE               Location/Qualifiers
source                1..17
                      mol_type = protein
                      organism = synthetic construct
SEQUENCE: 521
NIKKDGSEKY YVDSVRG                                                      17

SEQ ID NO: 522        moltype = AA  length = 11
FEATURE               Location/Qualifiers
source                1..11
                      mol_type = protein
                      organism = synthetic construct
SEQUENCE: 522
VRSGRYFALD D                                                            11

SEQ ID NO: 523        moltype = AA  length = 11
FEATURE               Location/Qualifiers
source                1..11
                      mol_type = protein
                      organism = synthetic construct
SEQUENCE: 523
GGDNIGSRPV H                                                            11
```

```
SEQ ID NO: 524           moltype = AA  length = 7
FEATURE                  Location/Qualifiers
source                   1..7
                         mol_type = protein
                         organism = synthetic construct
SEQUENCE: 524
DDSNRPS                                                              7

SEQ ID NO: 525           moltype = AA  length = 10
FEATURE                  Location/Qualifiers
source                   1..10
                         mol_type = protein
                         organism = synthetic construct
SEQUENCE: 525
QVWSSSTDHP                                                          10

SEQ ID NO: 526           moltype = AA  length = 10
FEATURE                  Location/Qualifiers
source                   1..10
                         mol_type = protein
                         organism = synthetic construct
SEQUENCE: 526
GFTFQNYWMT                                                          10

SEQ ID NO: 527           moltype = AA  length = 17
FEATURE                  Location/Qualifiers
source                   1..17
                         mol_type = protein
                         organism = synthetic construct
SEQUENCE: 527
NIKKDGSEKY YVDSVRG                                                  17

SEQ ID NO: 528           moltype = AA  length = 11
FEATURE                  Location/Qualifiers
source                   1..11
                         mol_type = protein
                         organism = synthetic construct
SEQUENCE: 528
VRSGRYFALD D                                                        11

SEQ ID NO: 529           moltype = AA  length = 11
FEATURE                  Location/Qualifiers
source                   1..11
                         mol_type = protein
                         organism = synthetic construct
SEQUENCE: 529
GGDNIGSRPV H                                                        11

SEQ ID NO: 530           moltype = AA  length = 7
FEATURE                  Location/Qualifiers
source                   1..7
                         mol_type = protein
                         organism = synthetic construct
SEQUENCE: 530
DDSNRPS                                                              7

SEQ ID NO: 531           moltype = AA  length = 10
FEATURE                  Location/Qualifiers
source                   1..10
                         mol_type = protein
                         organism = synthetic construct
SEQUENCE: 531
QVWSSSTDHP                                                          10

SEQ ID NO: 532           moltype = AA  length = 10
FEATURE                  Location/Qualifiers
source                   1..10
                         mol_type = protein
                         organism = synthetic construct
SEQUENCE: 532
GFTFNNYWMT                                                          10

SEQ ID NO: 533           moltype = AA  length = 17
FEATURE                  Location/Qualifiers
source                   1..17
                         mol_type = protein
                         organism = synthetic construct
SEQUENCE: 533
NIKKDGSEKY YVDSVRG                                                  17
```

```
SEQ ID NO: 534          moltype = AA  length = 11
FEATURE                 Location/Qualifiers
source                  1..11
                        mol_type = protein
                        organism = synthetic construct
SEQUENCE: 534
VRSGRYFALD D                                                            11

SEQ ID NO: 535          moltype = AA  length = 11
FEATURE                 Location/Qualifiers
source                  1..11
                        mol_type = protein
                        organism = synthetic construct
SEQUENCE: 535
GGDNIGSRPV H                                                            11

SEQ ID NO: 536          moltype = AA  length = 7
FEATURE                 Location/Qualifiers
source                  1..7
                        mol_type = protein
                        organism = synthetic construct
SEQUENCE: 536
DDSNRPS                                                                  7

SEQ ID NO: 537          moltype = AA  length = 10
FEATURE                 Location/Qualifiers
source                  1..10
                        mol_type = protein
                        organism = synthetic construct
SEQUENCE: 537
QVWSSSTDHP                                                              10

SEQ ID NO: 538          moltype = AA  length = 10
FEATURE                 Location/Qualifiers
source                  1..10
                        mol_type = protein
                        organism = synthetic construct
SEQUENCE: 538
GFTFNNYWMT                                                              10

SEQ ID NO: 539          moltype = AA  length = 17
FEATURE                 Location/Qualifiers
source                  1..17
                        mol_type = protein
                        organism = synthetic construct
SEQUENCE: 539
NIKKDGSEKY YVDSVRG                                                      17

SEQ ID NO: 540          moltype = AA  length = 11
FEATURE                 Location/Qualifiers
source                  1..11
                        mol_type = protein
                        organism = synthetic construct
SEQUENCE: 540
VRSGRYFALD D                                                            11

SEQ ID NO: 541          moltype = AA  length = 11
FEATURE                 Location/Qualifiers
source                  1..11
                        mol_type = protein
                        organism = synthetic construct
SEQUENCE: 541
GGDNIGSRPV H                                                            11

SEQ ID NO: 542          moltype = AA  length = 7
FEATURE                 Location/Qualifiers
source                  1..7
                        mol_type = protein
                        organism = synthetic construct
```

```
-continued

SEQUENCE: 542
DDSNRPS                                                                                    7

SEQ ID NO: 543         moltype = AA  length = 10
FEATURE                Location/Qualifiers
source                 1..10
                       mol_type = protein
                       organism = synthetic construct
SEQUENCE: 543
QVWSSSTDHP                                                                                10
```

What is claimed is:

1. An isolated antibody or antigen binding fragment thereof comprising:
    a heavy chain variable region (vH) that comprises (a) a HCDR1 (CDR-Complementarity Determining Region) of SEQ ID NO: 226, (b) a HCDR2 of SEQ ID NO: 227, and (c) a HCDR3 of SEQ ID NO: 228; and
    a light chain variable region (vL) that comprises: (d) a LCDR1 of SEQ ID NO: 236, (e) a LCDR2 of SEQ ID NO: 237, and (f) a LCDR3 of SEQ ID NO: 238.

2. The isolated antibody or antigen binding fragment thereof of claim 1, wherein the antibody or antigen binding fragment thereof comprises a heavy chain variable region (vH) that comprises SEQ ID NO:232, and a light chain variable region (vL) that comprises SEQ ID NO: 242.

3. The antibody or antigen binding fragment thereof of claim 1, wherein the antibody is a monoclonal antibody, a chimeric antibody, a humanized antibody, a human engineered antibody, a human antibody, or a single chain antibody (scFv).

4. The antibody or antigen binding fragment thereof of claim 1, wherein said antibody or antigen binding fragment thereof specifically binds to a VP1 epitope (SEQ ID NO:501).

5. The antibody or antigen binding fragment thereof of claim 1, wherein the antibody or fragment thereof has reduced glycosylation or no glycosylation or is hypofucosylated.

6. A pharmaceutical composition comprising the antibody or antigen binding fragment thereof of claim 1 further comprising a pharmaceutically acceptable carrier.

7. A pharmaceutical composition comprising a plurality of antibodies or antigen binding fragments thereof of claim 1, wherein at least 0.05%, 0.1%, 0.5%, 1%, 2%, 3%, 5% or more of the antibodies or antigen binding fragments thereof in the composition have an α2,3-linked sialic acid residue.

8. A pharmaceutical composition comprising a plurality of antibodies or antigen binding fragments thereof of claim 1, wherein none of the antibodies or antigen binding fragments thereof comprise a bisecting GlcNAc.

9. A pharmaceutical composition comprising the antibody or fragment thereof of claim 1, wherein the composition is a lyophilisate.

10. A method of neutralizing a BK virus (BKV) or John Cunningham (JC) virus (JCV) infection comprising administering, via injection or infusion to a patient in need thereof, an effective amount of the antibody or antigen-binding fragment thereof of claim 1.

11. The method of claim 10, wherein the patient in need thereof is diagnosed with BK viruria, BK viremia, JC viruria, or JC viremia.

12. A method of treating or reducing the likelihood of a BK virus or JC virus associated disorder, comprising administering, via injection or infusion to a patient in need thereof, an effective amount of the antibody or antigen binding fragment thereof of claim 1, and wherein the disorder is selected from the group consisting of: a nephropathy, a BKV-associated nephropathy (BKVAN), a hemorrhagic cystitis (HC), Progressive Multifocal Leukoencephalopathy (PML), a granule cell neuronopathy (GCN), an interstitial kidney disease, a ureteral stenosis, a vasculitis, a colitis, a retinitis, a meningitis, and an immune reconstitution inflammatory syndrome (IRIS).

13. The method of claim 12, wherein the antibody or antigen binding fragment thereof is administered in combination with another therapeutic agent.

14. The method of claim 13, wherein the another therapeutic agent is an immunosuppressive agent.

15. An isolated nucleic acid that encodes the antibody or antigen binding fragment thereof of claim 1.

16. A vector comprising the nucleic acid of claim 15.

17. A host cell comprising the vector of claim 16.

18. A process for producing an antibody or antigen binding fragment thereof comprising cultivating the host cell of claim 17 and recovering the antibody or antigen binding fragment thereof from the culture.

19. A diagnostic reagent comprising the antibody or antigen binding fragment thereof of claim 1, wherein the antibody or antigen binding fragment thereof is labeled.

20. The diagnostic reagent of claim 19, wherein the label is selected from the group consisting of: a radiolabel, a fluorophore, a chromophore, an imaging agent, and a metal ion.

* * * * *